(12) United States Patent
Bhalla et al.

(10) Patent No.: US 9,944,954 B2
(45) Date of Patent: Apr. 17, 2018

(54) GLYCEROL 3-PHOSPHATE DEHYDROGENASE FOR BUTANOL PRODUCTION

(71) Applicant: BUTAMAX ADVANCED BIOFUELS LLC, Wilmington, DE (US)

(72) Inventors: Ritu Bhalla, Tirmulgherry (IN); Gopal K. Chotani, Palo Alto, CA (US); Michael Dauner, Wilmington, DE (US); Mark J. Nelson, Newark, DE (US); Daniel P. O'Keefe, Ridley Park, PA (US); Caroline M. Peres, Palo Alto, CA (US); Jahnavi Chandra Prasad, Wilmington, DE (US); Jean-Francois Tomb, Wilmington, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days.

(21) Appl. No.: 15/228,770

(22) Filed: Aug. 4, 2016

(65) Prior Publication Data

US 2016/0376613 A1    Dec. 29, 2016

Related U.S. Application Data

(62) Division of application No. 14/208,474, filed on Mar. 13, 2014, now Pat. No. 9,441,250.

(60) Provisional application No. 61/782,651, filed on Mar. 14, 2013.

(51) Int. Cl.
| | |
|---|---|
| *C12P 7/16* | (2006.01) |
| *C12N 9/04* | (2006.01) |
| *C12N 1/20* | (2006.01) |
| *C12N 1/00* | (2006.01) |
| *C07H 21/02* | (2006.01) |
| *C07K 1/00* | (2006.01) |
| *C12N 15/52* | (2006.01) |
| *C12N 9/02* | (2006.01) |

(52) U.S. Cl.
CPC .............. *C12P 7/16* (2013.01); *C12N 9/0006* (2013.01); *C12N 9/0008* (2013.01); *C12N 15/52* (2013.01); *C12Y 101/01008* (2013.01); *C12Y 101/01094* (2013.01); *C12Y 101/05003* (2013.01); *C12Y 102/01012* (2013.01); *Y02E 50/10* (2013.01); *Y02P 20/52* (2015.11)

(58) Field of Classification Search
CPC .... C12N 9/0006; C12N 15/52; C12N 9/0008; C12P 7/16; Y02E 50/10; C12Y 102/01012; C12Y 101/01094; C12Y 101/01008; C12Y 101/05003; Y02P 20/52
USPC .......... 435/160, 190, 252.3, 252.31, 252.32, 435/252.33, 252.34, 254.11, 254.2, 435/254.21, 254.22; 536/23.1, 23.2; 530/350
See application file for complete search history.

(56) References Cited

U.S. PATENT DOCUMENTS

| | | |
|---|---|---|
| 4,683,202 A | 7/1987 | Mullis et al. |
| 5,514,583 A | 5/1996 | Picataggio et al. |
| 5,686,276 A | 11/1997 | Laffend et al. |
| 5,712,133 A | 1/1998 | Picataggio et al. |
| 6,013,494 A * | 1/2000 | Nakamura ........... C12N 9/0004 435/158 |
| 6,432,688 B1 | 8/2002 | Ito et al. |
| 7,223,575 B2 | 5/2007 | Zhang et al. |
| 7,541,173 B2 | 6/2009 | Bramucci et al. |
| 7,574,601 B2 | 8/2009 | Jahrorni et al. |
| 7,659,104 B2 | 2/2010 | Bramucci et al. |
| 7,741,119 B2 | 6/2010 | Viitanen et al. |
| 7,851,188 B2 | 12/2010 | Donaldson et al. |
| 7,910,342 B2 | 3/2011 | Liao et al. |
| 7,993,889 B1 | 8/2011 | Donaldson et al. |
| 8,017,364 B2 | 9/2011 | Bramucci et al. |
| 8,129,162 B2 | 3/2012 | Li et al. |
| 8,178,328 B2 | 5/2012 | Donaldson et al. |
| 8,188,250 B2 | 5/2012 | Bramucci et al. |

(Continued)

FOREIGN PATENT DOCUMENTS

| | | |
|---|---|---|
| WO | WO20090009142 | 1/2009 |
| WO | WO20110149353 | 12/2011 |

(Continued)

OTHER PUBLICATIONS

Albertyn, et al., Purification and characterization of glycerol-3-phosphate dehydrogenase of *Saccharomyces cerevisiae*, FEBS Lett 308:130-132, 1992.
Bell, Mutants of *Escherichia coli* defective in membrane phospholipid synthesis: macromolecular synthesis in an sn-glycerol 3-phosphate acyltransferase Km mutant, J. Bact. 117:1065-76, 1974.
Carmon and MacIntyre, The alpha-glycerophosphate cycle in *Drosophila melanogaster* VI. Structure and evolution of enzyme paralogs in the genus *Drosphila*, J. Heredity 101:225-234, 2010.
Database UniProtKB (Online), "Glycerol-3-phosphate dehydrogenase", XP002726310, Database accession No. B3LGS7 (Sep. 2, 2008) (Cited in ISR/WO).
Dickinson, et al., An Investigation of the Metabolism of Valine to isobutyl Alcohol in *Saccharomyces cerevisiae*,J. Biol. Chem. 273:25752-25756, 1998.
Edgar and Bell, Biosynthesis in *Escherichia coli* of sn-glycerol-3-phosphate, a precursor of phospholipid, J. Biol. Chem. 255: 3492-3497, 1980.

(Continued)

*Primary Examiner* — Ganapathirama Raghu

(57) ABSTRACT

Provided herein are glycerol-3-phosphate dehydrogenase (GPD) enzymes with increased $K_M$ for NADH and GPD enzymes with substantially the same affinity for NADH and NADPH and/or are feedback inhibited by glycerol-3-phosphate. Also provided herein are recombinant microorganisms comprising a heterologous gene encoding GPD and a deletion or disruption in an endogenous gene encoding GPD. Also provided are recombinant microorganisms comprising a heterologous gene encoding GPD and a butanol biosynthetic pathway. Further provided are methods of producing butanol comprising providing the recombinant microorganisms described herein and contacting the recombinant microorganism with at least one fermentable carbon substrate under conditions wherein butanol is produced.

11 Claims, 9 Drawing Sheets

(56) References Cited

U.S. PATENT DOCUMENTS

| | | |
|---|---|---|
| 8,206,970 B2 | 6/2012 | Eliot et al. |
| 8,222,017 B2 | 7/2012 | Li et al. |
| 8,241,878 B2 | 8/2012 | Anthony et al. |
| 8,247,208 B2 | 8/2012 | Caimi et al. |
| 8,273,558 B2 | 9/2012 | Donaldson et al. |
| 8,283,144 B2 | 10/2012 | Donaldson et al. |
| 8,372,612 B2 | 2/2013 | Larossa et al. |
| 8,389,252 B2 | 3/2013 | Larossa |
| 8,455,224 B2 | 6/2013 | Paul |
| 8,455,225 B2 | 6/2013 | Bramucci et al. |
| 8,455,239 B2 | 6/2013 | Feldman et al. |
| 8,465,964 B2 | 6/2013 | Anthony et al. |
| 8,518,678 B2 | 8/2013 | Flint et al. |
| 8,557,562 B2 | 10/2013 | Bramucci et al. |
| 8,614,085 B2 | 12/2013 | Van Dyk et al. |
| 8,637,281 B2 | 1/2014 | Paul et al. |
| 8,637,289 B2 | 1/2014 | Anthony et al. |
| 8,652,823 B2 | 2/2014 | Flint et al. |
| 8,889,385 B2 | 2/2014 | Donaldson et al. |
| 8,669,094 B2 | 3/2014 | Anthony et al. |
| 8,691,540 B2 | 4/2014 | Bramucci et al. |
| 8,735,114 B2 | 5/2014 | Donaldson et al. |
| 8,765,433 B2 | 7/2014 | Gude et al. |
| 8,785,166 B2 | 7/2014 | Anthony et al. |
| 8,795,992 B2 | 8/2014 | Bramucci et al. |
| 8,828,694 B2 | 9/2014 | Anthony et al. |
| 8,828,704 B2 | 9/2014 | Donaldson et al. |
| 8,871,488 B2 | 10/2014 | Dauner et al. |
| 8,895,307 B2 | 11/2014 | Li et al. |
| 8,906,666 B2 | 12/2014 | Alsaker |
| 8,911,981 B2 | 12/2014 | Li et al. |
| 8,940,511 B2 | 1/2015 | Larossa |
| 8,945,859 B2 | 2/2015 | Donaldson et al. |
| 8,945,899 B2 | 2/2015 | Li et al. |
| 8,951,774 B2 | 2/2015 | Donaldson et al. |
| 8,951,937 B2 | 2/2015 | Flint et al. |
| 8,956,850 B2 | 2/2015 | Anthony et al. |
| 8,962,298 B2 | 2/2015 | Donaldson et al. |
| 8,969,065 B2 | 3/2015 | Anthony et al. |
| 8,980,612 B2 | 3/2015 | Donaldson et al. |
| 9,163,266 B2 | 10/2015 | Anthony |
| 9,169,467 B2 | 10/2015 | Govindarajan et al. |
| 9,169,499 B2 | 10/2015 | Paul et al. |
| 9,181,566 B2 | 11/2015 | Dauner et al. |
| 9,206,447 B2 | 12/2015 | Anthony et al. |
| 9,238,801 B2 | 1/2016 | Li et al. |
| 9,238,828 B2 | 1/2016 | McElvain et al. |
| 9,260,708 B2 | 2/2016 | Anthony et al. |
| 9,267,157 B2 | 2/2016 | Anthony et al. |
| 9,273,330 B2 | 3/2016 | Bramucci et al. |
| 9,284,612 B2 | 3/2016 | Liao et al. |
| 9,297,016 B2 | 3/2016 | Flint et al. |
| 9,297,028 B2 | 3/2016 | Donaldson et al. |
| 9,297,029 B2 | 3/2016 | Donaldson et al. |
| 9,303,225 B2 | 4/2016 | Donaldson et al. |
| 9,365,872 B2 | 6/2016 | Donaldson et al. |
| 9,388,392 B2 | 7/2016 | Govindarajan et al. |
| 2007/0031918 A1 | 2/2007 | Dunson et al. |
| 2008/0182308 A1 | 7/2008 | Donaldson et al. |
| 2009/0155870 A1 | 6/2009 | Donaldson et al. |
| 2009/0203099 A1 | 8/2009 | Caimi et al. |
| 2009/0246846 A1 | 10/2009 | Viitanen et al. |
| 2009/0305370 A1 | 12/2009 | Grady et al. |
| 2010/0081154 A1 | 4/2010 | Flint et al. |
| 2010/0081179 A1 | 4/2010 | Anthony et al. |
| 2010/0081182 A1 | 4/2010 | Paul et al. |
| 2010/0093020 A1 | 4/2010 | Bramucci et al. |
| 2010/0120105 A1 | 5/2010 | Anthony et al. |
| 2011/0020889 A1 | 1/2011 | Feldman et al. |
| 2011/0097773 A1 | 4/2011 | Grady et al. |
| 2011/0124060 A1 | 5/2011 | Anthony et al. |
| 2011/0136192 A1 | 6/2011 | Paul et al. |
| 2011/0195505 A1 | 8/2011 | Euler et al. |
| 2011/0244536 A1 | 10/2011 | Nagarajan et al. |
| 2011/0250610 A1 | 10/2011 | Bramucci et al. |
| 2011/0275130 A1 | 11/2011 | Pronk et al. |
| 2012/0058541 A1 | 3/2012 | Alsaker et al. |
| 2012/0064561 A1 | 3/2012 | Flint et al. |
| 2012/0149080 A1 | 6/2012 | Bramucci et al. |
| 2012/0196341 A1 | 8/2012 | Donaldson et al. |
| 2012/0237988 A1 | 9/2012 | Anthony et al. |
| 2012/0258873 A1 | 10/2012 | Gibson et al. |
| 2012/0295319 A1 | 11/2012 | Nevoigt et al. |
| 2013/0035515 A1 | 2/2013 | Dobson et al. |
| 2013/0071898 A1 | 3/2013 | Anthony et al. |
| 2013/0171706 A1 | 7/2013 | Donaldson et al. |
| 2013/0203138 A1 | 8/2013 | McElvain et al. |
| 2013/0252296 A1 | 9/2013 | Maggio-Hall et al. |
| 2013/0316414 A1 | 11/2013 | Paul et al. |
| 2014/0004526 A1 | 1/2014 | Dauner et al. |
| 2014/0030782 A1 | 1/2014 | Anthony et al. |
| 2014/0030783 A1 | 1/2014 | Anthony et al. |
| 2014/0038263 A1 | 2/2014 | Flint et al. |
| 2014/0038268 A1 | 2/2014 | Flint et al. |
| 2014/0051133 A1 | 2/2014 | Govindarajan et al. |
| 2014/0051137 A1 | 2/2014 | Flint et al. |
| 2014/0057329 A1 | 2/2014 | Li et al. |
| 2014/0093930 A1 | 4/2014 | Li et al. |
| 2014/0096439 A1 | 4/2014 | Bramucci et al. |
| 2014/0141479 A1 | 5/2014 | Anthony et al. |
| 2014/0170732 A1 | 6/2014 | Bramucci et al. |
| 2014/0186910 A1 | 7/2014 | Rothman et al. |
| 2014/0186911 A1 | 7/2014 | Anthony et al. |
| 2014/0273116 A1 | 9/2014 | Kelly et al. |
| 2014/0273129 A1 | 9/2014 | Bhalla et al. |
| 2014/0308735 A1 | 10/2014 | Anthony et al. |
| 2014/0335582 A1 | 11/2014 | Donaldson et al. |
| 2014/0349349 A1 | 11/2014 | Dauner et al. |
| 2014/0377824 A1 | 12/2014 | Satagopan et al. |
| 2015/0037855 A1 | 2/2015 | Bhadra et al. |
| 2015/0111269 A1 | 4/2015 | Li et al. |
| 2015/0119608 A1 | 4/2015 | Donaldson et al. |
| 2015/0125920 A1 | 5/2015 | Anthony et al. |

FOREIGN PATENT DOCUMENTS

| | | |
|---|---|---|
| WO | WO20120138942 | 10/2012 |
| WO | WO20130141905 | 9/2013 |
| WO | WO20140081803 | 5/2014 |

OTHER PUBLICATIONS

Edgar and Bell, Biosynthesis in *Escherichia coli* of sn-glyceroi 3-hopshate, a precursor of phospholipid, J. Biol. Chem. 253:6354-63, 1978.

Feldmann, et al., Pentose metabolism in Zymomonas mobilis wild-type and recombinant strains, Appl. Microbiol. Biotechnol. 38:354-61, 1992.

Frohlich, et al, Rickettsia prowazekii uses an sn-glycerol-3-phosphate dehydrogenase and a novel dihydroxyacetone phosphate transport system to supply triose phosphate for phospholipit biosynthesis, J. Bacteriol ,192: 4281-4288, 2010.

Hahnai, et al., Engineered synthetic pathway for isopropanol production in *Escherichia coli*, Appl. Environ. 73:7814-7813, 2007.

Jain, et al., Effect of alternative NAD+–regenerating pathways on the formation of primary and secondary aroma compounds in a *Saccharomyces cerevisiae* glycerol-defective mutant, Appl. Microbiol. Biotechnol. 93:131-141, 2012.

Niesel, et al., sn-Glycerol-3-phosphate dehydrogenase (soluble) from *Drosophila melanogaster*, Methods Enzymol. 89:296-301, 1982.

Norbeck, Purification and characterization of two isoenzymes of DL-glycerol-3-phosphatase from *Saccharomyces cerevisiae*, J. Biol. Chem. 271:13875-13831, 1996.

Ohta, et al., Genetic improvement of *Escherichia coli* for ethanol production: chromosomal integration of mobilis genes encoding pyruvate decarboxylase and alcohol dehydrogenase II, Appl. Environ. Microbiol. 57:893-900, 1991.

Ou, et al, Crystal structures of human glycerol-3-phosphate dehydrogenase 1 (GPD1), J. Mol. Biol. 357: 858-869, 2005.

Ruijter, et al, Polyol accumulation by Aspergillus oryzae at low water activity in solid-state fermentation, Microbiology 150:1095-1101, 2004.

(56) References Cited

OTHER PUBLICATIONS

Sakasegawa, et al, Structural and functional analysis of the gpsA gene product of Archaeoglobus fulgidus: a glycerol-3-phopaste dehydrogenase with an unusual NADP+ preference, Protein Science 13:3161-3171, 2004.

Shen and Liao, Metabolic engineering of *Escherichia coli* for 1-butanol and 1-propanol production via the keto-acid pathways, Metab. Eng. 10:312-320, 2008.

Underwood, et al., Flux through citrate synthase limits the growth of ethanologenic *Escherichia coli* KO11 during xylose fermentation, Appl. Envrion. Microbiol. 68:1071-1081, 2002.

Valadi, et al, Distinct intracellular localization of GPD1p and GPD2p, the two yeast isoforms of NAD+ dependent glycerol-3-phosphate dehydrogenase, explains their different contributions to redox-driven glycerol production, J. Biol. Chem. 279:39677-39685, 2004.

Watanabe, et al, Expression of glycerol 3-phosphate dehydrogenase gene (CvGPD1) in salt-tolerant yeast Candida versatilis is stimulated by high concentrations of NaCl, Yeast 25:107-116, 2008.

Zhang, et al., Metabolic engineering of a pentose metabolism pathway in ethanologenic Zymomonas mobilis, Science 267:240-243, 1995.

Alarcon, et al., Structure of glycerol-3-phosphate dehydrogenase (GPD1) from *Saccharomyces cerevisiae* at 2.45A resolution, Acta Crystallographica F68:1279-1283, 2012.

Whisstock, et al., Prediction of protein function from protein sequence, Q. Rev. Biophysics. 36:307-340, 2003.

Witkowski, et al., Conversion of b-ketoacyl synthase to a Malonyl Decarboxylase by replacement of the active cysteine cysteine with glutamine, Biochemistry 38:11643-11650, 1999.

Broun, et al., Catalytic plasticity of fatty acid modification enzymes underlying chemical diversity of plant lipids, Science 282:1315-1317, 1998.

Devos, et al., Practical limits of function prediction, Proteins: Structure, Function, and Genetics 41:98-107, 2000.

Kisselev, Polypeptide release factors in prokaryotes and eukaryotes: same function, different structure, Structure 10:8-9. 2002.

Seffernick, et al., Melamine deaminase and Atrazine chlorohydrolase: 98 percent identical but functionally different, J. Bacteriol. 183:2405-2410, 2001.

International Search Report and Written Opinion, dated Jul. 11, 2014, in International Patent Application No. PCT/US2014/025714, filed on Mar. 13, 2014.

\* cited by examiner

```
                                            F41                                                        F97
                                             ↓                                                          ↓
Human-Truncated       (35) RVTMWVFEEDIGGKKLTETINTQHENVKYLEGHKLPPNVVAVPDVVQAAEDADILFVVPHQFIGK
Saccharomyces GP01    (67) TVQMWVFEEEINGEKLTEIINTRHQNVKYLPGTTLPDNLVANPDLIDSVKDVDIIVFNIPHQFLPR
Rickettsia            (29) NVTLFLRDEII----LKEILYKKTNAQYLGDIELPTNLQATTNLS-VLKDFELIIIAVPSYAFDD
Beggiatoa             (29) PIYLWGKDPAH----VHTLQIQRCNQRFLPNAVFPDNLYATFDFVTIMPIVEDIIVVPSHGFRE
Kangiella             (29) SVQLWARNSQH----VVEMQQAKQNTKYLPDVAFPDNLSVTDQHDVALKHHPILVAVPSHAFRD
```

FIG. 2

GLYCEROL 3-PHOSPHATE DEHYDROGENASE FOR BUTANOL PRODUCTION

CROSS REFERENCE TO RELATED APPLICATIONS

This application is a divisional of U.S. patent application Ser. No. 14/208,474, filed on Mar. 13, 2014, now U.S. Pat. No. 9,441,250, issued on Sep. 13, 2016, which claims benefit of priority from U.S. Provisional Application No. 61/782,651, filed Mar. 14, 2013, each of which is hereby incorporated by reference in its entirety.

FIELD OF THE INVENTION

The invention relates to the field of industrial microbiology and the fermentative production of butanol and isomers thereof. More specifically, the invention relates to glycerol-3-phosphate dehydrogenase (GPD) enzymes with a high $K_M$ for NADH, substantially the same affinity for NADH and NADPH and/or GPD enzymes that are feedback inhibited, recombinant microorganisms comprising such enzymes, and methods of using such enzymes to produce butanol.

REFERENCE TO SEQUENCE LISTING SUBMITTED ELECTRONICALLY

The content of the electronically submitted sequence listing in ASCII text file (Name: CL5707USDIV_SequenceListing_ST25) filed with the application is incorporated herein by reference in its entirety.

BACKGROUND

Butanol is an important industrial chemical, useful as a fuel additive, as a feedstock chemical in the plastics industry, and as a food grade extractant in the food and flavor industry. Each year 10 to 12 billion pounds of butanol are produced by petrochemical means and the need for this commodity chemical will likely increase in the future.

Methods for the chemical synthesis of isobutanol are known, such as oxo synthesis, catalytic hydrogenation of carbon monoxide (Ullmann's Encyclopedia of Industrial Chemistry, 6th edition, 2003, Wiley-VCH Verlag GmbH and Co., Weinheim, Germany, Vol. 5, pp. 716-719) and Guerbet condensation of methanol with n-propanol (Carlini et al., *J. Molec. Catal. A. Chem.* 220:215-220, 2004). These processes use starting materials derived from petrochemicals, are generally expensive, and are not environmentally friendly. The production of isobutanol from plant-derived raw materials would minimize greenhouse gas emissions and would represent an advance in the art.

Isobutanol is produced biologically as a by-product of yeast fermentation or by recombinantly engineered microorganisms modified to express a butanol biosynthetic pathway for producing butanol. See e.g., U.S. Pat. No. 7,851,188, which is incorporated herein by reference in its entirety. As a component of "fusel oil" that forms as a result of the incomplete metabolism of amino acids by fungi, isobutanol is specifically produced from catabolism of L-valine. After the amine group of L-valine is harvested as a nitrogen source, the resulting α-keto acid is decarboxylated and reduced to isobutanol by enzymes of the so-called Ehrlich pathway (Dickinson et al., *J. Biol. Chem.* 273:25752-25756, 1998).

One of the key yield loss mechanisms in yeast butanol production is the loss of carbon and reducing equivalents that are diverted from glycolysis by the conversion of dihydroxyacetone phosphate to glycerol. The first step in this conversion is catalyzed by an enzyme called glycerol-3-phosphate dehydrogenase (GPD). Eliminating GPD, and therefore glycerol production, in butanol-producing yeast, has been proposed previously. However, glycerol is required for growth and is an osmoprotectant.

Accordingly, methods of increasing butanol yield and decreasing glycerol production represent an advance in the art.

BRIEF SUMMARY OF THE INVENTION

Provided herein are GPD enzymes, recombinant microorganisms, and methods for production of butanol.

Provided herein are recombinant microorganisms comprising (a) an engineered butanol biosynthetic pathway comprising at least one polypeptide that is heterologous to the recombinant microorganism; (b) a heterologous glycerol-3-phosphate dehydrogenase (GPD), wherein the heterologous GPD has a higher $K_M$ for NADH as compared to the $K_M$ of the endogenous GPD of the microorganism; and (c) a deletion or disruption in an endogenous gene encoding GPD. In some embodiments, the recombinant microorganism has improved or increased production of butanol as compared to a control recombinant microorganism that lacks the heterologous GPD. In some embodiments, the recombinant microorganism has reduced or decreased production of glycerol as compared to a control recombinant microorganism that lacks the heterologous GPD. In some embodiments, the recombinant microorganism has an increased butanol to glycerol molar ratio as compared to a control recombinant microorganism that lacks the heterologous GPD. In some embodiments, the recombinant microorganism has an increased effective yield as compared to a control recombinant microorganism that lacks the heterologous GPD.

Also provided herein are recombinant microorganisms comprising (a) an engineered butanol biosynthetic pathway comprising at least one polypeptide that is heterologous to the recombinant microorganism; (b) a heterologous glycerol-3-phosphate dehydrogenase (GPD), wherein the heterologous GPD has substantially the same affinity for NADH and NADPH and/or is feedback inhibited; and (c) a deletion or disruption in an endogenous gene encoding GPD. In some embodiments, the recombinant microorganism has improved production of butanol as compared to a control recombinant microorganism that lacks the heterologous GPD. Optionally, the heterologous GPD is feedback inhibited by glycerol-3-phosphate. In some embodiments, the recombinant microorganism has reduced or decreased production of glycerol as compared to a control recombinant microorganism that lacks the heterologous GPD. In some embodiments, the recombinant microorganism has an increased butanol to glycerol molar ratio as compared to a control recombinant microorganism that lacks the heterologous GPD. In some embodiments, the recombinant microorganism has an increased effective yield as compared to a control recombinant microorganism that lacks the heterologous GPD.

In certain embodiments, the heterologous GPD is a naturally occurring GPD. In certain embodiments, the naturally occurring GPD is selected from EC number 1.1.1.8, 1.1.5.3, or 1.1.1.94. The naturally occurring GPD can be a GPD from an organism selected from the group consisting of *Leish-*

*mania mexicana, Dunaliella viridis, Jaculus orientalis, Archeoglobus fulgidus, Rickettsia prowazekii, Beggiatoa alba, Kangiella koreenis Aspergillus oryzae, Candida versatilis, Escherichia coli,* and *Oryctolagus cuniculu.*

In certain embodiments, the heterologous GPD is an engineered GPD. The engineered GPD can comprise at least one substitution corresponding to position 42, 44, 45, 71, 73, 75, 95, 124, 126, 129, 151, 152, 183, 184, 185, 246, 310, 336, 337, or 339 of SEQ ID NO: 195. In certain embodiments the engineered GPD comprises at least one substitution at a residue corresponding to position 73 of SEQ ID NO:195. In certain embodiments the engineered GPD comprises at least one substitution at a residue corresponding to position 129 of SEQ ID NO:195. In certain embodiments the engineered GPD comprises at least one substitution at a residue corresponding to position 73 of SEQ ID NO:195 and a substitution at a residue corresponding to position 129 of SEQ ID NO:195.

Also provided are engineered glycerol-3-phosphate dehydrogenase (GPD) enzymes. In certain embodiments, the engineered GPD enzyme has at least 85% identity to SEQ ID NO:195. In certain embodiments, the engineered GPD enzyme comprises at least one substitution at a residue corresponding to position 42, 44, 45, 71, 73, 75, 95, 124, 126, 129, 151, 152, 183, 184, 185, 246, 310, 336, 337, or 339 of SEQ ID NO: 195. In certain embodiments, the engineered GPD enzyme comprises at least one substitution corresponding to position 73 of SEQ ID NO:195. In certain embodiments, the engineered GPD enzyme comprises at least one substitution corresponding to position 129 of SEQ ID NO:195. In certain embodiments, the engineered GPD enzyme comprises at least one substitution corresponding to position 73 of SEQ ID NO:195 and a substitution corresponding to position 129 of SEQ ID NO:129. In certain embodiments, the engineered GPD enzyme has a $K_M$ for NADH from about 0.01 mM to 1 mM.

Also provided are recombinant microorganisms comprising any of the engineered GPD enzymes disclosed herein. Optionally, the recombinant microorganism can comprise an engineered butanol biosynthetic pathway that comprises at least one gene that is heterologous to the recombinant microorganism. The recombinant microorganism can, for example, comprise a deletion or disruption of an endogenous gene encoding GPD. In certain embodiments, the recombinant microorganism has improved or increased production of butanol compared to a microorganism that lacks the engineered GPD enzyme. In some embodiments, the recombinant microorganism has reduced or decreased production of glycerol as compared to a control recombinant microorganism that lacks the engineered GPD. In some embodiments, the recombinant microorganism has an increased butanol to glycerol molar ratio as compared to a control recombinant microorganism that lacks the engineered GPD. In some embodiments, the recombinant microorganism has an increased effective yield as compared to a control recombinant microorganism that lacks the engineered GPD.

Also provided are methods for the production of butanol. The methods comprise providing a recombinant microorganism comprising (i) an engineered butanol biosynthetic pathway, (ii) a deletion or disruption in an endogenous gene encoding GPD, and; (iii) at least one of (a) an engineered GPD enzyme; (b) a heterologous glycerol-3-phosphate dehydrogenase (GPD), wherein the heterologous GPD has a higher $K_M$ for NADH as compared to the $K_M$ of the microorganism's endogenous GPD; or (c) a heterologous GPD, wherein the heterologous GPD has substantially the same affinity for NADH and NADPH and/or is feedback inhibited; and contacting the recombinant microorganism with at least one fermentable carbon substrate under conditions wherein butanol is produced. Optionally, the heterologous GPD is feedback inhibited by glycerol-3-phosphate. In certain embodiments, the recombinant microorganism is grown under anaerobic conditions.

The recombinant microorganism can comprise an engineered butanol biosynthetic pathway selected from the group consisting of (a) a 1-butanol biosynthetic pathway; (b) a 2-butanol biosynthetic pathway; and (c) an isobutanol biosynthetic pathway.

Optionally, the 1-butanol biosynthetic pathway comprises at least one polypeptide that performs one of the following substrate to product conversions: (a) acetyl-CoA to acetoacetyl-CoA, as catalyzed by acetyl-CoA acetyltransferase; (b) acetoacetyl-CoA to 3-hydroxybutyryl-CoA, as catalyzed by 3-hydroxybutyryl-CoA dehydrogenase; (c) 3-hydroxybutyryl-CoA to crotonyl-CoA, as catalyzed by crotonase; (d) crotonyl-CoA to butyryl-CoA, as catalyzed by butyryl-CoA dehydrogenase; (e) butyryl-CoA to butyraldehyde, as catalyzed by butyraldehyde dehydrogenase; and (f) butyraldehyde to 1-butanol, as catalyzed by 1-butanol dehydrogenase.

Optionally, the 2-butanol biosynthetic pathway comprises at least one polypeptide that performs one of the following substrate to product conversions: (a) pyruvate to alpha-acetolactate, as catalyzed by acetolactate synthase; (b) alpha-acetolactate to acetoin, as catalyzed by acetolactate decarboxylase; (c) acetoin to 2,3-butanediol, as catalyzed by butanediol dehydrogenase; (d) 2,3-butanediol to 2-butanone, as catalyzed by butanediol dehydratase; and (e) 2-butanone to 2-butanol, as catalyzed by 2-butanol dehydrogenase.

Optionally, the isobutanol biosynthetic pathway comprises at least one polypeptide that performs one of the following substrate to product conversions: (a) pyruvate to acetolactate, as catalyzed by acetolactate synthase; (b) acetolactate to 2,3-dihydroxyisovalerate, as catalyzed by ketol-acid reductoisomerase; (c) 2,3-dihydroxyisovalerate to α-ketoisovalerate, as catalyzed by dihydroxyacid dehydratase; (d) α-ketoisovalerate to isobutyraldehyde, as catalyzed by a branched chain keto acid decarboxylase; and (e) isobutyraldehyde to isobutanol, as catalyzed by branched-chain alcohol dehydrogenase.

In certain embodiments, the recombinant microorganism is from a genus selected from the group consisting of *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Paenibacillus, Arthrobacter, Corynebacterium, Brevibacterium, Schizosaccharomyces, Kluveromyces, Yarrowia, Pichia, Zygosaccharomyces, Debaryomyces, Candida, Brettanomyces, Pachysolen, Hansenula, Issatchenkia, Trichosporon Yamadazyma,* and *Saccharomyces.*

Also provided are recombinant microorganisms comprising (a) a heterologous glycerol-3-phosphate dehydrogenase (GPD), wherein the heterologous GPD has a higher $K_M$ for NADH as compared to the $K_M$ of the endogenous GPD of the microorganism; and (b) a deletion or disruption in an endogenous gene encoding GPD. In some embodiments the microorganism has decreased production of glycerol as compared to a control recombinant microorganism that lacks the heterologous GPD.

Also provided are recombinant microorganisms comprising (a) a heterologous glycerol-3-phosphate dehydrogenase (GPD), wherein the heterologous GPD has substantially the same affinity for NADH and NADPH and/or is feedback inhibited; and (b) a deletion or disruption in an endogenous gene encoding GPD. Optionally, the heterologous GPD is feedback inhibited by glycerol-3-phosphate. In some embodiments the microorganism has decreased production of glycerol as compared to a control recombinant microorganism that lacks the heterologous GPD.

Also provided are recombinant microorganisms comprising a heterologous GPD, wherein the heterologous GPD has substantially the same affinity for NADH and NADPH and/or is feedback inhibited, and wherein the recombinant microorganism has decreased production of glycerol as compared to a control recombinant microorganism that lacks the heterologous GPD. Optionally, the heterologous GPD is feedback inhibited by glycerol-3-phosphate.

BRIEF DESCRIPTION OF THE DRAWINGS/FIGURES

FIG. 2 shows a partial alignment of the GPD sequences of human truncated (SEQ ID NO:190), Saccharomyces cerevisiae (GPD1) (SEQ ID NO:191), Rickettsia prowazekii (SEQ ID NO:192), Beggiatoa alba (SEQ ID NO:193), and Kangiella koreensis (SEQ ID NO:194) Asterisk (*) indicates the positions of the phe41 and phe97 in the human truncated sequence.

Figure 1:
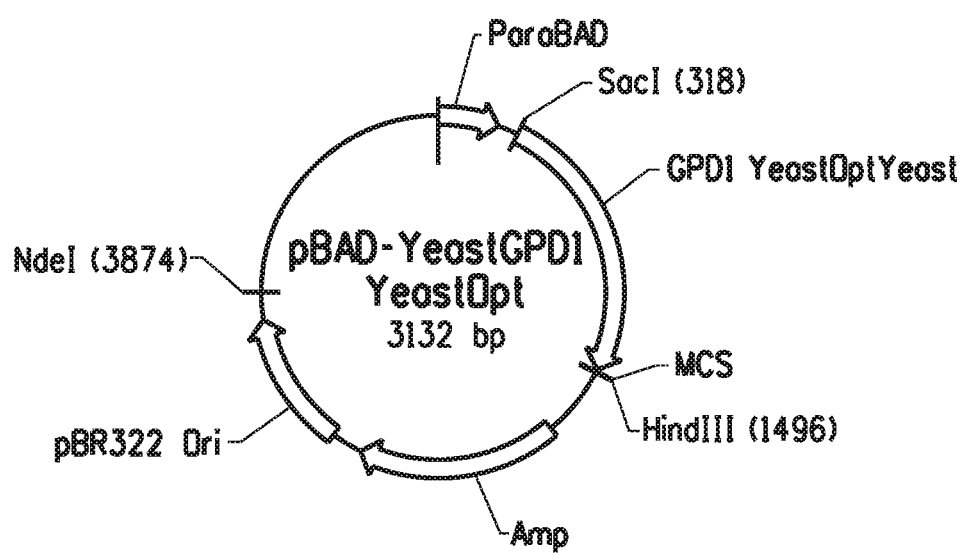
FIG. 1 shows a map of the plasmid used to express variant GPD proteins in E. coli.
Figure 3:
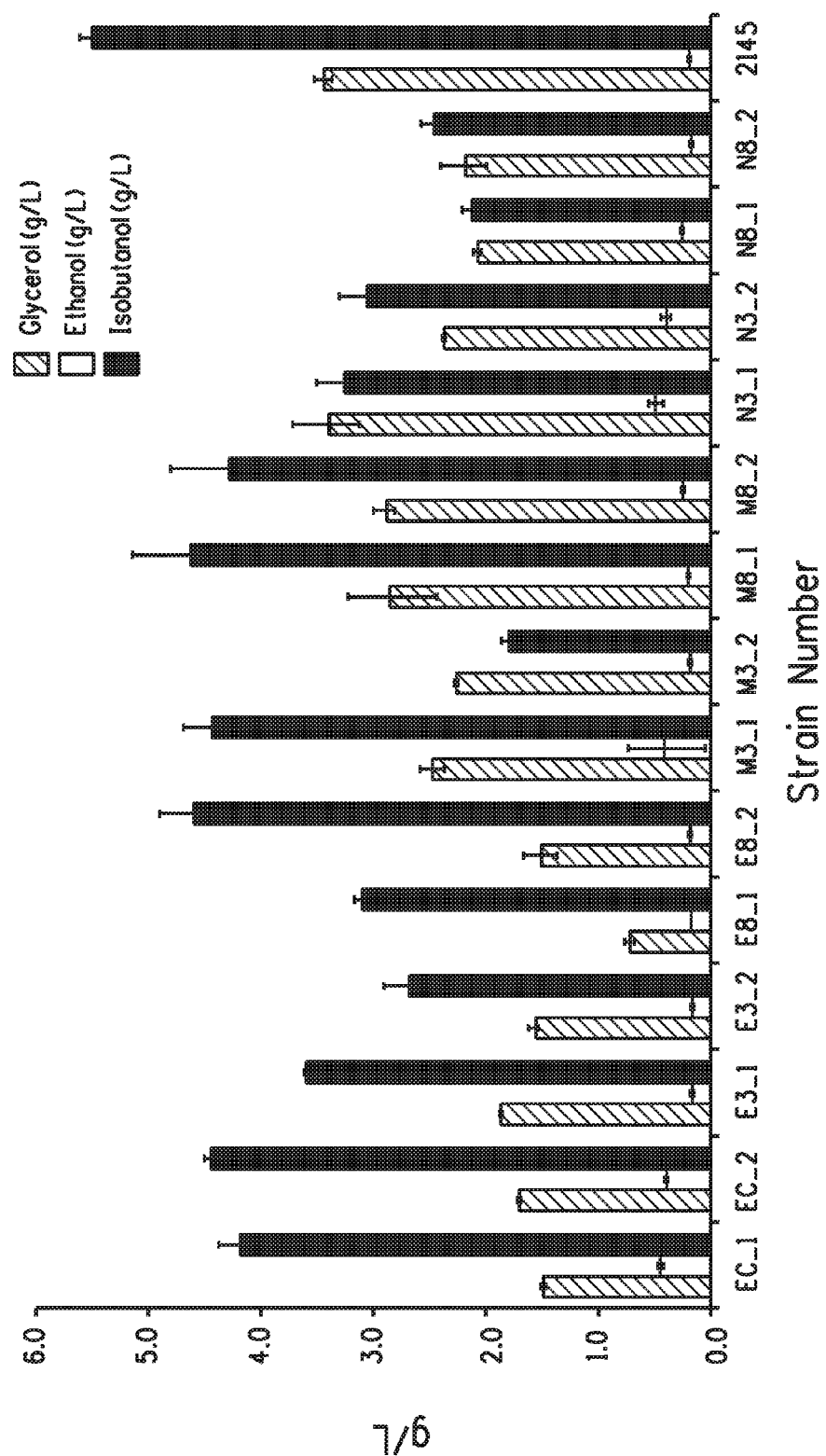

FIG. 3 shows a graph demonstrating 20 hour production data for the indicated GPD1 variant and control cell cultures. Two clones for each variant were tested in duplicate. 2145: isobutanologen control strain with WT GPD which is PNY2145 transformed with pLMH11-JM44; EC_1 and EC_2: E. coli optimized GPD; E3 and E8: E. coli optimized GPD1 variants; N3 and N8: yeast native codon-usage GPD variants; M3 and M8: Yeast codon optimized GPD variants. Variants E3, N3, and M3 has F73A substitution and variants E8, N8, and M8 have F73G/F129G substitutions.

Figure 4:
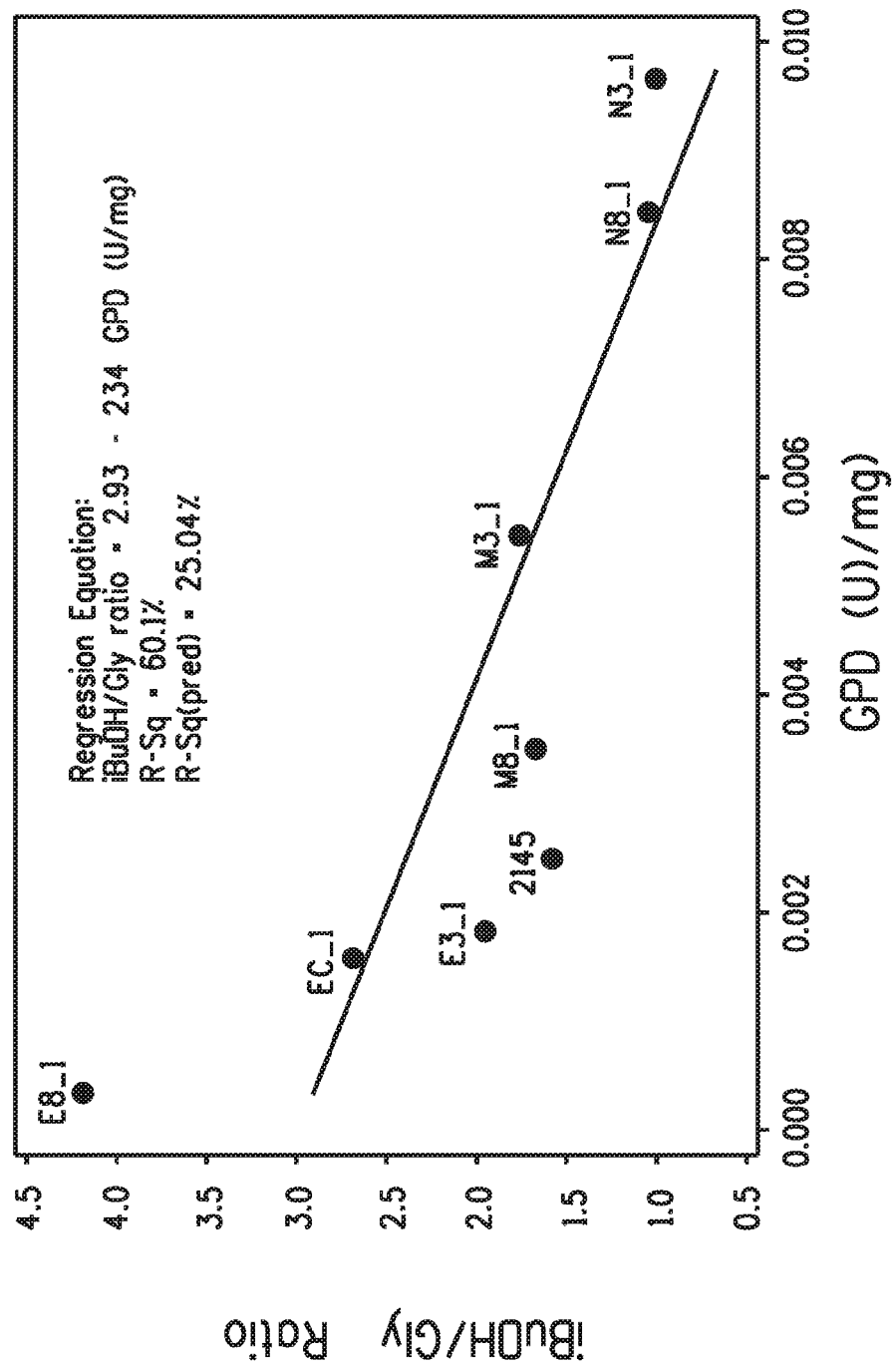

FIG. 4 shows a graph demonstrating a comparison of isobutanol (iBuOH)/glycerol (Gly) ratio with measured GPD activity (U/mg). The regression equation for the iBuOH/Gly ratio equals 2.93−234GPD (U/mg) (R-Sq=60.1%; R-Sq$_{(pred)}$=25.04%).

Figure 5:
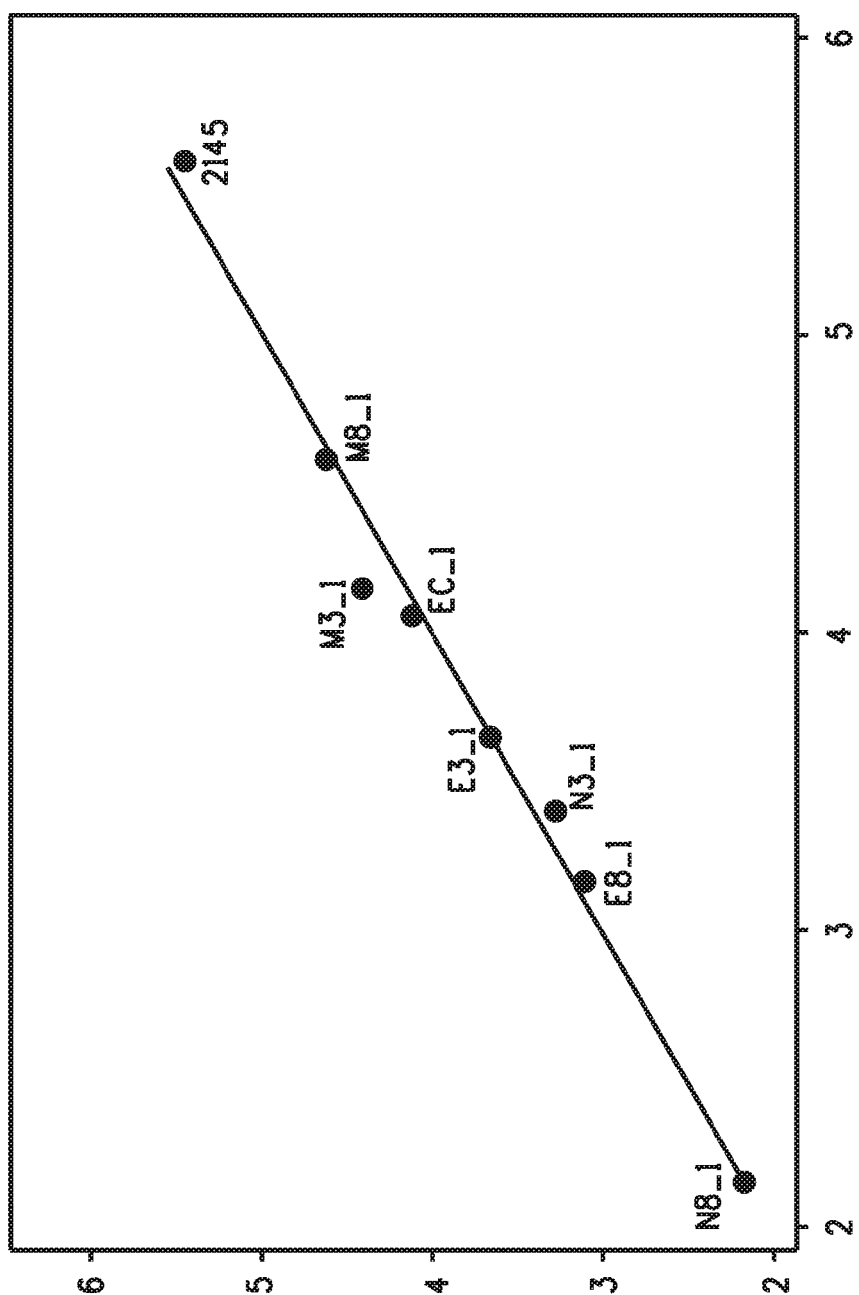

FIG. 5 shows a graph demonstrating a comparison of measured isobutanol titer to values calculated by the linear regression equation (FIT_2) (S=0.159277; R-Sq=98.6%; R-Sq$_{(adj)}$=97.6%; PRESS=0.415575; R-Sq$_{(pred)}$=94.32%). The constant and coefficients for the regression equation are provided in Table 12.

Figure 6:
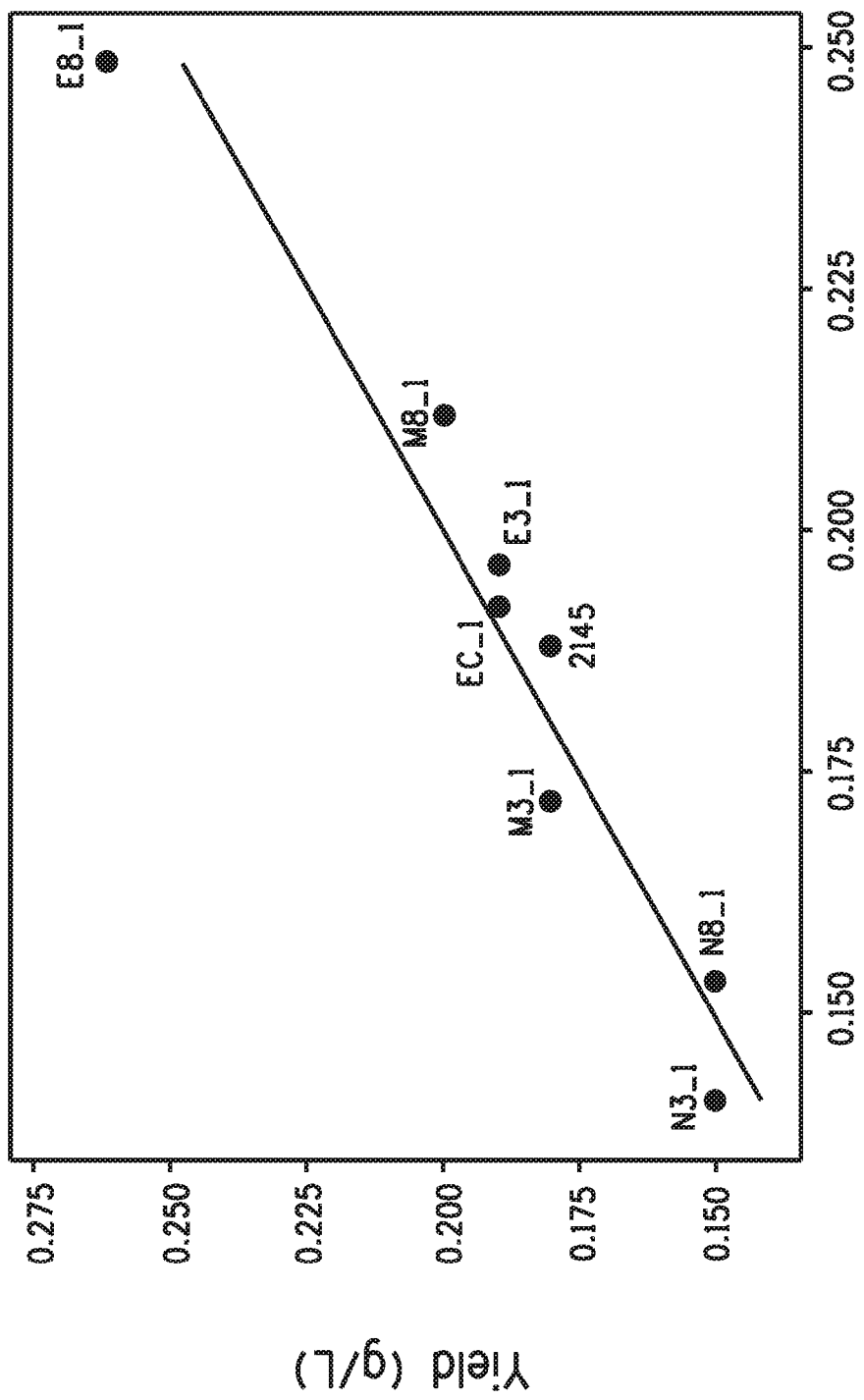

FIG. 6 shows a graph demonstrating a comparison of isobutanol yield (grams isobutanol/gram glucose consumed) to values calculated by the linear regression equation (FIT_4) (S=0.0101071; R-Sq=93.9%; R-Sq(adj)=91.4%; PRESS=0.00197878; R-Sq(pred)=76.30%). The constant and coefficients for the regression equation are provided in Table 13.

Figure 7:
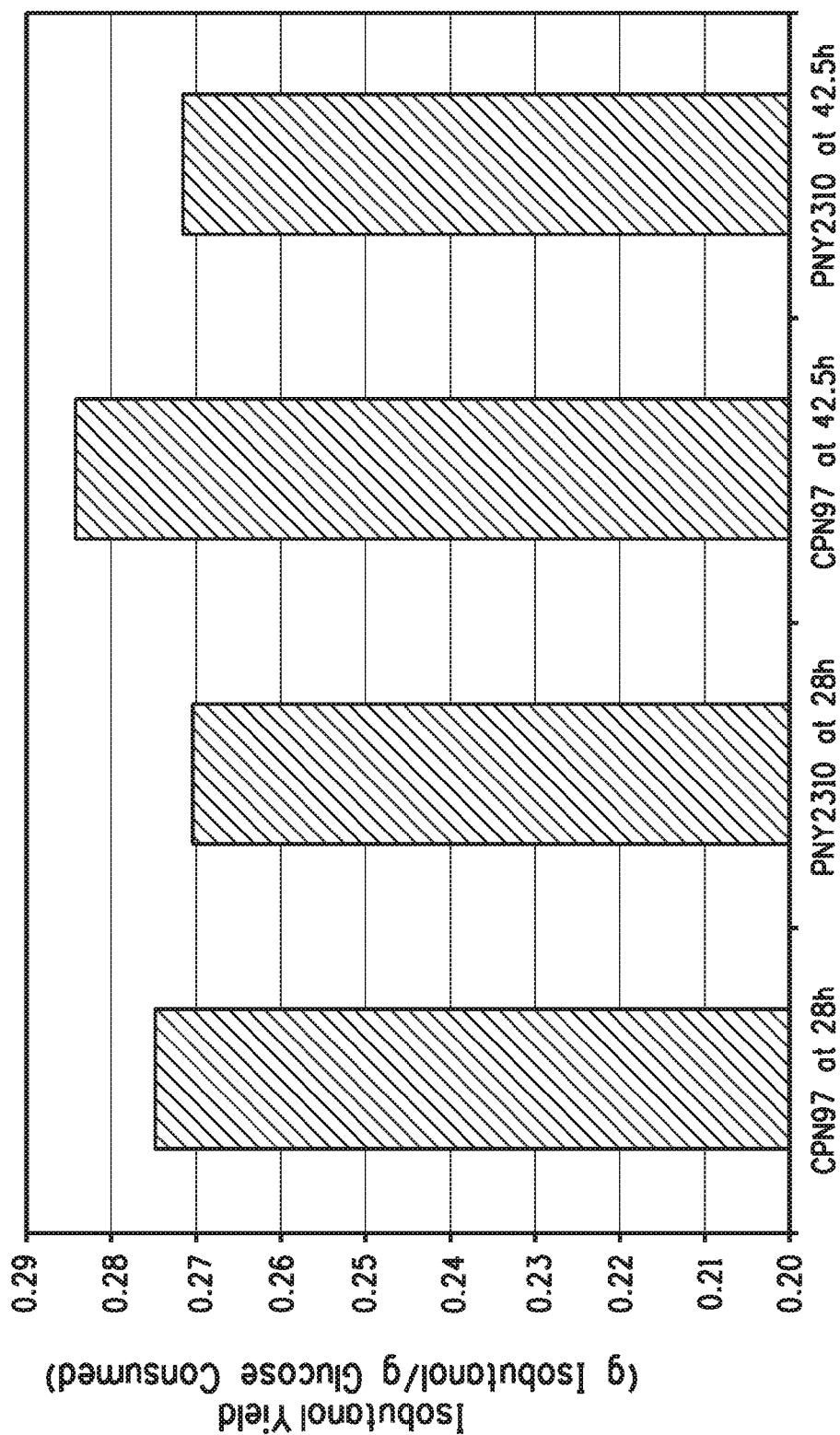

FIG. 7 shows a graph of the isobutanol yield (grams of isobutanol produced per gram of glucose consumed) at 28 and 42 hours for CPN97 and PNY2310 isobutanologen strains.

Figure 8:
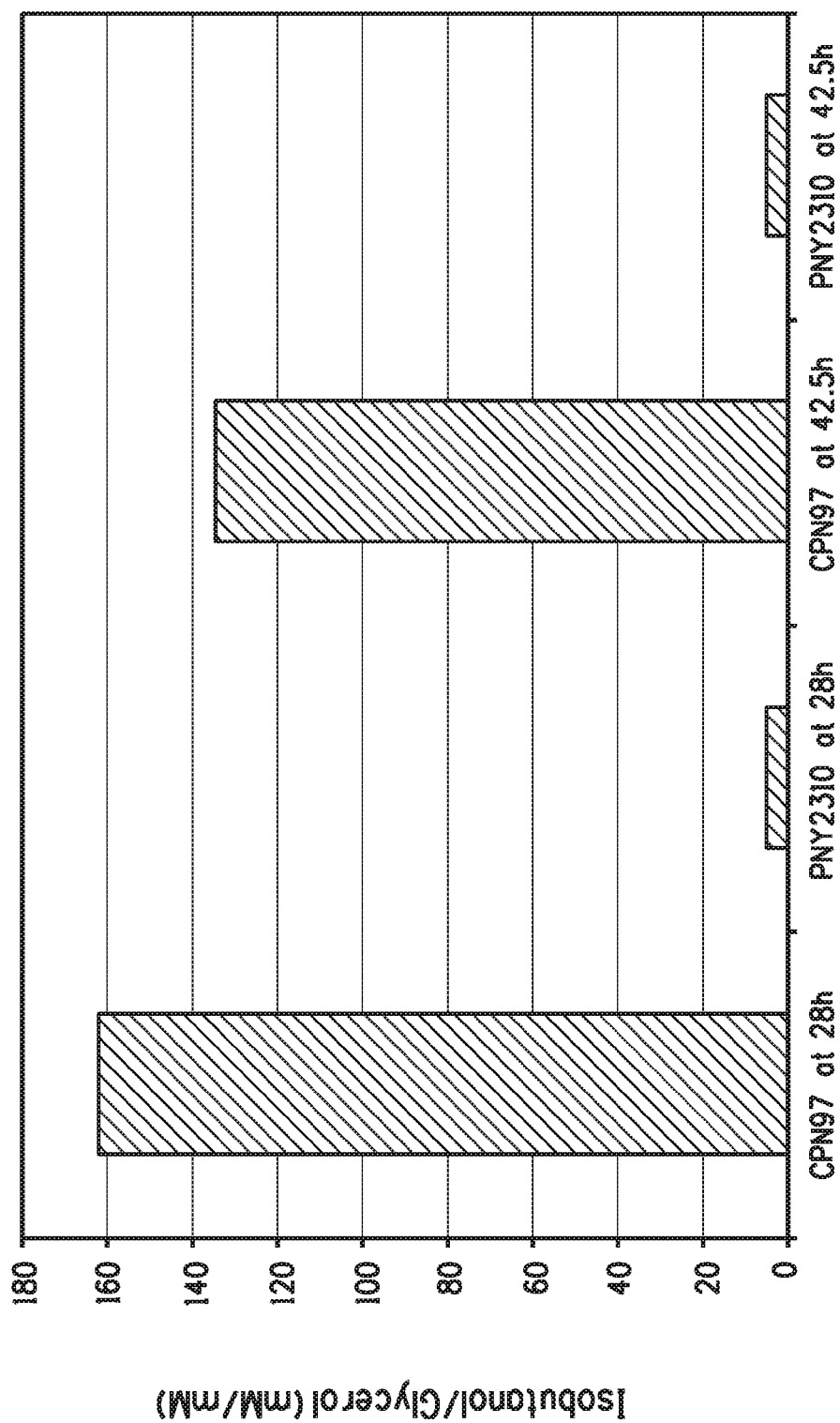

FIG. 8 shows a graph of the isobutanol/glycerol ratio at 28 and 42 hours for CPN97 and PNY2310 isobutanologen strains.

Figure 9:
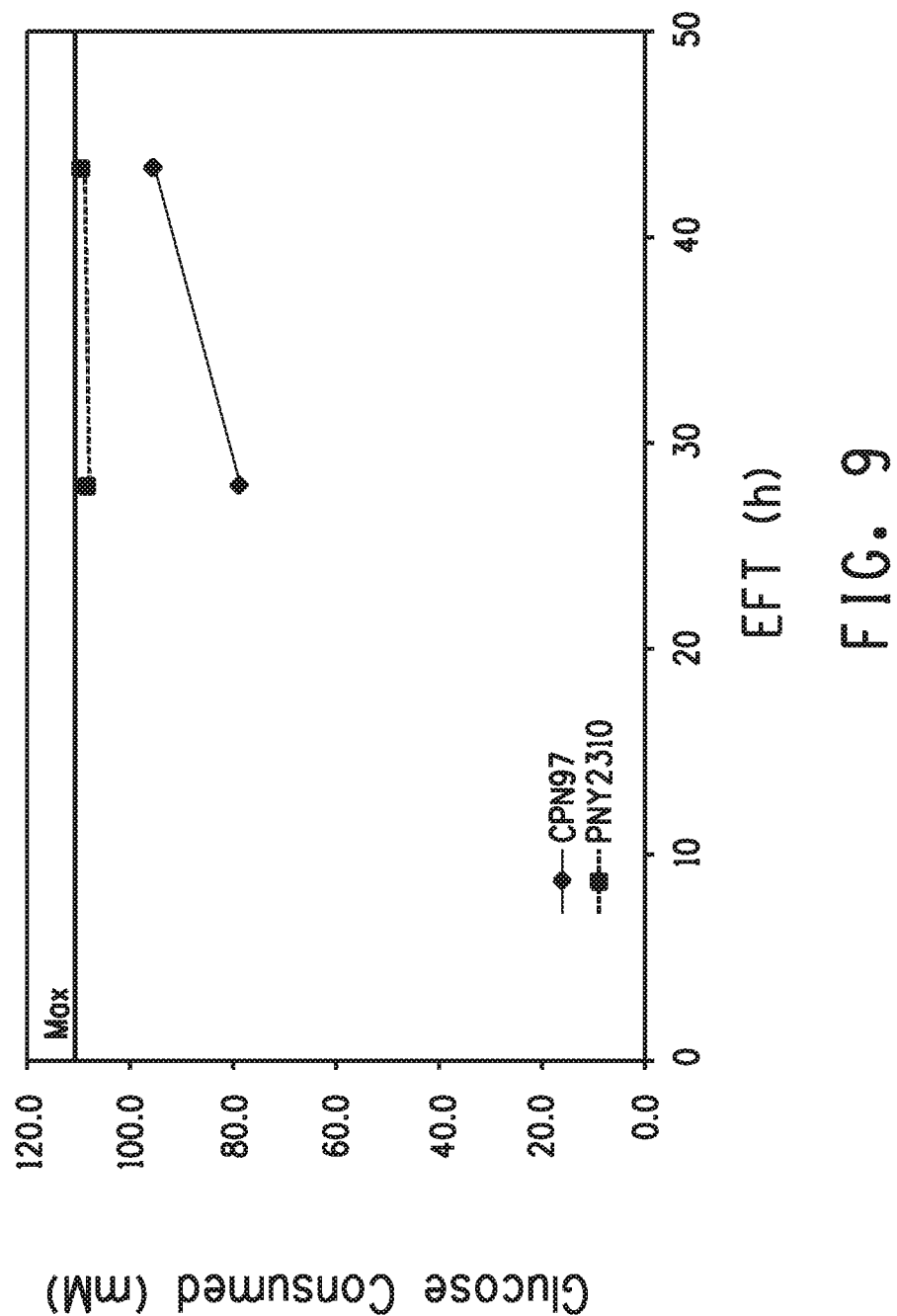

FIG. 9 shows a graph of glucose consumed as a function of time for CPN97 and PNY2310 isobutanologen strains.

DETAILED DESCRIPTION OF THE INVENTION

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference.

In order to further define this invention, the following terms, abbreviations and definitions are provided.

It will be understood that "derived from" with reference to polypeptides disclosed herein encompasses sequences synthesized based on the amino acid sequences of the GPDs, or other enzymes, present in the indicated organisms as well as those cloned directly from the genetic material of the organism.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. §2111.03.

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the claims as presented or as later amended and supplemented, or in the specification.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, or within 5% of the reported numerical value.

The term "butanol biosynthetic pathway" as used herein refers to the enzymatic pathway to produce 1-butanol, 2-butanol, or isobutanol.

The term "1-butanol biosynthetic pathway" refers to an enzymatic pathway to produce 1-butanol. A "1-butanol biosynthetic pathway" can refer to an enzyme pathway to produce 1-butanol from acetyl-coenzyme A (acetyl-CoA). For example, 1-butanol biosynthetic pathways are disclosed in U.S. Patent Application Publication No. 2008/0182308 and International Publication No. WO 2007/041269, which are herein incorporated by reference in their entireties.

The term "2-butanol biosynthetic pathway" refers to an enzymatic pathway to produce 2-butanol. A "2-butanol biosynthetic pathway" can refer to an enzyme pathway to produce 2-butanol from pyruvate. For example, 2-butanol biosynthetic pathways are disclosed in U.S. Pat. No. 8,206,970, U.S. Patent Application Publication No. 2007/0292927, International Publication Nos. WO 2007/130518 and WO 2007/130521, which are herein incorporated by reference in their entireties.

The term "isobutanol biosynthetic pathway" refers to an enzymatic pathway to produce isobutanol. An "isobutanol biosynthetic pathway" can refer to an enzyme pathway to produce isobutanol from pyruvate. For example, isobutanol biosynthetic pathways are disclosed in U.S. Pat. No. 7,851,188, U.S. Application Publication No. 2007/0092957, and International Publication No. WO 2007/050671, which are herein incorporated by reference in their entireties. From time to time "isobutanol biosynthetic pathway" is used synonymously with "isobutanol production pathway."

The term "butanol" as used herein refers to the butanol isomers 1-butanol (1-BuOH), 2-butanol (2-BuOH), tert-butanol (t-BuOH), and/or isobutanol (iBuOH or i-BuOH, also known as 2-methyl-1-propanol), either individually or as mixtures thereof. From time to time, as used herein the terms "biobutanol" and "bio-produced butanol" may be used synonymously with "butanol."

Uses for butanol can include, but are not limited to, fuels (e.g., biofuels), a fuel additive, an alcohol used for the production of esters that can be used as diesel or biodiesel fuel, as a chemical in the plastics industry, an ingredient in formulated products such as cosmetics, and a chemical intermediate. Butanol may also be used as a solvent for paints, coatings, varnishes, resins, gums, dyes, fats, waxes, resins, shellac, rubbers, and alkaloids.

As used herein, the term "bio-produced" means that the molecule (e.g., butanol) is produced from a renewable source (e.g., the molecule can be produced during a fermentation process from a renewable feedstock). Thus, for example, bio-produced isobutanol can be isobutanol produced by a fermentation process from a renewable feedstock. Molecules produced from a renewable source can further be defined by the $^{14}C/^{12}C$ isotope ratio. A $^{14}C/^{12}C$ isotope ratio in range of from 1:0 to greater than 0:1 indicates a bio-produced molecule, whereas a ratio of 0:1 indicates that the molecule is fossil derived.

A recombinant host cell comprising an "engineered alcohol production pathway" (such as an engineered butanol or isobutanol production pathway) refers to a host cell containing a modified pathway that produces alcohol in a manner different than that normally present in the host cell. Such differences include production of an alcohol not typically produced by the host cell, or increased or more efficient production.

The term "heterologous biosynthetic pathway" as used herein refers to an enzyme pathway to produce a product in which at least one of the enzymes is not endogenous to the host cell containing the biosynthetic pathway.

The term "extractant" as used herein refers to one or more organic solvents which can be used to extract alcohol (e.g., butanol) from a fermentation broth.

The term "effective isobutanol productivity" as used herein refers to the total amount in grams of isobutanol produced per gram of cells.

The term "effective titer" as used herein, refers to the total amount of a particular alcohol (e.g., butanol) produced by fermentation per liter of fermentation medium. The total amount of butanol includes: (i) the amount of butanol in the fermentation medium; (ii) the amount of butanol recovered from the organic extractant; and (iii) the amount of butanol recovered from the gas phase, if gas stripping is used.

The term "effective rate" as used herein, refers to the total amount of alcohol (e.g., butanol) produced by fermentation per liter of fermentation medium per hour of fermentation.

The term "effective yield" as used herein, refers to the amount of alcohol (e.g., butanol) produced per unit of fermentable carbon substrate consumed by the biocatalyst.

The term "separation" as used herein is synonymous with "recovery" and refers to removing a chemical compound from an initial mixture to obtain the compound in greater purity or at a higher concentration than the purity or concentration of the compound in the initial mixture.

The term "aqueous phase," as used herein, refers to the aqueous phase of a biphasic mixture obtained by contacting a fermentation broth with a water-immiscible organic extractant. In an embodiment of a process described herein that includes fermentative extraction, the term "fermentation broth" then specifically refers to the aqueous phase in biphasic fermentative extraction.

The term "organic phase," as used herein, refers to the non-aqueous phase of a biphasic mixture obtained by contacting a fermentation broth with a water-immiscible organic extractant.

The term "carbon substrate" or "fermentable carbon substrate" refers to a carbon source capable of being metabolized by host organisms of the present invention and particularly carbon sources selected from the group consisting of monosaccharides, oligosaccharides, polysaccharides, and one-carbon substrates or mixtures thereof. Non-limiting examples of carbon substrates are provided herein and include, but are not limited to, monosaccharides, disaccharides, oligosaccharides, polysaccharides, ethanol, lactate, succinate, glycerol, carbon dioxide, methanol, glucose, fructose, lactose, sucrose, xylose, arabinose, dextrose, cellulose, methane, amino acids, or mixtures thereof.

"Fermentation broth" as used herein means the mixture of water, sugars (fermentable carbon sources), dissolved solids (if present), microorganisms producing alcohol, product alcohol and all other constituents of the material in which product alcohol is being made by the reaction of sugars to alcohol, water and carbon dioxide ($CO_2$) by the microorganisms present. From time to time, as used herein the term "fermentation medium" and "fermented mixture" can be used synonymously with "fermentation broth."

As used herein a "fermentor" refers to any container, containers, or apparatus that are used to ferment a substrate. A fermentor can contain a fermentation medium and microorganism capable of fermentation. The term "fermentation vessel" refers to the vessel in which the fermentation reaction is carried out whereby alcohol such as butanol is made. "Fermentor" can be used herein interchangeably with "fermentation vessel."

The term "fermentation product" includes any desired product of interest, including, but not limited to 1-butanol, 2-butanol, isobutanol, etc.

"Biomass" as used herein refers to a natural product containing a hydrolysable starch that provides a fermentable sugar, including any cellulosic or lignocellulosic material and materials comprising cellulose, and optionally further comprising hemicellulose, lignin, starch, oligosaccharides, disaccharides, and/or monosaccharides. Biomass can also comprise additional components, such as protein and/or lipids. Biomass can be derived from a single source, or biomass can comprise a mixture derived from more than one source. For example, biomass can comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood, and forestry waste. Examples of biomass include, but are not limited to, corn grain, corn cobs, crop residues such as corn husks, corn stover, grasses, wheat, rye, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

"Feedstock" as used herein means a product containing a fermentable carbon source. Suitable feedstock include, but are not limited to, rye, wheat, corn, corn mash, cane, cane mash, sugar cane, barley, cellulosic material, lignocellulosic material, and mixtures thereof.

The term "biomass" as used herein, in some instances, refers to the mass of the culture, e.g., the amount of recombinant microorganisms, typically provided in units of grams per liter (g/l) dry cell weight (dcw).

The term "aerobic conditions" as used herein means growth conditions in the presence of oxygen.

The term "microaerobic conditions" as used herein means growth conditions with low levels of oxygen (i.e., below normal atmospheric oxygen levels).

The term "anaerobic conditions" as used herein means growth conditions in the absence of oxygen.

The term "polynucleotide" is intended to encompass a singular nucleic acid as well as plural nucleic acids, and refers to a nucleic acid molecule or construct, e.g., messenger RNA (mRNA) or plasmid DNA (pDNA). A polynucleotide can contain the nucleotide sequence of the full-length cDNA sequence, or a fragment thereof, including the untranslated 5' and 3' sequences and the coding sequences. The polynucleotide can be composed of any polyribonucleotide or polydeoxyribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. "Polynucleotide" embraces chemically, enzymatically, or metabolically modified forms.

A polynucleotide sequence can be referred to as "isolated," in which it has been removed from its native environment. For example, a heterologous polynucleotide encoding a polypeptide or polypeptide fragment having ALS activity contained in a vector is considered isolated for the purposes of the present invention. Further examples of an isolated polynucleotide include recombinant polynucleotides maintained in heterologous host cells or purified (partially or substantially) polynucleotides in solution. Isolated polynucleotides or nucleic acids according to the present invention further include such molecules produced synthetically. An isolated polynucleotide fragment in the form of a polymer of DNA can be comprised of one or more segments of cDNA, genomic DNA or synthetic DNA."

As used herein, "reduced activity" refers to any measurable decrease in a known biological activity of a polypeptide when compared to the same biological activity of the polypeptide prior to the change resulting in the reduced activity. Such a change can include a modification of a polypeptide or a polynucleotide encoding a polypeptide as described herein. A reduced activity of a polypeptide disclosed herein can be determined by methods well known in the art and disclosed herein. Reduced activity of an enzyme refers to down-regulation, whether partial or total, of the activity of the enzyme as compared to the activity of the wildtype enzyme. Down-regulation may occur when a native gene has a "disruption" or "modification," referring to an insertion, deletion, or targeted mutation within a portion of that gene, that results in e.g., a complete gene knockout such that the gene is deleted from the genome and no protein is translated or a translated subunit protein having an insertion, deletion, amino acid substitution or other targeted mutation. The location of the modification in the protein may be, for example, within the N-terminal portion of the protein or within the C-terminal portion of the protein. The modified protein will have impaired activity with respect to the protein that was not disrupted, and can be non-functional. Reduced activity in an enzyme could also result via manipulating the upstream regulatory domains or by use of sense, antisense or RNAi technology, etc. Another mechanism of reducing activity of an enzyme is introduction of a mutation that alters kinetic properties of the enzyme (e.g., reducing the affinity for a substrate, lowering the $k_{cat}$, etc.).

As used herein, "eliminated activity" refers to the complete abolishment of a known biological activity of a polypeptide when compared to the same biological activity of the polypeptide prior to the change resulting in the eliminated activity. Such a change can include a modification of a polypeptide or a polynucleotide encoding a polypeptide as described herein. An eliminated activity includes a biological activity of a polypeptide that is not measurable when compared to the same biological activity of the polypeptide prior to the change resulting in the eliminated activity. An eliminated activity of a polypeptide disclosed herein can be determined by methods well known in the art and disclosed herein.

The terms "PDC-," "PDC knockout," or "PDC-KO" as used herein refer to a cell that has a genetic modification to inactivate or reduce expression of a gene encoding pyruvate decarboxylase (PDC) so that the cell substantially or completely lacks pyruvate decarboxylase enzyme activity. If the cell has more than one expressed (active) PDC gene, then each of the active PDC genes can be inactivated or have minimal expression thereby producing a PDC-cell.

The term "specific activity" as used herein is defined as the units of activity in a given amount of protein. Thus, the specific activity is not directly measured but is calculated by dividing 1) the activity in units/ml of the enzyme sample by 2) the concentration of protein in that sample, so the specific activity is expressed as units/mg, where an enzyme unit is defined as moles of product formed/minute. The specific activity of a sample of pure, fully active enzyme is a characteristic of that enzyme. The specific activity of a sample of a mixture of proteins is a measure of the relative fraction of protein in that sample that is composed of the active enzyme of interest.

The terms "$k_{cat}$" and "$K_M$" are known to those skilled in the art and are described in Enzyme Structure and Mechanism, $2^{nd}$ ed. (Ferst; W. H. Freeman Press, NY, 1985; pp 98-120). $K_M$, the Michaelis constant, is the concentration of substrate that leads to half-maximal velocity. The term "$k_{cat}$", often called the "turnover number", is defined as the maximum number of substrate molecules converted to products per active site per unit time, or the number of times the enzyme turns over per unit time. $k_{cat}=V_{max}/[E]$, where [E] is the enzyme concentration (Ferst, supra). The terms "total turnover" and "total turnover number" are used herein to refer to the amount of product formed by the reaction of an enzyme with substrate.

The term "catalytic efficiency" is defined as the $k_{cat}/K_M$ of an enzyme. Catalytic efficiency is used to quantify the specificity of an enzyme for a substrate.

The term "isolated nucleic acid molecule", "isolated nucleic acid fragment" and "genetic construct" are used interchangeably and mean a polymer of RNA or DNA that is single or double-stranded, optionally containing synthetic, non natural or altered nucleotide bases. An isolated nucleic acid fragment in the form of a polymer of DNA can be comprised of one or more segments of cDNA, genomic DNA or synthetic DNA.

The term "amino acid" refers to the basic chemical structural unit of a protein or polypeptide. The abbreviations in Table 1 are used herein to identify specific amino acids.

TABLE 1

Amino acids and abbreviations thereof.

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene can comprise regulatory sequences and coding sequences that are derived from different sources, or regulatory sequences and coding sequences derived from the same source, but arranged in a manner different than that found in nature. "Endogenous gene" refers to a native gene in its natural location in the genome of a microorganism. A "foreign" gene refers to a gene not normally found in the host microorganism, but that is introduced into the host microorganism by gene transfer. Foreign genes can comprise native genes inserted into a non-native microorganism, or chimeric genes. A "transgene" is a gene that has been introduced into the genome by a transformation procedure.

As used herein, "native" refers to the form of a polynucleotide, gene, or polypeptide as found in nature with its own regulatory sequences, if present.

As used herein the term "coding sequence" or "coding region" refers to a DNA sequence that encodes for a specific amino acid sequence.

As used herein, "endogenous" refers to the native form of a polynucleotide, gene or polypeptide in its natural location in the organism or in the genome of an organism. "Endogenous polynucleotide" includes a native polynucleotide in its natural location in the genome of an organism. "Endogenous gene" includes a native gene in its natural location in the genome of an organism. "Endogenous polypeptide" includes a native polypeptide in its natural location in the organism transcribed and translated from a native polynucleotide or gene in its natural location in the genome of an organism.

The term "heterologous" when used in reference to a polynucleotide, a gene, or a polypeptide refers to a polynucleotide, gene, or polypeptide not normally found in the host organism. "Heterologous" also includes a native coding region, or portion thereof, that is reintroduced into the source organism in a form that is different from the corresponding native gene, e.g., not in its natural location in the organism's genome. The heterologous polynucleotide or gene can be introduced into the host organism by, e.g., gene transfer. A heterologous gene can include a native coding region with non-native regulatory regions that is reintroduced into the native host. For example, a heterologous gene can include a native coding region that is a portion of a chimeric gene including non-native regulatory regions that is reintroduced into the native host. "Heterologous polypeptide" includes a native polypeptide that is reintroduced into the source organism in a form that is different from the corresponding native polypeptide. A "heterologous" polypeptide or polynucleotide can also include an engineered polypeptide or polynucleotide that comprises a difference from the "native" polypeptide or polynucleotide, e.g., a point mutation within the endogenous polynucleotide can result in the production of a "heterologous" polypeptide. As used herein a "chimeric gene," a "foreign gene," and a "transgene," can all be examples of "heterologous" genes.

A "transgene" is a gene that has been introduced into the genome by a transformation procedure.

As used herein, the term "modification" refers to a change in a polynucleotide disclosed herein that results in reduced or eliminated activity of a polypeptide encoded by the polynucleotide, as well as a change in a polypeptide disclosed herein that results in reduced or eliminated activity of the polypeptide. Such changes can be made by methods well known in the art, including, but not limited to, deleting, mutating (e.g., spontaneous mutagenesis, random mutagenesis, mutagenesis caused by mutator genes, or transposon mutagenesis), substituting, inserting, down-regulating, altering the cellular location, altering the state of the polynucleotide or polypeptide (e.g., methylation, phosphorylation or ubiquitination), removing a cofactor, introduction of an antisense RNA/DNA, introduction of an interfering RNA/DNA, chemical modification, covalent modification, irradiation with UV or X-rays, homologous recombination, mitotic recombination, promoter replacement methods, and/or combinations thereof. Guidance in determining which nucleotides or amino acid residues can be modified can be found by comparing the sequence of the particular polynucleotide or polypeptide with that of homologous polynucleotides or polypeptides, e.g., yeast or bacterial, and maximizing the number of modifications made in regions of high homology (conserved regions) or consensus sequences.

The term "recombinant genetic expression element" refers to a nucleic acid fragment that expresses one or more specific proteins, including regulatory sequences preceding (5' non-coding sequences) and following (3' termination sequences) coding sequences for the proteins. A chimeric gene is a recombinant genetic expression element. The coding regions of an operon can form a recombinant genetic expression element, along with an operably linked promoter and termination region.

"Regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences can include promoters, enhancers, operators, repressors, transcription termination signals, translation leader sequences, introns, polyadenylation recognition sequences, RNA processing site, effector binding site and stem-loop structure.

The term "promoter" refers to a nucleic acid sequence capable of controlling the expression of a coding sequence or functional RNA. In general, a coding sequence is located 3' to a promoter sequence. Promoters can be derived in their entirety from a native gene, or be composed of different elements derived from different promoters found in nature, or even comprise synthetic nucleic acid segments. It is understood by those skilled in the art that different promoters can direct the expression of a gene in different tissues or cell types, or at different stages of development, or in response to different environmental or physiological conditions. Promoters which cause a gene to be expressed in most cell types at most times are commonly referred to as "constitutive promoters". "Inducible promoters," on the other hand, cause a gene to be expressed when the promoter is induced or turned on by a promoter-specific signal or molecule. It is further recognized that since in most cases the exact boundaries of regulatory sequences have not been completely defined, DNA fragments of different lengths can have identical promoter activity. For example, it will be understood that "FBA1 promoter" can be used to refer to a fragment derived from the promoter region of the FBA1 gene.

The term "terminator" as used herein refers to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence. It is recognized that since in most cases the exact boundaries of regulatory sequences have not been completely defined, DNA fragments of different lengths can have identical terminator activity. For example, it will be understood that "CYC1 terminator" can be used to refer to a fragment derived from the terminator region of the CYC1 gene.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression can also refer to translation of mRNA into a polypeptide.

The term "overexpression," as used herein, refers to expression that is higher than endogenous expression of the same or related gene. A heterologous gene is overexpressed if its expression is higher than that of a comparable endogenous gene.

The term overexpression refers to an increase in the level of nucleic acid or protein in a host cell. Thus, overexpression can result from increasing the level of transcription or translation of an endogenous sequence in a host cell or can result from the introduction of a heterologous sequence into a host cell. Overexpression can also result from increasing the stability of a nucleic acid or protein sequence.

As used herein the term "transformation" refers to the transfer of a nucleic acid fragment into the genome of a host microorganism, resulting in genetically stable inheritance. Host microorganisms containing the transformed nucleic acid fragments are referred to as "transgenic" or "recombinant" or "transformed" microorganisms.

The terms "plasmid", "vector" and "cassette" refer to an extra chromosomal element often carrying genes which are not part of the central metabolism of the cell, and usually in the form of circular double-stranded DNA fragments. Such elements can be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 2A. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at the "Codon Usage Database" available at the Kazusa DNA Research Institute, Japan, and these tables can be adapted in a number of ways. See Nakamura, Y., et al. *Nucl. Acids Res.* 28:292 (2000). Codon usage tables for yeast, calculated from GenBank Release 128.0 [15 Feb. 2002], are reproduced below as Table 2B. This table uses mRNA nomenclature, and so instead of thymine (T) which is found in DNA, the tables use uracil (U) which is found in RNA. The Table has been adapted so that frequencies are calculated for each amino acid, rather than for all 64 codons.

TABLE 2B

Codon Usage Table for *Saccharomyces cerevisiae*.

| Amino Acid | Codon | Number | Frequency per thousand |
|---|---|---|---|
| Phe | UUU | 170666 | 26.1 |
| Phe | UUC | 120510 | 18.4 |
| Leu | UUA | 170884 | 26.2 |
| Leu | UUG | 177573 | 27.2 |
| Leu | CUU | 80076 | 12.3 |

TABLE 2A

The Standard Genetic Code

| | T | C | A | G |
|---|---|---|---|---|
| T | TTT Phe (F) | TCT Ser (S) | TAT Tyr (Y) | TGT Cys (C) |
| | TTC " | TCC " | TAC " | TGC " |
| | TTA Leu (L) | TCA " | TAA Stop | TGA Stop |
| | TTG " | TCG " | TAG Stop | TGG Trp (W) |
| C | CTT Leu (L) | CCT Pro (P) | CAT His (H) | CGT Arg (R) |
| | CTC " | CCC " | CAC " | CGC " |
| | CTA " | CCA " | CAA Gln (Q) | CGA " |
| | CTG " | CCG " | CAG " | CGG " |
| A | ATT Ile (I) | ACT Thr (T) | AAT Asn (N) | AGT Ser (S) |
| | ATC " | ACC " | AAC " | AGC " |
| | ATA " | ACA " | AAA Lys (K) | AGA Arg (R) |
| | ATG Met (M) | ACG " | AAG " | AGG " |
| G | GTT Val (V) | GCT Ala (A) | GAT Asp (D) | GGT Gly (G) |
| | GTC " | GCC " | GAC " | GGC " |
| | GTA " | GCA " | GAA Gln (E) | GGA " |
| | GTG " | GCG " | GAG " | GGG " |

Many organisms display a bias for use of particular codons to code for insertion of a particular amino acid in a growing peptide chain. Codon preference, or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis.

TABLE 2B-continued

Codon Usage Table for *Saccharomyces cerevisiae*.

| Amino Acid | Codon | Number | Frequency per thousand |
|---|---|---|---|
| Leu | CUC | 35545 | 5.4 |
| Leu | CUA | 87619 | 13.4 |
| Leu | CUG | 68494 | 10.5 |

TABLE 2B-continued

Codon Usage Table for *Saccharomyces cerevisiae*.

| Amino Acid | Codon | Number | Frequency per thousand |
|---|---|---|---|
| Ile | AUU | 196893 | 30.1 |
| Ile | AUC | 112176 | 17.2 |
| Ile | AUA | 116254 | 17.8 |
| Met | AUG | 136805 | 20.9 |
| Val | GUU | 144243 | 22.1 |
| Val | GUC | 76947 | 11.8 |
| Val | GUA | 76927 | 11.8 |
| Val | GUG | 70337 | 10.8 |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Pro | CCU | 88263 | 13.5 |
| Pro | CCC | 44309 | 6.8 |
| Pro | CCA | 119641 | 18.3 |
| Pro | CCG | 34597 | 5.3 |
| Thr | ACU | 132522 | 20.3 |
| Thr | ACC | 83207 | 12.7 |
| Thr | ACA | 116084 | 17.8 |
| Thr | ACG | 52045 | 8.0 |
| Ala | GCU | 138358 | 21.2 |
| Ala | GCC | 82357 | 12.6 |
| Ala | GCA | 105910 | 16.2 |
| Ala | GCG | 40358 | 6.2 |
| Tyr | UAU | 122728 | 18.8 |
| Tyr | UAC | 96596 | 14.8 |
| His | CAU | 89007 | 13.6 |
| His | CAC | 50785 | 7.8 |
| Gln | CAA | 178251 | 27.3 |
| Gln | CAG | 79121 | 12.1 |
| Asn | AAU | 233124 | 35.7 |
| Asn | AAC | 162199 | 24.8 |
| Lys | AAA | 273618 | 41.9 |
| Lys | AAG | 201361 | 30.8 |
| Asp | GAU | 245641 | 37.6 |
| Asp | GAC | 132048 | 20.2 |
| Glu | GAA | 297944 | 45.6 |
| Glu | GAG | 125717 | 19.2 |
| Cys | UGU | 52903 | 8.1 |
| Cys | UGC | 31095 | 4.8 |
| Trp | UGG | 67789 | 10.4 |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Gly | GGU | 156109 | 23.9 |
| Gly | GGC | 63903 | 9.8 |
| Gly | GGA | 71216 | 10.9 |
| Gly | GGG | 39359 | 6.0 |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the VectorNTI Suite, available from InforMax, Inc., Bethesda, Md., and the "backtranslate" function in the GCG-Wisconsin Package, available from Accelrys, Inc., San Diego, Calif. In addition, various resources are publicly available to codon-optimize coding region sequences, e.g., the "backtranslation" function (Entelechon GmbH, Regensburg, Germany) and the "backtranseq" function (NRC Saskatoon Bioinformatics, Saskatoon, Saskatchewan, Canada). Constructing a rudimentary algorithm to assign codons based on a given frequency can also easily be accomplished with basic mathematical functions by one of ordinary skill in the art.

Codon-optimized coding regions can be designed by various methods known to those skilled in the art including software packages such as "synthetic gene designer" (University of Maryland, Baltimore, Md.).

A polynucleotide or nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. Molecular Cloning: A Laboratory Manual, 2nd ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2×SSC, 0.5% SDS was increased to 60° C. Another set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50 9.51). For hybridizations with shorter nucleic acids, i.e., oligonucleotides, the position of mismatches becomes more important, and the length of the oligonucleotide determines its specificity (see Sambrook et al., supra, 11.7 11.8). In one embodiment the length for a hybridizable nucleic acid is at least about 10 nucleotides. In one embodiment, a minimum length for a hybridizable nucleic acid is at least about 15 nucleotides; at least about 20 nucleotides; or the length is at least about 30 nucleotides. Furthermore, the skilled artisan will recognize that the temperature and wash solution salt concentration can be adjusted as necessary according to factors such as length of the probe.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. A polypeptide can be derived from a natural biological source or produced by recombinant technology, but is not necessarily translated from a designated nucleic acid sequence. It can be generated in any manner, including by chemical synthesis.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

As used herein, the terms "variant" and "mutant" are synonymous and refer to a polypeptide differing from a specifically recited polypeptide by one or more amino acid insertions, deletions, mutations, and substitutions, created using, e.g., recombinant DNA techniques, such as mutagenesis. Guidance in determining which amino acid residues can be replaced, added, or deleted without abolishing activities of interest, can be found by comparing the sequence of the particular polypeptide with that of homologous polypeptides, e.g., yeast or bacterial, and minimizing the number of amino acid sequence changes made in regions of high homology (conserved regions) or by replacing amino acids with consensus sequences.

"Engineered polypeptide" as used herein refers to a polypeptide that is synthetic, i.e., differing in some manner from a polypeptide found in nature.

Alternatively, recombinant polynucleotide variants encoding these same or similar polypeptides can be synthesized or selected by making use of the "redundancy" in the genetic code. Various codon substitutions, such as silent changes which produce various restriction sites, can be introduced to optimize cloning into a plasmid or viral vector for expression. Mutations in the polynucleotide sequence can be reflected in the polypeptide or domains of other peptides added to the polypeptide to modify the properties of any part of the polypeptide. For example, mutations can be used to reduce or eliminate expression of a target protein and include, but are not limited to, deletion of the entire gene or a portion of the gene, inserting a DNA fragment into the gene (in either the promoter or coding region) so that the protein is not expressed or expressed at lower levels, introducing a mutation into the coding region which adds a stop codon or frame shift such that a functional protein is not expressed, and introducing one or more mutations into the coding region to alter amino acids so that a non-functional or a less enzymatically active protein is expressed.

Amino acid "substitutions" can be the result of replacing one amino acid with another amino acid having similar structural and/or chemical properties, i.e., conservative amino acid replacements, or they can be the result of replacing one amino acid with an amino acid having different structural and/or chemical properties, i.e., non-conservative amino acid replacements. "Conservative" amino acid substitutions can be made on the basis of similarity in polarity, charge, solubility, hydrophobicity, hydrophilicity, or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Alternatively, "non-conservative" amino acid substitutions can be made by selecting the differences in polarity, charge, solubility, hydrophobicity, hydrophilicity, or the amphipathic nature of any of these amino acids. "Insertions" or "deletions" can be within the range of variation as structurally or functionally tolerated by the recombinant proteins. The variation allowed can be experimentally determined by systematically making insertions, deletions, or substitutions of amino acids in a polypeptide molecule using recombinant DNA techniques and assaying the resulting recombinant variants for activity.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Altschul, S. F., et al., *J. Mol. Biol.*, 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides can be used in sequence-dependent methods of gene identification (e.g., Southern hybridization) and isolation (e.g., in situ hybridization of bacterial colonies or bacteriophage plaques). In addition, short oligonucleotides of 12-15 bases can be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular proteins. The skilled artisan, having the benefit of the sequences as reported herein, can now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenine is complementary to thymine and cytosine is complementary to guanine, and with respect to RNA, adenine is complementary to uracil and cytosine is complementary to guanine.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton, N.Y. (1991).

Methods to determine identity are designed to give the best match between the sequences tested. Methods to determine identity and similarity are codified in publicly available computer programs. Sequence alignments and percent identity calculations can be performed using the MegAlign™ program of the LASERGENE bioinformatics computing suite (DNASTAR Inc., Madison, Wis.). Multiple alignments of the sequences are performed using the "Clustal method of alignment" which encompasses several varieties of the algorithm including the "Clustal V method of alignment" corresponding to the alignment method labeled Clustal V (described by Higgins and Sharp, *CABIOS*. 5:151-153 (1989); Higgins, D. G. et al., *Comput. Appl. Biosci.,* 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS*. 5:151-153 (1989); Higgins, D. G. et al., *Comput. Appl. Biosci.* 8:189-191(1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, such as from other species, wherein such polypeptides have the same or similar function or activity, or in describing the corresponding polynucleotides. Useful examples of percent identities include, but are not limited to: 55%, 60%, 65%, 70%, 75%, 80%, 85%, 90%, or 95%, or any integer percentage from 55% to 100% can be useful in describing the present invention, such as 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable polynucleotide fragments not only have the above homologies but typically comprise a polynucleotide having at least 50 nucleotides, at least 100 nucleotides, at least 150 nucleotides, at least 200 nucleotides, or at least 250 nucleotides. Further, suitable polynucleotide fragments having the above homologies encode a polypeptide having at least 50 amino acids, at least 100 amino acids, at least 150 amino acids, at least 200 amino acids, or at least 250 amino acids.

The term "sequence analysis software" refers to any computer algorithm or software program that is useful for the analysis of nucleotide or amino acid sequences. "Sequence analysis software" can be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.*, 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et al., *Current Protocols in Molecular Biology*, published by Greene Publishing Assoc. and Wiley-Interscience (1987). Additional methods used here are in *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif.). Other molecular tools and techniques are known in the art and include splicing by overlapping extension polymerase chain reaction (PCR) (Yu, et al. (2004) *Fungal Genet. Biol.* 41:973-981), positive selection for mutations at the URA3 locus of *Saccharomyces cerevisiae* (Boeke, J. D. et al. (1984) *Mol. Gen. Genet.* 197, 345-346; M A Romanos, et al. *Nucleic Acids Res.* 1991 Jan. 11; 19(1): 187), the cre-lox site-specific recombination system as well as mutant lox sites and FLP substrate mutations (Sauer, B. (1987) *Mol Cell Biol* 7: 2087-2096; Senecoff, et al. (1988) *Journal of Molecular Biology*, Volume 201, Issue 2, Pages 405-421; Albert, et al. (1995) *The Plant Journal. Volume* 7, Issue 4, pages 649-659), "seamless" gene deletion (Akada, et al. (2006) Yeast; 23(5):399-405), and gap repair methodology (Ma et al., *Genetics* 58:201-216; 1981).

Polypeptides with GPD Activity

Endogenous NAD-dependent "glycerol-3-phosphate dehydrogenase" or "GPD" is a key enzyme in glycerol synthesis, converting dihydroxyacetone phosphate (DHAP) to glycerol-3-phosphate. The terms "glycerol-3-phosphate dehydrogenase" and "GPD" refer to any polypeptide (or polypeptides) having the biological function of GPD. Such polypeptides include polypeptides having an enzyme activity that catalyzes the conversion of dihydroxyacetone phosphate to glycerol-3-phosphate. GPDs are widespread in nature and can fall into three categories. In the first category, EC 1.1.1.8, a GPD is a soluble cytoplasmic enzyme where the redox cofactor is the NAD/NADH couple, GPDs in the EC 1.1.1.8 category are described as NADH specific, but this does not preclude that some of the GPDs may have measurable activity with NADPH. *Saccharomyces cerevisiae* GPD1 is an example of this type of GPD (Albertyn et. Al, 1992, FEBS Lett 308: 130-132; Valadi, et al, 2004, J. Biol Chem 279: 39677-39685). Another example is the human GPD1, for which there are multiple 3-dimensional structural studies (Ou et al, 2005, J. Mol. Biol. 357: 858-869). Assays for enzymes in this category can utilize the spectrophotometric measurement of NADH oxidation in the presence of DHAP and the GPD enzyme (Niesel et al. 1982 Methods Enzymol 89: 296-301). The second category, EC 1.1.5.3, GPD enzymes are intrinsic membrane proteins of the mitochondrial inner membrane, and contain a flavin cofactor, and reducing equivalents are transferred to the quinone/quinol couple in the mitochondrion. There is a third minor category of GPDs, EC 1.1.1.94 which utilize either NADH or NADPH with substantially the same affinity. GPDs of the third minor category can also be feedback inhibited by glycerol-3-phosphate.

Recombinant microorganisms such as yeast can have one or more endogenous genes encoding glycerol-3-phosphate dehydrogenase (GPD). In some yeasts, such as *S. cerevisiae, S. pombe*, and *P. stipitis*, GPD1 and GPD2 are functional homologs. Any of the genes encoding GPD enzymes of yeast may be disrupted to reduce GPD activity in a yeast cell.

One of the key yield loss mechanisms in yeast butanol production is the loss of carbon and reducing equivalents that are diverted from glycolysis by the conversion of dihydroxyacetone phosphate to glycerol. Since GPD catalyzes the first step in this conversion of dihydroxyacetone phosphate to glycerol, the activity of GPD can contribute to the production of glycerol and the loss of butanol yield. As a result, some have considered eliminating the function of GPD (for example, by knocking out the gene encoding GPD protein) in butanol-producing yeast. However, glycerol is required for growth and is an important osmoprotectant. Thus, retaining the ability to make some glycerol offers certain advantages.

One way to retain the ability to make glycerol, but also improve the production of product alcohol is to alter the cofactor specificity of GPD. *Saccharomyces cerevisiae* GPD1 generally favors the cofactor nicotinamide adenine dinucleotide ("NADH") in catalyzing the first step in the conversion of dihydroxyacetone phosphate to glycerol in a yeast cell. However, as demonstrated herein, GPD enzymes can also use the cofactor nicotinamide adenine dinucleotide phosphate ("NADPH").

The use of GPD enzymes with preference for NADPH as compared to NADH can allow host cells to retain the ability to produce glycerol under different metabolic conditions when compared with enzymes with a preference for NADH. However, this glycerol production can advantageously be limited under anaerobic conditions when NADPH production is limited.

At the same time, decreasing the preference for NADH by GPD can increase the availability of NADH in a host cell. NADH is also used by other enzymes in a product alcohol production pathway, for example, in the isobutanol production pathway the available NADH can be utilized by KARI and alcohol dehydrogenase. Thus, decreasing the affinity of GPD for NADH can increase product alcohol (e.g., isobutanol) production. Accordingly, in some embodiments, a heterologous and/or engineered GPD is expressed in a recombinant microorganism that also expresses an NADH-utilizing enzyme, for example, an NADH-utilizing enzyme that acts in the isobutanol production pathway such as KARI and alcohol dehydrogenase.

An additional way to improve the production of a product alcohol (e.g., butanol) is to alter the GPD to decrease the $K_M$ for NADPH. Decreasing the $K_M$ for NADPH by altering GPD can increase the rate of NADPH oxidation catalyzed by GPD, thus allowing an increase in the availability of NADH in the host cell. The available NADH can be used by other enzymes in the product alcohol production pathway, for example, in the isobutanol production pathway the available NADH can be utilized by KARI and alcohol dehydrogenase. Thus, increasing the affinity of GPD for NADPH can increase product alcohol (e.g., isobutanol) production. Accordingly, in some embodiments, a heterologous and/or engineered GPD is expressed in recombinant microorganism that also expresses other NADH-utilizing enzymes, for example, an NADH-utilizing enzyme that acts in the isobutanol production pathway such as KARI and alcohol dehydrogenase.

Another way to retain the ability to make some glycerol and also improve the production of product alcohol is to use heterologous GPD enzymes that can reduce the amount of glycerol produced as compared to the amount produced by the endogenous GPD enzymes. An example heterologous enzyme is *E. coli* gpsA. Two mechanistic features of *E. coli* gpsA that may contribute to its ability to produce less glycerol include (1) gpsA is product inhibited by glycerol-3-phosphate, and (2) gpsA utilizes the cofactors NADH and NADPH with substantially the same affinity (Edgar and Bell, JBC 255:3492-7 (1980)) and under certain conditions this can also allow for the production of glycerol using NADPH, thus allowing for the availability of NADH in the host cell. Product inhibition by glycerol-3-phosphate in *Saccharomyces* may result in reduced glycerol production, especially if the glycerol-3-phosphate phosphatase enzymatic reaction is slower than the GPD enzymatic reaction. The published Michaelis constants for the *Saccharomyces* phosphatases GPP1 and GPP2 are 3.1 and 3.9, respectively (Norbeck, JBC 271:13875-81 (1996), which is nearly 1000-fold higher than the inhibition constant ($K_i$) of glycerol-3-phosphate on *E. coli* gpsA (Edgar and Bell, JBC 253:6345-63 (1978)). Most conditions are conducive to product inhibition by glycerol-3-phosphate.

GPD enzymes that can utilize NADH or NADPH and/or are feedback inhibited by glycerol-3-phosphate can include both naturally occurring proteins and engineered proteins. For instance, NADH-utilizing or NADPH-utilizing GPD enzymes are described by EC 1.1.1.94 and have been found in *Aspergillus oryzae, Candida versatilis, Escherichia coli,* and *Oryctolagus cuniculus*.

In some embodiments, the heterologous GPD used herein is a *Leishmania mexicana, Dunaliella viridis, Jaculus orientalis, Archeoglobus fulgidus, Rickettsia prowazekii, Beggiatoa alba, Kangiella koreenis Aspergillus oryzae, Candida versatilis, Escherichia coli,* or *Oryctolagus cuniculu* GPD.

In certain embodiments, the sequences of other GPD enzymes that can utilize either NADH or NADPH and/or are feedback inhibited by glycerol-3-phosphate can be identified in the literature and candidates can be identified in bioinformatics databases well known to the skilled person using sequences disclosed herein and available in the art. For example, such sequences can be identified through BLAST searching of publicly available databases with known GPD encoding polynucleotide or polypeptide sequences. In such a method, identities can be based on the Clustal W method of alignment using the default parameters of GAP PENALTY=10, GAP LENGTH PENALTY=0.1, and Gonnet 250 series of protein weight matrix.

Additionally, GPD polynucleotide or polypeptide sequences disclosed herein or known in the art can be used to identify other candidate GPD homologs in nature. For example, the GPD encoding nucleic acid sequences disclosed herein or known in the art can be used to isolate genes encoding homologous proteins. Isolation of homologous genes using sequence-dependent protocols include, but are not limited to (1) methods of nucleic acid hybridization; (2) methods of DNA and RNA amplification, as exemplified by various uses of nucleic acid amplification technologies (e.g., polymerase chain reaction (PCR), Mullis et al., U.S. Pat. No. 4,683,202; ligase chain reaction (LCR), Tabor, S. et al., *PNAS USA* 82:1074 (1985); or strand displacement amplification (SDA), Walker et al., *PNAS USA* 89:392 (1992)]; and (3) methods of library construction and screening by complementation.

Another way to improve the production of a product alcohol is to alter the GPD to increase the $K_M$ for NADH. Increasing the $K_M$ for NADH by altering GPD can decrease the rate of NADH oxidation catalyzed by GPD, thus allowing an increase in the availability of NADH in a host cell. The available NADH can be used by other enzymes in the product alcohol production pathway, for example, in the isobutanol production pathway the available NADH can be utilized by KARI and alcohol dehydrogenase. Thus, decreasing the affinity of GPD for NADH can increase product alcohol (e.g., isobutanol) production. Accordingly, in some embodiments, a heterologous and/or engineered GPD is expressed in recombinant microorganism that also expresses other NADH-utilizing enzymes, for example, an NADH-utilizing enzyme that acts in the isobutanol production pathway such as KARI and alcohol dehydrogenase.

GPD enzymes with an increased $K_M$ for NADH can also be produced by means of protein engineering. In some embodiments, the GPD has at least 50%, 55%, 60%, 65%, 70%, 75%, 80%, 85%, 90% or 95% identity to *Saccharomyces cerevisiae* GPD1 (SEQ ID NO: 195), but is not 100% identical to SEQ ID NO:195. In some embodiments, the GPD comprises at least one substitution at a residue corresponding to position 42, 44, 45, 71, 73, 75, 95, 124, 126, 129, 151, 152, 183, 184, 185, 246, 310, 336, 337, or 339 of *Saccharomyces cerevisiae* GPD1 (SEQ ID NO: 195).

For example, in some embodiments, the GPD comprises a substitution of the residue corresponding to position 44 of SEQ ID NO:195 (Asn in SEQ ID NO:195) to an amino acid selected from the group consisting of A, C, G, I, L, M, S, and V.

In some embodiments, the GPD comprises a substitution of the residue corresponding to position 45 of SEQ ID NO:195 (Trp in SEQ ID NO:195) to an amino acid selected from the group consisting of A, C, G, H, I, K, L, M, N, Q, R, S, T, and V.

In some embodiments, the GPD comprises a substitution of the residue corresponding to position 73 of SEQ ID NO:195 (Phe in SEQ ID NO:195) to an amino acid selected from the group consisting of G, A, R, and K.

In some embodiments, the GPD comprises a substitution of the residue corresponding to position 129 of SEQ ID NO:195 (Phe in SEQ ID NO:195) to an amino acid selected from the group consisting of G, A, R, and K.

In some embodiments, the GPD comprises a substitution of the residue corresponding to position 337 of SEQ ID NO:195 (Ser in SEQ ID NO:195) to an amino acid selected from the group consisting of A, C, D, E, G, I, L, M, N, Q, and V.

In some embodiments, the GPD comprises a substitution of the residue corresponding to position 339 of SEQ ID NO:195 (Gln in SEQ ID NO:195) to an amino acid selected from the group consisting of A, C, G, I, L, M, S, and V.

In some embodiments, the GPD comprises a substitution of the residue corresponding to position 42, 71, 75, 95, 124, 126, 151, 152, 183, 184, 185, 246, 310, and/or 336 of SEQ ID NO:195 (Ser, Trp, Glu, Tyr, Gln, Pro, Leu, Lys, Asn, Ile, Ala, Asn, Arg, Gln of SEQ ID NO: 195, respectively) to any other amino acid selected from the 19 naturally occurring amino acids.

In some embodiments, the GPD has a $K_M$ for NADH that is about 0.01 mM to about 1 mM. In some embodiments, the GPD has a $K_M$ for NADH that is about 0.05 mM to about 1 mM. In some embodiments, the GPD has a $K_M$ for NADH that is about 0.10 mM to about 1 mM. In some embodiments, the GPD has a $K_M$ for NADH that is about 0.15 mM to about 1 mM. In some embodiments, the GPD has a $K_M$ for NADH that is about 0.20 mM to about 1 mM. In some embodiments, the GPD has a $K_M$ for NADH that is about 0.30 mM to about 1 mM. In some embodiments, the GPD has a $K_M$ for NADH that is about 0.40 mM to about 1 mM. In some embodiments, the GPD has a $K_M$ for NADH that is about 0.50 mM to about 1 mM. Assays for measuring the $K_M$ for NADH of GPD are disclosed in Example 1 below and are known in the art, see, e.g., Niesel et al., Methods Enzymol. 89:296-301 (1982). Certain assays can be referred to as "NADH consumption assays," which refer to an enzyme assay for the determination of the specific activity of the GPD enzyme, involving measuring the disappearance of the GPD cofactor, NADH, from the enzyme reaction.

In some embodiments, the GPD has a $K_M$ for NADPH that is about 0.01 mM to about 1 mM. In some embodiments, the GPD has a $K_M$ for NADPH that is about 0.05 mM to about 1 mM. In some embodiments, the GPD has a $K_M$ for NADPH that is about 0.10 mM to about 1 mM. In some embodiments, the GPD has a $K_M$ for NADPH that is about 0.15 mM to about 1 mM. In some embodiments, the GPD has a $K_M$ for NADPH that is about 0.20 mM to about 1 mM. In some embodiments, the GPD has a $K_M$ for NADPH that is about 0.30 mM to about 1 mM. In some embodiments, the GPD has a $K_M$ for NADPH that is about 0.40 mM to about 1 mM. In some embodiments, the GPD has a $K_M$ for NADPH that is about 0.50 mM to about 1 mM. The NADH assays disclosed below in Example 1 can be adapted to measure the $K_M$ for NADPH of GPD by replacing NADH with NADPH. Additional assays for measuring the $K_M$ for NADPH of GPD are known in the art, see, e.g., Niesel et al., Methods Enzymol. 89:296-301 (1982). Certain assays can be referred to as "NADPH consumption assays," which refer to an enzyme assay for the determination of the specific activity of the GPD enzyme, involving measuring the disappearance of the GPD cofactor, NADH, from the enzyme reaction.

In some embodiments, the heterologous and/or engineered GPD can increase the growth of a recombinant microorganism comprising the heterologous and/or engineered GPD as compared to a recombinant microorganism that does not contain the heterologous and/or engineered GPD.

In some embodiments, the heterologous and/or engineered GPD can increase the product alcohol (e.g., isobutanol) production of a recombinant microorganism comprising the heterologous and/or engineered GPD as compared to a recombinant microorganism that does not contain the heterologous and/or engineered GPD.

In some embodiments, the heterologous and/or engineered GPD can decrease the glycerol production of a recombinant microorganism comprising the GPD as compared to a recombinant microorganism that does not contain the heterologous and/or engineered GPD.

In some embodiments, the heterologous and/or engineered GPD can increase the ratio of product alcohol (e.g., isobutanol) to glycerol produced by a recombinant microorganism comprising the heterologous and/or engineered GPD as compared to a recombinant microorganism that does not contain the heterologous and/or engineered GPD.

In some embodiments, the heterologous and/or engineered GPD can increase the yield (e.g., gram of isobutanol produced per gram of substrate consumed) of a recombinant microorganism comprising the heterologous and/or engineered GPD as compared to a recombinant microorganism that does not contain the heterologous and/or engineered GPD.

Thus in a recombinant microorganism comprising a butanol biosynthetic pathway, a heterologous and/or engineered GPD that has a higher $K_M$ for NADH than the microorganism's endogenous GPD, and a deletion or disruption of an endogenous gene encoding GPD, "improved production of butanol" can refer to increased production of butanol, a decreased production of glycerol, or both, as compared to a microorganism that lacks the heterologous and/or engineered GPD.

In a recombinant microorganisms comprising a heterologous and/or engineered GPD that has a higher $K_M$ for NADH than the microorganism's endogenous GPD, and a deletion or disruption in an endogenous gene encoding GPD, "improved production of alcohol" can refer to an increased production of alcohol, a decreased production of glycerol, or both, as compared to a microorganism that lacks the heterologous and/or engineered GPD.

Thus, in a recombinant microorganism comprising a butanol biosynthetic pathway, a heterologous GPD that has substantially the same affinity for NADH and NADPH and/or is feedback inhibited by glycerol-3-phosphate, and a deletion or disruption of an endogenous gene encoding GPD, "improved production of butanol" can refer to increased production of butanol, a decreased production of glycerol, or both, as compared to a microorganism that lacks the heterologous GPD.

In a recombinant microorganisms comprising a heterologous GPD that has substantially the same affinity for NADH and NAPDH and/or is feedback inhibited by glycerol-3-phosphate, and a deletion or disruption in an endogenous gene encoding GPD, "improved production of alcohol" can refer to an increased production of alcohol, a decreased production of glycerol, or both, as compared to a microorganism that lacks the heterologous GPD.

Recombinant Microorganisms

While not wishing to be bound by theory, it is believed that the processes described herein are useful in conjunction with any alcohol producing microorganism, particularly recombinant microorganisms which produce alcohol.

Recombinant microorganisms which produce alcohol are also known in the art (e.g., Ohta et al., Appl. Environ. Microbiol. 57:893-900 (1991); Underwood et al., Appl. Envrion. Microbiol. 68:1071-81 (2002); Shen and Liao, Metab. Eng. 10:312-20 (2008); Hahnai et al., Appl. Environ. 73:7814-8 (2007); U.S. Pat. No. 5,514,583; U.S. Pat. No. 5,712,133; International Publication No. WO 1995/028476; Feldmann et al., Appl. Microbiol. Biotechnol. 38:354-61 (1992); Zhang et al., Science 267:240-3 (1995); U.S. Patent Publication No. 2007/0031918A1; U.S. Pat. No. 7,223,575; U.S. Pat. No. 7,741,119; U.S. Patent Publication No. 2009/0203099A1; U.S. Patent Publication No. 2009/0246846A1; and International Publication No. WO 2010/075241, which are herein incorporated by reference).

For example, the metabolic pathways of microorganisms may be genetically modified to produce butanol. These pathways may also be modified to reduce or eliminate undesired metabolites, and thereby improve yield of the product alcohol. The production of butanol by a microorganism is disclosed, for example, in U.S. Pat. Nos. 7,851,188; 7,993,889; 8,178,328, 8,206,970; U.S. Patent Application Publication Nos. 2007/0292927; 2008/0182308; 2008/0274525; 2009/0305363; 2009/0305370; 2011/0250610; 2011/0313206; 2011/0111472; 2012/0258873; and 2013/0071898, the entire contents of each are herein incorporated by reference. In certain embodiments, the microorganism is genetically modified to comprise a butanol biosynthetic pathway or a biosynthetic pathway for a butanol isomer, such as 1-butanol, 2-butanol, or isobutanol. In certain embodiments, at least one, at least two, at least three, at least four, or at least five polypeptides catalyzing substrate to product conversions in the butanol biosynthetic pathway are encoded by heterologous polynucleotides in the microorganism. In certain embodiments, all the polypeptides catalyzing substrate to product conversions of the butanol biosynthetic pathway are encoded by heterologous polynucleotides in the microorganism. In will be appreciated that microorganisms comprising a butanol biosynthetic pathway may further comprise one or more additional genetic modifications as disclosed in U.S. Patent Application Publication No. 2013/0071898, which is herein incorporated by reference in its entirety.

In some embodiments, the microorganism may be bacteria, cyanobacteria, filamentous fungi, or yeasts. Suitable microorganisms capable of producing product alcohol (e.g., butanol) via a biosynthetic pathway include a member of the genera *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Paenibacillus, Arthrobacter, Corynebacterium, Brevibacterium, Schizosaccharomyces, Kluveromyces, Yarrowia, Pichia, Zygosaccharomyces, Debaryomyces, Candida, Brettanomyces, Pachysolen, Hansenula, Issatchenkia, Trichosporon, Yamadazyma*, or *Saccharomyces*. In one embodiment, recombinant microorganisms may be selected from the group consisting of *Escherichia coli, Alcaligenes eutrophus, Bacillus licheniformis, Paenibacillus macerans, Rhodococcus erythropolis, Pseudomonas putida, Lactobacillus plantarum, Enterococcus faecium, Enterococcus gallinarum, Enterococcus faecalis, Bacillus subtilis, Candida sonorensis, Candida methanosorbosa, Kluyveromyces lactis, Kluyveromyces marxianus, Kluyveromyces thermotolerans, Issatchenkia orientalis, Debaryomyces hansenii*, and *Saccharomyces cerevisiae*. In one embodiment, the genetically modified microorganism is yeast. In one embodiment, the genetically modified microorganism is a crabtree-positive yeast selected from *Saccharomyces, Zygosaccharomyces, Schizosaccharomyces, Dekkera, Torulopsis, Brettanomyces*, and some species of *Candida*. Species of crabtree-positive yeast include, but are not limited to, *Saccharomyces cerevisiae, Saccharomyces kluyveri, Schizosaccharomyces pombe, Saccharomyces bayanus, Saccharomyces mikitae, Saccharomyces paradoxus, Saccharomyces uvarum, Saccharomyces castelli, Zygosaccharomyces rouxii, Zygosaccharomyces bailli*, and *Candida glabrata*.

In some embodiments, the host cell is *Saccharomyces cerevisiae*. *Saccharomyces cerevisiae* are known in the art and are available from a variety of sources including, but not limited to, American Type Culture Collection (Rockville, Md.), Centraalbureau voor Schimmelcultures (CBS) Fungal Biodiversity Centre, LeSaffre, Gert Strand AB, Ferm Solutions, North American Bioproducts, Martrex, and Lallemand. *S. cerevisiae* include, but are not limited to, BY4741, CEN.PK 113-7D, Ethanol Red® yeast, Ferm Pro™ yeast, Bio-Ferm® XR yeast, Gert Strand Prestige Batch Turbo alcohol yeast, Gert Strand Pot Distillers yeast, Gert Strand Distillers Turbo yeast, FerMax™ Green yeast, FerMax™ Gold yeast, Thermosacc® yeast, BG-1, PE-2, CAT-1, CBS7959, CBS7960, and CBS7961.

In some embodiments, the microorganism may be immobilized or encapsulated. For example, the microorganism may be immobilized or encapsulated using alginate, calcium alginate, or polyacrylamide gels, or through the induction of biofilm formation onto a variety of high surface area support matrices such as diatomite, celite, diatomaceous earth, silica gels, plastics, or resins. In some embodiments, ISPR may be used in combination with immobilized or encapsulated microorganisms. This combination may improve productivity such as specific volumetric productivity, metabolic rate, product alcohol yields, tolerance to product alcohol. In addition, immobilization and encapsulation may minimize the effects of the process conditions such as shearing on the microorganisms.

Biosynthetic pathways for the production of isobutanol that may be used include those as described by Donaldson et al. in U.S. Pat. No. 7,851,188; U.S. Pat. No. 7,993,388; and International Publication No. WO 2007/050671, which are incorporated herein by reference. In one embodiment, the isobutanol biosynthetic pathway comprises the following substrate to product conversions:

a) pyruvate to acetolactate, which may be catalyzed, for example, by acetolactate synthase;

b) the acetolactate from step a) to 2,3-dihydroxyisovalerate, which may be catalyzed, for example, by ketol-acid reductoisomerase;

c) the 2,3-dihydroxyisovalerate from step b) to α-ketoisovalerate, which may be catalyzed, for example, by dihydroxyacid dehydratase;

d) the α-ketoisovalerate from step c) to isobutyraldehyde, which may be catalyzed, for example, by a branched-chain α-keto acid decarboxylase; and, e) the isobutyraldehyde from step d) to isobutanol, which may be catalyzed, for example, by a branched-chain alcohol dehydrogenase.

In another embodiment, the isobutanol biosynthetic pathway comprises the following substrate to product conversions:

a) pyruvate to acetolactate, which may be catalyzed, for example, by acetolactate synthase;

b) the acetolactate from step a) to 2,3-dihydroxyisovalerate, which may be catalyzed, for example, by ketol-acid reductoisomerase;

c) the 2,3-dihydroxyisovalerate from step b) to α-ketoisovalerate, which may be catalyzed, for example, by dihydroxyacid dehydratase;

d) the α-ketoisovalerate from step c) to valine, which may be catalyzed, for example, by transaminase or valine dehydrogenase;

e) the valine from step d) to isobutylamine, which may be catalyzed, for example, by valine decarboxylase;

f) the isobutylamine from step e) to isobutyraldehyde, which may be catalyzed by, for example, omega transaminase; and, g) the isobutyraldehyde from step f) to isobutanol, which may be catalyzed, for example, by a branched-chain alcohol dehydrogenase.

In another embodiment, the isobutanol biosynthetic pathway comprises the following substrate to product conversions:

a) pyruvate to acetolactate, which may be catalyzed, for example, by acetolactate synthase;

b) the acetolactate from step a) to 2,3-dihydroxyisovalerate, which may be catalyzed, for example, by ketol-acid reductoisomerase;

c) the 2,3-dihydroxyisovalerate from step b) to α-ketoisovalerate, which may be catalyzed, for example, by dihydroxyacid dehydratase;

d) the α-ketoisovalerate from step c) to isobutyryl-CoA, which may be catalyzed, for example, by branched-chain keto acid dehydrogenase;

e) the isobutyryl-CoA from step d) to isobutyraldehyde, which may be catalyzed, for example, by acylating aldehyde dehydrogenase; and, f) the isobutyraldehyde from step e) to isobutanol, which may be catalyzed, for example, by a branched-chain alcohol dehydrogenase.

Biosynthetic pathways for the production of 1-butanol that may be used include those described in U.S. Patent Application Publication No. 2008/0182308 and WO2007/041269, which are incorporated herein by reference. In one embodiment, the 1-butanol biosynthetic pathway comprises the following substrate to product conversions:

a) acetyl-CoA to acetoacetyl-CoA, which may be catalyzed, for example, by acetyl-CoA acetyltransferase;

b) the acetoacetyl-CoA from step a) to 3-hydroxybutyryl-CoA, which may be catalyzed, for example, by 3-hydroxybutyryl-CoA dehydrogenase;

c) the 3-hydroxybutyryl-CoA from step b) to crotonyl-CoA, which may be catalyzed, for example, by crotonase;

d) the crotonyl-CoA from step c) to butyryl-CoA, which may be catalyzed, for example, by butyryl-CoA dehydrogenase;

e) the butyryl-CoA from step d) to butyraldehyde, which may be catalyzed, for example, by butyraldehyde dehydrogenase; and, f) the butyraldehyde from step e) to 1-butanol, which may be catalyzed, for example, by butanol dehydrogenase.

Biosynthetic pathways for the production of 2-butanol that may be used include those described by Donaldson et al. in U.S. Pat. No. 8,206,970; U.S. Patent Application Publication Nos. 2007/0292927 and 2009/0155870; International Publication Nos. WO 2007/130518 and WO 2007/130521, all of which are incorporated herein by reference. In one embodiment, the 2-butanol biosynthetic pathway comprises the following substrate to product conversions:

a) pyruvate to alpha-acetolactate, which may be catalyzed, for example, by acetolactate synthase;

b) the alpha-acetolactate from step a) to acetoin, which may be catalyzed, for example, by acetolactate decarboxylase;

c) the acetoin from step b) to 3-amino-2-butanol, which may be catalyzed, for example, acetoin aminase;

d) the 3-amino-2-butanol from step c) to 3-amino-2-butanol phosphate, which may be catalyzed, for example, by aminobutanol kinase;

e) the 3-amino-2-butanol phosphate from step d) to 2-butanone, which may be catalyzed, for example, by aminobutanol phosphate phosphorylase; and, f) the 2-butanone from step e) to 2-butanol, which may be catalyzed, for example, by butanol dehydrogenase.

In another embodiment, the 2-butanol biosynthetic pathway comprises the following substrate to product conversions:

a) pyruvate to alpha-acetolactate, which may be catalyzed, for example, by acetolactate synthase;

b) the alpha-acetolactate from step a) to acetoin, which may be catalyzed, for example, by acetolactate decarboxylase;

c) the acetoin to 2,3-butanediol from step b), which may be catalyzed, for example, by butanediol dehydrogenase;

d) the 2,3-butanediol from step c) to 2-butanone, which may be catalyzed, for example, by diol dehydratase; and, e) the 2-butanone from step d) to 2-butanol, which may be catalyzed, for example, by butanol dehydrogenase.

Biosynthetic pathways for the production of 2-butanone that may be used include those described in U.S. Pat. No. 8,206,970 and U.S. Patent Application Publication Nos. 2007/0292927 and 2009/0155870, which are incorporated herein by reference. In one embodiment, the 2-butanone biosynthetic pathway comprises the following substrate to product conversions:

a) pyruvate to alpha-acetolactate, which may be catalyzed, for example, by acetolactate synthase;

b) the alpha-acetolactate from step a) to acetoin, which may be catalyzed, for example, by acetolactate decarboxylase;

c) the acetoin from step b) to 3-amino-2-butanol, which may be catalyzed, for example, acetoin aminase;

d) the 3-amino-2-butanol from step c) to 3-amino-2-butanol phosphate, which may be catalyzed, for example, by aminobutanol kinase; and, e) the 3-amino-2-butanol phosphate from step d) to 2-butanone, which may be catalyzed, for example, by aminobutanol phosphate phosphorylase.

In another embodiment, the 2-butanone biosynthetic pathway comprises the following substrate to product conversions:

a) pyruvate to alpha-acetolactate, which may be catalyzed, for example, by acetolactate synthase;

b) the alpha-acetolactate from step a) to acetoin which may be catalyzed, for example, by acetolactate decarboxylase;

c) the acetoin from step b) to 2,3-butanediol, which may be catalyzed, for example, by butanediol dehydrogenase;

d) the 2,3-butanediol from step c) to 2-butanone, which may be catalyzed, for example, by diol dehydratase.

The terms "acetohydroxyacid synthase," "acetolactate synthase," and "acetolactate synthetase" (abbreviated "ALS") are used interchangeably herein to refer to an enzyme that catalyzes the conversion of pyruvate to acetolactate and $CO_2$. Example acetolactate synthases are known by the EC number 2.2.1.6 (Enzyme Nomenclature 1992, Academic Press, San Diego). These enzymes are available from a number of sources, including, but not limited to, *Bacillus subtilis* (GenBank Nos: CAB07802.1, Z99122, NCBI (National Center for Biotechnology Information) amino acid sequence, NCBI nucleotide sequence, respectively), CAB15618, *Klebsiella pneumoniae* (GenBank Nos: AAA25079, M73842), and *Lactococcus lactis* (GenBank Nos: AAA25161, L16975).

The term "ketol-acid reductoisomerase" ("KARI"), "acetohydroxy acid isomeroreductase," and "acetohydroxy acid reductoisomerase" will be used interchangeably and refer to enzymes capable of catalyzing the reaction of (S)-acetolactate to 2,3-dihydroxyisovalerate. Example KARI enzymes may be classified as EC number EC 1.1.1.86 (Enzyme Nomenclature 1992, Academic Press, San Diego), and are available from a vast array of microorganisms, including, but not limited to, *Escherichia coli* (GenBank Nos: NP_418222, NC_000913), *Saccharomyces cerevisiae*

(GenBank Nos: NP_013459, NC_001144), *Methanococcus maripaludis* (GenBank Nos: CAF30210, BX957220), and *Bacillus subtilis* (GenBank Nos: CAB14789, Z99118). KARIs include *Anaerostipes caccae* KARI variants "K9G9" (SEQ ID NO:85), "K9D3" (SEQ ID NO:86), and "K9JB4P" (SEQ ID NO:87). Ketol-acid reductoisomerase (KARI) enzymes are described in U.S. Pat. Nos. 7,910,342 and 8,129,162; U.S. Patent Application Publication Nos. 2008/0261230, 2009/0163376, 2010/0197519, PCT Application Publication No. WO/2011/041415, PCT Application Publication No. WO2012/129555; and U.S. patent application Ser. No. 14/038,455, filed on Sep. 26, 2013, all of which are incorporated herein by reference. Examples of KARIs disclosed therein are those from *Lactococcus lactis, Vibrio cholera, Pseudomonas aeruginosa* PAO1, and *Pseudomonas fluorescens* PF5 mutants. In some embodiments, the KARI utilizes NADH. In some embodiments, the KARI utilizes NADPH. In some embodiments, the KARI utilizes NADH or NADPH.

The term "acetohydroxy acid dehydratase" and "dihydroxyacid dehydratase" ("DHAD") refers to an enzyme that catalyzes the conversion of 2,3-dihydroxyisovalerate to α-ketoisovalerate. Example acetohydroxy acid dehydratases are known by the EC number 4.2.1.9. Such enzymes are available from a vast array of microorganisms, including, but not limited to, *E. coli* (GenBank Nos: YP_026248, NC000913), *Saccharomyces cerevisiae* (GenBank Nos: NP_012550, NC 001142), *M. maripaludis* (GenBank Nos: CAF29874, BX957219), *B. subtilis* (GenBank Nos: CAB14105, Z99115), *L. lactis* (SEQ ID NO:88), and *N. crassa*. U.S. Patent Application Publication No. 2010/0081154, U.S. Pat. No. 7,851,188, and U.S. Pat. No. 8,241,878, which are incorporated herein by reference in their entireties, describe dihydroxyacid dehydratases (DHADs), including a DHAD from Streptococcus mutans (SEQ ID NO:89) and variants thereof.

The term "branched-chain α-keto acid decarboxylase," "α-ketoacid decarboxylase," "α-ketoisovalerate decarboxylase," or "2-ketoisovalerate decarboxylase" ("KIVD") refers to an enzyme that catalyzes the conversion of α-ketoisovalerate to isobutyraldehyde and $CO_2$. Example branched-chain α-keto acid decarboxylases are known by the EC number 4.1.1.72 and are available from a number of sources, including, but not limited to, *Lactococcus lactis* (GenBank Nos: AAS49166, AY548760; CAG34226, AJ746364), *Salmonella typhimurium* (GenBank Nos: NP_461346, NC_003197), *Clostridium acetobutylicum* (GenBank Nos: NP_149189, NC_001988), *M. caseolyticus*, and *L. grayi*. Suitable branched-chain α-keto acid decarboxylases can comprise SEQ ID NO:90 from *Lactococcus lactis* and SEQ ID NO:91 from *Listeria grayi*.

The term "branched-chain alcohol dehydrogenase" ("ADH") refers to an enzyme that catalyzes the conversion of isobutyraldehyde to isobutanol. Example branched-chain alcohol dehydrogenases are known by the EC number 1.1.1.265, but may also be classified under other alcohol dehydrogenases (specifically, EC 1.1.1.1 or 1.1.1.2). Alcohol dehydrogenases may be NADPH dependent or NADH dependent. Such enzymes are available from a number of sources, including, but not limited to, *S. cerevisiae* (GenBank Nos: NP_010656, NC_001136, NP_014051, NC_001145), *E. coli* (GenBank Nos: NP_417484, NC_000913), *C. acetobutylicum* (GenBank Nos: NP_349892, NC_003030; NP_349891, NC_003030). U.S. Patent Application Publication No. 2009/0269823 describes SadB, an alcohol dehydrogenase (ADH) from *Achromobacter xylosoxidans* (SEQ ID NO:92). Alcohol dehydrogenases also include horse liver ADH (SEQ ID NO:93) and *Beijerinkia indica* ADH (SEQ ID NO:94) (as described by U.S. Patent Application Publication No. 2011/0269199, which is incorporated herein by reference).

The term "butanol dehydrogenase" refers to a polypeptide (or polypeptides) having an enzyme activity that catalyzes the conversion of isobutyraldehyde to isobutanol or the conversion of 2-butanone and 2-butanol. Butanol dehydrogenases are a subset of a broad family of alcohol dehydrogenases. Butanol dehydrogenase may be NAD- or NADP-dependent. The NAD-dependent enzymes are known as EC 1.1.1.1 and are available, for example, from *Rhodococcus ruber* (GenBank Nos: CAD36475, AJ491307). The NADP dependent enzymes are known as EC 1.1.1.2 and are available, for example, from *Pyrococcus furiosus* (GenBank Nos: AAC25556, AF013169). Additionally, a butanol dehydrogenase is available from *Escherichia coli* (GenBank Nos: NP_417484, NC_000913) and a cyclohexanol dehydrogenase is available from *Acinetobacter* sp. (GenBank Nos: AAG10026, AF282240). The term "butanol dehydrogenase" also refers to an enzyme that catalyzes the conversion of butyraldehyde to 1-butanol, using either NADH or NADPH as cofactor. Butanol dehydrogenases are available from, for example, *C. acetobutylicum* (GenBank NOs: NP_149325, NC_001988; note: this enzyme possesses both aldehyde and alcohol dehydrogenase activity); NP_349891, NC_003030; and NP_349892, NC_003030) and *E. coli* (GenBank NOs: NP_417-484, NC_000913).

The term "branched-chain keto acid dehydrogenase" refers to an enzyme that catalyzes the conversion of α-ketoisovalerate to isobutyryl-CoA (isobutyryl-coenzyme A), typically using $NAD^+$ (nicotinamide adenine dinucleotide) as an electron acceptor. Example branched-chain keto acid dehydrogenases are known by the EC number 1.2.4.4. Such branched-chain keto acid dehydrogenases are comprised of four subunits and sequences from all subunits are available from a vast array of microorganisms, including, but not limited to, *B. subtilis* (GenBank Nos: CAB14336, Z99116; CAB14335, Z99116; CAB14334, Z99116; and CAB14337, Z99116) and *Pseudomonas putida* (GenBank Nos: AAA65614, M57613; AAA65615, M57613; AAA65617, M57613; and AAA65618, M57613).

The term "acylating aldehyde dehydrogenase" refers to an enzyme that catalyzes the conversion of isobutyryl-CoA to isobutyraldehyde, typically using either NADH or NADPH as an electron donor. Example acylating aldehyde dehydrogenases are known by the EC numbers 1.2.1.10 and 1.2.1.57. Such enzymes are available from multiple sources, including, but not limited to, *Clostridium beijerinckii* (GenBank Nos: AAD31841, AF157306), *C. acetobutylicum* (GenBank Nos: NP_149325, NC_001988; NP_149199, NC_001988), *P. putida* (GenBank Nos: AAA89106, U13232), and *Thermus thermophilus* (GenBank Nos: YP_145486, NC_006461).

The term "transaminase" refers to an enzyme that catalyzes the conversion of α-ketoisovalerate to L-valine, using either alanine or glutamate as an amine donor. Example transaminases are known by the EC numbers 2.6.1.42 and 2.6.1.66. Such enzymes are available from a number of sources. Examples of sources for alanine-dependent enzymes include, but are not limited to, *E. coli* (GenBank Nos: YP_026231, NC_000913) and *Bacillus licheniformis* (GenBank Nos: YP_093743, NC_006322). Examples of sources for glutamate-dependent enzymes include, but are not limited to, *E. coli* (GenBank Nos: YP_026247, NC_000913), *Saccharomyces cerevisiae* (GenBank Nos:

NP_012682, NC_001142) and *Methanobacterium thermoautotrophicum* (GenBank Nos: NP_276546, NC_000916).

The term "valine dehydrogenase" refers to an enzyme that catalyzes the conversion of α-ketoisovalerate to L-valine, typically using NAD(P)H as an electron donor and ammonia as an amine donor. Example valine dehydrogenases are known by the EC numbers 1.4.1.8 and 1.4.1.9 and such enzymes are available from a number of sources, including, but not limited to, *Streptomyces coelicolor* (GenBank Nos: NP_628270, NC_003888) and *B. subtilis* (GenBank Nos: CAB14339, Z99116).

The term "valine decarboxylase" refers to an enzyme that catalyzes the conversion of L-valine to isobutylamine and $CO_2$. Example valine decarboxylases are known by the EC number 4.1.1.14. Such enzymes are found in *Streptomyces*, such as for example, *Streptomyces viridifaciens* (GenBank Nos: AAN10242, AY116644).

The term "omega transaminase" refers to an enzyme that catalyzes the conversion of isobutylamine to isobutyraldehyde using a suitable amino acid as an amine donor. Example omega transaminases are known by the EC number 2.6.1.18 and are available from a number of sources, including, but not limited to, *Alcaligenes denitrificans* (AAP92672, AY330220), *Ralstonia eutropha* (GenBank Nos: YP_294474, NC_007347), *Shewanella oneidensis* (GenBank Nos: NP_719046, NC_004347), and *P. putida* (GenBank Nos: AAN66223, AE016776).

The term "acetyl-CoA acetyltransferase" refers to an enzyme that catalyzes the conversion of two molecules of acetyl-CoA to acetoacetyl-CoA and coenzyme A (CoA). Example acetyl-CoA acetyltransferases are acetyl-CoA acetyltransferases with substrate preferences (reaction in the forward direction) for a short chain acyl-CoA and acetyl-CoA and are classified as E.C. 2.3.1.9 [Enzyme Nomenclature 1992, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos: NP_416728, NC_000913; NCBI (National Center for Biotechnology Information) amino acid sequence, NCBI nucleotide sequence), *Clostridium acetobutylicum* (GenBank Nos: NP_349476.1, NC_003030; NP_149242, NC_001988, *Bacillus subtilis* (GenBank Nos: NP_390297, NC_000964), and *Saccharomyces cerevisiae* (GenBank Nos: NP_015297, NC_001148).

The term "3-hydroxybutyryl-CoA dehydrogenase" refers to an enzyme that catalyzes the conversion of acetoacetyl-CoA to 3-hydroxybutyryl-CoA. 3-Example hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA. Examples may be classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank NOs: NP_349314, NC_003030), *B. subtilis* (GenBank NOs: AAB09614, U29084), *Ralstonia eutropha* (GenBank Nos: YP_294481, NC_007347), and *Alcaligenes eutrophus* (GenBank NOs: AAA21973, J04987).

The term "crotonase" refers to an enzyme that catalyzes the conversion of 3-hydroxybutyryl-CoA to crotonyl-CoA and $H_2O$. Example crotonases may have a substrate preference for (S)-3-hydroxybutyryl-CoA or (R)-3-hydroxybutyryl-CoA and may be classified as E.C. 4.2.1.17 and E.C. 4.2.1.55, respectively. Crotonases are available from a number of sources, for example, *E. coli* (GenBank NOs: NP_415911, NC_000913), *C. acetobutylicum* (GenBank NOs: NP_349318, NC_003030), *B. subtilis* (GenBank NOs: CAB13705, Z99113), and *Aeromonas caviae* (GenBank NOs: BAA21816, D88825).

The term "butyryl-CoA dehydrogenase" refers to an enzyme that catalyzes the conversion of crotonyl-CoA to butyryl-CoA. Example butyryl-CoA dehydrogenases may be NADH-dependent, NADPH-dependent, or flavin-dependent and may be classified as E.C. 1.3.1.44, E.C. 1.3.1.38, and E.C. 1.3.99.2, respectively. Butyryl-CoA dehydrogenases are available from a number of sources, for example, *C. acetobutylicum* (GenBank NOs: NP_347102, NC_003030), *Euglena gracilis* (GenBank NOs: Q5EU90, AY741582), *Streptomyces collinus* (GenBank NOs: AAA92890, U37135), and *Streptomyces coelicolor* (GenBank NOs: CAA22721, AL939127).

The term "butyraldehyde dehydrogenase" refers to an enzyme that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank NOs: AAD31841, AF157306) and *C. acetobutylicum* (GenBank NOs: NP_149325, NC_001988).

The term "isobutyryl-CoA mutase" refers to an enzyme that catalyzes the conversion of butyryl-CoA to isobutyryl-CoA. This enzyme uses coenzyme $B_{12}$ as cofactor. Example isobutyryl-CoA mutases are known by the EC number 5.4.99.13. These enzymes are found in a number of *Streptomyces*, including, but not limited to, *Streptomyces cinnamonensis* (GenBank Nos: AAC08713, U67612; CAB59633, AJ246005), *S. coelicolor* (GenBank Nos: CAB70645, AL939123; CAB92663, AL939121), and *Streptomyces avermitilis* (GenBank Nos: NP_824008, NC_003155; NP_824637, NC_003155).

The term "acetolactate decarboxylase" refers to a polypeptide (or polypeptides) having an enzyme activity that catalyzes the conversion of alpha-acetolactate to acetoin. Example acetolactate decarboxylases are known as EC 4.1.1.5 and are available, for example, from *Bacillus subtilis* (GenBank Nos: AAA22223, L04470), *Klebsiella terrigena* (GenBank Nos: AAA25054, L04507) and *Klebsiella pneumoniae* (GenBank Nos: AAU43774, AY722056).

The term "acetoin aminase" or "acetoin transaminase" refers to a polypeptide (or polypeptides) having an enzyme activity that catalyzes the conversion of acetoin to 3-amino-2-butanol. Acetoin aminase may utilize the cofactor pyridoxal 5'-phosphate or NADH (reduced nicotinamide adenine dinucleotide) or NADPH (reduced nicotinamide adenine dinucleotide phosphate). The resulting product may have (R) or (S) stereochemistry at the 3-position. The pyridoxal phosphate-dependent enzyme may use an amino acid such as alanine or glutamate as the amino donor. The NADH- and NADPH-dependent enzymes may use ammonia as a second substrate. A suitable example of an NADH dependent acetoin aminase, also known as amino alcohol dehydrogenase, is described by Ito, et al. (U.S. Pat. No. 6,432,688). An example of a pyridoxal-dependent acetoin aminase is the amine:pyruvate aminotransferase (also called amine:pyruvate transaminase) described by Shin and Kim (*J. Org. Chem.* 67:2848-2853, 2002).

The term "acetoin kinase" refers to a polypeptide (or polypeptides) having an enzyme activity that catalyzes the conversion of acetoin to phosphoacetoin. Acetoin kinase may utilize ATP (adenosine triphosphate) or phosphoenolpyruvate as the phosphate donor in the reaction. Enzymes that catalyze the analogous reaction on the similar substrate dihydroxyacetone, for example, include enzymes known as EC 2.7.1.29 (Garcia-Alles, et al., *Biochemistry* 43:13037-13046, 2004).

The term "acetoin phosphate aminase" refers to a polypeptide (or polypeptides) having an enzyme activity that catalyzes the conversion of phosphoacetoin to 3-amino-2-butanol O-phosphate. Acetoin phosphate aminase may use the cofactor pyridoxal 5'-phosphate, NADH or NADPH. The resulting product may have (R) or (S) stereochemistry at the 3-position. The pyridoxal phosphate-dependent enzyme may use an amino acid such as alanine or glutamate. The NADH and NADPH-dependent enzymes may use ammonia as a second substrate. Although there are no reports of enzymes catalyzing this reaction on phosphoacetoin, there is a pyridoxal phosphate-dependent enzyme that is proposed to carry out the analogous reaction on the similar substrate serinol phosphate (Yasuta, et al., *Appl. Environ. Microbial.* 67:4999-5009, 2001).

The term "aminobutanol phosphate phospholyase," also called "amino alcohol O-phosphate lyase," refers to a polypeptide (or polypeptides) having an enzyme activity that catalyzes the conversion of 3-amino-2-butanol O-phosphate to 2-butanone. Amino butanol phosphate phospho-lyase may utilize the cofactor pyridoxal 5'-phosphate. There are reports of enzymes that catalyze the analogous reaction on the similar substrate 1-amino-2-propanol phosphate (Jones, et al., *Biochem J.* 134:167-182, 1973). U.S. Patent Application Publication No. 2007/0259410 describes an aminobutanol phosphate phospho-lyase from the organism *Erwinia carotovora*.

The term "aminobutanol kinase" refers to a polypeptide (or polypeptides) having an enzyme activity that catalyzes the conversion of 3-amino-2-butanol to 3-amino-2-butanol O-phosphate. Amino butanol kinase may utilize ATP as the phosphate donor. Although there are no reports of enzymes catalyzing this reaction on 3-amino-2-butanol, there are reports of enzymes that catalyze the analogous reaction on the similar substrates ethanolamine and 1-amino-2-propanol (Jones, et al., supra). U.S. Patent Application Publication No. 2009/0155870 describes, in Example 14, an amino alcohol kinase of *Erwinia carotovora* subsp. *Atroseptica*.

The term "butanediol dehydrogenase" also known as "acetoin reductase" refers to a polypeptide (or polypeptides) having an enzyme activity that catalyzes the conversion of acetoin to 2,3-butanediol. Butanedial dehydrogenases are a subset of the broad family of alcohol dehydrogenases. Butanediol dehydrogenase enzymes may have specificity for production of (R)- or (S)-stereochemistry in the alcohol product. (S)-specific butanediol dehydrogenases are known as EC 1.1.1.76 and are available, for example, from *Klebsiella pneumoniae* (GenBank Nos: BBA13085, D86412). (R)-specific butanediol dehydrogenases are known as EC 1.1.1.4 and are available, for example, from *Bacillus cereus* (GenBank Nos. NP_830481, NC_004722; AAP07682, AE017000), and *Lactococcus lactis* (GenBank Nos. AAK04995, AE006323).

The term "butanediol dehydratase," also known as "dial dehydratase" or "propanediol dehydratase" refers to a polypeptide (or polypeptides) having an enzyme activity that catalyzes the conversion of 2,3-butanediol to 2-butanone. Butanediol dehydratase may utilize the cofactor adenosyl cobalamin (also known as coenzyme Bw or vitamin $B_{12}$; although vitamin B12 may refer also to other forms of cobalamin that are not coenzyme B12). Adenosyl cobalamin-dependent enzymes are known as EC 4.2.1.28 and are available, for example, from *Klebsiella oxytoca* (GenBank Nos: AA08099 (alpha subunit), D45071; BAA08100 (beta subunit), D45071; and BBA08101 (gamma subunit), D45071 (Note all three subunits are required for activity), and *Klebsiella pneumonia* (GenBank Nos: AAC98384 (alpha subunit), AF102064; GenBank Nos: AAC98385 (beta subunit), AF102064, GenBank Nos: AAC98386 (gamma subunit), AF102064). Other suitable dial dehydratases include, but are not limited to, B12-dependent dial dehydratases available from *Salmonella typhimurium* (GenBank Nos: AAB84102 (large subunit), AF026270; GenBank Nos: AAB84103 (medium subunit), AF026270; GenBank Nos: AAB84104 (small subunit), AF026270); and *Lactobacillus collinoides* (GenBank Nos: CAC82541 (large subunit), AJ297723; GenBank Nos: CAC82542 (medium subunit); AJ297723; GenBank Nos: CAD01091 (small subunit), AJ297723); and enzymes from *Lactobacillus brevis* (particularly strains CNRZ 734 and CNRZ 735, Speranza, et al., *J. Agric. Food Chem.* 45:3476-3480, 1997), and nucleotide sequences that encode the corresponding enzymes. Methods of diol dehydratase gene isolation are well known in the art (e.g., U.S. Pat. No. 5,686,276).

The term "pyruvate decarboxylase" refers to an enzyme that catalyzes the decarboxylation of pyruvic acid to acetaldehyde and carbon dioxide. Pyruvate decarboxylases are known by the EC number 4.1.1.1. These enzymes are found in a number of yeast, including *Saccharomyces cerevisiae* (GenBank Nos: CAA97575, CAA97705, CAA97091).

It will be appreciated that host cells comprising an isobutanol biosynthetic pathway as provided herein may further comprise one or more additional modifications. U.S. Patent Application Publication No. 2009/0305363 (incorporated by reference) discloses increased conversion of pyruvate to acetolactate by engineering yeast for expression of a cytosol-localized acetolactate synthase and substantial elimination of pyruvate decarboxylase activity. In some embodiments, the host cells comprise modifications to reduce glycerol-3-phosphate dehydrogenase activity and/or disruption in at least one gene encoding a polypeptide having pyruvate decarboxylase activity or a disruption in at least one gene encoding a regulatory element controlling pyruvate decarboxylase gene expression as described in U.S. Patent Application Publication No. 2009/0305363 (incorporated herein by reference), modifications to a host cell that provide for increased carbon flux through an Entner-Doudoroff Pathway or reducing equivalents balance as described in U.S. Patent Application Publication No. 2010/0120105 (incorporated herein by reference). Other modifications include integration of at least one polynucleotide encoding a polypeptide that catalyzes a step in a pyruvate-utilizing biosynthetic pathway.

Other modifications include at least one deletion, mutation, and/or substitution in an endogenous polynucleotide encoding a polypeptide having acetolactate reductase activity. As used herein, "acetolactate reductase activity" refers to the activity of any polypeptide having the ability to catalyze the conversion of acetolactate to DHMB. Such polypeptides can be determined by methods well known in the art and disclosed herein. As used herein, "DHMB" refers to 2,3-dihydroxy-2-methyl butyrate. DHMB includes "fast DHMB," which has the 2S, 3S configuration, and "slow DHMB," which has the 2S, 3R configurate. See Kaneko et al., *Phytochemistry* 39: 115-120 (1995), which is herein incorporated by reference in its entirety and refers to fast DHMB as anglyceric acid and slow DHMB as tiglyceric acid. In embodiments, the polypeptide having acetolactate reductase activity is YMR226C of *Saccharomyces cerevisiae* or a homolog thereof.

Additional modifications include a deletion, mutation, and/or substitution in an endogenous polynucleotide encoding a polypeptide having aldehyde dehydrogenase and/or aldehyde oxidase activity. As used herein, "aldehyde dehydrogenase activity" refers to any polypeptide having a biological function of an aldehyde dehydrogenase. Such polypeptides include a polypeptide that catalyzes the oxidation (dehydrogenation) of aldehydes. Such polypeptides include a polypeptide that catalyzes the conversion of isobutyraldehyde to isobutyric acid. Such polypeptides also include a polypeptide that corresponds to Enzyme Commission Numbers EC 1.2.1.3, EC 1.2.1.4 or EC 1.2.1.5. Such polypeptides can be determined by methods well known in the art and disclosed herein. As used herein, "aldehyde oxidase activity" refers to any polypeptide having a biological function of an aldehyde oxidase. Such polypeptides include a polypeptide that catalyzes production of carboxylic acids from aldehydes. Such polypeptides include a polypeptide that catalyzes the conversion of isobutyraldehyde to isobutyric acid. Such polypeptides also include a polypeptide that corresponds to Enzyme Commission Number EC 1.2.3.1. Such polypeptides can be determined by methods well known in the art and disclosed herein. In some embodiments, the polypeptide having aldehyde dehydrogenase activity is ALD6 from *Saccharomyces cerevisiae* or a homolog thereof.

A genetic modification which has the effect of reducing glucose repression wherein the yeast production host cell is pdc- is described in U.S. Patent Application Publication No. 2011/0124060, incorporated herein by reference. In some embodiments, the pyruvate decarboxylase that is deleted or down-regulated is selected from the group consisting of: PDC1, PDC5, PDC6, and combinations thereof. In some embodiments, the pyruvate decarboxylase is selected from PDC1 pyruvate decarboxylase from *Saccharomyces cerevisiae*, PDC5 pyruvate decarboxylase from *Saccharomyces cerevisiae*, PDC6 pyruvate decarboxylase from *Saccharomyces cerevisiae*, pyruvate decarboxylase from *Candida glabrata*, PDC1 pyruvate decarboxylase from *Pichia stipites*, PDC2 pyruvate decarboxylase from *Pichia stipites*, pyruvate decarboxylase from *Kluveromyces lactis*, pyruvate decarboxylase from *Yarrowia lipolytica*, pyruvate decarboxylase from *Schizosaccharomyces pombe*, and pyruvate decarboxylase from *Zygosaccharomyces rouxii*. In some embodiments, host cells contain a deletion or down-regulation of a polynucleotide encoding a polypeptide that catalyzes the conversion of glyceraldehyde-3-phosphate to glycerate 1,3, bisphosphate. In some embodiments, the enzyme that catalyzes this reaction is glyceraldehyde-3-phosphate dehydrogenase.

WIPO publication number WO 2011/103300 discloses recombinant host cells comprising (a) at least one heterologous polynucleotide encoding a polypeptide having dihydroxy-acid dehydratase activity; and (b)(i) at least one deletion, mutation, and/or substitution in an endogenous gene encoding a polypeptide affecting Fe—S cluster biosynthesis; and/or (ii) at least one heterologous polynucleotide encoding a polypeptide affecting Fe—S cluster biosynthesis. In embodiments, the polypeptide affecting Fe—S cluster biosynthesis is encoded by AFT1, AFT2, FRA2, GRX3, or CCC1. In embodiments, the polypeptide affecting Fe—S cluster biosynthesis is constitutive mutant AFT1 L99A, AFT1 L102A, AFT1 C291F, or AFT/C293F.

Additionally, host cells may comprise heterologous polynucleotides encoding a polypeptide with phosphoketolase activity and/or a heterologous polynucleotide encoding a polypeptide with phosphotransacetylase activity as described in U.S. Patent Application No. 2012/0156735, incorporated herein by reference.

In some embodiments, any particular nucleic acid molecule or polypeptide may be at least 80%, 85%, 90%, 95%, 96%, 97%, 98%, or 99% identical to a nucleotide sequence or polypeptide sequence described herein. The term "percent identity" as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those disclosed in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton, N.Y. (1991).

Standard recombinant DNA and molecular cloning techniques are well known in the art and are described by Sambrook, et al. (Sambrook, J., Fritsch, E. F. and Maniatis, T. (Molecular Cloning: A Laboratory Manual; Cold Spring Harbor Laboratory Press, Cold Spring Harbor, 1989, here in referred to as Maniatis) and by Ausubel, et al. (Ausubel, et al., *Current Protocols in Molecular Biology*, pub. by Greene Publishing Assoc. and Wiley-Interscience, 1987). Examples of methods to construct microorganisms that comprise a butanol biosynthetic pathway are disclosed, for example, in U.S. Pat. No. 7,851,188, and U.S. Patent Application Publication Nos. 2007/0092957; 2007/0259410; 2007/0292927; 2008/0182308; 2008/0274525; 2009/0155870; 2009/0305363; and 2009/0305370, the entire contents of each are herein incorporated by reference.

Expression of a Butanol Biosynthetic Pathway in *Saccharomyces Cerevisiae*

Methods for gene expression in *Saccharomyces cerevisiae* are known in the art (e.g., *Methods in Enzymology*, Volume 194, *Guide to Yeast Genetics and Molecular and Cell Biology*, Part A, 2004, Christine Guthrie and Gerald R. Fink, eds., Elsevier Academic Press, San Diego, Calif.). Expression of genes in yeast typically requires a promoter, followed by the gene of interest, and a transcriptional terminator. A number of yeast promoters, including those used in the Examples herein, can be used in constructing expression cassettes for genes encoding an isobutanol biosynthetic pathway, including, but not limited to constitutive promoters FBA, GPD, ADH1, and GPM, and the inducible promoters GAL1, GAL10, and CUP1. Suitable transcriptional terminators include, but are not limited to FBAt, GPDt, GPMt, ERG10t, GAL1t, CYC1, and ADH1. For example, suitable promoters, transcriptional terminators, and the genes of an isobutanol biosynthetic pathway can be cloned into *E. coli*-yeast shuttle vectors and transformed into yeast cells as described in U.S. App. Pub. No. 2010/0129886. These vectors allow strain propagation in both *E. coli* and yeast strains. Typically the vector contains a selectable marker and sequences allowing autonomous replication or chromosomal integration in the desired host. Typically used plasmids in yeast are shuttle vectors pRS423, pRS424, pRS425, and pRS426 (American Type Culture Collection, Rockville, Md.), which contain an *E. coli* replication origin (e.g., pMB1), a yeast 2μ origin of replication, and a marker for nutritional selection. The selection markers for these four vectors are His3 (vector pRS423), Trp1 (vector pRS424), Leu2 (vector pRS425) and Ura3 (vector pRS426). Construction of expression vectors with genes encoding polypeptides of interest can be performed by either standard molecular cloning techniques in *E. coli* or by the gap repair recombination method in yeast.

The gap repair cloning approach takes advantage of the highly efficient homologous recombination in yeast. Typically, a yeast vector DNA is digested (e.g., in its multiple cloning site) to create a "gap" in its sequence. A number of insert DNAs of interest are generated that contain a ≥21 bp sequence at both the 5' and the 3' ends that sequentially overlap with each other, and with the 5' and 3' terminus of the vector DNA. For example, to construct a yeast expression vector for "Gene X", a yeast promoter and a yeast terminator are selected for the expression cassette. The promoter and terminator are amplified from the yeast genomic DNA, and Gene X is either PCR amplified from its source organism or obtained from a cloning vector comprising Gene X sequence. There is at least a 21 bp overlapping sequence between the 5' end of the linearized vector and the promoter sequence, between the promoter and Gene X, between Gene X and the terminator sequence, and between the terminator and the 3' end of the linearized vector. The "gapped" vector and the insert DNAs are then co-transformed into a yeast strain and plated on the medium containing the appropriate compound mixtures that allow complementation of the nutritional selection markers on the plasmids. The presence of correct insert combinations can be confirmed by PCR mapping using plasmid DNA prepared from the selected cells. The plasmid DNA isolated from yeast (usually low in concentration) can then be transformed into an *E. coli* strain, e.g., TOP10, followed by mini preps and restriction mapping to further verify the plasmid construct. Finally the construct can be verified by sequence analysis.

Like the gap repair technique, integration into the yeast genome also takes advantage of the homologous recombination system in yeast. Typically, a cassette containing a coding region plus control elements (promoter and terminator) and auxotrophic marker is PCR-amplified with a high-fidelity DNA polymerase using primers that hybridize to the cassette and contain 40-70 base pairs of sequence homology to the regions 5' and 3' of the genomic area where insertion is desired. The PCR product is then transformed into yeast and plated on medium containing the appropriate compound mixtures that allow selection for the integrated auxotrophic marker. For example, to integrate "Gene X" into chromosomal location "Y", the promoter-coding regionX-terminator construct is PCR amplified from a plasmid DNA construct and joined to an autotrophic marker (such as URA3) by either SOE PCR or by common restriction digests and cloning. The full cassette, containing the promoter-coding region X-terminator-URA3 region, is PCR amplified with primer sequences that contain 40-70 bp of homology to the regions 5' and 3' of location "Y" on the yeast chromosome. The PCR product is transformed into yeast and selected on growth media lacking uracil. Transformants can be verified either by colony PCR or by direct sequencing of chromosomal DNA.

Growth for Production

Recombinant host cells disclosed herein are contacted with suitable carbon substrates, typically in fermentation media. Additional carbon substrates may include, but are not limited to, monosaccharides such as fructose, oligosaccharides such as lactose, maltose, galactose, or sucrose, polysaccharides such as starch or cellulose or mixtures thereof and unpurified mixtures from renewable feedstocks such as cheese whey permeate, cornsteep liquor, sugar beet molasses, and barley malt. Other carbon substrates can include ethanol, lactate, succinate, or glycerol.

Additionally the carbon substrate may also be one-carbon substrates such as carbon dioxide, or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeasts are known to utilize the carbon from methylamine to form trehalose or glycerol (Bellion et al., *Microb. Growth C1 Compd.*, [Int. Symp.], $7^{th}$, (1993), 415-32, Editors: Murrell, J. Collin, Kelly, Don P.; Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, in some embodiments, the carbon substrates are glucose, fructose, and sucrose, or mixtures of these with C5 sugars such as xylose and/or arabinose for yeasts cells modified to use C5 sugars. Sucrose may be derived from renewable sugar sources such as sugar cane, sugar beets, cassava, sweet sorghum, and mixtures thereof. Glucose and dextrose can be derived from renewable grain sources through saccharification of starch based feedstocks including grains such as corn, wheat, rye, barley, oats, and mixtures thereof. In addition, fermentable sugars can be derived from renewable cellulosic or lignocellulosic biomass through processes of pretreatment and saccharification, as described, for example, in U.S. Patent Application Publication No. 2007/0031918 A1, which is herein incorporated by reference. Biomass, when used in reference to carbon substrate, refers to any cellulosic or lignocellulosic material and includes materials comprising cellulose, and optionally further comprising hemicellulose, lignin, starch, oligosaccharides and/or monosaccharides. Biomass can also comprise additional components, such as protein and/or lipid. Biomass can be derived from a single source, or biomass can comprise a mixture derived from more than one source; for example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

In addition to an appropriate carbon source, fermentation media must contain suitable minerals, salts, cofactors, buffers and other components, known to those skilled in the art, suitable for the growth of the cultures and promotion of an enzymatic pathway described herein.

Culture Conditions

Typically cells are grown at a temperature in the range of about 20° C. to about 40° C. in an appropriate medium. Suitable growth media in the present invention are common commercially prepared media such as Luria Bertani (LB) broth, Sabouraud Dextrose (SD) broth or Yeast Medium (YM) broth or broth that includes yeast nitrogen base, ammonium sulfate, and dextrose (as the carbon/energy source) or YPD Medium, a blend of peptone, yeast extract, and dextrose in optimal proportions for growing most *Saccharomyces cerevisiae* strains. Other defined or synthetic growth media can also be used, and the appropriate medium for growth of the particular microorganism will be known by one skilled in the art of microbiology or fermentation science. The use of agents known to modulate catabolite repression directly or indirectly, e.g., cyclic adenosine 2',3'-monophosphate (cAMP), can also be incorporated into the fermentation medium.

Suitable pH ranges for the fermentation are between pH 5.0 to pH 9.0, where pH 6.0 to pH 8.0 is preferred for the initial condition. Suitable pH ranges for the fermentation of yeast are typically between about pH 3.0 to about pH 9.0. In one embodiment, about pH 5.0 to about pH 8.0 is used for the initial condition. Suitable pH ranges for the fermentation of other microorganisms are between about pH 3.0 to about pH 7.5. In one embodiment, about pH 4.5 to about pH 6.5 is used for the initial condition.

Fermentations can be performed under aerobic or anaerobic conditions. In one embodiment, anaerobic or microaerobic conditions are used for fermentation.

Industrial Batch and Continuous Fermentations

Butanol, or other products, can be produced using a batch method of fermentation. A classical batch fermentation is a closed system where the composition of the medium is set at the beginning of the fermentation and not subject to artificial alterations during the fermentation. A variation on the standard batch system is the fed-batch system. Fed-batch fermentation processes are also suitable in the present invention and comprise a typical batch system with the exception that the substrate is added in increments at the fermentation progresses. Fed-batch systems are useful when catabolite repression is apt to inhibit the metabolism of the cells and where it is desirable to have limited amounts of substrate in the media. Batch and fed-batch fermentations are common and well known in the art and examples can be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36:227, (1992), herein incorporated by reference.

Butanol, or other products, may also be produced using continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth. Continuous fermentation allows for the modulation of one factor or any number of factors that affect cell growth or end product concentration. Methods of modulating nutrients and growth factors for continuous fermentation processes as well as techniques for maximizing the rate of product formation are well known in the art of industrial microbiology and a variety of methods are detailed by Brock, supra.

It is contemplated that the production of butanol, or other products, can be practiced using batch, fed-batch or continuous processes and that any known mode of fermentation would be suitable. Additionally, it is contemplated that cells can be immobilized on a substrate as whole cell catalysts and subjected to fermentation conditions for butanol production.

Methods for Butanol Isolation from the Fermentation Medium

Bioproduced butanol may be isolated from the fermentation medium using methods known in the art for ABE fermentations (see, e.g., Durre, *Appl. Microbiol. Biotechnol.* 49:639-648 (1998), Groot et al., *Process. Biochem.* 27:61-75 (1992), and references therein). For example, solids may be removed from the fermentation medium by centrifugation, filtration, decantation, or the like. The butanol may be isolated from the fermentation medium using methods such as distillation, azeotropic distillation, liquid-liquid extraction, adsorption, gas stripping, membrane evaporation, or pervaporation.

Because butanol forms a low boiling point, azeotropic mixture with water, distillation can be used to separate the mixture up to its azeotropic composition. Distillation may be used in combination with the processes described herein to obtain separation around the azeotrope. Methods that may be used in combination with distillation to isolate and purify butanol include, but are not limited to, decantation, liquid-liquid extraction, adsorption, and membrane-based techniques. Additionally, butanol may be isolated using azeotropic distillation using an entrainer (see, e.g., Doherty and Malone, *Conceptual Design of Distillation Systems*, McGraw Hill, New York, 2001).

The butanol-water mixture forms a heterogeneous azeotrope so that distillation may be used in combination with decantation to isolate and purify the isobutanol. In this method, the butanol containing fermentation broth is distilled to near the azeotropic composition. Then, the azeotropic mixture is condensed, and the butanol is separated from the fermentation medium by decantation. The decanted aqueous phase may be returned to the first distillation column as reflux or to a separate stripping column. The butanol-rich decanted organic phase may be further purified by distillation in a second distillation column.

The butanol can also be isolated from the fermentation medium using liquid-liquid extraction in combination with distillation. In this method, the butanol is extracted from the fermentation broth using liquid-liquid extraction with a suitable solvent. The butanol-containing organic phase is then distilled to separate the butanol from the solvent.

Distillation in combination with adsorption can also be used to isolate butanol from the fermentation medium. In this method, the fermentation broth containing the butanol is distilled to near the azeotropic composition and then the remaining water is removed by use of an adsorbent, such as molecular sieves (Aden et al., *Lignocellulosic Biomass to Ethanol Process Design and Economics Utilizing Co-Current Dilute Acid Prehydrolysis and Enzymatic Hydrolysis for Corn Stover*, Report NREL/TP-510-32438, National Renewable Energy Laboratory, June 2002).

Additionally, distillation in combination with pervaporation can be used to isolate and purify the butanol from the fermentation medium. In this method, the fermentation broth containing the butanol is distilled to near the azeotropic composition, and then the remaining water is removed by pervaporation through a hydrophilic membrane (Guo et al., *J. Membr. Sci.* 245, 199-210 (2004)).

In situ product removal (ISPR) (also referred to as extractive fermentation) can be used to remove butanol (or other fermentative alcohol) from the fermentation vessel as it is produced, thereby allowing the microorganism to produce butanol at high yields. One method for ISPR for removing fermentative alcohol that has been described in the art is liquid-liquid extraction. In general, with regard to butanol fermentation, for example, the fermentation medium, which includes the microorganism, is contacted with an organic extractant at a time before the butanol concentration reaches a toxic level. The organic extractant and the fermentation medium form a biphasic mixture. The butanol partitions into the organic extractant phase, decreasing the concentration in the aqueous phase containing the microorganism, thereby limiting the exposure of the microorganism to the inhibitory butanol.

Liquid-liquid extraction can be performed, for example, according to the processes described in U.S. Patent Appl. Pub. Nos. 2009/0305370 and 2011/0097773, the disclosures of which are hereby incorporated in their entirety. U.S. Patent Appl. Pub. Nos. 2009/0305370 and 2011/0097773 describe methods for producing and recovering butanol from a fermentation broth using liquid-liquid extraction, the methods comprising the step of contacting the fermentation broth with a water immiscible extractant to form a two-phase mixture comprising an aqueous phase and an organic phase. Typically, the extractant can be an organic extractant selected from the group consisting of saturated, mono-unsaturated, polyunsaturated (and mixtures thereof) $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, and mixtures thereof. The extractant(s) for ISPR can be non-alcohol extractants. The ISPR extractant can be an exogenous organic extractant such as oleyl alcohol, behenyl alcohol, cetyl alcohol, lauryl alcohol, myristyl alcohol, stearyl alcohol, 1-undecanol, oleic acid, lauric acid, myristic acid, stearic acid, methyl myristate, methyl oleate, undecanal, lauric aldehyde, 20-methylundecanal, and mixtures thereof.

In some embodiments, an alcohol ester can be formed by contacting the alcohol in a fermentation medium with an organic acid (e.g., fatty acids) and a catalyst capable of esterifying the alcohol with the organic acid. In such embodiments, the organic acid can serve as an ISPR extractant into which the alcohol esters partition. The organic acid can be supplied to the fermentation vessel and/or derived from the biomass supplying fermentable carbon fed to the fermentation vessel. Lipids present in the feedstock can be catalytically hydrolyzed to organic acid, and the same catalyst (e.g., enzymes) can esterify the organic acid with the alcohol. In certain embodiments, lipids present in the feedstock can be converted into fatty acids and glycerol utilizing the catalysts (e.g., enzymes) described above. The glycerol can, for example, be provided to the fermentation vessel to supplement the microorganisms with reduced glycerol production described herein. Supplementing the microorganisms can, for example, improve biomass production and microorganism cell health. The glycerol will be provided in sufficient amounts beyond that produced by yeast under fermentation conditions. Carboxylic acids that are produced during the fermentation can additionally be esterified with the alcohol produced by the same or a different catalyst. The catalyst can be supplied to the feedstock prior to fermentation, or can be supplied to the fermentation vessel before or contemporaneously with the supplying of the feedstock. When the catalyst is supplied to the fermentation vessel, alcohol esters can be obtained by hydrolysis of the lipids into organic acid and substantially simultaneous esterification of the organic acid with butanol present in the fermentation vessel. Organic acid and/or native oil not derived from the feedstock can also be fed to the fermentation vessel, with the native oil being hydrolyzed into organic acid. Any organic acid not esterified with the alcohol can serve as part of the ISPR extractant. The extractant containing alcohol esters can be separated from the fermentation medium, and the alcohol can be recovered from the extractant. The extractant can be recycled to the fermentation vessel. Thus, in the case of butanol production, for example, the conversion of the butanol to an ester reduces the free butanol concentration in the fermentation medium, shielding the microorganism from the toxic effect of increasing butanol concentration. In addition, unfractionated grain can be used as feedstock without separation of lipids therein, since the lipids can be catalytically hydrolyzed to organic acid, thereby decreasing the rate of build-up of lipids in the ISPR extractant.

In situ product removal can be carried out in a batch mode or a continuous mode. In a continuous mode of in situ product removal, product is continually removed from the reactor. In a batchwise mode of in situ product removal, a volume of organic extractant is added to the fermentation vessel and the extractant is not removed during the process. For in situ product removal, the organic extractant can contact the fermentation medium at the start of the fermentation forming a biphasic fermentation medium. Alternatively, the organic extractant can contact the fermentation medium after the microorganism has achieved a desired amount of growth, which can be determined by measuring the optical density of the culture. Further, the organic extractant can contact the fermentation medium at a time at which the product alcohol level in the fermentation medium reaches a preselected level. In the case of butanol production according to some embodiments of the present invention, the organic acid extractant can contact the fermentation medium at a time before the butanol concentration reaches a toxic level, so as to esterify the butanol with the organic acid to produce butanol esters and consequently reduce the concentration of butanol in the fermentation vessel. The ester-containing organic phase can then be removed from the fermentation vessel (and separated from the fermentation broth which constitutes the aqueous phase) after a desired effective titer of the butanol esters is achieved. In some embodiments, the ester-containing organic phase is separated from the aqueous phase after fermentation of the available fermentable sugar in the fermentation vessel is substantially complete.

Confirmation of Isobutanol Production

The presence and/or concentration of isobutanol in the culture medium can be determined by a number of methods known in the art (see, for example, U.S. Pat. No. 7,851,188, incorporated by reference). For example, a specific high performance liquid chromatography (HPLC) method utilizes a Shodex SH-1011 column with a Shodex SHG guard column, both may be purchased from Waters Corporation (Milford, Mass.), with refractive index (RI) detection. Chromatographic separation is achieved using 0.01 M $H_2SO_4$ as the mobile phase with a flow rate of 0.5 mL/min and a column temperature of 50° C. Isobutanol has a retention time of 46.6 min under the conditions used.

Alternatively, gas chromatography (GC) methods are available. For example, a specific GC method utilizes an HP-INNOWax column (30 m×0.53 mm id, 1 μm film thickness, Agilent Technologies, Wilmington, Del.), with a flame ionization detector (FID). The carrier gas is helium at a flow rate of 4.5 mL/min, measured at 150° C. with constant head pressure; injector split is 1:25 at 200° C.; oven temperature is 45° C. for 1 min, 45 to 220° C. at 10° C./min, and 220° C. for 5 min; and FID detection is employed at 240° C. with 26 mL/min helium makeup gas. The retention time of isobutanol is 4.5 min.

While various embodiments of the present invention have been described herein, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the claims and their equivalents.

All publications, patents, and patent applications mentioned in this specification are indicative of the level of those skilled in the art to which this invention pertains, and are herein incorporated by reference to the same extent as if each individual publication, patent, or patent application was specifically and individually indicated to be incorporated by reference.

EXAMPLES

The present invention is further defined in the following Examples. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA, molecular cloning techniques and transformation protocols used in the Examples are well known in the art and are described by Sambrook et al. (Sambrook, J., Fritsch, E. F. and Maniatis, T. (Molecular Cloning: A Laboratory Manual; Cold Spring Harbor Laboratory Press, Cold Spring Harbor, 1989, here in referred to as Maniatis), by Ausubel et al. (Ausubel et al., Current Protocols in Molecular Biology, pub. by Greene Publishing Assoc. and Wiley-Interscience, 1987) and by Amberg et al (Amberg, D. C., Burke, D. J. and Strathern, J. N. (Methods in Yeast Genetics: A Cold Spring Harbor Laboratory Course Manual, Cold Spring Harbor Press, 2005). Materials and methods suitable for the maintenance and growth of bacterial cultures are well known in the art. Techniques suitable for use in the following examples may be found as set out in Manual of Methods for General Bacteriology (Phillipp et al., eds., American Society for Microbiology, Washington, D.C., 1994) or by Thomas D. Brock in (Brock, Biotechnology: A Textbook of Industrial Microbiology, Second Edition, Sinauer Associates, Inc., Sunderland, Mass. (1989). All reagents, restriction enzymes and materials used for the growth and maintenance of bacterial cells were obtained from Sigma-Aldrich Chemicals (St. Louis, Mo.), BD Diagnostic Systems (Sparks, Md.), Invitrogen (Carlsbad, Calif.), HiMedia (Mumbai, India), SD Fine chemicals (India), or Takara Bio Inc. (Shiga, Japan), unless otherwise specified.

The meaning of abbreviations is as follows: "sec" means second(s), "min" means minute(s), "h" means hour(s), "nm" means nanometers, "uL" means microliter(s), "mL" means milliliter(s), "mg/mL" means milligram per milliliter, "L" means liter(s), "nm" means nanometers, "mM" means millimolar, "M" means molar, "mmol" means millimole(s), "µmole" means micromole(s), "kg" means kilogram, "g" means gram(s), "µg" means microgram(s) and "ng" means nanogram(s), "PCR" means polymerase chain reaction, "OD" means optical density, "OD600" means the optical density measured at a wavelength of 600 nm, "kDa" means kilodaltons, "g" can also mean the gravitation constant, "bp" means base pair(s), "kbp" means kilobase pair(s), "kb" means kilobase, "%" means percent, "% w/v" means weight/volume percent, "% v/v" means volume/volume percent, "HPLC" means high performance liquid chromatography, "g/L" means gram per liter, "µg/L" means microgram per liter, "ng/µL" means nanogram per microliter, "pmol/µL" means picomol per microliter, "RPM" means rotation per minute, "µmol/min/mg" means micromole per minute per milligram, "w/v" means weight per volume, "v/v" means volume per volume.

Strain Construction

Construction of Strain PNY2115

Saccharomyces cerevisiae strain PNY0827 is used as the host cell for further genetic manipulation for PNY2115. PNY0827 refers to a strain derived from Saccharomyces cerevisiae which has been deposited at the ATCC under the Budapest Treaty on Sep. 22, 2011 at the American Type Culture Collection, Patent Depository 10801 University Boulevard, Manassas, Va. 20110-2209 and has the patent deposit designation PTA-12105.

Deletion of URA3 and Sporulation into Haploids

In order to delete the endogenous URA3 coding region, a deletion cassette was PCR-amplified from pLA54 (SEQ ID NO: 95) which contains a $P_{TEF1}$-kanMX4-TEF1t cassette flanked by loxP sites to allow homologous recombination in vivo and subsequent removal of the KANMX4 marker. PCR was done by using Phusion High Fidelity PCR Master Mix (New England BioLabs; Ipswich, Mass.) and primers BK505 (SEQ ID NO: 96) and BK506 (SEQ ID NO: 97). The URA3 portion of each primer was derived from the 5' region 180 bp upstream of the URA3 ATG and 3' region 78 bp downstream of the coding region such that integration of the kanMX4 cassette results in replacement of the URA3 coding region. The PCR product was transformed into PNY0827 using standard genetic techniques (Methods in Yeast Genetics, 2005, Cold Spring Harbor Laboratory Press, Cold Spring Harbor, N.Y., pp. 201-202) and transformants were selected on YEP medium supplemented 2% glucose and 100 µg/ml Geneticin at 30° C. Transformants were screened by colony PCR with primers LA468 (SEQ ID NO: 98) and LA492 (SEQ ID NO: 99) to verify presence of the integration cassette. A heterozygous diploid was obtained: NYLA98, which has the genotype MATa/α URA3/ura3::loxP-kanMX4-loxP. To obtain haploids, NYLA98 was sporulated using standard methods (Codón A C, Gasent-Ramírez J M, Benítez T. Factors which affect the frequency of sporulation and tetrad formation in Saccharomyces cerevisiae baker's yeast. Appl Environ Microbiol. 1995 PMID: 7574601). Tetrads were dissected using a micromanipulator and grown on rich YPE medium supplemented with 2% glucose. Tetrads containing four viable spores were patched onto synthetic complete medium lacking uracil supplemented with 2% glucose, and the mating type was verified by multiplex colony PCR using primers AK109-1 (SEQ ID NO: 100), AK109-2 (SEQ ID NO: 101), and AK109-3 (SEQ ID NO: 102). The resulting identified haploid strain called NYLA103, which has the genotype: MATα ura3Δ::loxP-kanMX4-loxP, and NYLA106, which has the genotype: MATa ura3Δ::loxP-kanMX4-loxP.

Deletion of His3

To delete the endogenous HIS3 coding region, a scarless deletion cassette was used. The four fragments for the PCR cassette for the scarless HIS3 deletion were amplified using Phusion High Fidelity PCR Master Mix (New England BioLabs; Ipswich, Mass.) and CEN.PK 113-7D genomic DNA as template, prepared with a Gentra Puregene Yeast/Bact kit (Qiagen; Valencia, Calif.). HIS3 Fragment A was amplified with primer oBP452 (SEQ ID NO: 103) and primer oBP453 (SEQ ID NO: 104), containing a 5' tail with homology to the 5' end of HIS3 Fragment B. HIS3 Fragment B was amplified with primer oBP454 (SEQ ID NO: 105), containing a 5' tail with homology to the 3' end of HIS3 Fragment A, and primer oBP455 (SEQ ID NO: 106) containing a 5' tail with homology to the 5' end of HIS3 Fragment U. HIS3 Fragment U was amplified with primer oBP456 (SEQ ID NO: 107), containing a 5' tail with homology to the 3' end of HIS3 Fragment B, and primer oBP457 (SEQ ID NO: 108), containing a 5' tail with homology to the 5' end of HIS3 Fragment C. HIS3 Fragment C was amplified with primer oBP458 (SEQ ID NO: 109), containing a 5' tail with homology to the 3' end of HIS3 Fragment U, and primer oBP459 (SEQ ID NO: 110). PCR products were purified with a PCR Purification kit (Qiagen). HIS3 Fragment AB was created by overlapping PCR by mixing HIS3 Fragment A and HIS3 Fragment B and amplifying with primers oBP452 (SEQ ID NO: 103) and oBP455 (SEQ ID NO: 106). HIS3 Fragment UC was created by overlapping PCR by mixing HIS3 Fragment U and HIS3 Fragment C and amplifying with primers oBP456 (SEQ ID NO: 107) and oBP459 (SEQ ID NO: 110). The resulting PCR products were purified on an agarose gel followed by a Gel Extraction kit (Qiagen). The HIS3 ABUC cassette was created by overlapping PCR by mixing HIS3 Fragment AB and HIS3 Fragment UC and amplifying with primers oBP452 (SEQ ID NO: 103) and oBP459 (SEQ ID NO: 110). The PCR product was purified with a PCR Purification kit (Qiagen). Competent cells of NYLA106 were transformed with the HIS3 ABUC PCR cassette and were plated on synthetic complete medium lacking uracil supplemented with 2% glucose at 30° C. Transformants were screened to verify correct integration by replica plating onto synthetic complete medium lacking histidine and supplemented with 2% glucose at 30° C. Genomic DNA preps were made to verify the integration by PCR using primers oBP460 (SEQ ID NO: 111) and LA135 (SEQ ID NO: 112) for the 5' end and primers oBP461 (SEQ ID NO: 113) and LA92 (SEQ ID NO: 114) for the 3' end. The URA3 marker was recycled by plating on synthetic complete medium supplemented with 2% glucose and 5-FOA at 30° C. following standard protocols. Marker removal was confirmed by patching colonies from the 5-FOA plates onto SD-URA medium to verify the absence of growth. The resulting identified strain, called PNY2003 has the genotype: MATa ura3Δ::loxP-kanMX4-loxP his3Δ.

Deletion of PDC1

To delete the endogenous PDC1 coding region, a deletion cassette was PCR-amplified from pLA59 (SEQ ID NO: 115), which contains a URA3 marker flanked by degenerate loxP sites to allow homologous recombination in vivo and subsequent removal of the URA3 marker. PCR was done by using Phusion High Fidelity PCR Master Mix (New England BioLabs; Ipswich, Mass.) and primers LA678 (SEQ ID NO: 116) and LA679 (SEQ ID NO: 117). The PDC1 portion of each primer was derived from the 5' region 50 bp downstream of the PDC1 start codon and 3' region 50 bp upstream of the stop codon such that integration of the URA3 cassette results in replacement of the PDC1 coding region but leaves the first 50 bp and the last 50 bp of the coding region. The PCR product was transformed into PNY2003 using standard genetic techniques and transformants were selected on synthetic complete medium lacking uracil and supplemented with 2% glucose at 30° C. Transformants were screened to verify correct integration by colony PCR using primers LA337 (SEQ ID NO: 118), external to the 5' coding region and LA135 (SEQ ID NO: 112), an internal primer to URA3. Positive transformants were then screened by colony PCR using primers LA692 (SEQ ID NO: 119) and LA693 (SEQ ID NO: 120), internal to the PDC1 coding region. The URA3 marker was recycled by transforming with pLA34 (SEQ ID NO: 121) containing the CRE recombinase under the GAL1 promoter and plated on synthetic complete medium lacking histidine and supplemented with 2% glucose at 30° C. Transformants were plated on rich medium supplemented with 0.5% galactose to induce the recombinase. Marker removal was confirmed by patching colonies to synthetic complete medium lacking uracil and supplemented with 2% glucose to verify absence of growth. The resulting identified strain, called PNY2008 has the genotype: MATa ura3Δ::loxP-kanMX4-loxP his3Δpdc1Δ::loxP71/66.

Deletion of PDC5

To delete the endogenous PDC5 coding region, a deletion cassette was PCR-amplified from pLA59 (SEQ ID NO: 115), which contains a URA3 marker flanked by degenerate loxP sites to allow homologous recombination in vivo and subsequent removal of the URA3 marker. PCR was done by using Phusion High Fidelity PCR Master Mix (New England BioLabs; Ipswich, Mass.) and primers LA722 (SEQ ID NO: 122) and LA733 (SEQ ID NO: 123). The PDC5 portion of each primer was derived from the 5' region 50 bp upstream of the PDC5 start codon and 3' region 50 bp downstream of the stop codon such that integration of the URA3 cassette results in replacement of the entire PDC5 coding region. The PCR product was transformed into PNY2008 using standard genetic techniques and transformants were selected on synthetic complete medium lacking uracil and supplemented with 1% ethanol at 30° C. Transformants were screened to verify correct integration by colony PCR using primers LA453 (SEQ ID NO: 124), external to the 5' coding region and LA135 (SEQ ID NO: 112), an internal primer to URA3. Positive transformants were then screened by colony PCR using primers LA694 (SEQ ID NO: 125) and LA695 (SEQ ID NO: 126), internal to the PDC5 coding region. The URA3 marker was recycled by transforming with pLA34 (SEQ ID NO: 121) containing the CRE recombinase under the GAL1 promoter and plated on synthetic complete medium lacking histidine and supplemented with 1% ethanol at 30° C. Transformants were plated on rich YEP medium supplemented with 1% ethanol and 0.5% galactose to induce the recombinase. Marker removal was confirmed by patching colonies to synthetic complete medium lacking uracil and supplemented with 1% ethanol to verify absence of growth. The resulting identified strain, called PNY2009 has the genotype: MATa ura3Δ::loxP-kanMX4-loxP his3Δpdc1Δ::loxP71/66 pdc5Δ::loxP71/66.

Deletion of FRA2

The FRA2 deletion was designed to delete 250 nucleotides from the 3' end of the coding sequence, leaving the first 113 nucleotides of the FRA2 coding sequence intact. An in-frame stop codon was present 7 nucleotides downstream of the deletion. The four fragments for the PCR cassette for the scarless FRA2 deletion were amplified using Phusion High Fidelity PCR Master Mix (New England BioLabs; Ipswich, Mass.) and CEN.PK 113-7D genomic DNA as template, prepared with a Gentra Puregene Yeast/Bact kit (Qiagen; Valencia, Calif.). FRA2 Fragment A was amplified with primer oBP594 (SEQ ID NO: 127) and primer oBP595 (SEQ ID NO: 128), containing a 5' tail with homology to the 5' end of FRA2 Fragment B. FRA2 Fragment B was amplified with primer oBP596 (SEQ ID NO: 129), containing a 5' tail with homology to the 3' end of FRA2 Fragment A, and primer oBP597 (SEQ ID NO: 130), containing a 5' tail with homology to the 5' end of FRA2 Fragment U. FRA2 Fragment U was amplified with primer oBP598 (SEQ ID NO: 131), containing a 5' tail with homology to the 3' end of FRA2 Fragment B, and primer oBP599 (SEQ ID NO: 132), containing a 5' tail with homology to the 5' end of FRA2 Fragment C. FRA2 Fragment C was amplified with primer oBP600 (SEQ ID NO: 133), containing a 5' tail with homology to the 3' end of FRA2 Fragment U, and primer oBP601 (SEQ ID NO: 134). PCR products were purified with a PCR Purification kit (Qiagen). FRA2 Fragment AB was created by overlapping PCR by mixing FRA2 Fragment A and FRA2 Fragment B and amplifying with primers oBP594 (SEQ ID NO: 127) and oBP597 (SEQ ID NO: 130). FRA2 Fragment UC was created by overlapping PCR by mixing FRA2 Fragment U and FRA2 Fragment C and amplifying with primers oBP598 (SEQ ID NO: 131) and oBP601 (SEQ ID NO: 134). The resulting PCR products were purified on an agarose gel followed by a Gel Extraction kit (Qiagen). The FRA2 ABUC cassette was created by overlapping PCR by mixing FRA2 Fragment AB and FRA2 Fragment UC and amplifying with primers oBP594 (SEQ ID NO: 127) and oBP601 (SEQ ID NO: 134). The PCR product was purified with a PCR Purification kit (Qiagen).

To delete the endogenous FRA2 coding region, the scarless deletion cassette obtained above was transformed into PNY2009 using standard techniques and plated on synthetic complete medium lacking uracil and supplemented with 1% ethanol. Genomic DNA preps were made to verify the integration by PCR using primers oBP602 (SEQ ID NO: 135) and LA135 (SEQ ID NO: 112) for the 5' end, and primers oBP602 (SEQ ID NO: 135) and oBP603 (SEQ ID NO: 136) to amplify the whole locus. The URA3 marker was recycled by plating on synthetic complete medium supplemented with 1% ethanol and 5-FOA (5-Fluoroorotic Acid) at 30° C. following standard protocols. Marker removal was confirmed by patching colonies from the 5-FOA plates onto synthetic complete medium lacking uracil and supplemented with 1% ethanol to verify the absence of growth. The resulting identified strain, PNY2037, has the genotype: MATa ura3Δ::loxP-kanMX4-loxP his3Δpdc1Δ::loxP71/66 pdc5Δ::loxP71/66fra2Δ.

Addition of Native 2 Micron Plasmid

The loxP71-URA3-loxP66 marker was PCR-amplified using Phusion DNA polymerase (New England BioLabs; Ipswich, Mass.) from pLA59 (SEQ ID NO: 115), and transformed along with the LA811x817 (SEQ ID NOs: 137, 138) and LA812x818 (SEQ ID NOs: 139, 140) 2-micron plasmid fragments (amplified from the native 2-micron plasmid from CEN.PK 113-7D; Centraalbureau voor Schimmelcultures (CBS) Fungal Biodiversity Centre) into strain PNY2037 on SE-URA plates at 30° C. The resulting strain PNY2037 2μ::loxP71-URA3-loxP66 was transformed with pLA34 (pRS423::cre) (also called, pLA34) (SEQ ID NO: 121) and selected on SE-HIS-URA plates at 30° C. Transformants were patched onto YP-1% galactose plates and allowed to grow for 48 hrs at 30° C. to induce Cre recombinase expression. Individual colonies were then patched onto SE-URA, SE-HIS, and YPE plates to confirm URA3 marker removal. The resulting identified strain, PNY2050, has the genotype: MATa ura3Δ::loxP-kanMX4-loxP, his3Δpdc1Δ::loxP71/66 pdc5Δ::loxP71/66fra2Δ 2-micron.

Construction of PNY2115 from PNY2050

Construction of PNY2115 [MATa ura3Δ::loxP his3Δ pdc5Δ::loxP66/71 fra2Δ 2-micron plasmid (CEN.PK2) pdc1Δ::P[PDC1]-ALS|alsS_Bs-CYC1t-loxP71/66 pdc6Δ:: (UAS)PGK1-P[FBA1]-KIVD|Lg(y)-TDH3t-loxP71/66 adh1Δ::P[ADH1]-ADH|Bi(y)-ADHt-loxP71/66 fra2Δ::P[ILV5]-ADH|Bi(y)-ADHt-loxP71/66 gpd2Δ::loxP71/66] from PNY2050 was as follows.

Pdc1Δ::P[PDC1]-ALS|alsS_Bs-CYC1t-loxP71/66

To integrate alsS into the pdc1Δ::loxP66/71 locus of PNY2050 using the endogenous PDC1 promoter, An integration cassette was PCR-amplified from pLA71 (SEQ ID NO: 146), which contains the gene acetolactate synthase from the species *Bacillus subtilis* with a FBA1 promoter and a CYC1 terminator, and a URA3 marker flanked by degenerate loxP sites to allow homologous recombination in vivo and subsequent removal of the URA3 marker. PCR was done by using KAPA HiFi and primers 895 (SEQ ID NO: 149) and 679 (SEQ ID NO: 150). The PDC1 portion of each primer was derived from 60 bp of the upstream of the coding sequence and 50 bp that are 53 bp upstream of the stop codon. The PCR product was transformed into PNY2050 using standard genetic techniques and transformants were selected on synthetic complete media lacking uracil and supplemented with 1% ethanol at 30° C. Transformants were screened to verify correct integration by colony PCR using primers 681 (SEQ ID NO: 151), external to the 3' coding region and 92 (SEQ ID NO: 152), internal to the URA3 gene. Positive transformants were then prepped for genomic DNA and screened by PCR using primers N245 (SEQ ID NO: 153) and N246 (SEQ ID NO: 154). The URA3 marker was recycled by transforming with pLA34 (SEQ ID NO: 121) containing the CRE recombinase under the GAL1 promoter and plated on synthetic complete media lacking histidine and supplemented with 1% ethanol at 30° C. Transformants were plated on rich media supplemented with 1% ethanol and 0.5% galactose to induce the recombinase. Marker removal was confirmed by patching colonies to synthetic complete media lacking uracil and supplemented with 1% ethanol to verify absence of growth. The resulting identified strain, called PNY2090 has the genotype MATa ura3Δ::loxP, his3Δ, pdc1Δ::loxP71/66, pdc5Δ::loxP71/66 fra2Δ 2-micron pdc1Δ::P[PDC1]-ALS|alsS_Bs-CYC1t-loxP71/66.

Pdc6Δ:: (UAS)PGK1-P[FBA1]-KIVD|Lg(y)-TDH3t-loxP71/66

To delete the endogenous PDC6 coding region, an integration cassette was PCR-amplified from pLA78 (SEQ ID NO: 147), which contains the kivD gene from the species *Listeria grayi* with a hybrid FBA1 promoter and a TDH3 terminator, and a URA3 marker flanked by degenerate loxP sites to allow homologous recombination in vivo and subsequent removal of the URA3 marker. PCR was done by using KAPA HiFi and primers 896 (SEQ ID NO: 155) and 897 (SEQ ID NO: 156). The PDC6 portion of each primer was derived from 60 bp upstream of the coding sequence and 59 bp downstream of the coding region. The PCR product was transformed into PNY2090 using standard genetic techniques and transformants were selected on synthetic complete media lacking uracil and supplemented with 1% ethanol at 30° C. Transformants were screened to verify correct integration by colony PCR using primers 365 (SEQ ID NO: 157) and 366 (SEQ ID NO: 158), internal primers to the PDC6 gene. Transformants with an absence of product were then screened by colony PCR N638 (SEQ ID NO: 159), external to the 5' end of the gene, and 740 (SEQ ID NO: 160), internal to the FBA1 promoter. Positive transformants were than the prepped for genomic DNA and screened by PCR with two external primers to the PDC6 coding sequence. Positive integrants would yield a 4720 bp product, while PDC6 wild type transformants would yield a 2130 bp product. The URA3 marker was recycled by transforming with pLA34 containing the CRE recombinase under the GAL1 promoter and plated on synthetic complete media lacking histidine and supplemented with 1% ethanol at 30° C. Transformants were plated on rich media supplemented with 1% ethanol and 0.5% galactose to induce the recombinase. Marker removal was confirmed by patching colonies to synthetic complete media lacking uracil and supplemented with 1% ethanol to verify absence of growth. The resulting identified strain is called PNY2093 and has the genotype MATa ura3Δ::loxP his3Δ pdc5Δ::loxP71/66 fra2Δ 2-micron pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66. Adh1Δ::P[ADH1]-ADH|Bi(y)-ADHt-loxP71/66

To delete the endogenous ADH1 coding region and integrate BiADH using the endogenous ADH1 promoter, an integration cassette was PCR-amplified from pLA65 (SEQ ID NO: 148), which contains the alcohol dehydrogenase from the species *Beijerinckii* with an ILV5 promoter and a ADH1 terminator, and a URA3 marker flanked by degenerate loxP sites to allow homologous recombination in vivo and subsequent removal of the URA3 marker. PCR was done by using KAPA HiFi and primers 856 (SEQ ID NO: 161) and 857 (SEQ ID NO: 162). The ADH1 portion of each primer was derived from the 5' region 50 bp upstream of the ADH1 start codon and the last 50 bp of the coding region. The PCR product was transformed into PNY2093 using standard genetic techniques and transformants were selected on synthetic complete media lacking uracil and supplemented with 1% ethanol at 30° C. Transformants were screened to verify correct integration by colony PCR using primers BK415 (SEQ ID NO: 163), external to the 5' coding region and N1092 (SEQ ID NO: 164), internal to the BiADH gene. Positive transformants were then screened by colony PCR using primers 413 (SEQ ID NO: 169), external to the 3' coding region, and 92 (SEQ ID NO: 152), internal to the URA3 marker. The URA3 marker was recycled by transforming with pLA34 (SEQ ID NO: 121) containing the CRE recombinase under the GAL1 promoter and plated on synthetic complete media lacking histidine and supplemented with 1% ethanol at 30° C. Transformants were plated on rich media supplemented with 1% ethanol and 0.5% galactose to induce the recombinase. Marker removal was confirmed by patching colonies to synthetic complete media lacking uracil and supplemented with 1% ethanol to verify absence of growth. The resulting identified strain, called PNY2101 has the genotype MATa ura3Δ::loxP his3Δ pdc5Δ::loxP71/66 fra2Δ 2-micron pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66 adh1Δ::P[ADH1]-ADH|Bi(y)-ADHt-loxP71/66. Fra2Δ::P[ILV5]-ADH1Bi(y)-ADHt-loxP71/66

To integrate BiADH into the fra2Δ locus of PNY2101, an integration cassette was PCR-amplified from pLA65 (SEQ ID NO: 148), which contains the alcohol dehydrogenase from the species *Beijerinckii indica* with an ILV5 promoter and an ADH1 terminator, and a URA3 marker flanked by degenerate loxP sites to allow homologous recombination in vivo and subsequent removal of the URA3 marker. PCR was done by using KAPA HiFi and primers 906 (SEQ ID NO: 165) and 907 (SEQ ID NO: 166). The FRA2 portion of each primer was derived from the first 60 bp of the coding sequence starting at the ATG and 56 bp downstream of the stop codon. The PCR product was transformed into PNY2101 using standard genetic techniques and transformants were selected on synthetic complete media lacking uracil and supplemented with 1% ethanol at 30° C. Transformants were screened to verify correct integration by colony PCR using primers 667 (SEQ ID NO: 167), external to the 5' coding region and 749 (SEQ ID NO: 168), internal to the ILV5 promoter. The URA3 marker was recycled by transforming with pLA34 (SEQ ID NO: 121) containing the CRE recombinase under the GAL1 promoter and plated on synthetic complete media lacking histidine and supplemented with 1% ethanol at 30° C. Transformants were plated on rich media supplemented with 1% ethanol and 0.5% galactose to induce the recombinase. Marker removal was confirmed by patching colonies to synthetic complete media lacking uracil and supplemented with 1% ethanol to verify absence of growth. The resulting identified strain, called PNY2110 has the genotype MATa ura3Δ::loxP his3Δpdc5Δ::loxP66/71 2-micron pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66 adh1Δ::P[ADH1]-ADH|Bi(y)-ADHt-loxP71/66 fra2Δ::P[ILV5]-ADH|Bi(y)-ADHt-loxP71/66.

GPD2 Deletion

To delete the endogenous GPD2 coding region, a deletion cassette was PCR amplified from pLA59 (SEQ ID NO: 115), which contains a URA3 marker flanked by degenerate loxP sites to allow homologous recombination in vivo and subsequent removal of the URA3 marker. PCR was done by using KAPA HiFi and primers LA512 (SEQ ID NO: 141) and LA513 (SEQ ID NO: 142). The GPD2 portion of each primer was derived from the 5' region 50 bp upstream of the GPD2 start codon and 3' region 50 bp downstream of the stop codon such that integration of the URA3 cassette results in replacement of the entire GPD2 coding region. The PCR product was transformed into PNY2110 using standard genetic techniques and transformants were selected on synthetic complete medium lacking uracil and supplemented with 1% ethanol at 30° C. Transformants were screened to verify correct integration by colony PCR using primers LA516 (SEQ ID NO: 143) external to the 5' coding region and LA135 (SEQ ID NO: 112), internal to URA3. Positive transformants were then screened by colony PCR using primers LA514 (SEQ ID NO: 144) and LA515 (SEQ ID NO: 145), internal to the GPD2 coding region. The URA3 marker was recycled by transforming with pLA34 (SEQ ID NO: 121) containing the CRE recombinase under the GAL1 promoter and plated on synthetic complete medium lacking histidine and supplemented with 1% ethanol at 30° C. Transformants were plated on rich medium supplemented with 1% ethanol and 0.5% galactose to induce the recombinase. Marker removal was confirmed by patching colonies to synthetic complete medium lacking uracil and supplemented with 1% ethanol to verify absence of growth. The resulting identified strain, called PNY2115, has the genotype MATa ura3Δ::loxP his3Δ pdc5Δ::loxP66/71 fra2Δ 2-micron pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66 adh1Δ::P[ADH1]-ADH|Bi(y)-ADHt-loxP71/66 fra2Δ::P[ILV5]-ADH|Bi(y)-ADHt-loxP71/66 gpd2Δ::loxP71/66.

Creation of PNY2145 from PNY2115

PNY2145 was constructed from PNY2115 by the additional integration of a phosphoketolase gene cassette at the pdc5Δ locus and by replacing the native AMN1 gene with a codon optimized version of the ortholog from CEN.PK. Integration constructs are further described below.

pdc5Δ::FBA(L8)-xpk1-CYC1t-loxP71/66

The TEF(M4)-xpk1-CYC1t gene from pRS423::TEF(M4)-xpk1+ENO1-eutD (SEQ ID NO: 170) was PCR amplified using primers N1341 and N1338 (SEQ ID NOS: 171 and 172), generating a 3.1 kb product. The loxP-flanked URA3 gene cassette from pLA59 (SEQ ID NO: 115) was amplified with primers N1033c and N1342 (SEQ ID NOS: 173 and 174), generating a 1.6 kb product. The xpk1 and URA3 PCR products were fused by combining them without primers for an additional 10 cycles of PCR using Phusion DNA polymerase. The resulting reaction mix was then used as a template for a PCR reaction with KAPA Hi Fi and primers N1342 and N1364 (SEQ ID NOS: 174 and 175). A 4.2 kb PCR product was recovered by purification from an electrophoresis agarose gel (Zymo kit). FBA promoter variant L8 (SEQ ID NO: 176) was amplified using primers N1366 and N1368 (SEQ ID NOS: 177 and 178). The xpk1::URA3 PCR product was combined with the FBA promoter by additional rounds of PCR. The resulting product was phosphorylated with polynucleotide kinase and ligated into pBR322 that had been digested with EcoRV and treated with calf intestinal phosphatase. The ligation reaction was transformed into E. coli cells (Stbl3 competent cells from Invitrogen). The integration cassette was confirmed by sequencing. To prepare DNA for integration, the plasmid was used as a template in a PCR reaction with Kapa HiFi and primers N1371 and N1372 (SEQ ID NOS: 179 and 180). The PCR product was isolated by phenol-chloroform extraction and ethanol precipitation (using standard methods; eg. Maniatas, et al.). Five micrograms of DNA were used to transform strain PNY2115. Transformants were selected on medium lacking uracil (synthetic complete medium minus uracil with 1% ethanol as the carbon source). Colonies were screened for the integration event using PCR (JumpStart) with primers BK93 and N1114 (SEQ ID NOS: 181 and 182). Two clones were selected to carry forward. The URA3 marker was recycled by transforming with pJT254 (SEQ ID NO: 183) containing the CRE recombinase under the GAL1 promoter and plating on synthetic complete medium lacking histidine and supplemented with 1% ethanol at 30° C. Transformants were grown in rich medium supplemented with 1% ethanol to derepress the recombinase. Marker removal was confirmed for single colony isolates by patching to synthetic complete medium lacking uracil and supplemented with 1% ethanol to verify absence of growth. Loss of the recombinase plasmid, pJT254, was confirmed by patching the colonies to synthetic complete medium lacking histidine and supplemented with 1% ethanol. Proper marker removal was confirmed by PCR (primers N160SeqF5 (SEQ ID NO: 184) and BK380. One resulting clone was designated PNY2293.

amn1Δ::AMN1(y)-loxP71/66

To replace the endogenous copy of AMN1 with a codon-optimized version of the AMN1 gene from CEN.PK2, an integration cassette containing the CEN.PK AMN1 promoter, AMN1(y) gene (nucleic acid SEQ ID NO: 185; amino acid SEQ ID NO: 186), and CEN.PK AMN1 terminator was assembled by SOE PCR and subcloned into the shuttle vector pLA59. The AMN1(y) gene was ordered from DNA 2.0 with codon-optimization for S. cerevisiae. The completed pLA67 plasmid (SEQ ID NO: 187) contained: 1) pUC19 vector backbone sequence containing an E. coli replication origin and ampicillin resistance gene; 2) URA3 selection marker flanked by loxP71 and loxP66 sites; and 3) $P_{AMN1(CEN.PK)}$-AMN1(y)-term$_{AMN1(CEN.PK)}$ expression cassette. PCR amplification of the AMN1(y)-loxP71-URA3-loxP66 cassette was done by using KAPA HiFi from Kapa Biosystems, Woburn, Mass. and primers LA712 (SEQ ID NO: 188) and LA746 (SEQ ID NO: 189). The PCR product was transformed into PNY2293 using standard genetic techniques and transformants were selected on synthetic complete medium lacking uracil and supplemented with 1% ethanol at 30° C. Transformants were observed under magnification for the absence of a clumping phenotype with respect to the control (PNY2293). The URA3 marker was recycled using the pJT254 Cre recombinase plasmid as described above. After marker recycle, clones were again observed under magnification to confirm absence of the clumping phenotype. A resulting identified strain, PNY2145, has the genotype: MATa ura3Δ::loxP his3Δ pdc5Δ::P[FBA(L8)]-XPK|xpk1_Lp-CYCt-loxP66/71 fra2Δ 2-micron plasmid (CEN.PK2) pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66 adh1Δ::P[ADH1]-ADH|Bi(y)-ADHt-loxP71/66 fra2Δ::P[ILV5]-ADH|Bi(y)-ADHt-loxP71/66 gpd2Δ::loxP71/66 amn1Δ::AMN1(y).

Creation of PNY2310 from PNY2145

PNY2310 was generated by transforming strain PNY2145 with plasmids pLH804-L2V4 and pRS413::BiADH-kivD. Plasmid pLH804-L2V4 (SEQ ID NO: 12) is a yeast-E. coli shuttle vector based on pHR81 (ATCC #87541). It contains genes for the expression of KARI variant K9JB4P and DHAD variant L2V4. Plasmid pRS413::BiADH-kivD (SEQ ID NO: 13) is a yeast-E. coli shuttle vector based on pRS413 (ATCC #87518). It contains genes for the expression of BiADH and kivD. The positions of the relevant gene features in both plasmids are listed in the Tables 3 and 4. Plasmid transformants were selected by plating on synthetic complete medium lacking uracil and histidine with 1% (v/v) ethanol as the carbon source. Colonies were transferred to fresh plates by patching. After two days, cells from the patches were transferred to plates containing synthetic complete medium (minus uracil and histidine) with 2% (w/v) glucose as the carbon source. The resulting strain was designated PNY2310.

TABLE 3

Nucleotide positions of pathway gene features in plasmid pLH804-L2V4

| Element | Description | Start | End | Strand |
|---|---|---|---|---|
| Promoter | ILV5p | 427 | 1620 | T |
| CDS | JB4P | 1628 | 2659 | T |
| Terminator | ILV5t | 2685 | 3307 | T |
| Terminator | FBAt | 3320 | 3632 | B |
| CDS | ILVD-L2V4 | 3641 | 5356 | B |
| Promoter | TEF1(M7)p | 5366 | 5766 | B |

TABLE 4

Nucleotide positions of pathway gene features in plasmid pRS413::BiADH-kivD

| Element | Description | Start | End | Strand |
|---|---|---|---|---|
| Promoter | FBA1p | 2293 | 2893 | T |
| CDS | kivD_Lg(y) | 2902 | 4548 | T |

TABLE 4-continued

Nucleotide positions of pathway gene features
in plasmid pRS413::BiADH-kivD

| Element | Description | Start | End | Strand |
|---|---|---|---|---|
| Terminator | TDH3t | 4560 | 5139 | T |
| Promoter | PDC1p | 5983 | 6852 | T |
| CDS | adhBiy | 6853 | 7896 | T |
| Terminator | ADH1t | 7905 | 8220 | T |

Creation of CPN97 from PNY2145

To replace the endogenous GPD1 of *Saccharomyces cerevisiae* with *E. coli* gpsA, primers were designed to amplify the *E. coli* gpsA open reading frame to insert in the endogenous GPD1 chromosomal location maintaining the region upstream of the ATG start codon and the endogenous *Saccharomyces cerevisiae* GPD1 stop codon. Overlapping PCR was used to obtain a PCR product containing 50 base pairs upstream of the *Saccharomyces cerevisiae* GPD1 for recombination, the *E. coli* gpsA gene, a loxP-URA3-loxP cassette, and 50 base pairs downstream of the *Saccharomyces cerevisiae* GPD1 for recombination in PNY2145. The *E. coli* gpsA ORF (PCR product 1) was amplified utilizing *E. coli* BL21 chromosomal DNA as a template with primers F1 (SEQ ID NO: 234) and R1 (SEQ ID NO: 235). The loxP-URA3-loxP cassette (PCR product 2) was amplified utilizing pLA59 (SEQ ID NO:27) as a template using primers F2 (SEQ ID NO: 236) and R2 (SEQ ID NO: 237). The PCR product (PCR product 3) containing 50 base pairs upstream of the *Saccharomyces cerevisiae* GPD1, the *E. coli* gpsA gene, a loxP-URA3-loxP cassette, and 50 base pairs downstream of the *Saccharomyces cerevisiae* GPD1 was amplified utilizing the PCR products 1 and 2 as templates and primers F1 (SEQ ID NO: 234) and R2 (SEQ ID NO: 237). All PCR reactions were performed using the enzyme Herculase (Agilent; Santa Clara, Calif.) according to manufacturer's conditions.

PCR product 3 was recovered by purification and transformed into PNY2145 using a yeast transformation kit (Sigma-Aldrich; St. Louis, Mo.). Colonies were selected on yeast synthetic medium containing 1% ethanol but no uracil. Yeast synthetic medium: 6.7 g/L yeast nitrogen base without amino acids (Becton Dickinson; East Rutherford, N.J.), 1.85 g/L Kaiser dropout His-Ura (Formedium; Norfolk, UK). Histidine or uracil were added at 76 mg/L when needed.

To recycle the URA3 marker, one colony was selected and transformed with plasmid pJT254 (SEQ ID NO: 183) containing CRE recombinase under the GAL1 promoter and was plated on yeast synthetic medium containing 1% ethanol and no histidine. One colony was selected and grown overnight in YPE medium (20 g/L peptone, 10 g/L yeast extract, 10 g/L ethanol) and restreaked on YPE plates (20 g/L peptone, 10 g/L yeast extract, 10 g/L ethanol, 15 g/L agar). Colonies were selected and patched on plates of yeast synthetic medium containing 1% ethanol and no uracil, 1% ethanol and no histidine, and YPE plates. A colony unable to grow on plates lacking uracil and histidine was selected and screened for marker removal and insertion of *E. coli* gpsA by PCR. The colony was designated CPN82.

To produce a strain with an isobutanol production pathway, CPN82 was transformed with pLH804::L2V4 (SEQ ID NO: 12) and pRS413::BiADH-kivD (SEQ ID NO: 13), described above. The transformation was plated on yeast synthetic medium lacking uracil and histidine and with 1% ethanol, and three colonies were selected and restreaked on yeast synthetic medium lacking histidine and uracil with 3 g/L glucose, 3 g/L ethanol. The colonies were tested for isobutanol production, and one colony was selected and designated CPN97.

Creation of Yeast Codon Optimized GPD1 M, M3, and M8 Variant Strains from PNY2145 Integration of Yeast Codon Optimized GPD1 Variants In order to test GPD1 mutants in the host *Saccharomyces cerevisiae* strain, native GPD1 was swapped with a codon optimized version of GPD1 synthesized by DNA 2.0 using *S. cerevisiae* codon usage.

Preparation of Integration Cassette

The gene swap cassette was prepared by cloning 2 fragments (upstream GPD1 upstream homology region and codon optimized yeast GPD1 fragment) in vector pBP3518 (SEQ ID NO:9) containing the URA3 marker gene along with the promoter and terminator and GPD downstream homology region cloned downstream of the URA3 marker gene.

Fragment 1 for the integration cassette was amplified using Phusion High Fidelity PCR Master Mix (New England Biolabs Inc.; Ipswich, Mass.), primers oBP1329 (SEQ ID NO:1) and oBP1333 (SEQ ID NO:2) and PNY2145 genomic DNA as template prepared using YeaStar™ Genomic DNA kit (Zymo Research). Fragment 2 was amplified using primers oBP1334 (SEQ ID NO:3) and oBP1335 (SEQ ID NO:4) and synthetic codon optimized Yeast GPD1 or appropriate GPD1 variants as the templates. Primer oBP1333 (SEQ ID NO:2) has a 5' tail with homology to the 5' region of Fragment 2 (synthetic codon optimized GPD1) and primer oBP1334 (SEQ ID NO:3) has a 5' tail with homology to the 3' end of Fragment 1 (GPD upstream region). The two fragments were combined using overlap PCR using primer oBP1329 (SEQ ID NO:1) and oBP1335 (SEQ ID NO:4). This combined fragment was cloned in AscI and PmeI sites in vector pBP3518 (SEQ ID NO:9) and the resulting vector referred as pBP3518GPD* (SEQ ID NO:10) was transformed into Agilent XL1Blue competent cells (Agilent Technologies, USA).

Transformation of Integration Cassette in PNY2145

Plasmid oBP3518GPD* (SEQ ID NO:10) was isolated using QIAprep Spin miniprep Kit (Qiagen, GmbH) and restricted using SacI and PacI restriction enzymes (New England Biolabs Inc. Ipswich, Mass.). The resulting 4.2 kb fragments (containing the entire integration cassette, GPD Upstream homology region, Codon Opt GPD, URA3 marker gene and Downstream GPD region) was transformed into PNY2145 using Frozen EZ Yeast Transformation II Kit (Zymo Research). The transformation mix was plated on synthetic complete lacking Uracil with 0.5% ethanol at 30° C. for 48 hours. For confirmation of integration site, transformants were screened using two sets of primers oBP1342 (SEQ ID NO:6) and oBP1344 (SEQ ID NO:7) and oBP1341 (SEQ ID NO:5) and oBP1345 (SEQ ID NO:8) for confirmation of integration at both ends. The primers oBP1342 (SEQ ID NO:6) and oBP1345 (SEQ ID NO:8) were designed from a region outside the cassette to confirm integration at the right site.

Removal of URA3 Marker

The confirmed transformants (strain PNY2145 GPD14:: CO GPD1 URA3) were transformed with pRS423::P$_{GAL1}$-cre using a Frozen-EZ Yeast Transformation II™ kit (Zymo Research Corporation, Irvine, Calif.) and plating on synthetic complete medium lacking histidine and uracil supplemented with 0.5% ethanol and incubated at 30° C. for 48 hours. Transformants were grown in synthetic complete medium lacking histidine with 0.5% ethanol overnight and plated on synthetic complete medium with 0.5% ethanol and 0.1% 5FOA for URA3 marker. Marker removal was confirmed by colony PCR using primers oBP1341 (SEQ ID NO:5) and oBP1345 (SEQ ID NO:8).

Transformation of Pathway Plasmid

The strain PNY2145 GPD1Δ::CO GPD1 was then transformed with plasmid pLMH11-JM44 (SEQ ID NO:240) using Frozen-EZ Yeast Transformation W™ kit (Zymo Research Corporation, Irvine, Calif.) and plated on synthetic complete medium without uracil with 0.5% ethanol. The resulting strains were designated M, M3 (F73A), and M8 (F73G/F129G).

Creation of E. Coli Codon Optimized Yeast GPD1 EC1, E3, and E8 Strains from PNY2145 Integration of Yeast GPD1 Codon Optimized for E. coli In order to test GPD1 mutants in the host Saccharomyces cerevisiae strain, native GPD1 was swapped with an E. coli codon optimized version of GPD1 synthesized by DNA 2.0 using E. coli codon usage.

Preparation of Integration Cassette

The gene swap cassette was prepared by cloning 2 fragments (upstream GPD1 upstream homology region and codon optimized yeast GPD1 fragment) in vector pBP3518 (SEQ ID NO:9) containing the URA3 marker gene along with the promoter and terminator and GPD downstream homology region cloned downstream of the URA3 marker gene.

Fragment 1 for the integration cassette was amplified using Phusion High Fidelity PCR Master Mix (New England Biolabs Inc.; Ipswich, Mass.), primers oBP1329 (SEQ ID NO:1) and oBP1350 (SEQ ID NO:241) and PNY2145 genomic DNA as template prepared using YeaStar™ Genomic DNA kit (Zymo Research). Fragment 2 was amplified using primers oBP1351 (SEQ ID NO:242) and oBP1352 (SEQ ID NO:243) and synthetic E. coli codon Yeast optimized GPD1 gene and E3 and E8 variants as the templates. Primer oBP1350 (SEQ ID NO:241) has a 5' tail with homology to the 5' region of Fragment 2 (synthetic codon optimized GPD1) and primer oBP1351 (SEQ ID NO:242) has a 5' tail with homology to the 3' end of Fragment 1 (GPD upstream region). The two fragments were combined using overlap PCR using primer oBP1329 (SEQ ID NO:1) and oBP1352 (SEQ ID NO:243). This combined fragment was cloned in AscI and PmeI sites in vector pBP3518 (SEQ ID NO:9) and the resulting vector referred as pBP3518GPD1_EcOpt (SEQ ID NO:249) was transformed into Agilent XL1Blue competent cells (Agilent Technologies, USA).

Transformation of Integration Cassette in PNY2145

Plasmid pBP3518GPD1_EcOpt (SEQ ID NO:249) was isolated using QIAprep Spin miniprep Kit (Qiagen, GmbH) and restricted using SacI and PacI restriction enzymes (New England Biolabs Inc. Ipswich, Mass.). The resulting 4.2 kb fragments (containing the entire integration cassette, GPD Upstream homology region, E. coli codon optimized GPD1, URA3 marker gene and Downstream GPD region) was transformed into PNY2145 using Frozen EZ Yeast Transformation II Kit (Zymo Research). The transformation mix was plated on synthetic complete lacking Uracil with 0.5% ethanol at 30° C. for 48 hours. For confirmation of integration site, transformants were screened using two sets of primers oBP1342 (SEQ ID NO:6) and oBP1352 (SEQ ID NO:243) and oBP1357 (SEQ ID NO:248) and oBP1345 (SEQ ID NO:8) for confirmation of integration at both ends. The primers oBP1342 (SEQ ID NO:6) and oBP1345 (SEQ ID NO:8) were designed from a region outside the cassette to confirm integration at the right site.

Removal of URA3 Marker

The confirmed transformants (strain PNY2145 GPD1Δ:: EC CO GPD1 URA3) were transformed with pRS423:: P$_{GAL1}$-cre using a Frozen-EZ Yeast Transformation II™ kit (Zymo Research Corporation, Irvine, Calif.) and plating on synthetic complete medium lacking histidine and uracil supplemented with 0.5% ethanol and incubated at 30° C. for 48 hours. Transformants were grown in synthetic complete medium lacking histidine with 0.5% ethanol overnight and plated on synthetic complete medium with 0.5% ethanol and 0.1% 5FOA for URA3 marker. Marker removal was confirmed by colony PCR using primers oBP1357 (SEQ ID NO:248) and oBP1345 (SEQ ID NO:8).

Transformation of Pathway Plasmid

The strain PNY2145 GPD1Δ::EC CO GPD1 was then transformed with plasmid pLMH11-JM44 (SEQ ID NO:240) using Frozen-EZ Yeast Transformation II™ kit (Zymo Research Corporation, Irvine, Calif.) and plated on synthetic complete medium without uracil with 0.5% ethanol. The resulting strains were designated EC1, E3 (F73A), and E8 (F73G/F129G).

Creation of Native Yeast GPD1 N, N3, and N8 Strains from PNY2145 Integration of Yeast Native GPD1 Variants In order to test yeast native GPD1 mutants in the host Saccharomyces cerevisiae strain, yeast codon optimized GPD1 was swapped with yeast native version of GPD1 in strain PNY2145 GPD1Δ::CO GPD1.

Preparation of Integration Cassette

The gene swap cassette was prepared by cloning 2 fragments (upstream GPD1 upstream homology region and yeast native GPD1 fragment) in vector pBP3518 (SEQ ID NO:9) containing the URA3 marker gene along with the promoter and terminator and GPD downstream homology region cloned downstream of the URA3 marker gene.

Fragment 1 for the integration cassette was amplified using Phusion High Fidelity PCR Master Mix (New England Biolabs Inc.; Ipswich, Mass.), primers oBP1329 (SEQ ID NO:1) and oBP1353 (SEQ ID NO:244) and PNY2145 genomic DNA as template prepared using YeaStar™ Genomic DNA kit (Zymo Research). Fragment 2 was amplified using primers oBP1354 (SEQ ID NO:245) and oBP1355 (SEQ ID NO:246) and PNY2145 genomic DNA and appropriate variants as the templates. Primer oBP1353 (SEQ ID NO:244) has a 5' tail with homology to the 5' region of Fragment 2 (yeast native GPD1) and primer oBP1354 (SEQ ID NO:245) has a 5' tail with homology to the 3' end of Fragment 1 (GPD upstream region). The two fragments were combined using overlap PCR using primer oBP1329 (SEQ ID NO: 1) and oBP1355 (SEQ ID NO:246). This combined fragment was cloned in AscI and PmeI sites in vector pBP3518 (SEQ ID NO:9) and the resulting vector referred as pBP3518GPD1 Native (SEQ ID NO:250) was transformed into Agilent XL1Blue competent cells (Agilent Technologies, USA).

Transformation of Integration Cassette in PNY2145

Plasmid pBP3518GPD1 Native (SEQ ID NO:250) was isolated using QIAprep Spin miniprep Kit (Qiagen, GmbH) and restricted using SacI and PacI restriction enzymes (New England Biolabs Inc. Ipswich, Mass.). The resulting 4.2 kb fragments (containing the entire integration cassette, GPD upstream homology region, yeast native GPD1, URA3 marker gene and downstream GPD region) was transformed into PNY2145 GPD1Δ::CO GPD1 using Frozen EZ Yeast Transformation II Kit (Zymo Research). The transformation mix was plated on synthetic complete lacking Uracil with 0.5% ethanol at 30° C. for 48 hours. For confirmation of integration site, transformants were screened using two sets of primers oBP1342 (SEQ ID NO:6) and oBP1355 (SEQ ID NO:246) and oBP1356 (SEQ ID NO:247) and oBP1345 (SEQ ID NO:8) for confirmation of integration at both ends.

Removal of URA3 Marker

The confirmed transformants (strain PNY2145 CO GPD1Δ::Native GPD1 URA3) were transformed with pRS423::P$_{GAL1}$-cre using a Frozen-EZ Yeast Transformation II™ kit (Zymo Research Corporation, Irvine, Calif.) and plating on synthetic complete medium lacking histidine and uracil supplemented with 0.5% ethanol and incubated at 30° C. for 48 hours. Transformants were grown in synthetic complete medium lacking histidine with 0.5% ethanol overnight and plated on synthetic complete medium with 0.5% ethanol and 0.1% 5FOA for URA3 marker. Marker removal was confirmed by colony PCR using primers oBP1356 (SEQ ID NO:247) and oBP1345 (SEQ ID NO:8).

Transformation of Pathway Plasmids

The strain PNY2145 CO GPD1Δ::Native GPD1 was then transformed with plasmid pLMH11-JM44 (SEQ ID NO:240) using Frozen-EZ Yeast Transformation W™ kit (Zymo Research Corporation, Irvine, Calif.) and plated on synthetic complete medium without uracil with 0.5% ethanol. The resulting strains were designated N, N3 (F73A), and N8 (F73G/F129G).

Integration of GPD1 Variants

Integration cassettes for GPD1 variants were prepared in the same way as described above for codon optimized GPD1 swap except that the template used for amplifying fragment 2 for each GPD1 variant was the corresponding coding sequence with the mutation listed in Table 5.

TABLE 5

GPD variants with corresponding mutations

| GPD Variant | Mutation | Strain |
|---|---|---|
| GPD2 | F129G | |
| GPD3 | F73A | E3, M3, N3 |
| GPD4 | F73G | |

TABLE 5-continued

GPD variants with corresponding mutations

| GPD Variant | Mutation | Strain |
|---|---|---|
| GPD7 | F73A/F129G | |
| GPD8 | F73G/F129G | E8, M8, N8 |

E3 and E8 are variants of GPD1 using *E. coli* codon optimization; M3 and M8 are variants GPD1 using *S. cerevisiae* codon optimization; and N3 and N8 are variants GPD1 with native *S. cerevisiae* codon usage.

Integration of Heterologous GPDs

Integration cassettes for heterologous GPDs can be prepared in the same way as described above for codon optimized GPD1 except one skilled in the art would redesign the primers based on the heterologous GPD1 to be inserted to get proper assembly of the integration cassette.

Example 1: Variant GPD1 Enzymes

In this example, variant versions of *Saccharomyces GPD1* were created and tested by expression in *E. coli* followed by enzymatic assays on the crude cell extract.

GPD1 Mutagenesis

Mutagenesis of yeast GPD1 was directed by the desire to increase the $K_M$ for NADH without having an impact on other kinetic parameters of the enzyme. The approach to mutagenesis was based on the high resolution crystal structures of human GPD1 (Ou et al, 2005, J. Mol. Biol. 357: 858-869), which allowed for the determination of the amino acids within contact distance of NAD in the cofactor binding pocket. By analyzing the amino acid residues and the type of contact made, it was possible to limit the number of amino acid changes to result in an increase in the NADH $K_M$ value. Table 6 shows the results of this analysis, where the amino acid residues within 5 Angstroms of the bound NAD have been enumerated, and the role in NAD binding was interpreted. Because of their role in the pi-stacking stabilization of bound NAD, an initial focus was placed on mutagenesis of positions homologous to the phe41 and phe97 of truncated human GPD1 (SEQ ID NO:84) (phe73 and phe129 of yeast GPD1)

TABLE 6

Amino acid residues within 5 angstroms (Å) of bound NAD in the human crystal structure, and potential mutagenesis targets to increase NADH $K_M$ value.

| Residue (Number Human GPD1) | Yeast GPD Number (Residue if diff.) | No. of Contacts with NAD | Interaction Type | Possible Role | Equiv. Alt. Residues | Increase KM with | Rationale |
|---|---|---|---|---|---|---|---|
| Ser(11) | 42 | 3 | | | | | |
| Asn(13) | 44 | 18 | Polar | H-bonds with NAD | | A, C, G, I, L, M, S, V | A non-bulky non-polar residue can reduce attraction to NAD |
| Trp(14) | 45 | 66 | π-stacking | Possibly stabilizes pyrimidine ring for stable electron transfer | Phe, Tyr | A, C, G, H, I, K, L, M, N, Q, R, S, T, V | A non-ring residue which does not create too much of a Van der Waal clash and is non-negative can increase $K_M$ for NAD but destabilize the electron transfer by removing the π-stacking fixing. May also alter $K_{cat}$. |

TABLE 6-continued

Amino acid residues within 5 angstroms (Å) of bound NAD in the human crystal structure, and potential mutagenesis targets to increase NADH $K_M$ value.

| Residue (Number Human GPD1) | Yeast GPD Number (Residue if diff.) | No. of Contacts with NAD | Interaction Type | Possible Role | Equiv. Alt. Residues | Increase KM with | Rationale |
|---|---|---|---|---|---|---|---|
| Trp(39) | 71 | 6 | | | | | |
| Phe(41) | 73 | 64 | π-stacking | Stabilizes after binding | Tyr, Trp, possibly Arg, Lys due to cation-π | G, A, R, K | Small residues can increase adenine entropy. Large residues can make it difficult to get in. Long positive residues close gate with other ring due to cation-π. |
| Glu(43) | 75 | 2 | | | | | |
| Tyr(63) | 95 | 39 | | Water stabilization | | | |
| Val(92) | 124 (Gln) | 6 | | | | | |
| Pro(94) | 126 | 25 | | | | | |
| Phe(97) | 129 | 64 | π-stacking | Stabilizes after binding | Tyr, Trp, possibly Arg, Lys due to cation-π | G, A, R, K | Small residues can increase adenine entropy. Large residues can make it difficult to get in. Long positive residues close gate with other ring due to cation-π. |
| Ile(119) | 151 (leu) | 5 | | | | | |
| Lys(120) | 152 | 20 | Polar | H-bonds with DHAP and stabilizes it | | | Reversing or removing polarity can increase $K_M$ for NAD, but can alter $K_{cat}$ or $K_M$ for DHAP |
| Asn(151) | 183 | 3 | | | | | |
| Ile(152) | 184 | 2 | | | | | |
| Ala(153) | 185 | 4 | | | | | |
| Asn(205) | 246 | 1 | | Possibly assists in electron transfer | | | Can alter $K_{cat}$ or $K_M$ for DHAP |
| Arg(269) | 310 | 33 | | Stabilizes electron transfer. Likely can create attraction for diphosphate of NAD | | | Changing to a non-positive residue can make the diphosphate of NAD uneasy, but can alter $K_{cat}$ or $K_M$ for DHAP |
| Gln(295) | 336 | 14 | | | | | |
| Lys(296) | 337 (Ser) | 17 | | H-bonds with NAD | A, C, D, E, G, I, L, M, N, Q, S, V | | Prevent h-bond formation, reverse polarity and reduce attraction for NAD |
| Gln(298) | 339 | 14 | | H-bonds and stabilizes residues around NAD | A, C, G, I, L, M, S, V | | A non-bulky non-polar residue can reduce attraction to NAD |

Strain and Media

*Escherichia coli* TOP10 was obtained from Life Technologies Corp. (Cat. #C404003, Grand Island, N.Y.). Expression plasmid pBAD was previously described (U.S. Pat. No. 7,910,342). Synthetic yeast GPD1 gene, optimized for yeast expression, was obtained from DNA2.0 (Menlo Park, Calif.). Cells were grown at 37° C. in Miller's LB broth (Cat. #46-050-CM, Mediatech, Inc., Herndon, Va.) with 0.02% L-(+)-arabinose (Cat. #A3256, Sigma-Aldrich, Inc., St. Louis, Mo.) and 100 µg/mL ampicillin (Cat. #A1066, Sigma-Aldrich, Inc., St. Louis, Mo.). Cells were plated on LB agar plates with 100 µg/mL ampicillin (Cat. #L1004, Teknova, Inc., Hollister, Calif.).

Construction of GPD1 Variants

Mutations were introduced at 4 different amino acid positions, according to Table 7. Mutagenesis was performed using a QuikChange Lightning Kit (Cat. #210519, Agilent Technologies, La Jolla, Calif.), according to manufacturer's directions. Mutagenesis primers were obtained from Sigma-Aldrich Co. LLC, St. Louis, Mo. Reactions were thermocycled in a Gene Amp 9700 (Perkin Elmer Applied Biosystems, Norwalk, Conn.). *Escherichia coli* TOP10 were transformed with 1 µl of QuikChange reaction product according to manufacturer's directions, and transformants were selected on LB agar plates with 100 µg/mL ampicillin.

DNA sequences were obtained for multiple isolates from each transformation in order to identify those with the desired mutations.

Double mutants were constructed in the same manner, except that the template in the mutagenesis reaction already contained one of the mutations, and the appropriate primers were used to introduce the second mutation.

TABLE 7

GPD1 Variants and Primers Used in Their Construction

| Position | SEQ ID NO: | Forward Primer SEQ ID NO: | Reverse Primer SEQ ID NO: |
|---|---|---|---|
| Asn44 | | 20 | |
| N44A | 212 | 21 | 54 |
| N44C | 213 | 22 | 55 |
| N44G | 214 | 23 | 56 |
| N44I | 215 | 24 | 57 |
| N44L | 216 | 25 | 58 |
| N44M | 217 | 26 | 59 |
| N44S | 218 | 27 | 60 |
| N44V | 219 | 28 | 61 |
| Trp45 | | 29 | |
| W45A | 220 | 30 | 62 |
| W45C | 221 | 31 | 63 |
| W45G | 222 | 32 | 64 |
| W45H | 223 | 33 | 65 |
| W45I | 224 | 34 | 66 |
| W45K | 225 | 35 | 67 |
| W45L | 226 | 36 | 68 |
| W45M | 227 | 37 | 69 |
| W45N | 228 | 38 | 70 |
| W45Q | 229 | 39 | 71 |
| W45R | 230 | 40 | 72 |
| W45S | 231 | 41 | 73 |
| W45T | 232 | 42 | 74 |
| W45V | 233 | 43 | 75 |
| Phe73 | | 44 | |
| F73G | 196 | 45 | 76 |
| F73A | 197 | 46 | 77 |
| F73R | 198 | 47 | 78 |
| F73K | 199 | 48 | 79 |
| Phe129 | | 49 | |
| F129G | 200 | 50 | 80 |
| F129A | 201 | 51 | 81 |
| F129R | 202 | 52 | 82 |
| F129K | 203 | 53 | 83 |

GPD1 Assay

Soluble fraction cell extracts were prepared from 5 ml of culture by bead beating 2×10 seconds in 100 mM MOPS pH 6.8, 10 mM $MgCl_2$, 1 mM EDTA in a Mini-Bead-beater (Cat. #3110BX, Biospec Products, Bartlesville, Okla.). Cell extract protein concentration was determined by Pierce BCA assay (Cat. #23224 and 23228, Thermo Fisher Scientific, Inc., Rockford, Ill.).

Assays were performed in a 100 μl volume containing 100 mM MOPS pH6.8, 1 mM EDTA, 1 mM glucose-6-phosphate, 3 m U/μl glucose-6-phosphate dehydrogenase (Cat. #G8404, Sigma-Aldrich, Inc., St. Louis, Mo.), 1 mM dihydroxyacetone phosphate (Cat. #D7137, Sigma-Aldrich, Inc., St. Louis, Mo.), varying concentrations of NADH, and varying concentrations of cell extract. Reactions were terminated by 4-fold dilution into 0.1% formic acid (Suprapur, #1167-1, EMD Chemicals, Gibbstown, N.J.) in water (Omnisolv, #WX0001-1, EMD Chemicals, Gibbstown, N.J.). Glycerol-3-phosphate production was measured by LC/MS.

LC/MS Method

2 μL of each sample was injected on a Waters Acuity UPLC/SQD System, using a HSS T3 column (2.1×100 mm, 1.8 μm, #186003539, Waters, Milford, Mass.) at a temperature of 30° C. UPLC mobile phases consisted of 0.1% formic acid in water (Mobile A) and 0.1% formic acid in acetonitrile (Omnisolv, #AX0156-1, EMD Chemicals, Gibbstown, N.J.) (Mobile B) with a constant flow rate of 0.3 mL/min. The gradient consisted of an initial 1 minute period at 99% A, followed by a 0.5 minute linear gradient ending at 75% B, and then a 0.5 minute linear gradient back down to 99% A, before injecting the next sample. MS analysis was performed by electrospray negative ionization at a cone voltage of 30V and m/z=171. Retention time and peak intensities were determined using MassLynx4.1 software (Waters, Milford, Mass.). External standard (glycerol-3-phosphate, Cat. #G7886, Sigma-Aldrich, Inc., St. Louis, Mo.) was analyzed in the same manner was used for quantitation.

Analysis of GPD1 Variants

The activity of the GPD1 variants was initially screened by measuring the initial rate of formation of glycerol 3 phosphate (G3P) at two concentrations of NADH (30 and 300 μM). This serves as a measurement indicating the $K_M$ of the variants for NADH: for a $K_M$ much less than 30 μM, the ratio would be 1.0, for a $K_M$ much higher than 300 μM the ratio would be 10. The results for the individual single mutants are shown in Table 8.

TABLE 8

Activity of GPD1 Variants Measured by Initial G3P Formation Rate

| Variant | Activity Ratio |
|---|---|
| 129R | 78.0 |
| 129K | 73.1 |
| 129G | 67.8 |
| 129A | 65.9 |
| 44G | 2.4 |
| 44M | 2.4 |
| 44S | 2.3 |
| 45G | 2.2 |
| 44V | 2.2 |
| 73A | 2.0 |
| 44A | 1.8 |
| 73G | 1.8 |
| 44C | 1.8 |
| 44L | 1.8 |
| 44I | 1.7 |
| 45C | 1.7 |
| 73R | 1.5 |
| 45M | 1.4 |
| 45A | 1.4 |
| 45H | 1.3 |
| 73K | 1.2 |
| 45I | 1.0 |
| 45S | 1.0 |
| 45V | 1.0 |
| 45T | 0.9 |
| 45K | 0.8 |
| 45L | 0.7 |
| 45N | 0.6 |
| 45Q | 0.6 |
| 45R | 0.6 |
| GPD1 wt | 1.3 +/− 0.3 |

This data can be interpreted to indicate that any variant with a ratio greater than 1.6 (average value of three control measurements plus standard deviation) has a higher NADH $K_M$ than the wild-type GPD1. Double mutants of the individual high-$K_M$ single mutants were created as described above. Full-scale analysis of the NADH $K_M$ values for a selection of the double and single mutants is shown in Table 9.

TABLE 9

Michaelis constants ($K_M$) for NADH of GPD1 Variants

| Variant | Vmax (U/ml) | $K_M$ (µM) |
|---|---|---|
| GPD1 WT_y | 9 | 13 |
| F129A | 14 | 234 |
| F129G | 21 | 200 |
| F129K | 14 | 136 |
| F129R | 11 | 76 |
| F73A | 11 | 101 |
| F73G | 9 | 42 |
| N44A | 6 | 14 |
| N44C | 3 | 5 |
| N44G | 29 | 26 |
| N44L | 1 | 8 |
| N44M | 9 | 8 |
| N44S | 6 | 51 |
| N44V | 3 | 3 |
| F129A | 33 | 199 |
| F129R | 32 | 70 |
| F73A129G (SEQ ID NO: 204) | 30 | 605 |
| F73A129A (SEQ ID NO: 205) | 12 | 595 |
| F73A129R (SEQ ID NO: 206) | 14 | 734 |
| F73A129K (SEQ ID NO: 207) | 9 | 2989 |
| F73G129G (SEQ ID NO: 208) | 29 | 515 |
| F73G129A (SEQ ID NO: 209) | 15 | 554 |
| F73G129R (SEQ ID NO: 210) | 7 | 1364 |
| F73G129K (SEQ ID NO: 211) | 6 | 1671 |

These data indicate that mutations of amino acids corresponding to residues 44, 45, 73, and 129 (alone or in combination) of S. cerevisiae GPD can increase the $K_M$ of GPD for NADH. As shown in FIG. 2, amino acids 73 and 129 of S. cerevisiae GPD correspond to amino acids 41 and 97 of human GPD, respectively.

Example 2: Heterologous GPD Enzymes with Higher $K_M$ for NADH than S. Cerevisiae GPD In this example, alternate glycerol-3-phosphate dehydrogenase enzymes with Michaelis constants ($K_M$) for NADH that are higher than yeast GPD1 were identified.

One strategy to identify higher NADH $K_M$ enzymes is to use values published in literature for those enzymes that have been previously identified. Table 10 enumerates publications where the NADH $K_M$ is higher than that reported for Saccharomyces GPD1.

TABLE 10

Published NADH $K_M$ for GPDs

| NADH $K_M$ (mM) | Source | Reference |
|---|---|---|
| 0.023 | Saccharomyces Cerevisiae GPD1 | Albertyn et al. 1992, FEBS Lett. 308: 130 |
| 0.024 | Leishmania mexicana | Marche et al, 2000, Mol Biochem Parasitol. 106: 83-91 |
| 0.032 | Jaculus orientalis | Berrada et al, 2002 Mol Cell Biochem. 231: 117-27 |
| 0.0589 | Dunaliella viridis GPDH1 | He et al, 2009, Plant Mol Biol. 71: 193-205 |
| 0.0592 | Dunaliella viridis GPDH2 | He et al, 2009, Plant Mol Biol. 71: 193-205 |
| 0.078 | Drosophila melanogaster | Niesel et al, 1982, Methods Enzymol. 89, 296-301 |

The enzyme in the Drosophila melanogaster reference cited above identified "GPDH1" as coming from the Drosophila flight muscle. However, the reference predates sequence information about the gene encoding the enzyme. Subsequently, the sequence for this enzyme was identified (gi: 22945708) as glycerol 3 phosphate dehydrogenase, isoform C from the Drosophila genomic sequence (Carmon & MacIntyre, 2010, Journal of Heredity 101: 225-234). Using the techniques outlined in Example 1, this enzyme was expressed in E. coli, and the $K_M$ value was measured in parallel with, and under the same conditions, used to measure E. coli expressed Saccharomyces GPD1. In one experiment, the NADH $K_M$ was measured as 5 µM for both enzymes, i.e., not significantly different.

An alternate strategy to identify naturally occurring GPDs with a high $K_M$ for NADH is to evaluate members of the GPDs as defined by the enzyme commission nomenclature EC 1.1.1.94. While some of these enzymes use both NADH and NADPH equally well (e.g., Edgar & Bell, 1980, J Biol Chem 255: 3492-34-97), others have been characterized as having a preference for NADPH (Frohlich et al, 2010, J Bacteriol 192: 4281-4288; Watanabe et al, 2008, Yeast 25:107-116; Sakasegawa et al, 2004, Protein Science 13: 1361-1371; Ruijter et al, 2004, Microbiology 150: 1095-1101). It is possible that this preference might be manifest as a high $K_M$ for NADH (as compared to the $K_M$ for NADPH of the same enzyme). Using the techniques outlined in Example 1, synthetic genes in the pBad expression vector for the following GPD enzymes were prepared: (a) Archaeoglobus fulgidus DSM 4304 (gi|11497621:c775889-774882) (SEQ ID NO:14); (b) Candida versatilis CvGPD1 gene for glycerol-3-phosphate dehydrogenase (gi|157060214|dbj|AB296385.1) (SEQ ID NO:15); and (c) Rickettsia prowazekii str. BuV67-CWPP chromosome (gi|383499256:539930-540880) (SEQ ID NO:16).

As in Example 1, these proteins were expressed in E. coli, and crude cell extracts were used to measure NADH $K_M$ values. Candida versatilis GPD did not yield significant measurable activity. The Archeoglobus fulgidus enzyme had measurable activity with a $K_M$=7 µM for NADPH and 5 µM for NADH, and the Rickettsia prowazekii enzyme had measurable activity with a $K_M$=4 µM for NADPH and 664 µM for NADH.

The Rickettsia prowazekii enzyme $K_M$ for NADH was higher than the $K_M$ for Saccharomyces. In order to further evaluate what aspect of the enzyme might be contributing to this decreased affinity for NADH, the sequence of the Rickettsia enzyme was compared to the crystal structure of the human enzyme with NAD+ in the binding site. A notable feature of the human enzyme:NAD complex is the pi-stacking of phe41 and phe97 sandwiched around the adenine ring of NAD+ (pdb: 1X0X; Ou et al, 2006 J Mol Biol 357: 858-869). The pi-stacking is a very stable structure, and sequence alignment reveals that the homologous positions are conserved in yeast GPD1 sequence (phe73, phe129).

However in *Rickettsia*, the homologous positions in an alignment are arg35 and ala85 (see FIG. 2). These amino acids would be expected to destabilize NADH binding, thus leading to an increased NADH $K_M$. This was confirmed by mutagenesis at these positions in Example 1.

As further confirmation of the role of these amino acid positions in increasing NADH $K_M$, two of the most closely related GPD sequences outside of the *Rickettsia* genus were identified by BLAST search of the NCBI database. Two of the most closely related sequences are from *Beggiatoa alba* (BLAST E value=2e-51, 37% sequence identity; SEQ ID NO:17) and *Kangiella koreensis* (BLAST E value=2e-50, 37% sequence identity; SEQ ID NO:18). These proteins were synthesized and tested as previously described.

Although the expression level in *E. coli* for these enzymes was low, the values measured with the *Beggiatoa* enzyme were $K_M$=6 μM for NADPH and 101 μM for NADH, while the *Kangiella* enzyme values were $K_M$=1 μM for NADPH and 2018 μM for NADH. The amino acids in homologous positions to the two phenylalanines forming the pi-stacking in the human enzyme are lys85 and gly86 in the *Beggiatoa* enzyme, and arg35 and ala86 in the *Kangiella* enzyme (see FIG. 2).

These results confirm that certain GPDs from other organisms have a higher $K_M$ for NADH and also further support that the $K_M$ for NADH can be raised by engineering GPD enzymes, for example, by modification of amino acids involved in the pi-stacking phenylalanine pair.

Example 3: Isobutanol and Glycerol Production for Yeast Strains Comprising GPD1 Enzyme Variants In this example, yeast strains with variant GPD1 enzymes produced and described above were tested for isobutanol and glycerol production.

PNY2145 GPD and GPD variant strains with isobutanol pathway plasmid were plated on synthetic complete agar plates [1× yeast nitrogen base without amino acids (Difco), 1× amino acid drop-out without uracil (Clone-tech) containing 2% agar (Difco), 0.2% ethanol] and incubated for 72 hours at 300 C incubator (New Brunswick)

Cells were patched on synthetic complete medium [1× yeast nitrogen base without amino acids (Difco), 1× amino acid drop-out without uracil (Clonetech) containing 2% agar (Difco), 1% glucose (sigma), 0.2% ethanol] and incubated for 72 hours at 30° C. incubator (New Brunswick). Cells were adapted by repetitive plating every three days on same media for 30 days.

Patches of the adapted cells were inoculated in 10 ml of synthetic complete liquid medium [1× yeast nitrogen base without amino acids (Difco), 1× amino acid drop-out without uracil (Clonetech) containing 2% agar (Difco), 1% glucose (Sigma), 0.2% ethanol] as primary cultures in 125 ml flasks (BD) and incubated at 30° C. for 24 hours in an incubator shaker (New Brunswick) at 250 rpm. Secondary cultures were inoculated from the primary cultures in the same medium with an initial OD of 0.5 and allowed to grow for another 24 hours. After 24 hours tertiary cultures were inoculated in the same medium from the secondary cultures with an initial O.D of 0.5 and allowed to grow for another 24 hours. These cells were then used for evaluation studies of GPD variants.

Cells were harvested by centrifugation at 3600 rpm for 5 minutes at room temperature in a centrifuge (Eppendorf) and suspended in production medium (1× yeast nitrogen base without amino acids (Difco), 1× amino acid drop-out without uracil (Clonetech), 35 g/L glucose (Sigma), 2 g/L ethanol, 100 mM MES (Sigma) 1× peptone (Difco), 1× yeast extract (Difco), 1M HCL (Sigma) at pH 5.2) and initial OD of 2 in 15 ml falcon tubes. Cultures were then incubated at 30° C. in an incubator shaker (New Brunswick) at 225 rpm for 20 hours. Samples were collected at 20 hours and analyzed by HPLC (Agilent Life Sciences) (FIG. 3).

Sample Preparation

Cultures were harvested at the end of production at 20 hours and each cell pellet was resuspended in 100 mM of MOPS pH 6.8 which contains 1× protease inhibitor (Roche). Lysis was achieved by subjecting cells to bead beating (Mini-Beadbeater-16, Biospec) for 5 cycles of 30 seconds each with an interval of 2 min between each cycle. Lysed sample was subjected to centrifugation at 13,000 rpm for 30 min in centrifuge at 40° C. Supernatant was carefully transferred to another tube. Protein estimation was done using Bradford reagent (Cat. #500-0205, Bio-Rad). GPD assay was done immediately on fresh samples without any freeze-thaw step.

Assay Condition

Glycerol-3-phosphate (GPD) assays were performed using Cary 100 UV-Vis spectrophotometer in a 1 ml volume containing 100 mM MOPS (Sigma) pH 6.8, 1 mM EDTA, 1 mM glucose-6-phosphate, 3 mU/μl glucose-6-phosphate dehydrogenase (Cat. #G8404, Sigma-Aldrich, Inc., St. Louis, Mo.), 1 mM dihydroxyacetone phosphate (Cat. #D51269,Sigma-Aldrich, Inc., St. Louis, Mo.), 0.3 mM NADH, and varying concentrations of cell extract. Rate of the reaction was calculated by taking slope of first 1 min for decrease in NADH concentration at 340 nm. Extinction coefficient of NADH was taken as 6.22 $mM^{-1}cm^{-1}$. For variants N8_1, E8_1 and M8_1 (i.e. those with the double mutant F73G/F129G) the NADH concentration was increased to 0.45 mM. This is non-saturating level of NADH for these variants.

Regression Analysis of Results

The data used in this section are provided in Table 11, and includes measurements of the metabolic products and the in vitro measurements of GPD as described above. To account for differences in the measured GPD activity that arises from measurement at subsaturating amounts of NADH, the total activity at $V_{max}$ was calculated by solving the single substrate Michaelis-Menton equation for $V_{max}$, using GPD (U/mg) for rate and the $K_M$ value as determined in Table 9.

TABLE 11

In vitro measurement of metabolic products and specific activity of GPD in various control and variant isobutanologen strains harboring different substitution in heterologous/native GPD sequence.

| Strain | Glucose Cons. (g/L) | Gly (g/L) | EtOH (g/L) | iBuOH (g/L) | Yield (g/g) | iBuOH/Gly ratio | GPD (U/mg) | GPD $K_M$ (μM) | GPD $V_{max}$ (U/mg) |
|---|---|---|---|---|---|---|---|---|---|
| EC_1 | 21.52 | 1.55 | 0.4 | 4.14 | 0.19 | 2.67 | 0.0014 | 11 | 0.0015 |
| E3_1 | 18.82 | 1.91 | 0.13 | 3.63 | 0.19 | 1.90 | 0.0018 | 101 | 0.0024 |

TABLE 11-continued

In vitro measurement of metabolic products and specific activity of GPD in various control and variant isobutanologen strains harboring different substitution in heterologous/native GPD sequence.

| Strain | Glucose Cons. (g/L) | Gly (g/L) | EtOH (g/L) | iBuOH (g/L) | Yield (g/g) | iBuOH/Gly ratio | GPD (U/mg) | GPD $K_M$ (μM) | GPD $V_{max}$ (U/mg) |
|---|---|---|---|---|---|---|---|---|---|
| E8_1 | 12.16 | 0.75 | 0.13 | 3.11 | 0.26 | 4.15 | 0.0003 | 554 | 0.0007 |
| M3_1 | 23.81 | 2.44 | 0.35 | 4.36 | 0.18 | 1.79 | 0.0053 | 101 | 0.0071 |
| M8_1 | 22.91 | 2.89 | 0.2 | 4.64 | 0.20 | 1.61 | 0.0035 | 554 | 0.0078 |
| N3_1 | 22.32 | 3.4 | 0.49 | 3.3 | 0.15 | 0.97 | 0.0097 | 101 | 0.0130 |
| N8_1 | 13.95 | 2.1 | 0.19 | 2.16 | 0.15 | 1.03 | 0.0084 | 554 | 0.0187 |
| 2145 | 30.68 | 3.43 | 0.2 | 5.46 | 0.18 | 1.59 | 0.0025 | 11 | 0.0026 |

Initially, it was observed that integration of both unaltered and variant GPDs following the methods described above led to varying amounts of GPD activity, as analyzed in the yeast cell extract following isobutanol production. The specific activity of GPD could vary by as much as 10-fold. The isobutanol/glycerol ratio also exhibited an inverse correlation with the level of GPD activity detected as shown in FIG. 4. As shown in the figure, the $R^2$ value for the linear regression of this relationship was 60.1%, but the cross-validated R-$Sq_{(pred)}$ value, which indicates the ability of the GPD activity data to predict unknown values of the isobutanol/glycerol ratio, was only 25.04%. This result indicated that while there was a correlation, the GPD activity alone was not a good predictor of this ratio.

This factor made it difficult to detect changes in the contribution of the high $K_M$ GPD variants to the production of glycerol and isobutanol, as the beneficial effect of the increased NADH $K_M$ was masked by the unpredictable activity levels. In order to further understand these effects, multiple linear regression analysis was applied to the data in Table 11 to determine if the contribution of the variant properties could be more clearly quantified. Modeled parameters were subjected to multiple rounds of linear regression using Minitab (Minitab V16.2.1, Minitab Inc.; State College, Pa.), manually removing the contributing parameter with the greatest P value until the P value of the remaining coefficients were all below 0.05. This produced a regression equation with a maximum R-sq(pred) value, which indicated the ability of the model to predict the value of new observations. Two of the metabolic measurements in Table 11 yielded models with independent contributing parameters that could be interpreted physiologically.

Isobutanol titer was modeled using the following parameters from Table 11: glucose consumed, ethanol, glycerol, yield, GPD $K_M$, and GPD $V_{max}$. Eliminating the least significant parameters yielded a regression model with 3 parameters (predictors): glucose consumed, GPD $K_M$, and GPD $V_{max}$ (shown in the FIG. 5 and Table 12). The R-Sq value for this model is 98.6%. The R-$Sq_{(pred)}$ value for this model is 94.32% indicating that this regression equation provides a high degree of predictive value. Interpreting the regression model physiologically, it suggests that isobutanol titer is predicted by positive contributions from the glucose consumed and GPD $K_M$ values, and a negative contribution from the GPD $V_{max}$ value. Thus, at any amount of glucose consumed, a higher GPD $K_M$ will result in an increase in isobutanol titer. Similarly, increases in the level of the measured activity of the GPD enzyme (as $V_{max}$ value) will result in a decrease in the isobutanol titer.

TABLE 12

Regression model for isobutanol titer (g/L).

| Predictor | Coefficient | SE Coefficient | T | P | VIF |
|---|---|---|---|---|---|
| Constant | 0.3316 | 0.3499 | 0.95 | 0.397 | |
| Glucose Consumed (g/L) | 0.17741 | 0.01382 | 12.83 | 0.000 | 1.804 |
| GPD $K_M$ (μM) | 0.0013789 | 0.0003309 | 4.17 | 0.014 | 1.977 |
| GPD $V_{max}$ (U/mg) | −75.81 | 10.10 | −7.50 | 0.002 | 1.146 |

The regression model allowed an estimate of the magnitude of these effects. At a glucose consumption level of 30 g/L, and GPD $V_{max}$ of 0.0026 U/mg, increasing the $K_M$ from 11 μM (wild type) to 550 μM resulted in a 14% increase in isobutanol titer. However, at a glucose consumption level of 30 g/L, $K_M$ at 11 μM, and increase in the GPD level from 0.0015 U/mg to 0.019 U/mg (the maximum change in activity from Table 11) resulted in a 25% decrease in isobutanol titer. This regression model therefore demonstrated that decreasing GPD affinity for NADH (increased $K_M$), increased the isobutanol titer in the samples shown here.

Isobutanol yield (grams isobutanol/gram glucose consumed) was similarly modeled using the following parameters from Table 12: glucose consumed, ethanol, glycerol, isobutanol, GPD $K_M$, and GPD $V_{max}$. Elimination of the least significant parameters yielded a regression model using 2 parameters, GPD $K_M$, and GPD $V_{max}$ (see FIG. 6 and Table 13). This regression model had an R-Sq value of 93.9%. This regression model predicted yield with R-$Sq_{(pred)}$ value of 76.3%, and notably is solely dependent on the activity level and $K_M$ of the GPD enzyme. Similar to the regression model for isobutanol titer, the GPD $V_{max}$ has a negative contribution to yield. In this regression model, increasing the $K_M$ of GPD from 11 μM (wild type) to 550 μM, at the lowest observed GPD activity level of 0.0015 U/mg, resulted in a yield improvement of 28%. At the highest GPD activity level observed here (0.019 U/mg) the yield improvement was 78%.

TABLE 13

Regression model for yield (g/g).

| Predictor | Coefficient | SE Coefficient | T | P | VIF |
|---|---|---|---|---|---|
| Constant | 0.199176 | 0.005908 | 33.71 | 0.000 | |
| GPD $K_M$ (μM) | 0.00009410 | 0.00001597 | 5.89 | 0.002 | 1.144 |
| GPD $V_{max}$ (U/mg) | −5.2197 | 0.6404 | −8.15 | 0.000 | 1.144 |

Example 4: Prophetic

In this example, heterologous GPD1 yeast integrants described above are tested for isobutanol and glycerol production.

Growth Media and Procedure

Two types of media are used during the growth procedure of yeast strains: an aerobic pre-culture media and an anaerobic culture media. All chemicals are obtained from Sigma unless otherwise noted (St. Louis, Mo.)

Aerobic pre-culture media (SE-Ura-His): 6.7 g/L yeast nitrogen base without amino acids (Difco, 291940, Sparks, Md.), 1.4 g/L yeast synthetic drop-out medium supplement without histidine, leucine, tryptophan and uracil, 0.2% ethanol, 0.2% glucose, 0.01% w/v leucine and 0.002% w/v tryptophan.

Anaerobic culture media (SEG-Ura-His): 50 mM MES (pH 5.5, 6.7 g/L yeast nitrogen base without amino acids (Difco, 291940, Sparks, Md.), 1.4 g/L yeast synthetic drop-out medium supplement without histidine, leucine, tryptophan and uracil, 0.1% ethanol, 3% glucose, 0.01% leucine, 0.002% tryptophan, 30 mg/L nicotinic acid, 30 mg/L thiamine and 10 mg/L ergosterol made up in 50/50 v/v Tween/ethanol solution.

The patched cells are inoculated into 25 mL SEG-Ura,His media with 0.2% glucose and 0.2% ethanol, and grown under progressively oxygen-limited conditions with lid closed for approximately 48 hours at 30° C. with shaking, until a target $OD_{600}$ value of approximately 1.5 to 2 is achieved. $OD_{600}$ values are recorded. Cells are pelleted via centrifugation and the supernatant is discarded. Cell pellets are transferred into a Coy Anaerobic Bag (Grass Lake, Mich.) where pellets are resuspended in 1.0 mL anaerobic growth media (SEG-Ura-His). The resuspended cell pellets are used to inoculate 30 mL SEG-Ura-His media in 50 mL serum bottles (Wheaton, 223748, Millville, N.J.) to a target initial $OD_{600}$ value of 0.2. All anaerobic media, serum vials, stoppers and crimps are allowed to degas in the anaerobic bag for at least 24 hours prior to inoculation. Serum bottles are stoppered, crimped and transferred out of the anaerobic bag and grown at 30° C. with shaking at 240 rpm. Anaerobic cultures are grown for 24 to 72 hours with a target $OD_{600}$ value of at least 1.2. Additional anaerobic growth steps used the cells from the previous anaerobic culture step as inoculant. Three transformants were evaluated for each variant.

HPLC Analysis of Variant and Heterologous Yeast GPD1 Strains

Samples are taken for HPLC analysis and to obtain $OD_{600}$ values at the end of the anaerobic growth period. HPLC analysis is performed using a Waters 2695 separations unit, 2996 photodiode array detector, and 2414 refractive index detector (Waters, Milford, Mass.) with a Shodex Sugar SH-G pre-column and Shodex Sugar SH1011 separations column (Shodex, J M Science, Grand Island, N.Y.). Compounds are separated by isocratic elution at 0.01 N sulfuric acid with a flow rate of 0.5 mL/min. Chromatograms are analyzed using the Waters Empower Pro software.

Molar yields for glycerol, isobutanol and the isobutanol/glycerol ratio are determined. Mean and standard deviations are calculated from triplicate analyses for each variant and heterologous GPD. Student's t-test is employed to determine if the difference in the values are statistically significant from the codon-optimized GPD1 control values.

Example 5: Effect of gpsA on Isobutanol Production

Strains CPN97 and PNY2310 were grown on yeast synthetic medium containing 100 mM MES (2-(N-morpholino) ethanesulfonic acid), 3 g/L glucose and 3 g/L ethanol and lacking histidine and uracil. A colony from each strain was selected and inoculated in 10 ml yeast synthetic medium containing 10 g/l glucose and 100 mM MES without histidine and uracil and incubated overnight at 30° C. at 200 rpm. After overnight incubation, the cells were resuspended to an $OD_{600}$=0.4 in 10 mL yeast synthetic medium containing 20 g/l glucose and 100 mM MES without histidine and uracil and incubated for 4 hours at 30° C. and 200 rpm. The cells were then harvested and resuspended to an $OD_{600}$=0.2 in 10 mL yeast synthetic medium containing 20 g/l glucose and 100 mM MES without histidine and uracil in a 20 ml serum vial (Wheaton; Millville, N.J.), capped with a butylrubber stopper and sealed. Vials were placed in a 30° C. incubator, rotated at 200 rpm, and incubated for 28 and 42.5 hours. Two vials were prepared for each strain tested.

After 28 and 42.5 hours, the cap of one of the vials was opened, $OD_{600}$ was measured and the broth was analyzed by HPLC. HPLC analysis was performed on an Agilent 1100 series HPLC system containing a refractive index detector using a 300 mm×7.8 mm BioRad-Aminex HPX-87H exclusion column (BioRad; Hercules, Calif.) incubated at 50° C. and equipped with a BioRad-Microguard Cation H refill 30 mm×4.6 mm. Samples were run at a flow rate of 0.6 ml/min in 0.01 N sulfuric acid running buffer. From the HPLC analysis, it was observed that isobutanol yield (FIG. 7) and isobutanol/glycerol ratio (FIG. 8) were increased in CPN97 as compared to PNY2310 and glucose consumption was decreased (FIG. 9) in CPN97 as compared to PNY2310. While grown in aerobic conditions, the optical densities (ODs) as a function of time were similar.

Example 6: Generation of Feedback Resistant gpsA

Prophetic

The gpsA allele was amplified using *E. coli* MG1655 chromosomal DNA and primers Ptrc-gpsA NcoI F (SEQ ID NO:238) and Ptrc-gpsA PstI R (SEQ ID NO:239). The gpsA allele was cloned into NcoI/PstI-digested pTrcHis2B (Invitrogen; Carlsbad, Calif.) using the GeneArt seamless cloning and assembly kit (Life Technologies, Carlsbad, Calif.), to form pCPN124.

pCPN124 is submitted to error-prone mutagenesis using GeneMorphII Random Mutagenesis kit from Agilent (Santa Clara, Calif.). Plasmids that are obtained are transformed into strain BB26-36 (Bell, J. Bact. 117:1065-1076 (1974)). Strain BB26-36 contains a mutation in the plsB gene. Additionally, the strain does not have the glycerol-3-phosphate auxotrophy of parent strain BB26 because of the loss of inhibition of glycerol kinase (GlpK) by fructose-1,6-diphosphate (fru-1,6-diP), so BB26-36 can produce glycerol-3-phosphate and grow on minimal media M9 plus glycerol 3 g/L and glucose 3 g/L (M9 contains 12.8 g sodium phosphate heptahydrate, 3 g potassium phosphate monobasic, 0.5 g sodium chloride, 1 g ammonium chloride, 0.24 g magnesium sulfate, and 11.1 mg calcium chloride, per liter).

The transformation reaction is plated on M9 medium containing 5 g/L glucose and 50 mg/L carbenicillin. Plasmids are extracted from the colonies growing on these plates and the gpsA gene is sequenced. GpsA activity of the mutated protein was determined and the $K_i$ for glycerol-3-phosphate is measured. Proteins with increased $K_i$ compared to wild-type protein are then used to replace GPD1 in the yeast chromosome and isobutanol and glycerol production are measured.

What is claimed is:

1. A method for the production of isobutanol comprising:
   (a) providing a recombinant microorganism comprising
      i. an engineered isobutanol biosynthetic pathway,
      ii. a deletion or disruption in an endogenous gene encoding GPD1, and
      iii. an engineered glycerol-3-phosphate dehydrogenase (GPD) enzyme wherein the GPD has at least 90% identity to SEQ ID NO: 195 and comprises at least one substitution at a residue corresponding to position 44, 45, 73, or 129 of SEQ ID NO: 195, and wherein the engineered GPD has a higher $K_M$ for NADH as compared to the $K_M$ of the endogenous GPD of the microorganism; and
   (a) contacting the recombinant microorganism with at least one fermentable carbon substrate under conditions wherein isobutanol is produced.

2. The method of claim 1, wherein the recombinant microorganism is grown under anaerobic conditions.

3. The method of claim 1, wherein the enzyme comprises at least one substitution corresponding to position 73 of SEQ ID NO: 195.

4. The method of claim 1, wherein the enzyme comprises at least one substitution corresponding to position 129 of SEQ ID NO:195.

5. The method of claim 1, wherein the enzyme comprises a substitution corresponding to position 73 of SEQ ID NO:195 and a substitution corresponding to position 129 of SEQ ID NO:195.

6. The method of claim 1, wherein the isobutanol biosynthetic pathway comprises at least one gene encoding a polypeptide that performs at least one of the following substrate to product conversions:

(a) pyruvate to acetolactate, as catalyzed by acetolactate synthase;
   (b) acetolactate to 2,3-dihydroxyisovalerate, as catalyzed by acetohydroxy acid isomeroreductase;
   (c) 2,3-dihydroxyisovalerate to α-ketoisovalerate, as catalyzed by dihydroxyacid dehydratase;
   (d) α-ketoisovalerate to isobutyraldehyde, as catalyzed by a branched chain keto acid decarboxylase; and
   (e) isobutyraldehyde to isobutanol, as catalyzed by branched-chain alcohol dehydrogenase.

7. The method of claim 1, wherein the microorganism is from a genus selected from the group consisting of *Clostridium, Zymomonas, Escherichia, Salmonella, Serratia, Envinia, Klebsiella, Shigella, Rhodococcus, Pseudomonas, Bacillus, Lactobacillus, Enterococcus, Alcaligenes, Paenibacillus, Arthrobacter, Corynebacterium, Brevibacterium, Schizosaccharomyces, Kluveromyces, Yarrowia, Pichia, Zygosaccharomyces, Debaryomyces, Candida, Brettanomyces, Pachysolen, Hansenula, Issatchenkia, Trichosporon* Yamadazyma, and *Saccharomyces*.

8. The method of claim 7, wherein the microorganism is from the genus *Saccharomyces*.

9. The method of claim 1, wherein the microorganism comprises a ketol-acid reductoisomerase (KARI) that utilizes NADH.

10. The method of claim 1, further comprising recovering the isobutanol.

11. The method of claim 10, wherein the isobutanol is recovered by distillation, azeotropic distillation, liquid-liquid extraction, adsorption, gas stripping, membrane evaporation, pervaporation, or combinations thereof.

\* \* \* \* \*

SEQUENCE LISTING

<160> NUMBER OF SEQ ID NOS: 250

<210> SEQ ID NO 1
<211> LENGTH: 38
<212> TYPE: DNA
<213> ORGANISM: Artificial Sequence
<220> FEATURE:
<223> OTHER INFORMATION: oBP1329

<400> SEQUENCE: 1
aattggcgcg ccgtgtagac gtagtataac agtatatc        38

<210> SEQ ID NO 2
<211> LENGTH: 48
<212> TYPE: DNA
<213> ORGANISM: Artificial Sequence
<220> FEATURE:
<223> OTHER INFORMATION: oBP1333

<400> SEQUENCE: 2
atctgtcagc agcagcggac atctttatat tatcaatatt tgtgtttg        48

<210> SEQ ID NO 3
<211> LENGTH: 50
<212> TYPE: DNA
<213> ORGANISM: Artificial Sequence
<220> FEATURE:
<223> OTHER INFORMATION: oBP1334

<400> SEQUENCE: 3
aaacacaaat attgataata taaagatgtc cgctgctgct gacagattga        50

<210> SEQ ID NO 4
<211> LENGTH: 36
<212> TYPE: DNA
<213> ORGANISM: Artificial Sequence
<220> FEATURE:
<223> OTHER INFORMATION: oBP1335

<400> SEQUENCE: 4
ttaagtttaa acttagtcct cgtgtaagtc taattc        36

<210> SEQ ID NO 5
<211> LENGTH: 25
<212> TYPE: DNA
<213> ORGANISM: Artificial Sequence
<220> FEATURE:
<223> OTHER INFORMATION: oBP1341

<400> SEQUENCE: 5
gacctaataa ccacctgtgc tggtg        25

<210> SEQ ID NO 6
<211> LENGTH: 25
<212> TYPE: DNA
<213> ORGANISM: Artificial Sequence
<220> FEATURE:
<223> OTHER INFORMATION: oBP1342

<400> SEQUENCE: 6
agcccgaaag agttatcgtt actcc        25

<210> SEQ ID NO 7
<211> LENGTH: 21
<212> TYPE: DNA
<213> ORGANISM: Artificial Sequence

```
<220> FEATURE:
<223> OTHER INFORMATION: oBP1344

<400> SEQUENCE: 7
aatatcaacg tccttgacac t                                              21

<210> SEQ ID NO 8
<211> LENGTH: 25
<212> TYPE: DNA
<213> ORGANISM: Artificial Sequence
<220> FEATURE:
<223> OTHER INFORMATION: oBP1345

<400> SEQUENCE: 8
cacatctgaa atcatcgtaa ggaac                                          25

<210> SEQ ID NO 9
<211> LENGTH: 5036
<212> TYPE: DNA
<213> ORGANISM: Artificial Sequence
<220> FEATURE:
<223> OTHER INFORMATION: pBP3518

<400> SEQUENCE: 9
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt cgagctcggt acccggggat   420
ccggcgcgcc gtttaaactc atgtaattag ttatgtcacg cttacattca cgccctcctc   480
ccacatccgc tctaaccgaa aggaaggag ttagacaacc tgaagtctag gtccctattt   540 attttttta atagttatgt tagtattaag aacgttattt atatttcaaa ttttctttt    600 ttttctgtac aaacgcgtgt acgcatgtaa cattatactg aaaaccttgc ttgagaaggt   660
tttgggacgc tcgaaggctt taatttgcgg ggccggccgc attgcggatt acgtattcta   720
atgttcagta ccgttcgtat aatgtatgct atacgaagtt atgcagattg tactgagagt   780
gcaccatacc acctttttcaa ttcatcattt tttttttatt ctttttttg atttcggttt   840 ccttgaaatt tttttgattc ggtaatctcc gaacagaagg aagaacgaag gaaggagcac   900
agacttagat tggtatatat acgcatatgt agtgttgaag aaacatgaaa ttgcccagta   960
ttcttaaccc aactgcacag aacaaaaacc tgcaggaaac gaagataaat catgtcgaaa  1020
gctacatata aggaacgtgc tgctactcat cctagtcctg ttgctgccaa gctatttaat  1080
atcatgcacg aaaagcaaac aaacttgtgt gcttcattgg atgttcgtac caccaaggaa  1140
ttactggagt tagttgaagc attaggtccc aaaatttgtt tactaaaaac acatgtggat  1200
atcttgactg atttttccat ggagggcaca gttaagccgc taaaggcatt atccgccaag  1260
tacaattttt tactcttcga agacagaaaa tttgctgaca ttggtaatac agtcaaattg  1320
cagtactctg cggtgtata cagaatagca gaatgggcag acattacgaa tgcacacggt  1380
gtggtgggcc caggtattgt tagcggttg aagcaggcgg cagaagaagt aacaaaggaa  1440
cctagaggcc ttttgatgtt agcagaattg tcatgcaagg gctccctatc tactggagaa  1500
```

```
tatactaagg gtactgttga cattgcgaag agcgacaaag attttgttat cggctttatt      1560
gctcaaagag acatgggtgg aagagatgaa ggttacgatt ggttgattat gacacccggt      1620
gtgggtttag atgacaaggg agacgcattg ggtcaacagt atagaaccgt ggatgatgtg      1680
gtctctacag gatctgacat tattattgtt ggaagaggac tatttgcaaa gggaagggat      1740
gctaaggtag agggtgaacg ttacagaaaa gcaggctggg aagcatattt gagaagatgc      1800
ggccagcaaa actaaaaaac tgtattataa gtaaatgcat gtatactaaa ctcacaaatt      1860
agagcttcaa tttaattata tcagttatta ccctatgcgg tgtgaaatac cgcacagatg      1920
cgtaaggaga aaataccgca tcaggaaatt gtaagcgtta atattttgtt aaaattcgcg      1980
ttaaattttt gttaaatcag ctcatttttt aaccaatagg ccgaaatcgg caaaatccct      2040
tataaatcaa aagaatagac cgagataggg ttgagtgttg ttccagtttg gaacaagagt      2100
ccactattaa agaacgtgga ctccaacgtc aaagggcgaa aaaccgtcta tcagggcgat      2160
ggcccactac gtgaaccatc accctaatca agataacttc gtataatgta tgctatacga      2220
acggtaccag tgatgataca acgagttagc caaggtggcg gccgcattta ttggagaaag      2280
ataacatatc atactttccc ccactttttt cgaggctctt ctatatcata ttcataaatt      2340
agcattatgt catttctcat aactacttta tcacgttaga aattacttat tattattaaa      2400
ttaatacaaa atttagtaac caaataaata taaataaata tgcatattta aattttaaaa      2460
aaaaatccta tagagcaaaa ggattctcca ttataatatg agctatacac ctcttacgca      2520
ttttttgagg gtggttacaa caccactcat tcagaggctg tcggcacagt tgcttccagc      2580
atctggcgtc cgtatgtatg ggtgtatttt aaataataaa caaagtgcca caccttcacc      2640
aattatgtct ttaagaaatg gacaagttcc aaagagcttg cccaaggctc gacaaggatg      2700
tactttagaa tatctatatt caagtacgtg gcgcgcatat gtttgagtgt gcacacaata      2760
aaggttaatt aatctagagt cgacctgcag gcatgcaagc ttggcgtaat catggtcata      2820
gctgtttcct gtgtgaaatt gttatccgct cacaattcca cacaacatac gagccggaag      2880
cataaagtgt aaagcctggg gtgcctaatg agtgagctaa ctcacattaa ttgcgttgcg      2940
ctcactgccc gctttccagt cgggaaacct gtcgtgccag ctgcattaat gaatcggcca      3000
acgcgcgggg agaggcggtt tgcgtattgg gcgctcttcc gcttcctcgc tcactgactc      3060
gctgcgctcg gtcgttcggc tgcggcgagc ggtatcagct cactcaaagg cggtaatacg      3120
gttatccaca gaatcagggg ataacgcagg aaagaacatg tgagcaaaag gccagcaaaa      3180
ggccaggaac cgtaaaaagg ccgcgttgct ggcgtttttc cataggctcc gcccccctga      3240
cgagcatcac aaaaatcgac gctcaagtca gaggtggcga aacccgacag gactataaag      3300
ataccaggcg tttccccctg gaagctccct cgtgcgctct cctgttccga ccctgccgct      3360
taccggatac ctgtccgcct ttctcccttc gggaagcgtg gcgctttctc atagctcacg      3420
ctgtaggtat ctcagttcgg tgtaggtcgt tcgctccaag ctgggctgtg tgcacgaacc      3480
ccccgttcag cccgaccgct gcgccttatc cggtaactat cgtcttgagt ccaacccggt      3540
aagacacgac ttatcgccac tggcagcagc cactggtaac aggattagca gagcgaggta      3600
tgtaggcggt gctacagagt tcttgaagtg gtggcctaac tacggctaca ctagaaggac      3660
agtatttggt atctgcgctc tgctgaagcc agttaccttc ggaaaaagag ttggtagctc      3720
ttgatccggc aaacaaacca ccgctggtag cggtggtttt tttgtttgca agcagcagat      3780
tacgcgcaga aaaaaaggat ctcaagaaga tcctttgatc ttttctacgg ggtctgacgc      3840
tcagtggaac gaaaactcac gttaagggat tttggtcatg agattatcaa aaaggatctt      3900
```

```
cacctagatc cttttaaatt aaaaatgaag ttttaaatca atctaaagta tatatgagta    3960
aacttggtct gacagttacc aatgcttaat cagtgaggca cctatctcag cgatctgtct    4020
atttcgttca tccatagttg cctgactccc cgtcgtgtag ataactacga tacgggaggg    4080
cttaccatct ggccccagtg ctgcaatgat accgcgagac ccacgctcac cggctccaga    4140
tttatcagca ataaaccagc cagccggaag ggccgagcgc agaagtggtc ctgcaacttt    4200
atccgcctcc atccagtcta ttaattgttg ccgggaagct agagtaagta gttcgccagt    4260
taatagtttg cgcaacgttg ttgccattgc tacaggcatc gtggtgtcac gctcgtcgtt    4320
tggtatggct tcattcagct ccggttccca acgatcaagg cgagttacat gatcccccat    4380
gttgtgcaaa aaagcggtta gctccttcgg tcctccgatc gttgtcagaa gtaagttggc    4440
cgcagtgtta tcactcatgg ttatggcagc actgcataat tctcttactg tcatgccatc    4500
cgtaagatgc ttttctgtga ctggtgagta ctcaaccaag tcattctgag aatagtgtat    4560
gcggcgaccg agttgctctt gcccggcgtc aatacgggga ataccgcgc cacatagcag    4620 aactttaaaa gtgctcatca ttggaaaacg ttcttcgggg cgaaaactct caaggatctt    4680
accgctgttg agatccagtt cgatgtaacc cactcgtgca cccaactgat cttcagcatc    4740
ttttactttc accagcgttt ctgggtgagc aaaaacagga aggcaaaatg ccgcaaaaaa    4800
gggaataagg gcgacacgga aatgttgaat actcatactc ttccttttc aatattattg    4860 aagcatttat cagggttatt gtctcatgag cggatacata tttgaatgta tttagaaaaa    4920
taaacaaata ggggttccgc gcacatttcc ccgaaaagtg ccacctgacg tctaagaaac    4980
cattattatc atgacattaa cctataaaaa taggcgtatc acgaggccct ttcgtc        5036
```

<210> SEQ ID NO 10
<211> LENGTH: 7063
<212> TYPE: DNA
<213> ORGANISM: Artificial Sequence
<220> FEATURE:
<223> OTHER INFORMATION: pBP3518GPD*

<400> SEQUENCE: 10

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaagggg gatgtgctg caaggcgatt aagttgggta acgccagggt     360
tttcccagtc acgacgttgt aaaacgacgg ccagtgaatt cgagctcggt acccggggat     420
ccggcgcgcc gtgtagacgt agtataacag tatatctgac acgcacgtga tgaccacgta     480
atcgcatcgc ccctcacatc tcacctctca ccgctgactc agcttcacta aaaaggaaaa     540
tatatactct ttcccaggca aggtgacagc ggtccccgtc tcctccacaa aggcctctcc     600 tggggttga gcaagtctaa gtttacgtag cataaaaatt ctcggattgc gtcaaataat     660
aaaaaaagta actccacttc tacttctaca tcggaaaaac attccattca catatcgtct     720
ttggcctatc ttgttttgtc cttggtagat caggtcagta caaacgcaac acgaaagaac     780
aaaaaaagaa gaaaacagaa ggccaagaca gggtcaatga gactgttgtc ctcctactgt     840
ccctatgtct ctggccgatc acgcgccatt gtccctcaga aacaaatcaa acacccacac     900
```

```
cccgggcacc caaagtcccc acccacacca ccaatacgta aacggggcgc ccctgcagg      960
ccctcctgcg cgcggcctcc cgccttgctt ctctccctc cttttctt ttccagtttt      1020
ccctattttg tcccttttc cgcacaacaa gtatcagaat gggttcatca aatctatcca    1080
acctaattcg cacgtagact ggcttggtat tggcagtttc gcagttatat atatactacc    1140
atgagtgaaa ctgttacgtt accttaaatt cttctcct ttaattttct tttatcttac     1200
tctcctacat aagacatcaa gaaacaattg tatattgtac cccccccc tccacaaaca     1260
caaatattga taatataaag atgtccgctg ctgctgacag attgaacttg acatctggtc    1320
acttgaacgc tggtagaaag agatcatcct cctctgtctc tttgaaggct gccgaaaagc    1380
cattcaaggt caccgttatc ggttctggta actggggtac caccattgcc aaggtcgtcg    1440
ccgaaaactg caagggttac ccagaagttt ttgctccaat cgttcaaatg tgggttttg     1500
aagaggaaat taacggtgaa agttgactg aaattatcaa cactagacac caaaacgtga    1560
agtacttgcc cggtattacc ttgccagaca atttggttgc caatccagac ttgatcgata    1620
gtgtcaagga cgttgatatt atcgttttta acatcccaca ccaattccta ccacgtattt    1680
gttctcaatt gaagggtcat gtcgattctc acgttagagc tatctcctgc ttgaagggtt    1740
tcgaagttgg tgctaagggt gttcaattgt tatcctctta catcactgaa gagctaggta    1800
tccaatgtgg tgctttgtct ggtgctaaca tcgctaccga agtcgctcaa gagcactggt    1860
ctgaaaccac tgtcgcttac catatcccaa aggactttag aggtgaaggt aaagacgttg    1920
accacaaggt cctaaaggct ttgttccaca gaccatactt tcacgtttct gtcatcgaag    1980
atgtcgccgg tatctctatc tgtggcgctt taaagaacgt cgtcgccttg ggttgtggtt    2040
ttgttgaagg attgggttgg ggtaacaacg cctctgctgc tatccaacgt gtcggtttgg    2100
gtgaaatcat tagatttggt caaatgtttt tccctgaatc cagagaggaa acctactacc    2160
aagagtctgc cggtgttgct gacctaataa ccacctgtgc tggtggtaga aacgttaagg    2220
ttgccagatt gatggctact tccggtaagg acgcttggga atgtgaaaag gaattgttga    2280
acggtcaatc cgctcaaggt ttgattactt gtaaggaagt tcacgaatgg ttggaaactt    2340
gtggcagcgt tgaagatttt ccattattcg aagctgtcta ccaaatcgtc tacaataact    2400
accctatgaa aaacttgcca gatatgatcg aggaattaga cttacacgag gactaagttt    2460
aaactcatgt aattagttat gtcacgctta cattcacgcc ctcctcccac atccgctcta    2520
accgaaaagg aaggagttag acaacctgaa gtctaggtcc ctatttattt tttttaatag    2580
ttatgttagt attaagaacg ttatttatat ttcaaatttt tcttttttt ctgtacaaac    2640
gcgtgtacgc atgtaacatt atactgaaaa ccttgcttga aaggttttg ggacgctcga    2700
aggctttaat ttgcggggcc ggccgcattg cggattacgt attctaatgt tcagtaccgt    2760
tcgtataatg tatgctatac gaagttatgc agattgtact gagagtgcac cataccacct    2820
tttcaattca tcatttttt tttattcttt tttttgattt cggtttcctt gaaatttttt    2880
tgattcggta atctccgaac agaaggaaga acgaaggaag gagcacagac ttagattggt    2940
atatatacgc atatgtagtg ttgaagaaac atgaaattgc ccagtattct aacccaact    3000
gcacagaaca aaaacctgca ggaaacgaag ataaatcatg tcgaaagcta catataagga    3060
acgtgctgct actcatccta gtcctgttgc tgccaagcta tttaatatca tgcacgaaaa    3120
gcaaacaaac ttgtgtgctt cattggatgt tcgtaccacc aaggaattac tggagttagt    3180
tgaagcatta ggtcccaaaa tttgtttact aaaaacacat gtggatatct tgactgattt    3240
ttccatggag ggcacagtta agccgctaaa ggcattatcc gccaagtaca attttttact    3300
```

```
cttcgaagac agaaaatttg ctgacattgg taatacagtc aaattgcagt actctgcggg    3360
tgtatacaga atagcagaat gggcagacat tacgaatgca cacggtgtgg tgggcccagg    3420
tattgttagc ggtttgaagc aggcggcaga agaagtaaca aaggaaccta gaggcctttt    3480
gatgttagca gaattgtcat gcaagggctc cctatctact ggagaatata ctaagggtac    3540
tgttgacatt gcgaagagcg acaaagattt tgttatcggc tttattgctc aaagagacat    3600
gggtggaaga gatgaaggtt acgattggtt gattatgaca cccggtgtgg gtttagatga    3660
caagggagac gcattgggtc aacagtatag aaccgtggat gatgtggtct ctacaggatc    3720
tgacattatt attgttggaa gaggactatt tgcaaaggga agggatgcta aggtagaggg    3780
tgaacgttac agaaaagcag gctgggaagc atatttgaga agatgcggcc agcaaaacta    3840
aaaaactgta ttataagtaa atgcatgtat actaaactca caaattagag cttcaattta    3900
attatatcag ttattaccct atgcggtgtg aaataccgca cagatgcgta aggagaaaat    3960
accgcatcag gaaattgtaa gcgttaatat tttgttaaaa ttcgcgttaa attttttgtta   4020 aatcagctca ttttttaacc aataggccga atcggcaaa atcccttata aatcaaaaga    4080
atagaccgag atagggttga gtgttgttcc agtttggaac aagagtccac tattaaagaa    4140
cgtggactcc aacgtcaaag ggcgaaaaac cgtctatcag ggcgatggcc cactacgtga    4200
accatcaccc taatcaagat aacttcgtat aatgtatgct atacgaacgg taccagtgat    4260
gatacaacga gttagccaag gtggcggccg catttattgg agaaagataa catatcatac    4320
tttcccccac ttttttcgag gctcttctat atcatattca taaattagca tttatgtcatt    4380 tctcataact actttatcac gttagaaatt acttattatt attaaattaa tacaaaattt    4440
agtaaccaaa taaatataaa taaatatgca tatttaaatt ttaaaaaaaa aatcctatag    4500
agcaaaagga ttctccatta taatatgagc tatacacctc ttacgcattt tttgagggtg    4560
gttacaacac cactcattca gaggctgtcg gcacagttgc ttccagcatc tggcgtccgt    4620
atgtatgggt gtattttaaa taataaacaa agtgccacac cttcaccaat tatgtctttta   4680 agaaatggac aagttccaaa gagcttgccc aaggctcgac aaggatgtac tttagaatat    4740
ctatattcaa gtacgtggcg cgcatatgtt tgagtgtgca cacaataaag gttaattaat    4800
ctagagtcga cctgcaggca tgcaagcttg gcgtaatcat ggtcatagct gtttcctgtg    4860
tgaaattgtt atccgctcac aattccacac aacatacgag ccggaagcat aaagtgtaaa    4920
gcctggggtg cctaatgagt gagctaactc acattaattg cgttgcgctc actgcccgct    4980
ttccagtcgg gaaacctgtc gtgccagctg cattaatgaa tcggccaacg cgcgggaga    5040 ggcggtttgc gtattgggcg ctcttccgct tcctcgctca ctgactcgct gcgctcggtc    5100
gttcggctgc ggcgagcggt atcagctcac tcaaaggcgg taatacggtt atccacagaa    5160
tcaggggata acgcaggaaa gaacatgtga gcaaaaggcc agcaaaaggc caggaaccgt    5220
aaaaaggccg cgttgctggc gtttttccat aggctccgcc ccctgacga gcatcacaaa     5280 aatcgacgct caagtcagag gtggcgaaac ccgacaggac tataaagata ccaggcgttt    5340
ccccctggaa gctccctcgt gcgctctcct gttccgaccc tgccgcttac cggatacctg    5400 tccgccttc tcccttcggg aagcgtggcg ctttctcata gctcacgctg taggtatctc     5460
agttcggtgt aggtcgttcg ctccaagctg ggctgtgtgc acgaaccccc cgttcagccc    5520
gaccgctgcg ccttatccgg taactatcgt cttgagtcca acccgtaag acacgactta     5580 tcgccactgg cagcagccac tggtaacagg attagcagag cgaggtatgt aggcggtgct    5640
```

```
acagagttct tgaagtggtg gcctaactac ggctacacta gaaggacagt atttggtatc    5700
tgcgctctgc tgaagccagt taccttcgga aaaagagttg gtagctcttg atccggcaaa    5760
caaaccaccg ctggtagcgg tggttttttt gtttgcaagc agcagattac gcgcagaaaa    5820
aaaggatctc aagaagatcc tttgatcttt tctacggggt ctgacgctca gtggaacgaa    5880
aactcacgtt aagggatttt ggtcatgaga ttatcaaaaa ggatcttcac ctagatcctt    5940
ttaaattaaa aatgaagttt taaatcaatc taaagtatat atgagtaaac ttggtctgac    6000
agttaccaat gcttaatcag tgaggcacct atctcagcga tctgtctatt tcgttcatcc    6060
atagttgcct gactccccgt cgtgtagata actacgatac gggagggctt accatctggc    6120
cccagtgctg caatgatacc gcgagaccca cgctcaccgg ctccagattt atcagcaata    6180
aaccagccag ccggaagggc cgagcgcaga agtggtcctg caactttatc cgcctccatc    6240
cagtctatta attgttgccg ggaagctaga gtaagtagtt cgccagttaa tagtttgcgc    6300
aacgttgttg ccattgctac aggcatcgtg gtgtcacgct cgtcgtttgg tatggcttca    6360
ttcagctccg gttcccaacg atcaaggcga gttacatgat cccccatgtt gtgcaaaaaa    6420
gcggttagct ccttcggtcc tccgatcgtt gtcagaagta agttggccgc agtgttatca    6480
ctcatggtta tggcagcact gcataattct cttactgtca tgccatccgt aagatgcttt    6540
tctgtgactg gtgagtactc aaccaagtca ttctgagaat agtgtatgcg gcgaccgagt    6600
tgctcttgcc cggcgtcaat acgggataat accgcgccac atagcagaac tttaaaagtg    6660
ctcatcattg gaaaacgttc ttcggggcga aaactctcaa ggatcttacc gctgttgaga    6720
tccagttcga tgtaacccac tcgtgcaccc aactgatctt cagcatcttt tactttcacc    6780
agcgtttctg ggtgagcaaa aacaggaagg caaaatgccg caaaaaaggg aataagggcg    6840
acacggaaat gttgaatact catactcttc ctttttcaat attattgaag catttatcag    6900
ggttattgtc tcatgagcgg atacatattt gaatgtattt agaaaaataa acaaatag gg    6960 gttccgcgca catttccccg aaaagtgcca cctgacgtct aagaaaccat tattatcatg    7020
acattaacct ataaaaatag gcgtatcacg aggccctttc gtc                      7063
```

<210> SEQ ID NO 11
<211> LENGTH: 7555
<212> TYPE: DNA
<213> ORGANISM: Artificial Sequence
<220> FEATURE:
<223> OTHER INFORMATION: p423:Gal1p-CRE-ADHt

<400> SEQUENCE: 11

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accataaatt cccgttttaa gagcttggtg agcgctagga gtcactgcca ggtatcgttt     240
gaacacggca ttagtcaggg aagtcataac acagtccttt cccgcaattt tctttttcta     300
ttactcttgg cctcctctag tacactctat atttttttat gcctcggtaa tgattttcat     360 ttttttttt cccctagcgg atgactcttt tttttcttta gcgattggca ttatcacata     420
atgaattata cattatataa agtaatgtga tttcttcgaa gaatatacta aaaaatgagc     480
aggcaagata aacgaaggca aagatgacag agcagaaagc cctagtaaag cgtattacaa     540
atgaaaccaa gattcagatt gcgatctctt taaagggtgg tccccctagcg atagagcact     600 cgatcttccc agaaaaagag gcagaagcag tagcagaaca ggccacacaa tcgcaagtga     660
```

```
ttaacgtcca cacaggtata gggtttctgg accatatgat acatgctctg gccaagcatt    720
ccggctggtc gctaatcgtt gagtgcattg gtgacttaca catagacgac catcacacca    780
ctgaagactg cgggattgct ctcggtcaag cttttaaaga ggccctactg gcgcgtggag    840
taaaaaggtt tggatcagga tttgcgcctt tggatgaggc actttccaga gcggtggtag    900
atctttcgaa caggccgtac gcagttgtcg aacttggttt gcaaagggag aaagtaggag    960
atctctcttg cgagatgatc ccgcattttc ttgaaagctt tgcagaggct agcagaatta   1020
ccctccacgt tgattgtctg cgaggcaaga atgatcatca ccgtagtgag agtgcgttca   1080
aggctcttgc ggttgccata agagaagcca cctcgcccaa tggtaccaac gatgttccct   1140
ccaccaaagg tgttcttatg tagtgacacc gattatttaa agctgcagca tacgatatat   1200
atacatgtgt atatatgtat acctatgaat gtcagtaagt atgtatacga acagtatgat   1260
actgaagatg acaaggtaat gcatcattct atacgtgtca ttctgaacga ggcgcgcttt   1320 cctttttct ttttgctttt tcttttttt tctcttgaac tcgacggatc tatgcggtgt    1380
gaaataccgc acagatgcgt aaggagaaaa taccgcatca ggaaattgta aacgttaata   1440
ttttgttaaa attcgcgtta aattttttgtt aaatcagctc atttttttaac caataggccg   1500 aaatcggcaa aatcccttat aaatcaaaag aatagaccga gatagggttg agtgttgttc   1560
cagtttggaa caagagtcca ctattaaaga acgtggactc caacgtcaaa gggcgaaaaa   1620
ccgtctatca gggcgatggc ccactacgtg aaccatcacc ctaatcaagt tttttggggt   1680
cgaggtgccg taaagcacta atcggaacc ctaaagggag ccccgatttt agagcttgac    1740
ggggaaagcc ggcgaacgtg gcgagaaagg aagggaagaa agcgaaagga gcgggcgcta   1800
gggcgctggc aagtgtagcg gtcacgctgc gcgtaaccac cacacccgcc gcgcttaatg   1860
cgccgctaca gggcgcgtcg cgccattcgc cattcaggct gcgcaactgt tgggaagggc   1920
gatcggtgcg ggcctcttcg ctattacgcc agctggcgaa aggggatgt gctgcaaggc    1980 gattaagttg ggtaacgcca gggttttccc agtcacgacg ttgtaaaacg acggccagtg   2040
agcgcgcgta atacgactca ctataggcgc aattgggtac cgggcccccc ctcgaggtcg   2100
acggtatcga taagcttgat tagaagccgc cgagcgggcg acagccctcc gacggaagac   2160
tctcctccgt gcgtcctcgt cttcaccggt cgcgttcctg aaacgcagat gtgcctcgcg   2220
ccgcactgct ccgaacaata aagattctac aatactagct tttatggtta tgaagaggaa   2280
aaattggcag taacctggcc ccacaaacct tcaaattaac gaatcaaatt aacaaccata   2340
ggatgataat gcgattagtt ttttagcctt atttctgggg taattaatca gcgaagcgat   2400
gatttttgat ctattaacag atatataaat ggaaaagctg cataaccact ttaactaata   2460
cttccaacat tttcagtttg tattacttct tattcaaatg tcataaaagt atcaacaaaa   2520
aattgttaat atacctctat actttaacgt caaggagaaa aatgtccaat ttactgcccg   2580
tacaccaaaa tttgcctgca ttaccggtcg atgcaacgag tgatgaggtt cgcaagaacc   2640
tgatggacat gttcagggat cgccaggcgt tttctgagca tacctggaaa atgcttctgt   2700
ccgtttgccg gtcgtgggcg gcatggtgca agttgaataa ccggaaatgg tttcccgcag   2760
aacctgaaga tgttcgcgat tatcttctat atcttcaggc gcgcggtctg gcagtaaaaa   2820
ctatccagca acatttgggc cagctaaaca tgcttcatcg tcggtccggg ctgccacgac   2880
caagtgacag caatgctgtt tcactggtta tgcggcggat ccgaaaagaa aacgttgatg   2940
ccggtgaacg tgcaaaacag gctctagcgt tcgaacgcac tgatttcgac caggttcgtt   3000
```

```
cactcatgga aaatagcgat cgctgccagg atatacgtaa tctggcattt ctggggattg     3060
cttataacac cctgttacgt atagccgaaa ttgccaggat cagggttaaa gatatctcac     3120
gtactgacgg tgggagaatg ttaatccata ttggcagaac gaaaacgctg gttagcaccg     3180
caggtgtaga gaaggcactt agcctggggg taactaaact ggtcgagcga tggatttccg     3240
tctctggtgt agctgatgat ccgaataact acctgttttg ccgggtcaga aaaatggtg      3300 ttgccgcgcc atctgccacc agccagctat caactcgcgc cctggaaggg atttttgaag     3360
caactcatcg attgatttac ggcgctaagg atgactctgg tcagagatac ctggcctggt     3420
ctggacacag tgcccgtgtc ggagccgcgc gagatatggc ccgcgctgga gtttcaatac     3480
cggagatcat gcaagctggt ggctggacca atgtaaatat tgtcatgaac tatatccgta     3540
acctggatag tgaaacaggg gcaatggtgc gcctgctgga agatggcgat taggagtaag     3600
cgaatttctt atgatttatg attttttatta ttaaataagt tataaaaaaa ataagtgtat     3660
acaaatttta aagtgactct taggttttaa aacgaaaatt cttattcttg agtaactctt     3720
tcctgtaggt caggttgctt tctcaggtat agcatgaggt cgctcttatt gaccacacct     3780
ctaccggcat gccgagcaaa tgcctgcaaa tcgctcccca tttcacccaa ttgtagatat     3840
gctaactcca gcaatgagtt gatgaatctc ggtgtgtatt ttatgtcctc agaggacaac     3900
acctgtggtg ttctagagcg gccgccaccg cggtggagct ccagcttttg ttcccttttag    3960 tgagggttaa ttgcgcgctt ggcgtaatca tggtcatagc tgtttcctgt gtgaaattgt     4020
tatccgctca caattccaca acatagga gccggaagca taaagtgtaa agcctggggt       4080
gcctaatgag tgaggtaact cacattaatt gcgttgcgct cactgcccgc tttccagtcg     4140
ggaaacctgt cgtgccagct gcattaatga atcggccaac gcgcggggag aggcggtttg     4200
cgtattgggc gctcttccgc ttcctcgctc actgactcgc tgcgctcggt cgttcggctg     4260
cggcgagcgg tatcagctca ctcaaaggcg gtaatacggt tatccacaga atcaggggat     4320
aacgcaggaa agaacatgtg agcaaaaggc cagcaaaagg ccaggaaccg taaaaaggcc     4380
gcgttgctgg cgttttttcca taggctccgc cccctgacg agcatcacaa aaatcgacgc     4440
tcaagtcaga ggtggcgaaa cccgacagga ctataaagat accaggcgtt ccccctgga     4500 agctccctcg tgcgctctcc tgttccgacc ctgccgctta ccggatacct gtccgccttt     4560
ctcccttcgg gaagcgtggc gctttctcat agctcacgct gtaggtatct cagttcggtg    4620
taggtcgttc gctccaagct gggctgtgtg cacgaacccc ccgttcagcc cgaccgctgc    4680
gccttatccg gtaactatcg tcttgagtcc aacccggtaa gacacgactt atcgccactg    4740
gcagcagcca ctggtaacag gattagcaga gcgaggtatg taggcggtgc tacagagttc    4800
ttgaagtggt ggcctaacta cggctacact agaaggacag tatttggtat ctgcgctctg    4860
ctgaagccag ttaccttcgg aaaaagagtt ggtagctctt gatccggcaa acaaaccacc    4920
gctggtagcg gtggtttttt tgtttgcaag cagcagatta cgcgcagaaa aaaaggatct    4980
caagaagatc ctttgatctt ttctacgggg tctgacgctc agtggaacga aaactcacgt    5040
taagggattt tggtcatgag attatcaaaa aggatcttca cctagatcct tttaaattaa    5100
aaatgaagtt ttaaatcaat ctaaagtata tatgagtaaa cttggtctga cagttaccaa    5160
tgcttaatca gtgaggcacc tatctcagcg atctgtctat ttcgttcatc catagttgcc    5220
tgactccccg tcgtgtagat aactacgata cgggagggct taccatctgg ccccagtgct    5280
gcaatgatac cgcgagaccc acgctcaccg gctccagatt tatcagcaat aaaccagcca    5340
gccggaaggg ccgagcgcag aagtggtcct gcaactttat ccgcctccat ccagtctatt    5400
```

```
aattgttgcc gggaagctag agtaagtagt tcgccagtta atagtttgcg caacgttgtt    5460
gccattgcta caggcatcgt ggtgtcacgc tcgtcgtttg gtatggcttc attcagctcc    5520
ggttcccaac gatcaaggcg agttacatga tcccccatgt tgtgcaaaaa agcggttagc    5580
tccttcggtc ctccgatcgt tgtcagaagt aagttggccg cagtgttatc actcatggtt    5640
atggcagcac tgcataattc tcttactgtc atgccatccg taagatgctt ttctgtgact    5700
ggtgagtact caaccaagtc attctgagaa tagtgtatgc ggcgaccgag ttgctcttgc    5760
ccggcgtcaa tacgggataa taccgcgcca catagcagaa ctttaaaagt gctcatcatt    5820
ggaaaacgtt cttcggggcg aaaactctca aggatcttac cgctgttgag atccagttcg    5880
atgtaaccca ctcgtgcacc caactgatct tcagcatctt ttactttcac cagcgtttct    5940
gggtgagcaa aaacaggaag gcaaaatgcc gcaaaaaagg gaataagggc gacacggaaa    6000
tgttgaatac tcatactctt ccttttcaa tattattgaa gcatttatca gggttattgt     6060
ctcatgagcg gatacatatt tgaatgtatt tagaaaaata acaaataggg gttccgcgc     6120
acatttcccc gaaaagtgcc acctgaacga agcatctgtg cttcattttg tagaacaaaa    6180
atgcaacgcg agagcgctaa ttttcaaac aaagaatctg agctgcattt ttacagaaca     6240
gaaatgcaac gcgaaagcgc tattttacca acgaagaatc tgtgcttcat ttttgtaaaa    6300
caaaaatgca acgcgagagc gctaatttt caaacaaaga atctgagctg cattttaca     6360
gaacagaaat gcaacgcgag agcgctattt taccaacaaa gaatctatac ttcttttttg    6420
ttctacaaaa atgcatcccg agagcgctat tttctaaca aagcatctta gattactttt     6480
tttctccttt gtgcgctcta taatgcagtc tcttgataac ttttgcact gtaggtccgt     6540
taaggttaga agaaggctac tttggtgtct attttctctt ccataaaaaa agcctgactc    6600
cacttcccgc gtttactgat tactagcgaa gctgcgggtg catttttca agataaaggc     6660
atccccgatt atattctata ccgatgtgga ttgcgcatac tttgtgaaca gaaagtgata    6720
gcgttgatga ttcttcattg gtcagaaaat tatgaacggt ttcttctatt tgtctctat     6780
atactacgta taggaaatgt ttacattttc gtattgtttt cgattcactc tatgaatagt    6840
tcttactaca attttttgt ctaaagagta atactagaga taaacataaa aaatgtagag      6900
gtcgagttta gatgcaagtt caaggagcga aaggtggatg ggtaggttat atagggatat    6960
agcacagaga tatatagcaa agagatactt ttgagcaatg tttgtggaag cggtattcgc    7020
aatattttag tagctcgtta cagtccggtg cgttttggt tttttgaaag tgcgtcttca     7080
gagcgctttt ggttttcaaa agcgctctga agttcctata ctttctagag aataggaact    7140
tcggaatagg aacttcaaag cgtttccgaa aacgagcgct tccgaaaatg caacgcgagc    7200
tgcgcacata cagctcactg ttcacgtcgc acctatatct gcgtgttgcc tgtatatata    7260
tatacatgag aagaacggca tagtgcgtgt ttatgcttaa atgcgtactt atatgcgtct    7320
atttatgtag gatgaaaggt agtctagtac ctcctgtgat attatcccat tccatgcggg    7380
gtatcgtatg cttccttcag cactacccctt tagctgttct atatgctgcc actcctcaat   7440
tggattagtc tcatccttca atgctatcat ttcctttgat attggatcat ctaagaaacc    7500
attattatca tgacattaac ctataaaat aggcgtatca cgaggccctt tcgtc          7555
```

<210> SEQ ID NO 12
<211> LENGTH: 12298
<212> TYPE: DNA
<213> ORGANISM: Artificial Sequence
<220> FEATURE:

<223> OTHER INFORMATION: pLH804::L2V4

<400> SEQUENCE: 12

```
tcccattacc gacatttggg cgctatacgt gcatatgttc atgtatgtat ctgtatttaa      60
aacacttttg tattattttt cctcatatat gtgtataggt ttatacggat gatttaatta     120
ttacttcacc acccttttatt tcaggctgat atcttagcct tgttactaga ttaatcatgt     180
aattagttat gtcacgctta cattcacgcc ctccccccac atccgctcta accgaaaagg     240
aaggagttag acaacctgaa gtctaggtcc ctatttattt ttttatagtt atgttagtat     300
taagaacgtt atttatattt caaattttc ttttttttct gtacagacgc gtgtacgcat     360
gtaacattat actgaaaacc ttgcttgaga aggttttggg acgctcgaag gctttaattt     420
gcgggcggcc gcacctggta aaacctctag tggagtagta gatgtaatca atgaagcgga     480
agccaaaaga ccagagtaga ggcctataga agaaactgcg ataccttttg tgatggctaa     540
acaaacagac atcttttat atgtttttac ttctgtatat cgtgaagtag taagtgataa     600
gcgaatttgg ctaagaacgt tgtaagtgaa caagggacct cttttgcctt tcaaaaaagg     660
attaaatgga gttaatcatt gagatttagt tttcgttaga ttctgtatcc ctaaataact     720
cccttacccg acgggaaggc acaaaagact tgaataatag caaacggcca gtagccaaga     780
ccaaataata ctagagttaa ctgatggtct taaacaggca ttacgtggtg aactccaaga     840
ccaatataca aaatatcgat aagttattct tgcccaccaa tttaaggagc ctacatcagg     900
acagtagtac cattcctcag agaagaggta tacataacaa gaaaatcgcg tgaacacctt     960
atataactta gcccgttatt gagctaaaaa accttgcaaa atttcctatg aataagaata    1020
cttcagacgt gataaaaatt tactttctaa ctcttctcac gctgccccta tctgttcttc    1080
cgctctaccg tgagaaataa agcatcgagt acggcagttc gctgtcactg aactaaaaca    1140
ataaggctag ttcgaatgat gaacttgctt gctgtcaaac ttctgagttg ccgctgatgt    1200
gacactgtga caataaattc aaaccggtta tagcggtctc ctccggtacc ggttctgcca    1260
cctccaatag agctcagtag gagtcagaac ctctgcggtg gctgtcagtg actcatccgc    1320
gtttcgtaag ttgtgcgcgt gcacatttcg cccgttcccg ctcatcttgc agcaggcgga    1380
aattttcatc acgctgtagg acgcaaaaaa aaaataatta atcgtacaag aatcttggaa    1440
aaaaaattga aaattttgt ataaaaggga tgacctaact tgactcaatg gcttttacac    1500
ccagtatttt ccctttcctt gtttgttaca attatagaag caagacaaaa acatatagac    1560
aacctattcc taggagttat attttttttac cctaccagca atataagtaa aaaactgttt    1620
aaacagtatg gaagaatgta agatggctaa gatttactac caagaagact gtaacttgtc    1680
cttgttggat ggtaagacta tcgccgttat cggttacggt tctcaaggtc acgctcatgc    1740
cctgaatgct aaggaatccg gttgtaacgt tatcattggt ttatacgaag gtgcggagga    1800
gtggaaaaga gctgaagaac aaggtttcga agtctacacc gctgctgaag ctgctaagaa    1860
ggctgacatc attatgatct tgatcccaga tgaaaagcag gctaccatgt acaaaaacga    1920
catcgaacca aacttggaag ccggtaacat gttgatgttc gctcacggtt tcaacatcca    1980
tttcggttgt attgttccac caaggacgt tgatgtcact atgatcgctc caaagggtcc    2040
aggtcacacc gttagatccg aatacgaaga aggtaaaggt gtcccatgct tggttgctgt    2100
cgaacaagac gctactggca aggctttgga tatggctttg gcctacgctt tagccatcgg    2160
tggtgctaga gccggtgtct tggaaactac cttcagaacc gaaactgaaa ccgacttgtt    2220
cggtgaacaa gctgttttat gtggtggtgt ctgcgctttg atgcaggccg gttttgaaac    2280
```

```
cttggttgaa gccggttacg acccaagaaa cgcttacttc gaatgtatcc acgaaatgaa    2340
gttgatcgtt gacttgatct accaatctgg tttctccggt atgcgttact ctatctccaa    2400
cactgctgaa tacggtgact acattaccgg tccaaagatc attactgaag ataccaagaa    2460
ggctatgaag aagattttgt ctgacattca agatggtacc tttgccaagg acttcttggt    2520
tgacatgtct gatgctggtt cccaggtcca cttcaaggct atgagaaagt tggcctccga    2580
acacccagct gaagttgtcg gtgaagaaat tagatccttg tactcctggt ccgacgaaga    2640
caagttgatt aacaactgag gccctgcagg ccagaggaaa ataatatcaa gtgctggaaa    2700 cttttttctct tggaattttt gcaacatcaa gtcatagtca attgaattga cccaatttca    2760
catttaagat tttttttttt tcatccgaca tacatctgta cactaggaag ccctgttttt    2820
ctgaagcagc ttcaaatata tatttttttt acatatttat tatgattcaa tgaacaatct    2880
aattaaatcg aaaacaagaa ccgaaacgcg aataaataat ttatttagat ggtgacaagt    2940
gtataagtcc tcatcgggac agctacgatt tctctttcgg ttttggctga gctactggtt    3000
gctgtgacgc agcggcatta gcgcggcgtt atgagctacc ctcgtggcct gaaagatggc    3060
gggaataaag cggaactaaa aattactgac tgagccatat tgaggtcaat ttgtcaactc    3120
gtcaagtcac gtttggtgga cggccccttt ccaacgaatc gtatatacta acatgcgcgc    3180
gcttcctata tacacatata catatatata tatatatata tgtgtgcgtg tatgtgtaca    3240
cctgtattta atttccttac tcgcgggttt ttctttttttc tcaattcttg gcttcctctt    3300
tctcgagcgg accggatcct cgcgaactcc aaaatgagct atcaaaaacg atagatcgat    3360
taggatgact ttgaaatgac tccgcagtgg actggccgtt aatttcaagc gtgagtaaaa    3420
tagtgcatga caaagatga gctaggcttt tgtaaaaata tcttacgttg taaaatttta    3480
gaaatcatta tttccttcat atcatttttgt cattgaccttt cagaagaaaa gagccgacca    3540
ataatataaa taaataaata aaaataatat tccattattt ctaaacagat tcaatactca    3600
ttaaaaaact atatcaatta atttgaatta acttaattaa ttattttttg ccagtttctt    3660
caggcttcca aaagtctgtt acggctcccc tagaagcaga cgaaacgatg tgagcatatt    3720
taccaaggat accgcgtgaa tagagcggtg gcaattcaat ggtctcttga cgatgtttta    3780
actcttcatc ggagatatca aagtgtaatt ccttagtgtc ttggtcaata gtgactatgt    3840
ctcctgtttg caggtaggcg attggaccgc catcttgtgc ttcaggagcg atatgaccca    3900
cgacaagacc ataagtacca cctgagaagc ggccatctgt cagaagggca acttttttcac    3960 cttgcccttt accaacaatc attgatgaaa gggaaagcat ttcaggcata ccaggaccgc    4020
cctttggtcc tacaaaacgt acgacaacaa catcaccatc aacaatatca tcattcaaga    4080
cagcttcaat ggcttcttct tcagaattaa agaccttagc aggaccgaca tgacgacgca    4140
cttttacacc agaaactttg gcaacggcac cgtctggagc caagttacca tggagaataa    4200
tgaccggacc atcttcacgt ttaggatttt caagcggcat aataaccttt tgaccaggtg    4260
ttaaatcatc aaaagccttc aaattttcag cgactgtttt gccagtacaa gtgatacggt    4320
caccatgaag gaagccattt ttaaggagat atttcataac tgctggtacc cctccgacct    4380
tgtaaaggtc ttggaataca tattgaccag aaggttcaa atcagccaaa tgaggaactt    4440
tttcttggaa agtattgaaa tcatcaagtg tcaattccac attagcagca tgggcaatag    4500
ctaagaggtg aagggttgag ttggttgaac ctcccagagc catagttaca gtaatagcat    4560
cttcaaaagc ttcacgcgtt aaaatgtcag aaggttttaa gcccatttcg agcattttga    4620
```

```
caacagcgcg accagcttct tcaatatctg ctttcttttc tgcggattca gccgggtgag    4680
aagatgaacc cggaaggcta agtcccaaaa cttcaatagc tgtcgccatt gtgttagcag    4740
tatacatacc accgcagcct ccaggaccgg gacaagcatt acattccaaa gctttaactt    4800
cttctttggt catatcgccg tggttccaat ggccgacacc ttcaaagaca gagactaaat    4860
cgatatcttt gccgtctaaa ttaccaggtg caattgttcc gccgtaagca aaaatggctg    4920
ggatatccat gttagccata gcgataacag aaccgggcat gttttttatca caaccgccaa    4980 tggctacaaa agcatccgca ttatgacctc ccatggctgc ttcaatagaa tctgcaataa    5040
tatcacgaga tgtcaaggag aaacgcattc cttgggttcc catggcgatt ccatcagaaa    5100
ccgtgattgt tccgaactga actggccaag caccagcttc cttaacaccg actttggcta    5160
gtttaccaaa gtcatgtaag tggatattac aaggtgtgtt ttcagcccaa gttgaaatga    5220
caccgacgat aggttttttca aagtcttcat cttgcatacc agttgcacgc aacatagcac    5280
gattaggtga tttaaccatt gaatcgtaaa cagaactacg atttcttaag tctttaagag    5340 ttttttttgtc agtcatactc acgtgaaact tagattagat tgctatgctt tctttccaat    5400
gagcaagaag taaaaaaagt tgtaatagaa caggaaaaat gaagctgaaa cttgagaaat    5460
tgaagaccgt ttgttaactc aaatatcaat gggaggtcgt cgaaagagaa caaaatcgaa    5520
aaaaagtttt tcaagagaaa gaaacgtgat aaaaatttttt attgccttct ccgacgaaga    5580
aaaagggacg aggcggtctc ttttttcctttt tccaaacctt tagtacgggt aattaacggc    5640
accctagagg aaggaggagg gggaatttag tatgctgtgc ttgggtgttt tgaagtggta    5700
cggcggtgcg cggagtccga gaaaatctgg aagagtaaaa aaggagtaga gacatttttga    5760 agctatgccg gcagatctat ttaaatggcg cgccgacgtc aggtggcact tttcggggaa    5820 atgtgcgcg aaccctatt tgtttatttt tctaaataca ttcaaatatg tatccgctca    5880
tgagacaata accctgataa atgcttcaat aatattgaaa aaggaagagt atgagtattc    5940
aacatttccg tgtcgccctt attcccttttt ttgcggcatt ttgccttcct gttttttgctc    6000 acccagaaac gctggtgaaa gtaaaagatg ctgaagatca gttgggtgca cgagtgggtt    6060
acatcgaact ggatctcaac agcggtaaga tccttgagag ttttcgcccc gaagaacgtt    6120
ttccaatgat gagcactttt aaagttctgc tatgtggcgc ggtattatcc cgtattgacg    6180
ccgggcaaga gcaactcggt cgccgcatac actattctca gaatgacttg gttgagtact    6240
caccagtcac agaaaagcat cttacggatg gcatgacagt aagagaatta tgcagtgctg    6300
ccataaccat gagtgataac actgcggcca acttacttct gacaacgatc ggaggaccga    6360
aggagctaac cgcttttttttg cacaacatgg gggatcatgt aactcgcctt gatcgttggg    6420
aaccggagct gaatgaagcc ataccaaacg acgagcgtga caccacgatg cctgtagcaa    6480
tggcaacaac gttgcgcaaa ctattaactg gcgaactact tactctagct tcccggcaac    6540
aattaataga ctggatggag gcggataaag ttgcaggacc acttctgcgc tcggcccttc    6600
cggctggctg gtttattgct gataaatctg gagccggtga gcgtgggtct cgcggtatca    6660
ttgcagcact ggggccagat ggtaagccct cccgtatcgt agttatctac acgacgggga    6720
gtcaggcaac tatggatgaa cgaaatagac agatcgctga gataggtgcc tcactgatta    6780
agcattggta actgtcagac caagtttact catatatact ttagattgat ttaaaacttc    6840
atttttaatt taaaaggatc taggtgaaga tcctttttga atctctcatg accaaaatcc    6900
cttaacgtga gttttcgttc cactgagcgt cagaccccgt agaaaagatc aaaggatctt    6960
cttgagatcc ttttttttctg cgcgtaatct gctgcttgca acaaaaaaaa ccaccgctac    7020
```

```
cagcggtggt tgtttgccg gatcaagagc taccaactct tttccgaag gtaactggct      7080 tcagcagagc gcagatacca aatactgttc ttctagtgta gccgtagtta ggccaccact      7140
tcaagaactc tgtagcaccg cctacatacc tcgctctgct aatcctgtta ccagtggctg      7200
ctgccagtgg cgataagtcg tgtcttaccg ggttggactc aagacgatag ttaccggata      7260
aggcgcagcg gtcgggctga acggggggtt cgtgcacaca gcccagcttg gagcgaacga      7320
cctacaccga actgagatac ctacagcgtg agctatgaga aagcgccacg cttcccgaag      7380
ggagaaaggc ggacaggtat ccggtaagcg gcagggtcgg aacaggagag cgcacgaggg      7440
agcttccagg gggaaacgcc tggtatcttt atagtcctgt cgggtttcgc cacctctgac      7500
ttgagcgtcg attttgtga tgctcgtcag ggggcggag cctatggaaa aacgccagca      7560
acgcggcctt tttacggttc ctggccttt gctggccttt tgctcacatg ttctttcctg      7620
cgttatcccc tgattctgtg gataaccgta ttaccgcctt tgagtgagct gataccgctc      7680
gccgcagccg aacgaccgag cgcagcgagt cagtgagcga ggaagcggaa gagcgcccaa      7740
tacgcaaacc gcctctcccc gcgcgttggc cgattcatta atgcagctgg cacgacaggt      7800
ttcccgactg gaaagcgggc agtgagcgca acgcaattaa tgtgagttag ctcactcatt      7860
aggcacccca ggctttacac tttatgcttc cggctcgtat gttgtgtgga attgtgagcg      7920
gataacaatt tcacacagga aacagctatg accatgatta cgccaagctt tttctttcca      7980
attttttttt tttcgtcatt ataaaaatca ttacgaccga gattcccggg taataactga      8040
tataattaaa ttgaagctct aatttgtgag tttagtatac atgcatttac ttataataca      8100
gttttttagt tttgctggcc gcatcttctc aaatatgctt cccagcctgc ttttctgtaa      8160
cgttcaccct ctaccttagc atcccttccc tttgcaaata gtcctcttcc aacaataata      8220
atgtcagatc ctgtagagac cacatcatcc acggttctat actgttgacc caatgcgtct      8280
cccttgtcat ctaaacccac accgggtgtc ataatcaacc aatcgtaacc ttcatctctt      8340
ccacccatgt ctctttgagc aataaagccg ataacaaaat ctttgtcgct cttcgcaatg      8400
tcaacagtac ccttagtata ttctccagta gatagggagc ccttgcatga caattctgct      8460
aacatcaaaa ggcctctagg ttcctttgtt acttcttctg ccgcctgctt caaaccgcta      8520
acaatacctg ggcccaccac accgtgtgca ttcgtaatgt ctgcccattc tgctattctg      8580
tatacacccg cagagtactg caatttgact gtattaccaa tgtcagcaaa ttttctgtct      8640
tcgaagagta aaaaattgta cttggcggat aatgccttta gcggcttaac tgtgccctcc      8700
atggaaaaat cagtcaagat atccacatgt gttttagta aacaaatttt gggacctaat      8760
gcttcaacta actccagtaa ttccttggtg gtacgaacat ccaatgaagc acacaagttt      8820
gtttgctttt cgtgcatgat attaaatagc ttggcagcaa caggactagg atgagtagca      8880
gcacgttcct tatatgtagc tttcgacatg atttatcttc gtttcctgca ggtttttgtt      8940
ctgtgcagtt gggttaagaa tactgggcaa tttcatgttt cttcaacact acatatgcgt      9000
atatatacca atctaagtct gtgctccttc cttcgttctt ccttctgttc ggagattacc      9060
gaatcaaaaa aatttcaagg aaaccgaaat caaaaaaaag aataaaaaaa aaatgatgaa      9120
ttgaaaagct tgcatgcctg caggtcgact ctagtatact ccgtctactg tacgatacac      9180
ttccgctcag gtccttgtcc tttaacgagg ccttaccact cttttgttac tctattgatc      9240
cagctcagca aaggcagtgt gatctaagat tctatcttcg cgatgtagta aaactagcta      9300
gaccgagaaa gagactagaa atgcaaaagg cacttctaca atggctgcca tcattattat      9360
```

```
ccgatgtgac gctgcatttt tttttttttt tttttttttt tttttttttt tttttttttt    9420
ttttttttgt acaaatatca taaaaaaaga gaatctttt  aagcaaggat tttcttaact    9480
tcttcggcga cagcatcacc gacttcggtg gtactgttgg aaccacctaa atcaccagtt    9540
ctgatacctg catccaaaac cttttaact  gcatcttcaa tggctttacc ttcttcaggc    9600
aagttcaatg acaatttcaa catcattgca gcagacaaga tagtggcgat agggttgacc    9660
ttattctttg gcaaatctgg agcggaacca tggcatggtt cgtacaaacc aaatgcggtg    9720
ttcttgtctg gcaaagaggc caaggacgca gatggcaaca acccaagga  gcctgggata    9780
acggaggctt catcggagat gatatcacca aacatgttgc tggtgattat aataccattt    9840
aggtgggttg ggttcttaac taggatcatg gcggcagaat caatcaattg atgttgaact    9900
ttcaatgtag ggaattcgtt cttgatggtt cctccacag  ttttctcca  taatcttgaa    9960
gaggccaaaa cattagcttt atccaaggac caaataggca atggtggctc atgttgtagg   10020
gccatgaaag cggccattct tgtgattctt tgcacttctg gaacggtgta ttgttcacta   10080
tcccaagcga caccatcacc atcgtcttcc tttctcttac caaagtaaat acctcccact   10140
aattctctaa caacaacgaa gtcagtacct ttagcaaatt gtggcttgat tggagataag   10200
tctaaaagag agtcggatgc aaagttacat ggtcttaagt tggcgtacaa ttgaagttct   10260
ttacggattt ttagtaaacc ttgttcaggt ctaacactac cggtacccca tttaggacca   10320
cccacagcac ctaacaaaac ggcatcagcc ttcttggagg cttccagcgc ctcatctgga   10380
agtggaacac ctgtagcatc gatagcagca ccaccaatta atgattttc  gaaatcgaac   10440
ttgacattgg aacgaacatc agaaatagct ttaagaacct taatggcttc ggctgtgatt   10500
tcttgaccaa cgtggtcacc tggcaaaacg acgatcttct tagggg caga cattacaatg   10560
gtatatcctt gaaatatata taaaaaaaaa aaaaaaaaaa aaaaaaaaaa atgcagcttc   10620
tcaatgatat tcgaatacgc tttgaggaga tacagcctaa tatccgacaa actgttttac   10680
agatttacga tcgtacttgt tacccatcat tgaattttga acatccgaac ctgggagttt   10740
tccctgaaac agatagtata tttgaacctg tataataata tatagtctag cgctttacgg   10800
aagacaatgt atgtatttcg gttcctggag aaactattgc atctattgca taggtaatct   10860
tgcacgtcgc atccccggtt cattttctgc gtttccatct tgcacttcaa tagcatatct   10920
ttgttaacga agcatctgtg cttcattttg tagaacaaaa atgcaacgcg agagcgctaa   10980
tttttcaaac aaagaatctg agctgcattt ttacagaaca gaaatgcaac gcgaaagcgc   11040
tattttacca acgaagaatc tgtgcttcat ttttgtaaaa caaaaatgca acgcgagagc   11100
gctaatttt  caaacaaaga atctgagctg catttttaca gaacagaaat gcaacgcgag   11160
agcgctattt taccaacaaa gaatctatac ttcttttttg ttctacaaaa atgcatcccg   11220
agagcgctat ttttctaaca aagcatctta gattactttt tttctccttt gtgcgctcta   11280
taatgcagtc tcttgataac tttttgcact gtaggtccgt taaggttaga agaaggctac   11340
tttggtgtct attttctctt ccataaaaaa agcctgactc acttcccgc  gtttactgat   11400
tactagcgaa gctgcgggtg catttttca  agataaaggc atccccgatt atattctata   11460
ccgatgtgga ttgcgcatac tttgtgaaca gaaagtgata gcgttgatga ttcttcattg   11520
gtcagaaaat tatgaacggt ttcttctatt ttgtctctat atactacgta taggaaatgt   11580
ttacattttc gtattgtttt cgattcactc tatgaatagt tcttactaca atttttttgt   11640
ctaaagagta atactagaga taaacataaa aaatgtagag gtcgagttta gatgcaagtt   11700
caaggagcga aaggtggatg ggtaggttat atagggatat agcacagaga tatatagcaa   11760
```

```
agagatactt tgagcaatg tttgtggaag cggtattcgc aatattttag tagctcgtta    11820
cagtccggtg cgttttttggt tttttgaaag tgcgtcttca gagcgctttt ggttttcaaa    11880
agcgctctga agttcctata ctttctagag aataggaact tcggaatagg aacttcaaag    11940
cgtttccgaa aacgagcgct tccgaaaatg caacgcgagc tgcgcacata cagctcactg    12000
ttcacgtcgc acctatatct gcgtgttgcc tgtatatata tatacatgag aagaacggca    12060
tagtgcgtgt ttatgcttaa atgcgtactt atatgcgtct atttatgtag gatgaaaggt    12120
agtctagtac ctcctgtgat attatcccat tccatgcggg gtatcgtatg cttccttcag    12180 cactacccctt tagctgttct atatgctgcc actcctcaat tggattagtc tcatccttca    12240
atgctatcat ttcctttgat attggatcat atgcatagta ccgagaaact agaggatc     12298
```

<210> SEQ ID NO 13
<211> LENGTH: 11013
<212> TYPE: DNA
<213> ORGANISM: Artificial Sequence
<220> FEATURE:
<223> OTHER INFORMATION: pRS413::BiADH-KivD Lg(y)

<400> SEQUENCE: 13

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgcgtg     120
ttggcgggtg tcgggctgg cttaactatg cggcatcaga gcagattgta ctgagagtgc     180
accataaatt cccgttttaa gagcttggtg agcgctagga gtcactgcca ggtatcgttt     240
gaacacggca ttagtcaggg aagtcataac acagtccttt cccgcaattt tcttttttcta    300 ttactcttgg cctcctctag tacactctat atttttttat gcctcggtaa tgattttcat     360 ttttttttttt cccctagcgg atgactcttt ttttttctta gcgattggca ttatcacata     420
atgaattata cattatataa agtaatgtga tttcttcgaa gaatatacta aaaaatgagc     480
aggcaagata aacgaaggca aagatgacag agcagaaagc cctagtaaag cgtattacaa     540
atgaaaccaa gattcagatt gcgatctctt taaagggtgg tcccctagcg atagagcact     600
cgatcttccc agaaaaagag gcagaagcag tagcagaaca ggccacacaa tcgcaagtga    660
ttaacgtcca cacaggtata gggtttctgg accatatgat acatgctctg gccaagcatt     720
ccggctggtc gctaatcgtt gagtgcattg gtgacttaca catagacgac catcacacca     780
ctgaagactg cgggattgct ctcggtcaag ctttttaaaga ggccctactg gcgcgtggag     840
taaaaaggtt tggatcagga tttgcgcctt tggatgaggc actttccaga gcggtggtag     900
atctttcgaa caggccgtac gcagttgtcg aacttggttt gcaaagggag aaagtaggag    960
atctctcttg cgagatgatc ccgcattttc ttgaaagctt tgcagaggct agcagaatta    1020
ccctccacgt tgattgtctg cgaggcaaga atgatcatca ccgtagtgag agtgcgttca    1080
aggctcttgc ggttgccata agagaagcca cctcgcccaa tggtaccaac gatgttccct    1140
ccaccaaagg tgttcttatg tagtgacacc gattatttaa agctgcagca tacgatatat    1200
atacatgtgt atatatgtat acctatgaat gtcagtaagt atgtatacga acagtatgat    1260
actgaagatg acaaggtaat gcatcattct atacgtgtca ttctgaacga ggcgcgcttt    1320 ccttttttcct ttttgctttt tcttttttttt tctcttgaac tcgacggatc tatgcggtgt    1380
gaaataccgc acagatgcgt aaggagaaaa taccgcatca ggaaattgta acgttaata    1440 ttttgttaaa attcgcgtta aattttttgtt aaatcagctc attttttaac caataggccg    1500
```

```
aaatcggcaa aatcccttat aaatcaaaag aatagaccga gatagggttg agtgttgttc    1560
cagtttggaa caagagtcca ctattaaaga acgtggactc caacgtcaaa gggcgaaaaa    1620
ccgtctatca gggcgatggc ccactacgtg aaccatcacc ctaatcaagt ttttgggggt    1680
cgaggtgccg taaagcacta aatcggaacc ctaaagggag cccccgattt agagcttgac    1740
ggggaaagcc ggcgaacgtg gcgagaaagg aagggaagaa agcgaaagga gcgggcgcta    1800
gggcgctggc aagtgtagcg gtcacgctgc gcgtaaccac cacacccgcc gcgcttaatg    1860
cgccgctaca gggcgcgtcg cgccattcgc cattcaggct gcgcaactgt tgggaagggc    1920
gatcggtgcg ggcctcttcg ctattacgcc agctggcgaa aggggatgt gctgcaaggc    1980 gattaagttg ggtaacgcca gggttttccc agtcacgacg ttgtaaaacg acggccagtg    2040
agcgcgcgta atacgactca ctatagggcg aattgggtac cgggcccccc ctgtacgcat    2100
gtaacattat actgaaaacc ttgcttgaga aggttttggg acgtcgaag gctttaattt     2160 cctgcaggaa ttaccgtcgc tcgtgatttg tttgcaaaaa gaacaaaact gaaaaaaccc    2220
agacacgctc gacttcctgt cttcctattg attgcagctt ccaatttcgt cacacaacaa    2280
ggtcctgtcg acgcctactt ggcttcacat acgttgcata cgtcgatata gataataatg    2340
ataatgacag caggattatc gtaatacgta atagttgaaa atctcaaaaa tgtgtgggtc    2400
attacgtaaa taatgatagg aatgggattc ttctatttt ccttttttcca ttctagcagc    2460 cgtcgggaaa acgtggcatc ctctctttcg ggctcaattg gagtcacgct gccgtgagca    2520
tcctctcttt ccatatctaa caactgagca cgtaaccaat ggaaaagcat gagcttagcg    2580
ttgctccaaa aaagtattgg atggttaata ccatttgtct gttctcttct gactttgact    2640
cctcaaaaaa aaaaatcta caatcaacag atcgcttcaa ttacgccctc acaaaaactt    2700
ttttccttct tcttcgccca cgttaaattt tatccctcat gttgtctaac ggatttctgc    2760
acttgattta ttataaaaag acaaagacat aatacttctc tatcaatttc agttattgtt    2820
cttccttgcg ttattcttct gttcttcttt ttcttttgtc atatataacc ataaccaagt    2880
aatacatatt caagtttaaa catgtatacc gtaggacagt acttggtaga tagactagaa    2940
gagattggta tcgataaggt tttcggtgtg ccagggatt acaatttgac ttttctagat     3000
tacattcaaa atcacgaagg actttcctgg caagggaata ctaatgaact aaacgcagca    3060
tatgcagcag atggctacgc ccgtgaaaga ggcgtatcag ctcttgttac tacattcgga    3120
gtgggtgaac tgtcagccat taacggaaca gctggtagtt ttgcagaaca agtccctgtc    3180
atccacatcg tgggttctcc aactatgaat gtgcaatcca acaaaaagct ggttcatcat    3240
tccttaggaa tgggtaactt tcataacttt agtgaaatgg ctaaggaagt cactgccgct    3300
acaaccatgc ttactgaaga gaatgcagct tcagagatcg acagagtatt agaaacagcc    3360
ttgttggaaa agaggccagt atacatcaat cttccaattg atatagctca taaagcaata    3420
gttaaacctg caaagcact acaaacagag aaatcatctg gtgagagaga ggcacaactt    3480
gcagaaatca tactatcaca cttagaaaag gccgctcaac ctatcgtaat cgccggtcat    3540
gagatcgccc gtttccagat aagagaaaga tttgaaaact ggataaacca aacaagttg    3600 ccagtaacca atttggcata tggcaaaggc tctttcaatg aagagaacga acatttcatt    3660
ggtacctatt acccagcttt ttctgacaaa aacgttctgg attacgttga caatagtgac    3720
ttcgttttac attttggtgg gaaaatcatt gacaattcta cctcctcatt ttctcaaggc    3780
tttaagacta aaaacacttt aaccgctgca aatgacatca ttatgctgcc agatgggtct    3840
acttactctg gatttctct taacggtctt ttggcagagc tggaaaaact aaactttact    3900
```

```
tttgctgata ctgctgctaa acaagctgaa ttagctgttt tcgaaccaca ggccgaaaca    3960
ccactaaagc aagacagatt tcaccaagct gttatgaact ttttgcaagc tgatgatgtg    4020
ttggtcactg agcaggggac atcatctttc ggtttgatgt tggcacctct gaaaaagggt    4080
atgaatttga tcagtcaaac attatggggc tccataggat acacattacc tgctatgatt    4140
ggttcacaaa ttgctgcccc agaaaggaga cacattctat ccatcggtga tggatctttt    4200
caactgacag cacaggaaat gtccaccatc ttcagagaga aattgacacc agtgatattc    4260
attatcaata cgatggcta tacagtcgaa agagccatcc atggagagga tgagagttac    4320
aatgatatac caacttggaa cttgcaatta gttgctgaaa catttggtgg tgatgccgaa    4380
actgtcgaca ctcacaacgt tttcacagaa acagacttcg ctaatacttt agctgctatc    4440
gatgctactc ctcaaaaagc acatgtcgtt gaagttcata tggaacaaat ggatatgcca    4500
gaatcattga gacagattgg cttagcctta tctaagcaaa actcttaacc tgcagggccg    4560
tgaatttact ttaaatcttg catttaaata aattttcttt ttatagcttt atgacttagt    4620
ttcaatttat atactatttt aatgacattt tcgattcatt gattgaaagc tttgtgtttt    4680
ttcttgatgc gctattgcat tgttcttgtc ttttcgcca catgtaatat ctgtagtaga    4740
tacctgatac attgtggatg ctgagtgaaa tttagttaa taatggaggc gctcttaata    4800
attttgggga tattggcttt ttttttaaa gtttacaaat gaattttttc cgccaggata    4860
acgattctga agttactctt agcgttccta tcggtacagc catcaaatca tgcctataaa    4920
tcatgcctat atttgcgtgc agtcagtatc atctacatga aaaaactcc cgcaatttct    4980
tatagaatac gttgaaaatt aaatgtacgc gccaagataa gataacatat atctagatgc    5040
agtaatatac acagattccc gcggacgtgg aaggaaaaa attagataac aaaatctgag    5100
tgatatggaa attccgctgt atagctcata tctttcccta cctggtaaaa cctctagtgg    5160
agtagtagat gtaatcaatg aagcggaagc caaaagacca gagtagaggc ctatagaaga    5220
aactgcgata ccttttgtga tggctaaaca aacagacatc ttttatatg tttttacttc    5280
tgtatatcgt gaagtagtaa gtgataagcg aatttggcta agaacgttgt aagtgaacaa    5340
gggacctctt ttgcctttca aaaaaggatt aaatggagtt aatcattgag atttagtttt    5400
cgttagattc tgtatcccta ataactccc ttacccgacg ggaaggcaca aaagacttga    5460
ataatagcaa acgccagta gccaagacca aataatacta gagttaactg atggtcttaa    5520
acaggcatta cgtggtgaac tccaagacca atatacaaaa tatcgataag ttattcttgc    5580
ccaccaattt aaggagccta catcaggaca gtagtaccat tcctcagaga agaggtatac    5640
ataacaagaa aatcgcgtga acaccttata taacttagcc cgttattgag ctaaaaaacc    5700
ttgcaaaatt tcctatgaat aagaatactt cagacgtgat aaaaatttac tttctaactc    5760
ttctcacgct gccctatct gttcttccgc tctaccgtga gaaataaagc atcgagtacg    5820
gcagttcgct gtcactgaac taaaacaata aggctagttc gaatgatgaa cttgcttgct    5880
gtcaaacttc tgagttgccg ctgatgtgac actgtgacaa taaattcaaa ccggttatag    5940
cggtctcctc cggtaccggt tctgccacct ccaatagagc tcccgcacgc cgaaatgcat    6000
gcaagtaacc tattcaaagt aatatctcat acatgtttca tgagggtaac aacatgcgac    6060
tgggtgagca tatgttccgc tgatgtgatg tgcaagataa acaagcaagg cagaaactaa    6120
cttcttcttc atgtaataaa cacaccccg gtttatttac ctatctctaa acttcaacac    6180
cttatatcat aactaatatt tcttgagata agcacactgc acccataccct tccttaaaaa    6240
```

```
cgtagcttcc agttttttggt ggttccggct tccttcccga ttccgcccgc taaacgcata    6300 ttttttgttgc ctggtggcat ttgcaaaatg cataacctat gcatttaaaa gattatgtat    6360
gctcttctga cttttcgtgt gatgaggctc gtggaaaaaa tgaataattt atgaatttga    6420
gaacaatttt gtgttgttac ggtattttac tatggaataa tcaatcaatt gaggatttta    6480
tgcaaatatc gtttgaatat ttttccgacc ctttgagtac ttttcttcat aattgcataa    6540
tattgtccgc tgccccttttt tctgttagac ggtgtcttga tctacttgct atcgttcaac    6600
accaccttat tttctaacta tttttttttt agctcatttg aatcagctta tggtgatggc    6660
acatttttgc ataaacctag ctgtcctcgt tgaacatagg aaaaaaaaat atataaacaa    6720
ggctctttca ctctccttgc aatcagattt gggtttgttc cctttatttt catatttctt    6780
gtcatattcc tttctcaatt attattttct actcataacc tcacgcaaaa taacacagtc    6840
aaatcaatca aaatgaaagc attagtgtat aggggcccag ccagaagtt  ggtggaagag    6900 agacagaagc cagagcttaa ggaacctggt gacgctatag tgaaggtaac aaagactaca    6960
atttgcggaa ccgatctaca cattcttaaa ggtgacgttg cgacttgtaa acccggtcgt    7020
gtattagggc atgaaggagt gggggttatt gaatcagtcg gatctggggt tactgctttc    7080
caaccaggcg atagagtttt gatatcatgt atatcgagtt gcggaaagtg ctcatttttgt   7140 agaagaggaa tgttcagtca ctgtacgacc ggggggttgga ttctgggcaa cgaaattgat    7200
ggtacccaag cagagtacgt aagagtacca catgctgaca catcccttta tcgtattccg    7260
gcaggtgcgg atgaagaggc cttagtcatg ttatcagata ttctaccaac gggttttgag    7320
tgcggagtcc taaacggcaa agtcgcacct ggttcttcgg tggctatagt aggtgctggt    7380
cccgttggtt tggccgcctt actgacagca caattctact ccccagctga aatcataatg    7440
atcgatcttg atgataacag gctgggatta gccaaacaat ttggtgccac cagaacagta    7500
aactccacgg gtggtaacgc cgcagccgaa gtgaaagctc ttactgaagg cttaggtgtt    7560
gatactgcga ttgaagcagt tgggatacct gctacatttg aattgtgtca gaatatcgta    7620
gctcccggtg aactatcgc  taatgtcggc gttcacggta gcaaagttga tttgcatctt    7680
gaaagtttat ggtcccataa tgtcacgatt actacaaggt tggttgacac ggctaccacc    7740
ccgatgttac tgaaaactgt tcaaagtcac aagctagatc catctagatt gataacacat    7800
agattcagcc tggaccagat cttggacgca tatgaaactt ttggccaagc tgcgtctact    7860
caagcactaa aagtcatcat ttcgatggag gcttgattaa ttaagagtaa gcgaatttct    7920
tatgatttat gattttttatt attaaataag ttataaaaaa aataagtgta tacaaatttt    7980
aaagtgactc ttaggttttta aaacgaaaat tcttattctt gagtaactct ttcctgtagg    8040
tcaggttgct ttctcaggta tagcatgagg tcgctcttat tgaccacacc tctaccggca    8100
tgccgagcaa atgcctgcaa atcgctcccc atttcaccca attgtagata tgctaactcc    8160
agcaatgagt tgatgaatct cggtgtgtat tttatgtcct cagaggacaa cacctgtggt    8220
gagctccagc ttttgttccc tttagtgagg gttaattgcg cgcttggcgt aatcatggtc    8280
atagctgttt cctgtgtgaa attgttatcc gctcacaatt ccacacaaca taggagccgg    8340
aagcataaag tgtaaagcct ggggtgccta atgagtgagg taactcacat taattgcgtt    8400
gcgctcactg cccgctttcc agtcgggaaa cctgtcgtgc cagctgcatt aatgaatcgg    8460
ccaacgcgcg gggagaggcg gtttgcgtat tgggcgctct tccgcttcct cgctcactga    8520
ctcgctgcgc tcggtcgttc ggctgcggcg agcggtatca gctcactcaa aggcggtaat    8580
acggttatcc acagaatcag gggataacgc aggaaagaac atgtgagcaa aaggccagca    8640
```

```
aaaggccagg aaccgtaaaa aggccgcgtt gctggcgttt ttccataggc tccgccccccc   8700 tgacgagcat cacaaaaatc gacgctcaag tcagaggtgg cgaaacccga caggactata   8760
aagataccag gcgttttcccc ctggaagctc cctcgtgcgc tctcctgttc cgaccctgcc   8820
gcttaccgga tacctgtccg cctttctccc ttcgggaagc gtggcgcttt ctcatagctc   8880
acgctgtagg tatctcagtt cggtgtaggt cgttcgctcc aagctgggct gtgtgcacga   8940
accccccgtt cagcccgacc gctgcgcctt atccggtaac tatcgtcttg agtccaaccc   9000
ggtaagacac gacttatcgc cactggcagc agccactggt aacaggatta gcagagcgag   9060
gtatgtaggc ggtgctacag agttcttgaa gtggtggcct aactacggct acactagaag   9120
gacagtattt ggtatctgcg ctctgctgaa gccagttacc ttcggaaaaa gagttggtag   9180
ctcttgatcc ggcaaacaaa ccaccgctgg tagcggtggt ttttttgttt gcaagcagca   9240
gattacgcgc agaaaaaaag gatctcaaga agatcctttg atcttttcta cggggtctga   9300
cgctcagtgg aacgaaaact cacgttaagg gattttggtc atgagattat caaaaaggat   9360
cttcacctag atccttttaa attaaaaatg aagttttaaa tcaatctaaa gtatatatga   9420
gtaaacttgg tctgacagtt accaatgctt aatcagtgag gcacctatct cagcgatctg   9480
tctatttcgt tcatccatag ttgcctgact ccccgtcgtg tagataacta cgatacggga   9540
gggcttacca tctggcccca gtgctgcaat gataccgcga gacccacgct caccggctcc   9600
agatttatca gcaataaacc agccagccgg aagggccgag cgcagaagtg gtcctgcaac   9660
tttatccgcc tccatccagt ctattaattg ttgccgggaa gctagagtaa gtagttcgcc   9720
agttaatagt ttgcgcaacg ttgttgccat tgctacaggc atcgtggtgt cacgctcgtc   9780
gtttggtatg gcttcattca gctccggttc ccaacgatca aggcgagtta catgatcccc   9840
catgttgtgc aaaaaagcgg ttagctcctt cggtcctccg atcgttgtca gaagtaagtt   9900
ggccgcagtg ttatcactca tggttatggc agcactgcat aattctctta ctgtcatgcc   9960
atccgtaaga tgcttttctg tgactggtga gtactcaacc aagtcattct gagaatagtg  10020
tatgcggcga ccgagttgct cttgcccggc gtcaatacgg gataataccg cgccacatag  10080
cagaacttta aaagtgctca tcattggaaa acgttcttcg gggcgaaaac tctcaaggat  10140
cttaccgctg ttgagatcca gttcgatgta acccactcgt gcacccaact gatcttcagc  10200
atcttttact ttcaccagcg tttctgggtg agcaaaaaca ggaaggcaaa atgccgcaaa  10260
aaagggaata agggcgacac ggaaatgttg aatactcata ctcttccttt ttcaatatta  10320
ttgaagcatt tatcagggtt attgtctcat gagcggatac atatttgaat gtatttagaa  10380
aaataaacaa ataggggttc cgcgcacatt tccccgaaaa gtgccacctg gtccttttc   10440 atcacgtgct ataaaaataa ttataattta aatttttttaa tataaatata taaattaaaa  10500
atagaaagta aaaaagaaa ttaaagaaaa atagttttt gttttccgaa gatgtaaaag  10560
actctagggg gatcgccaac aaatactacc ttttatcttg ctcttcctgc tctcaggtat  10620
taatgccgaa ttgtttcatc ttgtctgtgt agaagaccac acacgaaaat cctgtgattt  10680
tacattttac ttatcgttaa tcgaatgtat atctatttaa tctgcttttc ttgtctaata  10740
aatatatatg taaagtacgc ttttttgttga aattttttaa acctttgttt atttttttttt  10800 cttcattccg taactcttct accttcttta tttactttct aaaatccaaa tacaaaacat  10860
aaaaataaat aaacacagag taaattccca aattattcca tcattaaaag atacgaggcg  10920
cgtgtaagtt acaggcaagc gatccgtcct aagaaaccat tattatcatg acattaacct  10980
```

| | |
|---|---|
| ataaaaatag gcgtatcacg aggcccttttc gtc | 11013 |

<210> SEQ ID NO 14
<211> LENGTH: 1008
<212> TYPE: DNA
<213> ORGANISM: Archaeoglobus fulgidus

<400> SEQUENCE: 14

| | |
|---|---|
| atgattgttt cgatactggg agcgggtgca atgggctcag ccctctccgt cccgctcgta | 60 |
| gataacggca acgaagtgag aatctggggg accgagttcg atacggagat tttaaaatca | 120 |
| atctcagccg gcagagagca tccaaggctt ggtgtaaagc tcaatggcgt ggaaattttc | 180 |
| tggccagagc agcttgaaaa atgtttggag aatgcagagg ttgtacttct gggtgttagc | 240 |
| acggatggcg tgctgcccgt aatgagcaga attctcccgt atctcaagga ccagtacatc | 300 |
| gtactcatct ctaaagggct gattgatttt gataacagtg ttctgacggt tcccgaagct | 360 |
| gtatggaggt taaagcacga tttgagggaa aggactgtgg cgataaccgg gcccgctatt | 420 |
| gcaagagagg tggcgaaacg catgcccaca accgttgttt tcagcagccc atccgaaagc | 480 |
| tcggccaata aaatgaaaga aatctttgag acagagtact tggcgttga agtaacaaca | 540 |
| gacataattg gcacggaaat aacctccgcc ctcaaaaacg tttattccat agccattgca | 600 |
| tggataaggg gctacgagag cagaaaaaac gttgagatga gcaatgcaaa gggagtgatt | 660 |
| gcaacgagag ccataaacga gatggcagag ctgatagaga ttctcggagg ggatagagag | 720 |
| accgcctttg gcctttccgg atttggagac ctcatcgcaa ccttcagggg aggaaggaac | 780 |
| gggatgctgg gagagctgct tggaaagggg cttagcatcg atgaggcgat ggaggagctt | 840 |
| gagaggagag gagttggtgt ggttgagggc tacaaaacgg cagagaaagc atacaggctg | 900 |
| tccagcaaaa taaatgcaga cacaaagctg ctcgacagca tctacagagt cctttatgaa | 960 |
| ggactgaagg ttgaggaagt gctgtttgaa ctcgctacat ttaaataa | 1008 |

<210> SEQ ID NO 15
<211> LENGTH: 1137
<212> TYPE: DNA
<213> ORGANISM: Candida versatilis

<400> SEQUENCE: 15

| | |
|---|---|
| atgcctactc ctcaagagag actcgctcag ttgcgtggaa atgaagacgc gccagcgtcg | 60 |
| gtagcatcga aatataacaa aagattccgt gtaggtgtca ttggttctgg taactggggt | 120 |
| acggcagtcg cgaagattgt cgccgaaaac tgcctggaaa agccatatct gtttcaccgt | 180 |
| gatgtgaaga tgtgggttcg tgaggaagag gtctctgaca tgaagctgac ggacatcatt | 240 |
| aattcctacc atgagaacgt gaagtacctg ccggaggtaa ctctgccgtt taatctgttt | 300 |
| gctgagccag acattcgcaa ggttgctgat ggtgcagacc tgctggttat caatctgccc | 360 |
| caccagttct tggggtctgt atgcgaccag atgaagggca tcgacttctc taagtcctca | 420 |
| gccatttctt gtctaaaggg tatcaatgta tctgcagatg gtgtggagct tcttcatgat | 480 |
| gtcgtggaaa agaagcttgg cttgcattgc ggtgtcctga gtggtgcgaa tattgcgtcc | 540 |
| gaggtggccc gtgaacgttg gtctgagacc accattgcct tcccattgcc ttcgtggtac | 600 |
| cagcagggtg atgctgatga taatctgatc aaggagttgt tctacaggcc ctatttccat | 660 |
| gttcaagtat cggatgatgt gtgtggtgcg tcaattagcg gtgcacttaa gaacgtggtc | 720 |
| gctcttggcg caggtcttgt tgagggcgca ggctggggta taatgccaa ggctgctgtc | 780 |
| atgcgtcgtg gcttgctcga agtgattatg ttcggcaacg ttttcttccc aggtaagtgc | 840 |

```
cgcccagaga ccttcaccac tgaatcggca ggtgtggccg atttgatcac ctcgtgtgct    900
ggtggacgta acgtcaaggt tggacgtgca tttgctcgta caggaaagcc acttgaggtc    960
atcgagaagg agctcctaaa tggccagtca gcccagggta ttattaccgg acgtgaggtg   1020
atggagcttc taacggcaac caagaaggag gacgagttcc ctctgcttgg tgctatttac   1080
gatattgtgc ataacaagtt gcacatctca aatctgccag agcggatcgc agactaa     1137
```

<210> SEQ ID NO 16
<211> LENGTH: 951
<212> TYPE: DNA
<213> ORGANISM: Rickettsia prowazekii

<400> SEQUENCE: 16

```
atgaacaaat ttaagaatat tgcagtttat ggaggaggta gtttcggcac tagtcttgct     60
tctttagtag cacgaaactg taataatgtt actttatttt tacgtgacga gataattta    120 aaagaaattt tatataaaaa aactaacgca caatacttag gtgatattga attacctact    180
aatttgcaag ctactacaaa cttaagtgta atcaaggatt ttgaattaat tattattgca    240
gtgccatctt atgcttttga tgattcaata aaattattga aaacgtacgg catctctaaa    300
gagcatacta ttctagtagc gacaaaaggc ttggctgata atcctactga attattttct    360
gatagactta acactttatt acccgataat cctataggat ttttatctgg tccaaatcta    420
gcaaaggaac ttgctaaaaa tttgcctgct tcggcaagta ttgcaagttt agatatagat    480
atcgcaaata aaatagctta aacttcagt tcaaaaactt tttcaacaaa tacgaccata    540
gatattgtaa cgttacaaat tgctggagct ttaaaaaata tttttgctat taaaagtgga    600
attgatttag caagagagca gggagcaaat tcaagagcaa cgcttatagt aggggcctta    660
aaagaaatta ctactttatc taaggttctt ggaggtatgc aaaaaaattc tgatattta    720 cttgaagcag gagtattagg cgatttagta cttacttgtt actctttagg ttcgcgtaat    780 acaaatttg gttatgaatt tgaaattagt agggataaaa agaaattttt atgcgaatat    840
aaagaattag tagaaggacg agaagcatta aaattagttt tggatctaat aaaaaaatat    900
aatttacaca tgcctatagt tgctgaagta gcttcactca ttttaatttg a            951
```

<210> SEQ ID NO 17
<211> LENGTH: 1008
<212> TYPE: DNA
<213> ORGANISM: Beggiatoa alba

<400> SEQUENCE: 17

```
atgttatcgc cgtccgcctt attagtctta ggggcagggt catggggcac tgcactggct     60
cttgcgcttg cccgtcgaca ataccctatt tacctttggg gtaaagaccc tgcgcatgtt    120
catactttac aaatacaacg ttgtaatcaa cgattttttgc cgaatgcggt ttttcccgat    180
aatttatacg ccattacgga cttcgtaacc ctcatgccga ttgtggaaga cattattatt    240
gtcgttccta gccatggctt ccgcgaaacc ttaaaaaaaa taaagcccta cattacaaaa    300
aatcatcgtt tatgctgggc aacaaaaggc ttggaatatc aaacagggtt gcttttacac    360
gaagtagcgc gtgcagaatt aggcgataac atccctctcg cggttttgtc aggtccttca    420
tttgccggtg aagtcgctgc cgccttaccg acagcggtca cgattgccgc acaagacatc    480
gaaaacgctc atcatgtcgc ccaattattt catcaagcct cattccgtgc ttataccagt    540
aatgacatgg tcggggtaca aattgggggc gcggttaaaa atgtcattgc cattgctgca    600
```

| | |
|---|---|
| ggtatcgcag atggtttaaa aatgggagca ataccccgtg ccgctttaat tacacgtgga | 660 |
| ctgagcgaaa ttgtacgttt aggcattgcc ctcggtggac aacgcgaaac ctttatgggt | 720 |
| ttagcaggct taggcgattt agtcctaact tgcactgata accaatcccg caatcgacgc | 780 |
| tttggctacg cactcgcgca aggcatcagc ctagaagctg cacaagctca agttggacaa | 840 |
| gtggtcgaag gcatacatgc tgcaaccatc acccaccaac tcgcccaaca gcacggtgta | 900 |
| gaaatgccca tagtcaacca tgtcaaccaa gtattaacag gacaaagcac cccactagaa | 960 |
| gccgctcaag ccctgttagc ccgtgaaccc aagccagaaa tgctataa | 1008 |

<210> SEQ ID NO 18
<211> LENGTH: 1005
<212> TYPE: DNA
<213> ORGANISM: Kangiella koreensis

<400> SEQUENCE: 18

| | |
|---|---|
| atgtctgcac aactttcctt tgcggttctt ggggcaggtt cttatggaac cgcattggca | 60 |
| gttttgcttg cccgtaatgg ccatagtgtt cagttatggg ctcgcaactc tcagcatgtt | 120 |
| gttgaaatgc agcaggcaaa acagaatacg aaataccttc ctgatgtcgc tttccctgac | 180 |
| aatctatcag taaccgatca aattgatgta gctttaaagc atcatcctat tattcttgta | 240 |
| gcggtcccaa gtcatgcgtt tcgcgataca ctgtacctca tcaaacctct tgtaaaccaa | 300 |
| gatagtaagc tagtatgggc gagcaaaggg ctcgatcccg atagtggtga tttgttaggt | 360 |
| aatgtgctga aaaatatttt aggcgataat atgccacacg ccatttatc tgggccaact | 420 |
| ttcgccaagg aaatggctat tggtatgcct accgctatca ctttagcagc taataatgac | 480 |
| gactttgctg agcaattagc tttggcttta cataatgagc gtttcagagt ctataccagt | 540 |
| gatgacatcg ttggtgttca gtcggtggt gcggttaaaa atgtagtagc tatcggtgct | 600 |
| ggaattgctg acggactagg ttatggtgcg aacgcaagaa cagccttgat cactcgggt | 660 |
| ttggctgaaa tgactcgctt aggtgttgcc gcaggcggaa agcaggaaac ttcaatgga | 720 |
| atggcaggca tgggcgattt ggtcttaacc tgtaccgata tcagtcgcg taataggcgt | 780 |
| tttggtttag ctttaggtaa aggtgctaat agagatgagg ctgagcatgc cattgggcag | 840 |
| gtagtagaag gtgttcgtaa tgccaaggaa gttaagatgc tggcggagcg actaggggtc | 900 |
| gaaatgccaa tcagcgatgc gatttatcgc ataatttatg aaggcgtcga cgcccgtcag | 960 |
| gccgcacatg aattattaac tcgagaccctt aaatctgaag gttag | 1005 |

<210> SEQ ID NO 19
<211> LENGTH: 1176
<212> TYPE: DNA
<213> ORGANISM: Artificial Sequence
<220> FEATURE:
<223> OTHER INFORMATION: Yeast GPD1_opt

<400> SEQUENCE: 19

| | |
|---|---|
| atgtccgctg ctgctgacag attgaacttg acatctggtc acttgaacgc tggtagaaag | 60 |
| agatcatcct cctctgtctc tttgaaggct gccgaaaagc cattcaaggt caccgttatc | 120 |
| ggttctggta actgggggtac caccattgcc aaggtcgtcg ccgaaaactg caagggttac | 180 |
| ccagaagttt ttgctccaat cgttcaaatg tgggttttg aagaggaaat taacggtgaa | 240 |
| aagttgactg aaattatcaa cactagacac caaaacgtga agtacttgcc cggtattacc | 300 |
| ttgccagaca atttggttgc caatccagac ttgatcgata tgtcaagga cgttgatatt | 360 |
| atcgttttta acatcccaca ccaattccta ccacgtattt gttctcaatt gaagggtcat | 420 |

```
gtcgattctc acgttagagc tatctcctgc ttgaagggtt tcgaagttgg tgctaagggt    480
gttcaattgt tatcctctta catcactgaa gagctaggta tccaatgtgg tgctttgtct    540
ggtgctaaca tcgctaccga agtcgctcaa gagcactggt ctgaaaccac tgtcgcttac    600
catatcccaa aggactttag aggtgaaggt aaagacgttg accacaaggt cctaaaggct    660
ttgttccaca gaccatactt tcacgtttct gtcatcgaag atgtcgccgg tatctctatc    720
tgtggcgctt taaagaacgt cgtcgccttg ggttgtggtt ttgttgaagg attgggttgg    780
ggtaacaacg cctctgctgc tatccaacgt gtcggtttgg gtgaaatcat tagatttggt    840
caaatgtttt tccctgaatc cagagaggaa acctactacc aagagtctgc cggtgttgct    900
gacctaataa ccacctgtgc tggtggtaga aacgttaagg ttgccagatt gatggctact    960
tccggtaagg acgcttggga atgtgaaaag gaattgttga acggtcaatc cgctcaaggt   1020
ttgattactt gtaaggaagt tcacgaatgg ttggaaactt gtggcagcgt tgaagatttt   1080
ccattattcg aagctgtcta ccaaatcgtc tacaataact accctatgaa aaacttgcca   1140
gatatgatcg aggaattaga cttacacgag gactaa                             1176
```

```
<210> SEQ ID NO 20
<211> LENGTH: 38
<212> TYPE: DNA
<213> ORGANISM: Artificial Sequence
<220> FEATURE:
<223> OTHER INFORMATION: Asn44F

<400> SEQUENCE: 20
ccgttatcgg ttctggtaac tggggtacca ccattgcc                              38

<210> SEQ ID NO 21
<211> LENGTH: 38
<212> TYPE: DNA
<213> ORGANISM: Artificial Sequence
<220> FEATURE:
<223> OTHER INFORMATION: N44AF

<400> SEQUENCE: 21
ccgttatcgg ttctggtgct tggggtacca ccattgcc                              38

<210> SEQ ID NO 22
<211> LENGTH: 38
<212> TYPE: DNA
<213> ORGANISM: Artificial Sequence
<220> FEATURE:
<223> OTHER INFORMATION: N44CF

<400> SEQUENCE: 22
ccgttatcgg ttctggttgt tggggtacca ccattgcc                              38

<210> SEQ ID NO 23
<211> LENGTH: 38
<212> TYPE: DNA
<213> ORGANISM: Artificial Sequence
<220> FEATURE:
<223> OTHER INFORMATION: N44GF

<400> SEQUENCE: 23
ccgttatcgg ttctggtggt tggggtacca ccattgcc                              38

<210> SEQ ID NO 24
<211> LENGTH: 38
<212> TYPE: DNA
```

```
<213> ORGANISM: Artificial Sequence
<220> FEATURE:
<223> OTHER INFORMATION: N44IF

<400> SEQUENCE: 24
ccgttatcgg ttctggtatc tggggtacca ccattgcc                              38

<210> SEQ ID NO 25
<211> LENGTH: 38
<212> TYPE: DNA
<213> ORGANISM: Artificial Sequence
<220> FEATURE:
<223> OTHER INFORMATION: N44LF

<400> SEQUENCE: 25
ccgttatcgg ttctggtcta tggggtacca ccattgcc                              38

<210> SEQ ID NO 26
<211> LENGTH: 38
<212> TYPE: DNA
<213> ORGANISM: Artificial Sequence
<220> FEATURE:
<223> OTHER INFORMATION: N44MF

<400> SEQUENCE: 26
ccgttatcgg ttctggtatg tggggtacca ccattgcc                              38

<210> SEQ ID NO 27
<211> LENGTH: 38
<212> TYPE: DNA
<213> ORGANISM: Artificial Sequence
<220> FEATURE:
<223> OTHER INFORMATION: N44SF

<400> SEQUENCE: 27
ccgttatcgg ttctggttct tggggtacca ccattgcc                              38

<210> SEQ ID NO 28
<211> LENGTH: 38
<212> TYPE: DNA
<213> ORGANISM: Artificial Sequence
<220> FEATURE:
<223> OTHER INFORMATION: N44VF

<400> SEQUENCE: 28
ccgttatcgg ttctggtgtt tggggtacca ccattgcc                              38

<210> SEQ ID NO 29
<211> LENGTH: 38
<212> TYPE: DNA
<213> ORGANISM: Artificial Sequence
<220> FEATURE:
<223> OTHER INFORMATION: Trp45F

<400> SEQUENCE: 29
ccgttatcgg ttctggtaac tggggtacca ccattgcc                              38

<210> SEQ ID NO 30
<211> LENGTH: 38
<212> TYPE: DNA
<213> ORGANISM: Artificial Sequence
<220> FEATURE:
<223> OTHER INFORMATION: W45AF

<400> SEQUENCE: 30
ccgttatcgg ttctggtaac gctggtacca ccattgcc                              38
```

```
<210> SEQ ID NO 31
<211> LENGTH: 38
<212> TYPE: DNA
<213> ORGANISM: Artificial Sequence
<220> FEATURE:
<223> OTHER INFORMATION: W45CF

<400> SEQUENCE: 31
ccgttatcgg ttctggtaac tgtggtacca ccattgcc                              38

<210> SEQ ID NO 32
<211> LENGTH: 38
<212> TYPE: DNA
<213> ORGANISM: Artificial Sequence
<220> FEATURE:
<223> OTHER INFORMATION: W45GF

<400> SEQUENCE: 32
ccgttatcgg ttctggtaac ggtggtacca ccattgcc                              38

<210> SEQ ID NO 33
<211> LENGTH: 38
<212> TYPE: DNA
<213> ORGANISM: Artificial Sequence
<220> FEATURE:
<223> OTHER INFORMATION: W45HF

<400> SEQUENCE: 33
ccgttatcgg ttctggtaac cacggtacca ccattgcc                              38

<210> SEQ ID NO 34
<211> LENGTH: 38
<212> TYPE: DNA
<213> ORGANISM: Artificial Sequence
<220> FEATURE:
<223> OTHER INFORMATION: W45IF

<400> SEQUENCE: 34
ccgttatcgg ttctggtaac atcggtacca ccattgcc                              38

<210> SEQ ID NO 35
<211> LENGTH: 38
<212> TYPE: DNA
<213> ORGANISM: Artificial Sequence
<220> FEATURE:
<223> OTHER INFORMATION: W45RF

<400> SEQUENCE: 35
ccgttatcgg ttctggtaac aagggtacca ccattgcc                              38

<210> SEQ ID NO 36
<211> LENGTH: 38
<212> TYPE: DNA
<213> ORGANISM: Artificial Sequence
<220> FEATURE:
<223> OTHER INFORMATION: W45LF

<400> SEQUENCE: 36
ccgttatcgg ttctggtaac ctaggtacca ccattgcc                              38

<210> SEQ ID NO 37
<211> LENGTH: 38
<212> TYPE: DNA
<213> ORGANISM: Artificial Sequence
<220> FEATURE:
```

<223> OTHER INFORMATION: W45MF

<400> SEQUENCE: 37
ccgttatcgg ttctggtaac atgggtacca ccattgcc                                   38

<210> SEQ ID NO 38
<211> LENGTH: 38
<212> TYPE: DNA
<213> ORGANISM: Artificial Sequence
<220> FEATURE:
<223> OTHER INFORMATION: W45NF

<400> SEQUENCE: 38
ccgttatcgg ttctggtaac aacggtacca ccattgcc                                   38

<210> SEQ ID NO 39
<211> LENGTH: 38
<212> TYPE: DNA
<213> ORGANISM: Artificial Sequence
<220> FEATURE:
<223> OTHER INFORMATION: W45QF

<400> SEQUENCE: 39
ccgttatcgg ttctggtaac caaggtacca ccattgcc                                   38

<210> SEQ ID NO 40
<211> LENGTH: 38
<212> TYPE: DNA
<213> ORGANISM: Artificial Sequence
<220> FEATURE:
<223> OTHER INFORMATION: W45RF

<400> SEQUENCE: 40
ccgttatcgg ttctggtaac cgtggtacca ccattgcc                                   38

<210> SEQ ID NO 41
<211> LENGTH: 38
<212> TYPE: DNA
<213> ORGANISM: Artificial Sequence
<220> FEATURE:
<223> OTHER INFORMATION: W45SF

<400> SEQUENCE: 41
ccgttatcgg ttctggtaac tctggtacca ccattgcc                                   38

<210> SEQ ID NO 42
<211> LENGTH: 38
<212> TYPE: DNA
<213> ORGANISM: Artificial Sequence
<220> FEATURE:
<223> OTHER INFORMATION: W45TF

<400> SEQUENCE: 42
ccgttatcgg ttctggtaac accggtacca ccattgcc                                   38

<210> SEQ ID NO 43
<211> LENGTH: 38
<212> TYPE: DNA
<213> ORGANISM: Artificial Sequence
<220> FEATURE:
<223> OTHER INFORMATION: W45VF

<400> SEQUENCE: 43
ccgttatcgg ttctggtaac gttggtacca ccattgcc                                   38

-continued

```
<210> SEQ ID NO 44
<211> LENGTH: 43
<212> TYPE: DNA
<213> ORGANISM: Artificial Sequence
<220> FEATURE:
<223> OTHER INFORMATION: Phe73F

<400> SEQUENCE: 44
ccaatcgttc aaatgtgggt ttttgaagag gaaattaacg gtg            43

<210> SEQ ID NO 45
<211> LENGTH: 43
<212> TYPE: DNA
<213> ORGANISM: Artificial Sequence
<220> FEATURE:
<223> OTHER INFORMATION: F73GF

<400> SEQUENCE: 45
ccaatcgttc aaatgtgggt tggtgaagag gaaattaacg gtg            43

<210> SEQ ID NO 46
<211> LENGTH: 43
<212> TYPE: DNA
<213> ORGANISM: Artificial Sequence
<220> FEATURE:
<223> OTHER INFORMATION: F73AF

<400> SEQUENCE: 46
ccaatcgttc aaatgtgggt tgctgaagag gaaattaacg gtg            43

<210> SEQ ID NO 47
<211> LENGTH: 43
<212> TYPE: DNA
<213> ORGANISM: Artificial Sequence
<220> FEATURE:
<223> OTHER INFORMATION: F73RF

<400> SEQUENCE: 47
ccaatcgttc aaatgtgggt tcgtgaagag gaaattaacg gtg            43

<210> SEQ ID NO 48
<211> LENGTH: 43
<212> TYPE: DNA
<213> ORGANISM: Artificial Sequence
<220> FEATURE:
<223> OTHER INFORMATION: F73KF

<400> SEQUENCE: 48
ccaatcgttc aaatgtgggt taaggaagag gaaattaacg gtg            43

<210> SEQ ID NO 49
<211> LENGTH: 43
<212> TYPE: DNA
<213> ORGANISM: Artificial Sequence
<220> FEATURE:
<223> OTHER INFORMATION: Phe129F

<400> SEQUENCE: 49
gtttttaaca tcccacacca attcctacca cgtatttgtt ctc            43

<210> SEQ ID NO 50
<211> LENGTH: 43
<212> TYPE: DNA
<213> ORGANISM: Artificial Sequence
<220> FEATURE:
<223> OTHER INFORMATION: F129GF
```

<400> SEQUENCE: 50
gtttttaaca tcccacacca aggtctacca cgtatttgtt ctc                43

<210> SEQ ID NO 51
<211> LENGTH: 43
<212> TYPE: DNA
<213> ORGANISM: Artificial Sequence
<220> FEATURE:
<223> OTHER INFORMATION: F129AF

<400> SEQUENCE: 51
gtttttaaca tcccacacca agctctacca cgtatttgtt ctc                43

<210> SEQ ID NO 52
<211> LENGTH: 43
<212> TYPE: DNA
<213> ORGANISM: Artificial Sequence
<220> FEATURE:
<223> OTHER INFORMATION: F129RF

<400> SEQUENCE: 52
gtttttaaca tcccacacca acgtctacca cgtatttgtt ctc                43

<210> SEQ ID NO 53
<211> LENGTH: 43
<212> TYPE: DNA
<213> ORGANISM: Artificial Sequence
<220> FEATURE:
<223> OTHER INFORMATION: F129KF

<400> SEQUENCE: 53
gtttttaaca tcccacacca aaagctacca cgtatttgtt ctc                43

<210> SEQ ID NO 54
<211> LENGTH: 38
<212> TYPE: DNA
<213> ORGANISM: Artificial Sequence
<220> FEATURE:
<223> OTHER INFORMATION: N44AR

<400> SEQUENCE: 54
ggcaatggtg gtaccccaag caccagaacc gataacgg                      38

<210> SEQ ID NO 55
<211> LENGTH: 38
<212> TYPE: DNA
<213> ORGANISM: Artificial Sequence
<220> FEATURE:
<223> OTHER INFORMATION: N44CR

<400> SEQUENCE: 55
ggcaatggtg gtacccccaac aaccagaacc gataacgg                     38

<210> SEQ ID NO 56
<211> LENGTH: 38
<212> TYPE: DNA
<213> ORGANISM: Artificial Sequence
<220> FEATURE:
<223> OTHER INFORMATION: N44GR

<400> SEQUENCE: 56
ggcaatggtg gtaccccaac caccagaacc gataacgg                      38

<210> SEQ ID NO 57
<211> LENGTH: 38

```
<212> TYPE: DNA
<213> ORGANISM: Artificial Sequence
<220> FEATURE:
<223> OTHER INFORMATION: N44IR

<400> SEQUENCE: 57
ggcaatggtg gtaccccaga taccagaacc gataacgg        38

<210> SEQ ID NO 58
<211> LENGTH: 38
<212> TYPE: DNA
<213> ORGANISM: Artificial Sequence
<220> FEATURE:
<223> OTHER INFORMATION: N44LR

<400> SEQUENCE: 58
ggcaatggtg gtacccata gaccagaacc gataacgg         38

<210> SEQ ID NO 59
<211> LENGTH: 38
<212> TYPE: DNA
<213> ORGANISM: Artificial Sequence
<220> FEATURE:
<223> OTHER INFORMATION: N44MR

<400> SEQUENCE: 59
ggcaatggtg gtacccaca taccagaacc gataacgg         38

<210> SEQ ID NO 60
<211> LENGTH: 38
<212> TYPE: DNA
<213> ORGANISM: Artificial Sequence
<220> FEATURE:
<223> OTHER INFORMATION: N44SR

<400> SEQUENCE: 60
ggcaatggtg gtacccaag aaccagaacc gataacgg         38

<210> SEQ ID NO 61
<211> LENGTH: 38
<212> TYPE: DNA
<213> ORGANISM: Artificial Sequence
<220> FEATURE:
<223> OTHER INFORMATION: N44VR

<400> SEQUENCE: 61
ggcaatggtg gtacccaaa caccagaacc gataacgg         38

<210> SEQ ID NO 62
<211> LENGTH: 38
<212> TYPE: DNA
<213> ORGANISM: Artificial Sequence
<220> FEATURE:
<223> OTHER INFORMATION: W45AR

<400> SEQUENCE: 62
ggcaatggtg gtaccagcgt taccagaacc gataacgg        38

<210> SEQ ID NO 63
<211> LENGTH: 38
<212> TYPE: DNA
<213> ORGANISM: Artificial Sequence
<220> FEATURE:
<223> OTHER INFORMATION: W45CR

<400> SEQUENCE: 63
```

```
ggcaatggtg gtaccacagt taccagaacc gataacgg                    38
```

<210> SEQ ID NO 64
<211> LENGTH: 38
<212> TYPE: DNA
<213> ORGANISM: Artificial Sequence
<220> FEATURE:
<223> OTHER INFORMATION: W45GR

<400> SEQUENCE: 64

```
ggcaatggtg gtaccaccgt taccagaacc gataacgg                    38
```

<210> SEQ ID NO 65
<211> LENGTH: 38
<212> TYPE: DNA
<213> ORGANISM: Artificial Sequence
<220> FEATURE:
<223> OTHER INFORMATION: W45HR

<400> SEQUENCE: 65

```
ggcaatggtg gtaccgtggt taccagaacc gataacgg                    38
```

<210> SEQ ID NO 66
<211> LENGTH: 38
<212> TYPE: DNA
<213> ORGANISM: Artificial Sequence
<220> FEATURE:
<223> OTHER INFORMATION: W45IR

<400> SEQUENCE: 66

```
ggcaatggtg gtaccgatgt taccagaacc gataacgg                    38
```

<210> SEQ ID NO 67
<211> LENGTH: 38
<212> TYPE: DNA
<213> ORGANISM: Artificial Sequence
<220> FEATURE:
<223> OTHER INFORMATION: W45KR

<400> SEQUENCE: 67

```
ggcaatggtg gtacccttgt taccagaacc gataacgg                    38
```

<210> SEQ ID NO 68
<211> LENGTH: 38
<212> TYPE: DNA
<213> ORGANISM: Artificial Sequence
<220> FEATURE:
<223> OTHER INFORMATION: W45LR

<400> SEQUENCE: 68

```
ggcaatggtg gtacctaggt taccagaacc gataacgg                    38
```

<210> SEQ ID NO 69
<211> LENGTH: 38
<212> TYPE: DNA
<213> ORGANISM: Artificial Sequence
<220> FEATURE:
<223> OTHER INFORMATION: W45MR

<400> SEQUENCE: 69

```
ggcaatggtg gtacccatgt taccagaacc gataacgg                    38
```

<210> SEQ ID NO 70
<211> LENGTH: 38
<212> TYPE: DNA
<213> ORGANISM: Artificial Sequence -continued

```
<220> FEATURE:
<223> OTHER INFORMATION: W45NR

<400> SEQUENCE: 70
ggcaatggtg gtaccgttgt taccagaacc gataacgg                                  38

<210> SEQ ID NO 71
<211> LENGTH: 38
<212> TYPE: DNA
<213> ORGANISM: Artificial Sequence
<220> FEATURE:
<223> OTHER INFORMATION: W45QR

<400> SEQUENCE: 71
ggcaatggtg gtaccttggt taccagaacc gataacgg                                  38

<210> SEQ ID NO 72
<211> LENGTH: 38
<212> TYPE: DNA
<213> ORGANISM: Artificial Sequence
<220> FEATURE:
<223> OTHER INFORMATION: W45RR

<400> SEQUENCE: 72
ggcaatggtg gtaccacggt taccagaacc gataacgg                                  38

<210> SEQ ID NO 73
<211> LENGTH: 38
<212> TYPE: DNA
<213> ORGANISM: Artificial Sequence
<220> FEATURE:
<223> OTHER INFORMATION: W45SR

<400> SEQUENCE: 73
ggcaatggtg gtaccagagt taccagaacc gataacgg                                  38

<210> SEQ ID NO 74
<211> LENGTH: 38
<212> TYPE: DNA
<213> ORGANISM: Artificial Sequence
<220> FEATURE:
<223> OTHER INFORMATION: W45TR

<400> SEQUENCE: 74
ggcaatggtg gtaccggtgt taccagaacc gataacgg                                  38

<210> SEQ ID NO 75
<211> LENGTH: 38
<212> TYPE: DNA
<213> ORGANISM: Artificial Sequence
<220> FEATURE:
<223> OTHER INFORMATION: W45VR

<400> SEQUENCE: 75
ggcaatggtg gtaccaacgt taccagaacc gataacgg                                  38

<210> SEQ ID NO 76
<211> LENGTH: 43
<212> TYPE: DNA
<213> ORGANISM: Artificial Sequence
<220> FEATURE:
<223> OTHER INFORMATION: F73GR

<400> SEQUENCE: 76
caccgttaat ttcctcttca ccaacccaca tttgaacgat tgg                            43
```

<210> SEQ ID NO 77
<211> LENGTH: 43
<212> TYPE: DNA
<213> ORGANISM: Artificial Sequence
<220> FEATURE:
<223> OTHER INFORMATION: F73AR

<400> SEQUENCE: 77
caccgttaat tcctcttca gcaacccaca tttgaacgat tgg          43

<210> SEQ ID NO 78
<211> LENGTH: 43
<212> TYPE: DNA
<213> ORGANISM: Artificial Sequence
<220> FEATURE:
<223> OTHER INFORMATION: F73RR

<400> SEQUENCE: 78
caccgttaat tcctcttca cgaacccaca tttgaacgat tgg          43

<210> SEQ ID NO 79
<211> LENGTH: 43
<212> TYPE: DNA
<213> ORGANISM: Artificial Sequence
<220> FEATURE:
<223> OTHER INFORMATION: F73KR

<400> SEQUENCE: 79
caccgttaat tcctcttcc ttaacccaca tttgaacgat tgg          43

<210> SEQ ID NO 80
<211> LENGTH: 43
<212> TYPE: DNA
<213> ORGANISM: Artificial Sequence
<220> FEATURE:
<223> OTHER INFORMATION: F129GR

<400> SEQUENCE: 80
gagaacaaat acgtggtaga ccttggtgtg ggatgttaaa aac          43

<210> SEQ ID NO 81
<211> LENGTH: 43
<212> TYPE: DNA
<213> ORGANISM: Artificial Sequence
<220> FEATURE:
<223> OTHER INFORMATION: F129AR

<400> SEQUENCE: 81
gagaacaaat acgtggtaga gcttggtgtg ggatgttaaa aac          43

<210> SEQ ID NO 82
<211> LENGTH: 43
<212> TYPE: DNA
<213> ORGANISM: Artificial Sequence
<220> FEATURE:
<223> OTHER INFORMATION: F129RR

<400> SEQUENCE: 82
gagaacaaat acgtggtaga cgttggtgtg ggatgttaaa aac          43

<210> SEQ ID NO 83
<211> LENGTH: 43
<212> TYPE: DNA
<213> ORGANISM: Artificial Sequence
<220> FEATURE:
<223> OTHER INFORMATION: F129KR

<400> SEQUENCE: 83
gagaacaaat acgtggtagc ttttggtgtg ggatgttaaa aac                43

<210> SEQ ID NO 84
<211> LENGTH: 349
<212> TYPE: PRT
<213> ORGANISM: Homo sapiens

<400> SEQUENCE: 84

```
Met Ala Ser Lys Lys Val Cys Ile Val Gly Ser Gly Asn Trp Gly Ser
 1               5                  10                  15

Ala Ile Ala Lys Ile Val Gly Gly Asn Ala Ala Gln Leu Ala Gln Phe
            20                  25                  30

Asp Pro Arg Val Thr Met Trp Val Phe Glu Glu Asp Ile Gly Gly Lys
        35                  40                  45

Lys Leu Thr Glu Ile Ile Asn Thr Gln His Glu Asn Val Lys Tyr Leu
    50                  55                  60

Pro Gly His Lys Leu Pro Pro Asn Val Val Ala Val Pro Asp Val Val
65                  70                  75                  80

Gln Ala Ala Glu Asp Ala Asp Ile Leu Ile Phe Val Val Pro His Gln
                85                  90                  95

Phe Ile Gly Lys Ile Cys Asp Gln Leu Lys Gly His Leu Lys Ala Asn
            100                 105                 110

Pro Thr Gly Ile Ser Leu Ile Lys Gly Val Asp Glu Gly Pro Asn Gly
        115                 120                 125

Leu Lys Leu Ile Ser Glu Val Ile Gly Glu Arg Leu Gly Ile Pro Met
    130                 135                 140

Ser Val Leu Met Gly Ala Asn Ile Ala Ser Glu Val Ala Asp Glu Lys
145                 150                 155                 160

Phe Cys Glu Thr Thr Ile Gly Cys Lys Asp Pro Ala Gln Gly Gln Leu
                165                 170                 175

Leu Lys Glu Leu Met Gln Thr Pro Asn Phe Arg Ile Thr Val Val Gln
            180                 185                 190

Glu Val Asp Thr Val Glu Ile Cys Gly Ala Leu Lys Asn Val Val Ala
        195                 200                 205

Val Gly Ala Gly Phe Cys Asp Gly Leu Gly Phe Gly Asp Asn Thr Lys
    210                 215                 220

Ala Ala Val Ile Arg Leu Gly Leu Met Glu Met Ile Ala Phe Ala Lys
225                 230                 235                 240

Leu Phe Cys Ser Gly Pro Val Ser Ser Ala Thr Phe Leu Glu Ser Cys
                245                 250                 255

Gly Val Ala Asp Leu Ile Thr Thr Cys Tyr Gly Gly Arg Asn Arg Lys
            260                 265                 270

Val Ala Glu Ala Phe Ala Arg Thr Gly Lys Ser Ile Glu Gln Leu Glu
        275                 280                 285

Lys Glu Leu Leu Asn Gly Gln Lys Leu Gln Gly Pro Glu Thr Ala Arg
    290                 295                 300

Glu Leu Tyr Ser Ile Leu Gln His Lys Gly Leu Val Asp Lys Phe Pro
305                 310                 315                 320

Leu Phe Met Ala Val Tyr Lys Val Cys Tyr Glu Gly Gln Pro Val Gly
                325                 330                 335

Glu Phe Ile His Cys Leu Gln Asn His Pro Glu His Met
            340                 345
```

<210> SEQ ID NO 85
<211> LENGTH: 343
<212> TYPE: PRT
<213> ORGANISM: Artificial Sequence
<220> FEATURE:
<223> OTHER INFORMATION: KG9G

<400> SEQUENCE: 85

Met Glu Glu Cys Lys Met Ala Lys Ile Tyr Tyr Gln Glu Asp Cys Asn
1               5                   10                  15

Leu Ser Leu Leu Asp Gly Lys Thr Ile Ala Val Ile Gly Tyr Gly Ser
            20                  25                  30

Gln Gly His Ala His Ala Leu Asn Ala Lys Ser Gly Cys Asn Val
        35                  40                  45

Ile Ile Gly Leu Tyr Glu Gly Ala Lys Glu Trp Lys Arg Ala Glu Glu
50                  55                  60

Gln Gly Phe Glu Val Tyr Thr Ala Ala Glu Ala Ala Lys Lys Ala Asp
65                  70                  75                  80

Ile Ile Met Ile Leu Ile Asn Asp Glu Lys Gln Ala Thr Met Tyr Lys
                85                  90                  95

Asn Asp Ile Glu Pro Asn Leu Glu Ala Gly Asn Met Leu Met Phe Ala
            100                 105                 110

His Gly Phe Asn Ile His Phe Gly Cys Ile Val Pro Pro Lys Asp Val
        115                 120                 125

Asp Val Thr Met Ile Ala Pro Lys Gly Pro Gly His Thr Val Arg Ser
130                 135                 140

Glu Tyr Glu Glu Gly Lys Gly Val Pro Cys Leu Val Ala Val Glu Gln
145                 150                 155                 160

Asp Ala Thr Gly Lys Ala Leu Asp Met Ala Leu Ala Tyr Ala Leu Ala
                165                 170                 175

Ile Gly Gly Ala Arg Ala Gly Val Leu Glu Thr Thr Phe Arg Thr Glu
            180                 185                 190

Thr Glu Thr Asp Leu Phe Gly Glu Gln Ala Val Leu Cys Gly Gly Val
        195                 200                 205

Cys Ala Leu Met Gln Ala Gly Phe Glu Thr Leu Val Glu Ala Gly Tyr
210                 215                 220

Asp Pro Arg Asn Ala Tyr Phe Glu Cys Ile His Glu Met Lys Leu Ile
225                 230                 235                 240

Val Asp Leu Ile Tyr Gln Ser Gly Phe Ser Gly Met Arg Tyr Ser Ile
                245                 250                 255

Ser Asn Thr Ala Glu Tyr Gly Asp Tyr Ile Thr Gly Pro Lys Ile Ile
            260                 265                 270

Thr Glu Asp Thr Lys Lys Ala Met Lys Lys Ile Leu Ser Asp Ile Gln
        275                 280                 285

Asp Gly Thr Phe Ala Lys Asp Phe Leu Val Asp Met Ser Asp Ala Gly
290                 295                 300

Ser Gln Val His Phe Lys Ala Met Arg Lys Leu Ala Ser Glu His Pro
305                 310                 315                 320

Ala Glu Val Val Gly Glu Glu Ile Arg Ser Leu Tyr Ser Trp Ser Asp
                325                 330                 335

Glu Asp Lys Leu Ile Asn Asn
            340

<210> SEQ ID NO 86
<211> LENGTH: 343

<212> TYPE: PRT
<213> ORGANISM: Artificial Sequence
<220> FEATURE:
<223> OTHER INFORMATION: K9D3

<400> SEQUENCE: 86

```
Met Glu Glu Cys Lys Met Ala Lys Ile Tyr Tyr Gln Glu Asp Cys Asn
1               5                   10                  15

Leu Ser Leu Leu Asp Gly Lys Thr Ile Ala Val Ile Gly Tyr Gly Ser
            20                  25                  30

Gln Gly His Ala His Ala Leu Asn Ala Lys Glu Ser Gly Cys Asn Val
        35                  40                  45

Ile Ile Gly Leu Tyr Glu Gly Ala Lys Asp Trp Lys Arg Ala Glu Glu
50                  55                  60

Gln Gly Phe Glu Val Tyr Thr Ala Ala Glu Ala Ala Lys Lys Ala Asp
65                  70                  75                  80

Ile Ile Met Ile Leu Ile Asn Asp Glu Lys Gln Ala Thr Met Tyr Lys
                85                  90                  95

Asn Asp Ile Glu Pro Asn Leu Glu Ala Gly Asn Met Leu Met Phe Ala
            100                 105                 110

His Gly Phe Asn Ile His Phe Gly Cys Ile Val Pro Pro Lys Asp Val
        115                 120                 125

Asp Val Thr Met Ile Ala Pro Lys Gly Pro Gly His Thr Val Arg Ser
130                 135                 140

Glu Tyr Glu Glu Gly Lys Gly Val Pro Cys Leu Val Ala Val Glu Gln
145                 150                 155                 160

Asp Ala Thr Gly Lys Ala Leu Asp Met Ala Leu Ala Tyr Ala Leu Ala
                165                 170                 175

Ile Gly Gly Ala Arg Ala Gly Val Leu Glu Thr Thr Phe Arg Thr Glu
            180                 185                 190

Thr Glu Thr Asp Leu Phe Gly Glu Gln Ala Val Leu Cys Gly Gly Val
        195                 200                 205

Cys Ala Leu Met Gln Ala Gly Phe Glu Thr Leu Val Glu Ala Gly Tyr
210                 215                 220

Asp Pro Arg Asn Ala Tyr Phe Glu Cys Ile His Glu Met Lys Leu Ile
225                 230                 235                 240

Val Asp Leu Ile Tyr Gln Ser Gly Phe Ser Gly Met Arg Tyr Ser Ile
                245                 250                 255

Ser Asn Thr Ala Glu Tyr Gly Asp Tyr Ile Thr Gly Pro Lys Ile Ile
            260                 265                 270

Thr Glu Asp Thr Lys Lys Ala Met Lys Lys Ile Leu Ser Asp Ile Gln
        275                 280                 285

Asp Gly Thr Phe Ala Lys Asp Phe Leu Val Asp Met Ser Asp Ala Gly
290                 295                 300

Ser Gln Val His Phe Lys Ala Met Arg Lys Leu Ala Ser Glu His Pro
305                 310                 315                 320

Ala Glu Val Val Gly Glu Glu Ile Arg Ser Leu Tyr Ser Trp Ser Asp
                325                 330                 335

Glu Asp Lys Leu Ile Asn Asn
            340
```

<210> SEQ ID NO 87
<211> LENGTH: 343
<212> TYPE: PRT
<213> ORGANISM: Artificial Sequence
<220> FEATURE:

<223> OTHER INFORMATION: K9JB4P

<400> SEQUENCE: 87

```
Met Glu Glu Cys Lys Met Ala Lys Ile Tyr Tyr Gln Glu Asp Cys Asn
1               5                   10                  15
Leu Ser Leu Leu Asp Gly Lys Thr Ile Ala Val Ile Gly Tyr Gly Ser
            20                  25                  30
Gln Gly His Ala His Ala Leu Asn Ala Lys Glu Ser Gly Cys Asn Val
        35                  40                  45
Ile Ile Gly Leu Tyr Glu Gly Ala Glu Glu Trp Lys Arg Ala Glu Glu
    50                  55                  60
Gln Gly Phe Glu Val Tyr Thr Ala Ala Glu Ala Lys Lys Ala Asp
65                  70                  75                  80
Ile Ile Met Ile Leu Ile Pro Asp Glu Lys Gln Ala Thr Met Tyr Lys
                85                  90                  95
Asn Asp Ile Glu Pro Asn Leu Glu Ala Gly Asn Met Leu Met Phe Ala
            100                 105                 110
His Gly Phe Asn Ile His Phe Gly Cys Ile Val Pro Pro Lys Asp Val
        115                 120                 125
Asp Val Thr Met Ile Ala Pro Lys Gly Pro Gly His Thr Val Arg Ser
    130                 135                 140
Glu Tyr Glu Glu Gly Lys Gly Val Pro Cys Leu Val Ala Val Glu Gln
145                 150                 155                 160
Asp Ala Thr Gly Lys Ala Leu Asp Met Ala Leu Ala Tyr Ala Leu Ala
                165                 170                 175
Ile Gly Gly Ala Arg Ala Gly Val Leu Glu Thr Thr Phe Arg Thr Glu
            180                 185                 190
Thr Glu Thr Asp Leu Phe Gly Glu Gln Ala Val Leu Cys Gly Gly Val
        195                 200                 205
Cys Ala Leu Met Gln Ala Gly Phe Glu Thr Leu Val Glu Ala Gly Tyr
    210                 215                 220
Asp Pro Arg Asn Ala Tyr Phe Glu Cys Ile His Glu Met Lys Leu Ile
225                 230                 235                 240
Val Asp Leu Ile Tyr Gln Ser Gly Phe Ser Gly Met Arg Tyr Ser Ile
                245                 250                 255
Ser Asn Thr Ala Glu Tyr Gly Asp Tyr Ile Thr Gly Pro Lys Ile Ile
            260                 265                 270
Thr Glu Asp Thr Lys Lys Ala Met Lys Lys Ile Leu Ser Asp Ile Gln
        275                 280                 285
Asp Gly Thr Phe Ala Lys Asp Phe Leu Val Asp Met Ser Asp Ala Gly
    290                 295                 300
Ser Gln Val His Phe Lys Ala Met Arg Lys Leu Ala Ser Glu His Pro
305                 310                 315                 320
Ala Glu Val Val Gly Glu Glu Ile Arg Ser Leu Tyr Ser Trp Ser Asp
                325                 330                 335
Glu Asp Lys Leu Ile Asn Asn
            340
```

<210> SEQ ID NO 88
<211> LENGTH: 570
<212> TYPE: PRT
<213> ORGANISM: Lactococcus lactis

<400> SEQUENCE: 88

Met Glu Phe Lys Tyr Asn Gly Lys Val Glu Ser Ile Glu Leu Asn Lys

-continued

```
1               5                   10                  15
Tyr Ser Lys Thr Leu Thr Gln Asp Pro Thr Gln Pro Ala Thr Gln Ala
            20                  25                  30

Met His Tyr Gly Ile Gly Phe Lys Asp Glu Asp Phe Lys Lys Ala Gln
            35                  40                  45

Val Gly Ile Val Ser Met Asp Trp Asp Gly Asn Pro Cys Asn Met His
50                  55                  60

Leu Gly Thr Leu Gly Ser Lys Ile Lys Asn Ser Val Asn Gln Thr Asp
65                  70                  75                  80

Gly Leu Ile Gly Leu Gln Phe His Thr Ile Gly Val Ser Asp Gly Ile
                85                  90                  95

Ala Asn Gly Lys Leu Gly Met Arg Tyr Ser Leu Val Ser Arg Glu Val
            100                 105                 110

Ile Ala Asp Ser Ile Glu Thr Asn Ala Gly Ala Glu Tyr Tyr Asp Ala
            115                 120                 125

Ile Val Ala Val Pro Gly Cys Asp Lys Asn Met Pro Gly Ser Ile Ile
130                 135                 140

Gly Met Ala Arg Leu Asn Arg Pro Ser Ile Met Val Tyr Gly Gly Thr
145                 150                 155                 160

Ile Glu His Gly Glu Tyr Lys Gly Glu Lys Leu Asn Ile Val Ser Ala
                165                 170                 175

Phe Glu Ala Leu Gly Gln Lys Ile Thr Gly Asn Ile Ser Glu Glu Asp
            180                 185                 190

Tyr His Gly Val Ile Cys Asn Ala Ile Pro Gly Gln Gly Ala Cys Gly
            195                 200                 205

Gly Met Tyr Thr Ala Asn Thr Leu Ala Ser Ala Ile Glu Thr Leu Gly
210                 215                 220

Met Ser Leu Pro Tyr Ser Ala Ser Asn Pro Ala Val Ser Gln Glu Lys
225                 230                 235                 240

Glu Asp Glu Cys Asp Glu Ile Gly Leu Ala Ile Lys Asn Leu Leu Glu
                245                 250                 255

Lys Asp Ile Lys Pro Ser Asp Ile Met Thr Lys Glu Ala Phe Glu Asn
            260                 265                 270

Ala Ile Thr Ile Val Met Val Leu Gly Gly Ser Thr Asn Ala Val Leu
            275                 280                 285

His Ile Ile Ala Met Ala Asn Ala Ile Gly Val Glu Ile Thr Gln Asp
290                 295                 300

Asp Phe Gln Arg Ile Ser Asp Val Thr Pro Val Leu Gly Asp Phe Lys
305                 310                 315                 320

Pro Ser Gly Lys Tyr Met Met Glu Asp Leu His Lys Ile Gly Gly Val
                325                 330                 335

Pro Ala Val Leu Lys Tyr Leu Leu Lys Glu Gly Lys Leu His Gly Asp
            340                 345                 350

Cys Leu Thr Val Thr Gly Lys Thr Leu Ala Glu Asn Val Glu Thr Ala
            355                 360                 365

Leu Asp Leu Asp Phe Asp Ser Gln Asp Ile Ile Arg Pro Leu Glu Asn
370                 375                 380

Pro Ile Lys Ala Thr Gly His Leu Gln Ile Leu Tyr Gly Asn Leu Ala
385                 390                 395                 400

Glu Gly Gly Ser Val Ala Lys Ile Ser Gly Lys Glu Gly Glu Phe Phe
                405                 410                 415

Lys Gly Thr Ala Arg Val Phe Asp Gly Glu Gln His Phe Ile Asp Gly
            420                 425                 430
```

-continued

```
Ile Glu Ser Gly Arg Leu His Ala Gly Asp Val Ala Val Ile Arg Asn
            435                 440                 445

Ile Gly Pro Val Gly Gly Pro Gly Met Pro Glu Met Leu Lys Pro Thr
450                 455                 460

Ser Ala Leu Ile Gly Ala Gly Leu Gly Lys Ser Cys Ala Leu Ile Thr
465                 470                 475                 480

Asp Gly Arg Phe Ser Gly Gly Thr His Gly Phe Val Val Gly His Ile
                485                 490                 495

Val Pro Glu Ala Val Glu Gly Gly Leu Ile Gly Leu Val Glu Asp Asp
                500                 505                 510

Asp Ile Ile Glu Ile Asp Ala Val Asn Asn Ser Ile Ser Leu Lys Val
            515                 520                 525

Ala Asp Asp Glu Ile Ala Arg Arg Ala Asn Tyr Gln Lys Pro Ala
            530                 535                 540

Pro Lys Ala Thr Arg Gly Val Leu Ala Lys Phe Ala Lys Leu Thr Arg
545                 550                 555                 560

Pro Ala Ser Glu Gly Cys Val Thr Asp Leu
                565                 570

<210> SEQ ID NO 89
<211> LENGTH: 571
<212> TYPE: PRT
<213> ORGANISM: Streptococcus mutans

<400> SEQUENCE: 89

Met Thr Asp Lys Lys Thr Leu Lys Asp Leu Arg Asn Arg Ser Ser Val
1               5                   10                  15

Tyr Asp Ser Met Val Lys Ser Pro Asn Arg Ala Met Leu Arg Ala Thr
                20                  25                  30

Gly Met Gln Asp Glu Asp Phe Glu Lys Pro Ile Val Gly Val Ile Ser
            35                  40                  45

Thr Trp Ala Glu Asn Thr Pro Cys Asn Ile His Leu His Asp Phe Gly
    50                  55                  60

Lys Leu Ala Lys Val Gly Val Lys Glu Ala Gly Ala Trp Pro Val Gln
65                  70                  75                  80

Phe Gly Thr Ile Thr Val Ser Asp Gly Ile Ala Met Gly Thr Gln Gly
                85                  90                  95

Met Arg Phe Ser Leu Thr Ser Arg Asp Ile Ile Ala Asp Ser Ile Glu
            100                 105                 110

Ala Ala Met Gly Gly His Asn Ala Asp Ala Phe Val Ala Ile Gly Gly
        115                 120                 125

Cys Asp Lys Asn Met Pro Gly Ser Val Ile Ala Met Ala Asn Met Asp
    130                 135                 140

Ile Pro Ala Ile Phe Ala Tyr Gly Gly Thr Ile Ala Pro Gly Asn Leu
145                 150                 155                 160

Asp Gly Lys Asp Ile Asp Leu Val Ser Val Phe Glu Gly Val Gly His
                165                 170                 175

Trp Asn His Gly Asp Met Thr Lys Glu Glu Val Lys Ala Leu Glu Cys
            180                 185                 190

Asn Ala Cys Pro Gly Pro Gly Gly Cys Gly Gly Met Tyr Thr Ala Asn
        195                 200                 205

Thr Met Ala Thr Ala Ile Glu Val Leu Gly Leu Ser Leu Pro Gly Ser
    210                 215                 220

Ser Ser His Pro Ala Glu Ser Ala Glu Lys Lys Ala Asp Ile Glu Glu
```

```
               225                 230                 235                 240
Ala Gly Arg Ala Val Val Lys Met Leu Glu Met Gly Leu Lys Pro Ser
                245                 250                 255
Asp Ile Leu Thr Arg Glu Ala Phe Glu Asp Ala Ile Thr Val Thr Met
                260                 265                 270
Ala Leu Gly Gly Ser Thr Asn Ser Thr Leu His Leu Ala Ile Ala
                275                 280                 285
His Ala Ala Asn Val Glu Leu Thr Leu Asp Asp Phe Asn Thr Phe Gln
                290                 295                 300
Glu Lys Val Pro His Leu Ala Asp Leu Lys Pro Ser Gly Gln Tyr Val
305                 310                 315                 320
Phe Gln Asp Leu Tyr Lys Val Gly Val Pro Ala Val Met Lys Tyr
                325                 330                 335
Leu Leu Lys Asn Gly Phe Leu His Gly Asp Arg Ile Thr Cys Thr Gly
                340                 345                 350
Lys Thr Val Ala Glu Asn Leu Lys Ala Phe Asp Asp Leu Thr Pro Gly
                355                 360                 365
Gln Lys Val Ile Met Pro Leu Glu Asn Pro Lys Arg Glu Asp Gly Pro
                370                 375                 380
Leu Ile Ile Leu His Gly Asn Leu Ala Pro Asp Gly Ala Val Ala Lys
385                 390                 395                 400
Val Ser Gly Val Lys Val Arg Arg His Val Gly Pro Ala Lys Val Phe
                405                 410                 415
Asn Ser Glu Glu Glu Ala Ile Glu Ala Val Leu Asn Asp Asp Ile Val
                420                 425                 430
Asp Gly Asp Val Val Val Arg Phe Val Gly Pro Lys Gly Gly Pro
                435                 440                 445
Gly Met Pro Glu Met Leu Ser Leu Ser Ser Met Ile Val Gly Lys Gly
                450                 455                 460
Gln Gly Glu Lys Val Ala Leu Leu Thr Asp Gly Arg Phe Ser Gly Gly
465                 470                 475                 480
Thr Tyr Gly Leu Val Val Gly His Ile Ala Pro Glu Ala Gln Asp Gly
                485                 490                 495
Gly Pro Ile Ala Tyr Leu Gln Thr Gly Asp Ile Val Thr Ile Asp Gln
                500                 505                 510
Asp Thr Lys Glu Leu His Phe Asp Ile Ser Asp Glu Glu Leu Lys His
                515                 520                 525
Arg Gln Glu Thr Ile Glu Leu Pro Pro Leu Tyr Ser Arg Gly Ile Leu
                530                 535                 540
Gly Lys Tyr Ala His Ile Val Ser Ser Ala Ser Arg Gly Ala Val Thr
545                 550                 555                 560
Asp Phe Trp Lys Pro Glu Glu Thr Gly Lys Lys
                565                 570

<210> SEQ ID NO 90
<211> LENGTH: 548
<212> TYPE: PRT
<213> ORGANISM: Lactococcus lactis

<400> SEQUENCE: 90

Met Tyr Thr Val Gly Asp Tyr Leu Leu Asp Arg Leu His Glu Leu Gly
1               5                   10                  15
Ile Glu Glu Ile Phe Gly Val Pro Gly Asp Tyr Asn Leu Gln Phe Leu
                20                  25                  30
```

-continued

```
Asp Gln Ile Ile Ser His Lys Asp Met Lys Trp Val Gly Asn Ala Asn
         35                  40                  45
Glu Leu Asn Ala Ser Tyr Met Ala Asp Gly Tyr Ala Arg Thr Lys Lys
 50                  55                  60
Ala Ala Ala Phe Leu Thr Thr Phe Gly Val Gly Glu Leu Ser Ala Val
 65                  70                  75                  80
Asn Gly Leu Ala Gly Ser Tyr Ala Glu Asn Leu Pro Val Val Glu Ile
                 85                  90                  95
Val Gly Ser Pro Thr Ser Lys Val Gln Asn Glu Gly Lys Phe Val His
            100                 105                 110
His Thr Leu Ala Asp Gly Asp Phe Lys His Phe Met Lys Met His Glu
        115                 120                 125
Pro Val Thr Ala Ala Arg Thr Leu Leu Thr Ala Glu Asn Ala Thr Val
    130                 135                 140
Glu Ile Asp Arg Val Leu Ser Ala Leu Leu Lys Glu Arg Lys Pro Val
145                 150                 155                 160
Tyr Ile Asn Leu Pro Val Asp Val Ala Ala Lys Ala Glu Lys Pro
                165                 170                 175
Ser Leu Pro Leu Lys Lys Glu Asn Ser Thr Ser Asn Thr Ser Asp Gln
            180                 185                 190
Glu Ile Leu Asn Lys Ile Gln Glu Ser Leu Lys Asn Ala Lys Lys Pro
        195                 200                 205
Ile Val Ile Thr Gly His Glu Ile Ile Ser Phe Gly Leu Glu Lys Thr
    210                 215                 220
Val Thr Gln Phe Ile Ser Lys Thr Lys Leu Pro Ile Thr Thr Leu Asn
225                 230                 235                 240
Phe Gly Lys Ser Ser Val Asp Glu Ala Leu Pro Ser Phe Leu Gly Ile
                245                 250                 255
Tyr Asn Gly Thr Leu Ser Glu Pro Asn Leu Lys Glu Phe Val Glu Ser
            260                 265                 270
Ala Asp Phe Ile Leu Met Leu Gly Val Lys Leu Thr Asp Ser Ser Thr
        275                 280                 285
Gly Ala Phe Thr His His Leu Asn Glu Asn Lys Met Ile Ser Leu Asn
    290                 295                 300
Ile Asp Glu Gly Lys Ile Phe Asn Glu Arg Ile Gln Asn Phe Asp Phe
305                 310                 315                 320
Glu Ser Leu Ile Ser Ser Leu Leu Asp Leu Ser Glu Ile Glu Tyr Lys
                325                 330                 335
Gly Lys Tyr Ile Asp Lys Lys Gln Glu Asp Phe Val Pro Ser Asn Ala
            340                 345                 350
Leu Leu Ser Gln Asp Arg Leu Trp Gln Ala Val Glu Asn Leu Thr Gln
        355                 360                 365
Ser Asn Glu Thr Ile Val Ala Glu Gln Gly Thr Ser Phe Phe Gly Ala
    370                 375                 380
Ser Ser Ile Phe Leu Lys Ser Lys Ser His Phe Ile Gly Gln Pro Leu
385                 390                 395                 400
Trp Gly Ser Ile Gly Tyr Thr Phe Pro Ala Ala Leu Gly Ser Gln Ile
                405                 410                 415
Ala Asp Lys Glu Ser Arg His Leu Leu Phe Ile Gly Asp Gly Ser Leu
            420                 425                 430
Gln Leu Thr Val Gln Glu Leu Gly Leu Ala Ile Arg Glu Lys Ile Asn
        435                 440                 445
Pro Ile Cys Phe Ile Ile Asn Asn Asp Gly Tyr Thr Val Glu Arg Glu
```

```
                  450                 455                 460
Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
                500                 505                 510

Gln Ala Asp Pro Asn Arg Met Tyr Trp Ile Glu Leu Ile Leu Ala Lys
                515                 520                 525

Glu Gly Ala Pro Lys Val Leu Lys Lys Met Gly Lys Leu Phe Ala Glu
                530                 535                 540

Gln Asn Lys Ser
545

<210> SEQ ID NO 91
<211> LENGTH: 548
<212> TYPE: PRT
<213> ORGANISM: Listeria grayi

<400> SEQUENCE: 91

Met Tyr Thr Val Gly Gln Tyr Leu Val Asp Arg Leu Glu Glu Ile Gly
1               5                   10                  15

Ile Asp Lys Val Phe Gly Val Pro Gly Asp Tyr Asn Leu Thr Phe Leu
                20                  25                  30

Asp Tyr Ile Gln Asn His Glu Gly Leu Ser Trp Gln Gly Asn Thr Asn
            35                  40                  45

Glu Leu Asn Ala Ala Tyr Ala Ala Asp Gly Tyr Ala Arg Glu Arg Gly
50                  55                  60

Val Ser Ala Leu Val Thr Thr Phe Gly Val Gly Glu Leu Ser Ala Ile
65                  70                  75                  80

Asn Gly Thr Ala Gly Ser Phe Ala Glu Gln Val Pro Val Ile His Ile
                85                  90                  95

Val Gly Ser Pro Thr Met Asn Val Gln Ser Asn Lys Lys Leu Val His
                100                 105                 110

His Ser Leu Gly Met Gly Asn Phe His Asn Phe Ser Glu Met Ala Lys
            115                 120                 125

Glu Val Thr Ala Ala Thr Thr Met Leu Thr Glu Glu Asn Ala Ala Ser
130                 135                 140

Glu Ile Asp Arg Val Leu Glu Thr Ala Leu Leu Glu Lys Arg Pro Val
145                 150                 155                 160

Tyr Ile Asn Leu Pro Ile Asp Ile Ala His Lys Ala Ile Val Lys Pro
                165                 170                 175

Ala Lys Ala Leu Gln Thr Glu Lys Ser Ser Gly Glu Arg Glu Ala Gln
                180                 185                 190

Leu Ala Glu Ile Ile Leu Ser His Leu Glu Lys Ala Ala Gln Pro Ile
            195                 200                 205

Val Ile Ala Gly His Glu Ile Ala Arg Phe Gln Ile Arg Glu Arg Phe
210                 215                 220

Glu Asn Trp Ile Asn Gln Thr Lys Leu Pro Val Thr Asn Leu Ala Tyr
225                 230                 235                 240

Gly Lys Gly Ser Phe Asn Glu Asn Glu His Phe Ile Gly Thr Tyr
                245                 250                 255

Tyr Pro Ala Phe Ser Asp Lys Asn Val Leu Asp Tyr Val Asp Asn Ser
                260                 265                 270
```

```
Asp Phe Val Leu His Phe Gly Lys Ile Ile Asp Asn Ser Thr Ser
            275                 280                 285

Ser Phe Ser Gln Gly Phe Lys Thr Glu Asn Thr Leu Thr Ala Ala Asn
290                 295                 300

Asp Ile Ile Met Leu Pro Asp Gly Ser Thr Tyr Ser Gly Ile Ser Leu
305                 310                 315                 320

Asn Gly Leu Leu Ala Glu Leu Glu Lys Leu Asn Phe Thr Phe Ala Asp
            325                 330                 335

Thr Ala Ala Lys Gln Ala Glu Leu Ala Val Phe Glu Pro Gln Ala Glu
            340                 345                 350

Thr Pro Leu Lys Gln Asp Arg Phe His Gln Ala Val Met Asn Phe Leu
            355                 360                 365

Gln Ala Asp Asp Val Leu Val Thr Glu Gln Gly Thr Ser Ser Phe Gly
370                 375                 380

Leu Met Leu Ala Pro Leu Lys Lys Gly Met Asn Leu Ile Ser Gln Thr
385                 390                 395                 400

Leu Trp Gly Ser Ile Gly Tyr Thr Leu Pro Ala Met Ile Gly Ser Gln
            405                 410                 415

Ile Ala Ala Pro Glu Arg Arg His Ile Leu Ser Ile Gly Asp Gly Ser
            420                 425                 430

Phe Gln Leu Thr Ala Gln Glu Met Ser Thr Ile Phe Arg Glu Lys Leu
435                 440                 445

Thr Pro Val Ile Phe Ile Ile Asn Asn Asp Gly Tyr Thr Val Glu Arg
            450                 455                 460

Ala Ile His Gly Glu Asp Glu Ser Tyr Asn Asp Ile Pro Thr Trp Asn
465                 470                 475                 480

Leu Gln Leu Val Ala Glu Thr Phe Gly Gly Asp Ala Glu Thr Val Asp
            485                 490                 495

Thr His Asn Val Phe Thr Glu Thr Asp Phe Ala Asn Thr Leu Ala Ala
            500                 505                 510

Ile Asp Ala Thr Pro Gln Lys Ala His Val Val Glu Val His Met Glu
            515                 520                 525

Gln Met Asp Met Pro Glu Ser Leu Arg Gln Ile Gly Leu Ala Leu Ser
530                 535                 540

Lys Gln Asn Ser
545

<210> SEQ ID NO 92
<211> LENGTH: 348
<212> TYPE: PRT
<213> ORGANISM: Achromobacter xyloxidans

<400> SEQUENCE: 92

Met Lys Ala Leu Val Tyr His Gly Asp His Lys Ile Ser Leu Glu Asp
1               5                   10                  15

Lys Pro Lys Pro Thr Leu Gln Lys Pro Thr Asp Val Val Arg Val
            20                  25                  30

Leu Lys Thr Thr Ile Cys Gly Thr Asp Leu Gly Ile Tyr Lys Gly Lys
            35                  40                  45

Asn Pro Glu Val Ala Asp Gly Arg Ile Leu Gly His Glu Gly Val Gly
50                  55                  60

Val Ile Glu Glu Val Gly Glu Ser Val Thr Gln Phe Lys Lys Gly Asp
65                  70                  75                  80

Lys Val Leu Ile Ser Cys Val Thr Ser Cys Gly Ser Cys Asp Tyr Cys
            85                  90                  95
```

```
Lys Lys Gln Leu Tyr Ser His Cys Arg Asp Gly Gly Trp Ile Leu Gly
                100                 105                 110

Tyr Met Ile Asp Gly Val Gln Ala Glu Tyr Val Arg Ile Pro His Ala
            115                 120                 125

Asp Asn Ser Leu Tyr Lys Ile Pro Gln Thr Ile Asp Asp Glu Ile Ala
        130                 135                 140

Val Leu Leu Ser Asp Ile Leu Pro Thr Gly His Glu Ile Gly Val Gln
145                 150                 155                 160

Tyr Gly Asn Val Gln Pro Gly Asp Ala Val Ala Ile Val Gly Ala Gly
                165                 170                 175

Pro Val Gly Met Ser Val Leu Leu Thr Ala Gln Phe Tyr Ser Pro Ser
            180                 185                 190

Thr Ile Ile Val Ile Asp Met Asp Glu Asn Arg Leu Gln Leu Ala Lys
        195                 200                 205

Glu Leu Gly Ala Thr His Thr Ile Asn Ser Gly Thr Glu Asn Val Val
210                 215                 220

Glu Ala Val His Arg Ile Ala Ala Glu Gly Val Asp Val Ala Ile Glu
225                 230                 235                 240

Ala Val Gly Ile Pro Ala Thr Trp Asp Ile Cys Gln Glu Ile Val Lys
                245                 250                 255

Pro Gly Ala His Ile Ala Asn Val Gly Val His Gly Val Lys Val Asp
            260                 265                 270

Phe Glu Ile Gln Lys Leu Trp Ile Lys Asn Leu Thr Ile Thr Thr Gly
        275                 280                 285

Leu Val Asn Thr Asn Thr Thr Pro Met Leu Met Lys Val Ala Ser Thr
290                 295                 300

Asp Lys Leu Pro Leu Lys Lys Met Ile Thr His Arg Phe Glu Leu Ala
305                 310                 315                 320

Glu Ile Glu His Ala Tyr Gln Val Phe Leu Asn Gly Ala Lys Glu Lys
                325                 330                 335

Ala Met Lys Ile Ile Leu Ser Asn Ala Gly Ala Ala
            340                 345

<210> SEQ ID NO 93
<211> LENGTH: 375
<212> TYPE: PRT
<213> ORGANISM: Equus ferus caballus

<400> SEQUENCE: 93

Met Ser Thr Ala Gly Lys Val Ile Lys Cys Lys Ala Ala Val Leu Trp
1               5                   10                  15

Glu Glu Lys Lys Pro Phe Ser Ile Glu Glu Val Glu Val Ala Pro Pro
            20                  25                  30

Lys Ala His Glu Val Arg Ile Lys Met Val Ala Thr Gly Ile Cys Arg
        35                  40                  45

Ser Asp Asp His Val Val Ser Gly Thr Leu Val Thr Pro Leu Pro Val
    50                  55                  60

Ile Ala Gly His Glu Ala Ala Gly Ile Val Glu Ser Ile Gly Glu Gly
65                  70                  75                  80

Val Thr Thr Val Arg Pro Gly Asp Lys Val Ile Pro Leu Phe Thr Pro
                85                  90                  95

Gln Cys Gly Lys Cys Arg Val Cys Lys His Pro Glu Gly Asn Phe Cys
            100                 105                 110

Leu Lys Asn Asp Leu Ser Met Pro Arg Gly Thr Met Gln Asp Gly Thr
```

```
                115                 120                 125
Ser Arg Phe Thr Cys Arg Gly Lys Pro Ile His His Phe Leu Gly Thr
    130                 135                 140

Ser Thr Phe Ser Gln Tyr Thr Val Val Asp Glu Ile Ser Val Ala Lys
145                 150                 155                 160

Ile Asp Ala Ala Ser Pro Leu Glu Lys Val Cys Leu Ile Gly Cys Gly
                165                 170                 175

Phe Ser Thr Gly Tyr Gly Ser Ala Val Lys Val Ala Lys Val Thr Gln
            180                 185                 190

Gly Ser Thr Cys Ala Val Phe Gly Leu Gly Gly Val Gly Leu Ser Val
        195                 200                 205

Ile Met Gly Cys Lys Ala Ala Gly Ala Ala Arg Ile Ile Gly Val Asp
    210                 215                 220

Ile Asn Lys Asp Lys Phe Ala Lys Ala Lys Glu Val Gly Ala Thr Glu
225                 230                 235                 240

Cys Val Asn Pro Gln Asp Tyr Lys Lys Pro Ile Gln Glu Val Leu Thr
                245                 250                 255

Glu Met Ser Asn Gly Gly Val Asp Phe Ser Phe Glu Val Ile Gly Arg
            260                 265                 270

Leu Asp Thr Met Val Thr Ala Leu Ser Cys Cys Gln Glu Ala Tyr Gly
        275                 280                 285

Val Ser Val Ile Val Gly Val Pro Pro Asp Ser Gln Asn Leu Ser Met
    290                 295                 300

Asn Pro Met Leu Leu Leu Ser Gly Arg Thr Trp Lys Gly Ala Ile Phe
305                 310                 315                 320

Gly Gly Phe Lys Ser Lys Asp Ser Val Pro Lys Leu Val Ala Asp Phe
                325                 330                 335

Met Ala Lys Lys Phe Ala Leu Asp Pro Leu Ile Thr His Val Leu Pro
            340                 345                 350

Phe Glu Lys Ile Asn Glu Gly Phe Asp Leu Leu Arg Ser Gly Glu Ser
        355                 360                 365

Ile Arg Thr Ile Leu Thr Phe
    370                 375

<210> SEQ ID NO 94
<211> LENGTH: 347
<212> TYPE: PRT
<213> ORGANISM: Beijerinckia indica

<400> SEQUENCE: 94

Met Lys Ala Leu Val Tyr Arg Gly Pro Gly Gln Lys Leu Val Glu Glu
1               5                   10                  15

Arg Gln Lys Pro Glu Leu Lys Glu Pro Gly Asp Ala Ile Val Lys Val
                20                  25                  30

Thr Lys Thr Thr Ile Cys Gly Thr Asp Leu His Ile Leu Lys Gly Asp
            35                  40                  45

Val Ala Thr Cys Lys Pro Gly Arg Val Leu Gly His Glu Gly Val Gly
        50                  55                  60

Val Ile Glu Ser Val Gly Ser Gly Val Thr Ala Phe Gln Pro Gly Asp
65                  70                  75                  80

Arg Val Leu Ile Ser Cys Ile Ser Ser Cys Gly Lys Cys Ser Phe Cys
                85                  90                  95

Arg Arg Gly Met Phe Ser His Cys Thr Thr Gly Gly Trp Ile Leu Gly
            100                 105                 110
```

```
Asn Glu Ile Asp Gly Thr Gln Ala Glu Tyr Val Arg Val Pro His Ala
            115                 120                 125
Asp Thr Ser Leu Tyr Arg Ile Pro Ala Gly Ala Asp Glu Glu Ala Leu
        130                 135                 140
Val Met Leu Ser Asp Ile Leu Pro Thr Gly Phe Glu Cys Gly Val Leu
145                 150                 155                 160
Asn Gly Lys Val Ala Pro Gly Ser Ser Val Ala Ile Val Gly Ala Gly
                165                 170                 175
Pro Val Gly Leu Ala Ala Leu Leu Thr Ala Gln Phe Tyr Ser Pro Ala
            180                 185                 190
Glu Ile Ile Met Ile Asp Leu Asp Asp Asn Arg Leu Gly Leu Ala Lys
        195                 200                 205
Gln Phe Gly Ala Thr Arg Thr Val Asn Ser Thr Gly Gly Asn Ala Ala
    210                 215                 220
Ala Glu Val Lys Ala Leu Thr Glu Gly Leu Gly Val Asp Thr Ala Ile
225                 230                 235                 240
Glu Ala Val Gly Ile Pro Ala Thr Phe Glu Leu Cys Gln Asn Ile Val
                245                 250                 255
Ala Pro Gly Gly Thr Ile Ala Asn Val Gly Val His Gly Ser Lys Val
            260                 265                 270
Asp Leu His Leu Glu Ser Leu Trp Ser His Asn Val Thr Ile Thr Thr
        275                 280                 285
Arg Leu Val Asp Thr Ala Thr Thr Pro Met Leu Leu Lys Thr Val Gln
    290                 295                 300
Ser His Lys Leu Asp Pro Ser Arg Leu Ile Thr His Arg Phe Ser Leu
305                 310                 315                 320
Asp Gln Ile Leu Asp Ala Tyr Glu Thr Phe Gly Gln Ala Ala Ser Thr
                325                 330                 335
Gln Ala Leu Lys Val Ile Ile Ser Met Glu Ala
            340                 345
```

<210> SEQ ID NO 95
<211> LENGTH: 4519
<212> TYPE: DNA
<213> ORGANISM: Artificial Sequence
<220> FEATURE:
<223> OTHER INFORMATION: pLA54

<400> SEQUENCE: 95

| | | | | | | |
|---|---|---|---|---|---|---|
| caccttggct | aactcgttgt | atcatcactg | gataacttcg | tataatgtat | gctatacgaa | 60 |
| gttatcgaac | agagaaacta | aatccacatt | aattgagagt | tctatctatt | agaaaatgca | 120 |
| aactccaact | aaatgggaaa | acagataacc | tcttttatt | ttttttaatg | tttgatattc | 180 |
| gagtcttttt | cttttgttag | gtttatattc | atcatttcaa | tgaataaaag | aagcttctta | 240 |
| ttttggttgc | aaagaatgaa | aaaaaggat | tttttcatac | ttctaaagct | tcaattataa | 300 |
| ccaaaaattt | tataaatgaa | gagaaaaaat | ctagtagtat | caagttaaac | ttagaaaaac | 360 |
| tcatcgagca | tcaaatgaaa | ctgcaattta | ttcatatcag | gattatcaat | accatatttt | 420 |
| tgaaaaagcc | gtttctgtaa | tgaaggagaa | aactcaccga | ggcagttcca | taggatggca | 480 |
| agatcctggt | atcggtctgc | gattccgact | cgtccaacat | caatacaacc | tattaatttc | 540 |
| ccctcgtcaa | aaataaggtt | atcaagtgag | aaatcaccat | gagtgacgac | tgaatccggt | 600 |
| gagaatggca | aaagcttatg | catttctttc | cagacttgtt | caacaggcca | gccattacgc | 660 |
| tcgtcatcaa | aatcactcgc | atcaaccaaa | ccgttattca | ttcgtgattg | cgcctgagcg | 720 |

```
agacgaaata cgcgatcgct gttaaaagga caattacaaa caggaatcga atgcaaccgg    780
cgcaggaaca ctgccagcgc atcaacaata ttttcacctg aatcaggata ttcttctaat    840
acctggaatg ctgttttgcc ggggatcgca gtggtgagta accatgcatc atcaggagta    900
cggataaaat gcttgatggt cggaagaggc ataaattccg tcagccagtt tagtctgacc    960
atctcatctg taacatcatt ggcaacgcta cctttgccat gtttcagaaa caactctggc   1020
gcatcgggct tcccatacaa tcgatagatt gtcgcacctg attgcccgac attatcgcga   1080
gcccatttat acccatataa atcagcatcc atgttggaat ttaatcgcgg cctcgaaacg   1140
tgagtctttt ccttacccat ctcgagtttt aatgttactt ctcttgcagt tagggaacta   1200
taatgtaact caaaataaga ttaaacaaac taaaataaaa agaagttata cagaaaaacc   1260
catataaacc agtactaatc cataataata atacacaaaa aaactatcaa ataaaaccag   1320
aaaacagatt gaatagaaaa attttttcga tctcctttta tattcaaaat tcgatatatg   1380
aaaaagggaa ctctcagaaa atcaccaaat caatttaatt agattttcct tttccttcta   1440
gcgttggaaa gaaaaatttt tctttttttt tttagaaatg aaaaattttt gccgtaggaa   1500
tcaccgtata aaccctgtat aaacgctact ctgttcacct gtgtaggcta tgattgaccc   1560
agtgttcatt gttattgcga gagagcggga gaaagaacc gatacaagag atccatgctg   1620
gtatagttgt ctgtccaaca ctttgatgaa cttgtaggac gatgatgtgt atttagacga   1680
gtacgtgtgt gactattaag tagttatgat agagaggttt gtacggtgtg ttctgtgtaa   1740
ttcgattgag aaaatggtta tgaatcccta gataacttcg tataatgtat gctatacgaa   1800
gttatctgaa cattagaata cgtaatccgc aatgcgggga tcctctagag tcgacctgca   1860
ggcatgcaag cttggcgtaa tcatggtcat agctgtttcc tgtgtgaaat tgttatccgc   1920
tcacaattcc acacaacata cgagccggaa gcataaagtg taaagcctgg ggtgcctaat   1980
gagtgagcta actcacatta attgcgttgc gctcactgcc cgctttccag tcgggaaacc   2040
tgtcgtgcca gctgcattaa tgaatcggcc aacgcgcggg gagaggcggt ttgcgtattg   2100
ggcgctcttc cgcttcctcg ctcactgact cgctgcgctc ggtcgttcgg ctgcggcgag   2160
cggtatcagc tcactcaaag gcggtaatac ggttatccac agaatcaggg gataacgcag   2220
gaaagaacat gtgagcaaaa ggccagcaaa aggccaggaa ccgtaaaaag gccgcgttgc   2280
tggcgttttt ccataggctc cgcccccctg acgagcatca caaaaatcga cgctcaagtc   2340
agaggtggcg aaacccgaca ggactataaa gataccaggc gtttccccct ggaagctccc   2400
tcgtgcgctc tcctgttccg accctgccgc ttaccggata cctgtccgcc tttctccctt   2460
cgggaagcgt ggcgctttct catagctcac gctgtaggta tctcagttcg gtgtaggtcg   2520
ttcgctccaa gctgggctgt gtgcacgaac cccccgttca gcccgaccgc tgcgccttat   2580
ccggtaacta tcgtcttgag tccaacccgg taagacacga cttatcgcca ctggcagcag   2640
ccactggtaa caggattagc agagcgaggt atgtaggcgg tgctacagag ttcttgaagt   2700
ggtggcctaa ctacggctac actagaagga cagtatttgg tatctgcgct ctgctgaagc   2760
cagttacctt cggaaaaaga gttggtagct cttgatccgg caaacaaacc accgctggta   2820
gcggtggttt ttttgtttgc aagcagcaga ttacgcgcag aaaaaaagga tctcaagaag   2880
atcctttgat cttttctacg gggtctgacg ctcagtggaa cgaaaactca cgttaaggga   2940
ttttggtcat gagattatca aaaaggatct tcacctagat ccttttaaat taaaaatgaa   3000
gttttaaatc aatctaaagt atatatgagt aaacttggtc tgacagttac caatgcttaa   3060
tcagtgaggc acctatctca gcgatctgtc tatttcgttc atccatagtt gcctgactcc   3120
```

```
ccgtcgtgta gataactacg atacgggagg gcttaccatc tggccccagt gctgcaatga    3180
taccgcgaga cccacgctca ccggctccag atttatcagc aataaaccag ccagccgaa     3240 gggccgagcg cagaagtggt cctgcaactt tatccgcctc catccagtct attaattgtt    3300
gccgggaagc tagagtaagt agttcgccag ttaatagttt gcgcaacgtt gttgccattg    3360
ctacaggcat cgtggtgtca cgctcgtcgt ttggtatggc ttcattcagc tccggttccc    3420
aacgatcaag gcgagttaca tgatccccca tgttgtgcaa aaaagcggtt agctccttcg    3480
gtcctccgat cgttgtcaga agtaagttgg ccgcagtgtt atcactcatg gttatggcag    3540
cactgcataa ttctcttact gtcatgccat ccgtaagatg cttttctgtg actggtgagt    3600
actcaaccaa gtcattctga gaatagtgta tgcggcgacc gagttgctct tgcccggcgt    3660
caatacggga taataccgcg ccacatagca gaactttaaa agtgctcatc attggaaaac    3720
gttcttcggg gcgaaaactc tcaaggatct taccgctgtt gagatccagt tcgatgtaac    3780
ccactcgtgc acccaactga tcttcagcat cttttacttt caccagcgtt tctgggtgag    3840
caaaaacagg aaggcaaaat gccgcaaaaa agggaataag ggcgacacgg aaatgttgaa    3900
tactcatact cttccttttt caatattatt gaagcattta tcagggttat tgtctcatga    3960
gcggatacat atttgaatgt atttagaaaa ataaacaaat aggggttccg cgcacatttc    4020
cccgaaaagt gccacctgac gtctaagaaa ccattattat catgacatta acctataaaa    4080
ataggcgtat cacgaggccc tttcgtctcg cgcgtttcgg tgatgacggt gaaaacctct    4140
gacacatgca gctcccggag acggtcacag cttgtctgta agcggatgcc gggagcagac    4200
aagcccgtca gggcgcgtca gcgggtgttg gcgggtgtcg ggctggctt aactatgcgg    4260 catcagagca gattgtactg agagtgcacc atatgcggtg tgaaataccg cacagatgcg    4320
taaggagaaa ataccgcatc aggcgccatt cgccattcag gctgcgcaac tgttgggaag    4380
ggcgatcggt gcgggcctct tcgctattac gccagctggc gaaaggggga tgtgctgcaa    4440
ggcgattaag ttgggtaacg ccagggtttt cccagtcacg acgttgtaaa acgacggcca    4500
gtgaattcga gctcggtac                                                 4519
```

<210> SEQ ID NO 96
<211> LENGTH: 80
<212> TYPE: DNA
<213> ORGANISM: Artificial Sequence
<220> FEATURE:
<223> OTHER INFORMATION: BK505

<400> SEQUENCE: 96

```
ttccggtttc tttgaaattt ttttgattcg gtaatctccg agcagaagga gcattgcgga    60
ttacgtattc taatgttcag                                                80
```

<210> SEQ ID NO 97
<211> LENGTH: 81
<212> TYPE: DNA
<213> ORGANISM: Artificial Sequence
<220> FEATURE:
<223> OTHER INFORMATION: BK506

<400> SEQUENCE: 97

```
gggtaataac tgatataatt aaattgaagc tctaatttgt gagtttagta caccttggct    60
aactcgttgt atcatcactg g                                              81
```

<210> SEQ ID NO 98

```
<211> LENGTH: 38
<212> TYPE: DNA
<213> ORGANISM: Artificial Sequence
<220> FEATURE:
<223> OTHER INFORMATION: LA468

<400> SEQUENCE: 98
gcctcgagtt ttaatgttac ttctcttgca gttaggga                              38

<210> SEQ ID NO 99
<211> LENGTH: 31
<212> TYPE: DNA
<213> ORGANISM: Artificial Sequence
<220> FEATURE:
<223> OTHER INFORMATION: LA492

<400> SEQUENCE: 99
gctaaattcg agtgaaacac aggaagacca g                                     31

<210> SEQ ID NO 100
<211> LENGTH: 23
<212> TYPE: DNA
<213> ORGANISM: Artificial Sequence
<220> FEATURE:
<223> OTHER INFORMATION: AK109-1

<400> SEQUENCE: 100
agtcacatca agatcgttta tgg                                              23

<210> SEQ ID NO 101
<211> LENGTH: 23
<212> TYPE: DNA
<213> ORGANISM: Artificial Sequence
<220> FEATURE:
<223> OTHER INFORMATION: AK109-2

<400> SEQUENCE: 101
gcacggaata tgggactact tcg                                              23

<210> SEQ ID NO 102
<211> LENGTH: 23
<212> TYPE: DNA
<213> ORGANISM: Artificial Sequence
<220> FEATURE:
<223> OTHER INFORMATION: AK109-3

<400> SEQUENCE: 102
actccacttc aagtaagagt ttg                                              23

<210> SEQ ID NO 103
<211> LENGTH: 24
<212> TYPE: DNA
<213> ORGANISM: Artificial Sequence
<220> FEATURE:
<223> OTHER INFORMATION: oBP452

<400> SEQUENCE: 103
ttctcgacgt gggccttttt cttg                                             24

<210> SEQ ID NO 104
<211> LENGTH: 49
<212> TYPE: DNA
<213> ORGANISM: Artificial Sequence
<220> FEATURE:
<223> OTHER INFORMATION: oBP453

<400> SEQUENCE: 104
```
tgcagcttta aataatcggt gtcactactt tgccttcgtt tatcttgcc    49

<210> SEQ ID NO 105
<211> LENGTH: 49
<212> TYPE: DNA
<213> ORGANISM: Artificial Sequence
<220> FEATURE:
<223> OTHER INFORMATION: oBP454

<400> SEQUENCE: 105
gagcaggcaa gataaacgaa ggcaaagtag tgacaccgat tatttaaag    49

<210> SEQ ID NO 106
<211> LENGTH: 49
<212> TYPE: DNA
<213> ORGANISM: Artificial Sequence
<220> FEATURE:
<223> OTHER INFORMATION: oBP455

<400> SEQUENCE: 106
tatggaccct gaaaccacag ccacattgta accaccacga cggttgttg    49

<210> SEQ ID NO 107
<211> LENGTH: 49
<212> TYPE: DNA
<213> ORGANISM: Artificial Sequence
<220> FEATURE:
<223> OTHER INFORMATION: oBP457

<400> SEQUENCE: 107
tttagcaaca accgtcgtgg tggttacaat gtggctgtgg tttcagggt    49

<210> SEQ ID NO 108
<211> LENGTH: 49
<212> TYPE: DNA
<213> ORGANISM: Artificial Sequence
<220> FEATURE:
<223> OTHER INFORMATION: oBP457

<400> SEQUENCE: 108
ccagaaaccc tatacctgtg tggacgtaag gccatgaagc ttttttcttt    49

<210> SEQ ID NO 109
<211> LENGTH: 49
<212> TYPE: DNA
<213> ORGANISM: Artificial Sequence
<220> FEATURE:
<223> OTHER INFORMATION: oBP458

<400> SEQUENCE: 109
attggaaaga aaaagcttca tggccttacg tccacacagg tatagggtt    49

<210> SEQ ID NO 110
<211> LENGTH: 22
<212> TYPE: DNA
<213> ORGANISM: Artificial Sequence
<220> FEATURE:
<223> OTHER INFORMATION: oBP459

<400> SEQUENCE: 110
cataagaaca cctttggtgg ag    22

<210> SEQ ID NO 111
<211> LENGTH: 22
<212> TYPE: DNA

```
<213> ORGANISM: Artificial Sequence
<220> FEATURE:
<223> OTHER INFORMATION: oBP460

<400> SEQUENCE: 111
aggattatca ttcataagtt tc                                              22

<210> SEQ ID NO 112
<211> LENGTH: 20
<212> TYPE: DNA
<213> ORGANISM: Artificial Sequence
<220> FEATURE:
<223> OTHER INFORMATION: LA135

<400> SEQUENCE: 112
cttggcagca acaggactag                                                 20

<210> SEQ ID NO 113
<211> LENGTH: 23
<212> TYPE: DNA
<213> ORGANISM: Artificial Sequence
<220> FEATURE:
<223> OTHER INFORMATION: oBP461

<400> SEQUENCE: 113
ttcttggagc tgggacatgt ttg                                             23

<210> SEQ ID NO 114
<211> LENGTH: 22
<212> TYPE: DNA
<213> ORGANISM: Artificial Sequence
<220> FEATURE:
<223> OTHER INFORMATION: LA92

<400> SEQUENCE: 114
gagaagatgc ggccagcaaa ac                                              22

<210> SEQ ID NO 115
<211> LENGTH: 4242
<212> TYPE: DNA
<213> ORGANISM: Artificial Sequence
<220> FEATURE:
<223> OTHER INFORMATION: pLA59

<400> SEQUENCE: 115
aaacgccagc aacgcggcct ttttacggtt cctggccttt tgctggcctt ttgctcacat     60
gttctttcct gcgttatccc ctgattctgt ggataaccgt attaccgcct ttgagtgagc    120
tgataccgct cgccgcagcc gaacgaccga gcgcagcgag tcagtgagcg aggaagcgga    180
agagcgccca atacgcaaac cgcctctccc cgcgcgttgg ccgattcatt aatgcagctg    240
gcacgacagg tttcccgact ggaaagcggg cagtgagcgc aacgcaatta atgtgagtta    300
gctcactcat taggcacccc aggctttaca ctttatgctt ccggctcgta tgttgtgtgg    360
aattgtgagc ggataacaat ttcacacagg aaacagctat gaccatgatt acgccaagct    420
tgcatgcctg caggtcgact ctagaggatc cgcaatgcgg atccgcattg cggattacgt    480
attctaatgt tcagtaccgt tcgtataatg tatgctatac gaagttatgc agattgtact    540
gagagtgcac cataccacct tttcaattca tcattttttt ttattctttt tttttgattt    600
cggtttcctt gaaattttt tgattcggta atctccgaac agaaggaaga acgaaggaag    660
gagcacagac ttagattggt atatatacgc atatgtagtg ttgaagaaac atgaaattgc    720
ccagtattct taacccaact gcacagaaca aaaacctgca ggaaacgaag ataaatcatg    780
```

```
tcgaaagcta catataagga acgtgctgct actcatccta gtcctgttgc tgccaagcta     840
tttaatatca tgcacgaaaa gcaaacaaac ttgtgtgctt cattggatgt tcgtaccacc     900
aaggaattac tggagttagt tgaagcatta ggtcccaaaa tttgtttact aaaaacacat     960
gtggatatct tgactgattt ttccatggag ggcacagtta agccgctaaa ggcattatcc    1020
gccaagtaca atttttact cttcgaagac agaaaatttg ctgacattgg taatacagtc    1080
aaattgcagt actctgcggg tgtatacaga atagcagaat gggcagacat tacgaatgca    1140
cacggtgtgg tgggcccagg tattgttagc ggtttgaagc aggcggcaga agaagtaaca    1200
aaggaaccta gaggccttt gatgttagca gaattgtcat gcaagggctc cctatctact    1260
ggagaatata ctaagggtac tgttgacatt gcgaagagcg acaaagattt tgttatcggc    1320
tttattgctc aaagagacat gggtggaaga gatgaaggtt acgattggtt gattatgaca    1380
cccggtgtgg gtttagatga caagggagac gcattgggtc aacagtatag aaccgtggat    1440
gatgtggtct ctacaggatc tgacattatt attgttggaa gaggactatt tgcaaaggga    1500
agggatgcta aggtagaggg tgaacgttac agaaaagcag gctgggaagc atatttgaga    1560
agatgcggcc agcaaaacta aaaaactgta ttataagtaa atgcatgtat actaaactca    1620
caaattagag cttcaattta attatatcag ttattaccct atgcggtgtg aaataccgca    1680
cagatgcgta aggagaaaat accgcatcag gaaattgtaa acgttaatat ttgttaaaa    1740 ttcgcgttaa attttgtta aatcagctca ttttttaacc aataggccga atcggcaaa    1800 atcccttata aatcaaaaga ataggccgag atagggttga gtgttgttcc agtttggaac    1860
aagagtccac tattaaagaa cgtggactcc aacgtcaaag ggcgaaaaac cgtctatcag    1920
ggcgatggcc cactacgtga accatcaccc taatcaagat aacttcgtat aatgtatgct    1980
atacgaacgg taccagtgat gatacaacga gttagccaag gtgaattcac tggccgtcgt    2040
tttacaacgt cgtgactggg aaaaccctgg cgttacccaa cttaatcgcc ttgcagcaca    2100 tcccccttc gccagctggc gtaatagcga agaggcccgc accgatcgcc cttcccaaca    2160
gttgcgcagc ctgaatggcg aatggcgcct gatgcggtat tttctcctta cgcatctgtg    2220
cggtatttca caccgcatat ggtgcactct cagtacaatc tgctctgatg ccgcatagtt    2280
aagccagccc cgacacccgc caacacccgc tgacgcgccc tgacgggctt gtctgctccc    2340
ggcatccgct tacagacaag ctgtgaccgt ctccggagc tgcatgtgtc agaggttttc    2400
accgtcatca ccgaaacgcg cgagacgaaa gggcctcgtg atacgcctat ttttataggt    2460
taatgtcatg ataataatgg tttcttagac gtcaggtggc acttttcggg gaaatgtgcg    2520
cggaacccct atttgtttat ttttctaaat acattcaaat atgtatccgc tcatgagaca    2580
ataaccctga taaatgcttc aataatattg aaaaaggaag agtatgagta ttcaacattt    2640
ccgtgtcgcc cttattccct ttttgcggc attttgcctt cctgttttg ctcacccaga    2700 aacgctggtg aaagtaaaag atgctgaaga tcagttgggt gcacgagtgg gttacatcga    2760
actggatctc aacagcggta agatccttga gttttcgc cccgaagaac gttttccaat    2820
gatgagcact tttaaagttc tgctatgtgg cgcggtatta tcccgtattg acgccgggca    2880
agagcaactc ggtcgccgca tacactattc tcagaatgac ttggttgagt actcaccagt    2940
cacagaaaag catcttacgg atggcatgac agtaagagaa ttatgcagtg ctgccataac    3000
catgagtgat aacactgcgg ccaacttact tctgacaacg atcggaggac cgaaggagct    3060
aaccgctttt ttgcacaaca tgggggatca tgtaactcgc cttgatcgtt gggaaccgga    3120
```

```
gctgaatgaa gccataccaa acgacgagcg tgacaccacg atgcctgtag caatggcaac    3180
aacgttgcgc aaactattaa ctggcgaact acttactcta gcttcccggc aacaattaat    3240
agactggatg gaggcggata aagttgcagg accacttctg cgctcggccc ttccggctgg    3300
ctggtttatt gctgataaat ctggagccgg tgagcgtggg tctcgcggta tcattgcagc    3360
actggggcca gatggtaagc cctcccgtat cgtagttatc tacacgacgg ggagtcaggc    3420
aactatggat gaacgaaata gacagatcgc tgagataggt gcctcactga ttaagcattg    3480
gtaactgtca gaccaagttt actcatatat actttagatt gatttaaaac ttcatttttta   3540 atttaaaagg atctaggtga agatcctttt tgataatctc atgaccaaaa tcccttaacg    3600
tgagttttcg ttccactgag cgtcagaccc cgtagaaaag atcaaggat cttcttgaga     3660 tccttttttt ctgcgcgtaa tctgctgctt gcaaacaaaa aaaccaccgc taccagcggt    3720
ggtttgtttg ccggatcaag agctaccaac tcttttccg aaggtaactg gcttcagcag     3780
agcgcagata ccaaatactg tccttctagt gtagccgtag ttaggccacc acttcaagaa    3840
ctctgtagca ccgcctacat acctcgctct gctaatcctg ttaccagtgg ctgctgccag    3900
tggcgataag tcgtgtctta ccgggttgga ctcaagacga tagttaccgg ataaggcgca    3960
gcggtcgggc tgaacggggg gttcgtgcac acagcccagc ttggagcgaa cgacctacac    4020
cgaactgaga tacctacagc gtgagctatg agaaagcgcc acgcttcccg aagggagaaa    4080
ggcggacagg tatccggtaa gcggcagggt cggaacagga gagcgcacga gggagcttcc    4140
agggggaaac gcctggtatc tttatagtcc tgtcgggttt cgccacctct gacttgagcg    4200
tcgatttttg tgatgctcgt caggggggcg gagcctatgg aa                       4242

<210> SEQ ID NO 116
<211> LENGTH: 80
<212> TYPE: DNA
<213> ORGANISM: Artificial Sequence
<220> FEATURE:
<223> OTHER INFORMATION: LA678

<400> SEQUENCE: 116
caacgttaac accgtttttcg gtttgccagg tgacttcaac ttgtccttgt gcattgcgga    60
ttacgtattc taatgttcag                                                80

<210> SEQ ID NO 117
<211> LENGTH: 81
<212> TYPE: DNA
<213> ORGANISM: Artificial Sequence
<220> FEATURE:
<223> OTHER INFORMATION: LA679

<400> SEQUENCE: 117
gtggagcatc gaagactggc aacatgattt caatcattct gatcttagag caccttggct    60
aactcgttgt atcatcactg g                                              81

<210> SEQ ID NO 118
<211> LENGTH: 23
<212> TYPE: DNA
<213> ORGANISM: Artificial Sequence
<220> FEATURE:
<223> OTHER INFORMATION: LA337

<400> SEQUENCE: 118
ctcatttgaa tcagcttatg gtg                                            23
```

<210> SEQ ID NO 119
<211> LENGTH: 24
<212> TYPE: DNA
<213> ORGANISM: Artificial Sequence
<220> FEATURE:
<223> OTHER INFORMATION: LA692

<400> SEQUENCE: 119
ggaagtcatt gacaccatct tggc                                          24

<210> SEQ ID NO 120
<211> LENGTH: 24
<212> TYPE: DNA
<213> ORGANISM: Artificial Sequence
<220> FEATURE:
<223> OTHER INFORMATION: LA693

<400> SEQUENCE: 120
agaagctggg acagcagcgt tagc                                          24

<210> SEQ ID NO 121
<211> LENGTH: 7523
<212> TYPE: DNA
<213> ORGANISM: Artificial Sequence
<220> FEATURE:
<223> OTHER INFORMATION: pLA34

<400> SEQUENCE: 121
ccagcttttg ttcccttag tgagggttaa ttgcgcgctt ggcgtaatca tggtcatagc      60
tgtttcctgt gtgaaattgt tatccgctca caattccaca caacatagga gccggaagca    120
taaagtgtaa agcctggggt gcctaatgag tgaggtaact cacattaatt gcgttgcgct    180
cactgcccgc tttccagtcg ggaaacctgt cgtgccagct gcattaatga atcggccaac    240
gcgcggggag aggcggtttg cgtattgggc gctcttccgc ttcctcgctc actgactcgc    300
tgcgctcggt cgttcggctg cggcgagcgg tatcagctca ctcaaaggcg gtaatacggt    360
tatccacaga atcaggggat aacgcaggaa agaacatgtg agcaaaaggc cagcaaaagg    420
ccaggaaccg taaaaaggcc gcgttgctgg cgttttttcca taggctccgc cccctgacg    480 agcatcacaa aaatcgacgc tcaagtcaga ggtggcgaaa cccgacagga ctataaagat    540
accaggcgtt tcccctggaa gctccctcg tgcgctctcc tgttccgacc ctgccgctta    600
ccggatacct gtccgccttt ctcccttcgg aagcgtggc gctttctcat agctcacgct    660
gtaggtatct cagttcggtg taggtcgttc gctccaagct gggctgtgtg cacgaacccc    720
ccgttcagcc cgaccgctgc gccttatccg gtaactatcg tcttgagtcc aacccggtaa    780
gacacgactt atcgccactg gcagcagcca ctggtaacag gattagcaga gcgaggtatg    840
taggcggtgc tacagagttc ttgaagtggt ggcctaacta cggctacact agaaggacag    900
tatttggtat ctgcgctctg ctgaagccag ttaccttcgg aaaaagagtt ggtagctctt    960
gatccggcaa acaaaccacc gctggtagcg gtggtttttt tgtttgcaag cagcagatta   1020
cgcgcagaaa aaaaggatct caagaagatc ctttgatctt ttctacgggg tctgacgctc   1080
agtggaacga aaactcacgt taagggattt tggtcatgag attatcaaaa aggatcttca   1140
cctagatcct tttaaattaa aaatgaagtt ttaaatcaat ctaaagtata tatgagtaaa   1200
cttggtctga cagttaccaa tgcttaatca gtgaggcacc tatctcagcg atctgtctat   1260
ttcgttcatc catagttgcc tgactccccg tcgtgtagat aactacgata cgggagggct   1320
taccatctgg ccccagtgct gcaatgatac cgcgagaccc acgctcaccg gctccagatt   1380

```
tatcagcaat aaaccagcca gccggaaggg ccgagcgcag aagtggtcct gcaactttat  1440
ccgcctccat ccagtctatt aattgttgcc gggaagctag agtaagtagt tcgccagtta  1500
atagtttgcg caacgttgtt gccattgcta caggcatcgt ggtgtcacgc tcgtcgtttg  1560
gtatggcttc attcagctcc ggttcccaac gatcaaggcg agttacatga tcccccatgt  1620
tgtgcaaaaa agcggttagc tccttcggtc ctccgatcgt tgtcagaagt aagttggccg  1680
cagtgttatc actcatggtt atggcagcac tgcataattc tcttactgtc atgccatccg  1740
taagatgctt ttctgtgact ggtgagtact caaccaagtc attctgagaa tagtgtatgc  1800
ggcgaccgag ttgctcttgc ccggcgtcaa tacgggataa taccgcgcca catagcagaa  1860
ctttaaaagt gctcatcatt ggaaaacgtt cttcggggcg aaaactctca aggatcttac  1920
cgctgttgag atccagttcg atgtaaccca ctcgtgcacc caactgatct tcagcatctt  1980
ttactttcac cagcgtttct gggtgagcaa aaacaggaag gcaaaatgcc gcaaaaaagg  2040
gaataagggc gacacggaaa tgttgaatac tcatactctt cctttttcaa tattattgaa  2100
gcatttatca gggttattgt ctcatgagcg gatacatatt tgaatgtatt tagaaaaata  2160
aacaaatagg ggttccgcgc acatttcccc gaaaagtgcc acctgaacga agcatctgtg  2220
cttcattttg tagaacaaaa atgcaacgcg agagcgctaa ttttttcaaac aaagaatctg  2280 agctgcattt ttacagaaca gaaatgcaac gcgaaagcgc tattttacca acgaagaatc  2340
tgtgcttcat ttttgtaaaa caaaaatgca acgcgagagc gctaattttt caaacaaaga  2400
atctgagctg catttttaca gaacagaaat gcaacgcgag agcgctattt taccaacaaa  2460
gaatctatac ttcttttttg ttctacaaaa atgcatcccg agagcgctat ttttctaaca  2520
aagcatctta gattactttt tttctccttt gtgcgctcta taatgcagtc tcttgataac  2580
tttttgcact gtaggtccgt taaggttaga agaaggctac tttggtgtct attttctctt  2640
ccataaaaaa agcctgactc acttcccgc gtttactgat tactagcgaa gctgcgggtg  2700
cattttttca agataaaggc atccccgatt atattctata ccgatgtgga ttgcgcatac  2760
tttgtgaaca gaaagtgata gcgttgatga ttcttcattg gtcagaaaat tatgaacggt  2820
ttcttctatt ttgtctctat atactacgta taggaaatgt ttacattttc gtattgtttt  2880
cgattcactc tatgaatagt tcttactaca attttttttgt ctaaagagta atactagaga  2940
taaacataaa aaatgtagag gtcgagttta gatgcaagtt caaggagcga aaggtggatg  3000
ggtaggttat atagggatat agcacagaga tatatagcaa agagatactt ttgagcaatg  3060
tttgtggaag cggtattcgc aatatttag tagctcgtta cagtccggtg cgttttggt  3120 ttttgaaag tgcgtcttca gagcgctttt ggttttcaaa agcgctctga agttcctata  3180
ctttctagag aataggaact tcggaatagg aacttcaaag cgtttccgaa aacgagcgct  3240
tccgaaaatg caacgcgagc tgcgcacata cagctcactg ttcacgtcgc acctatatct  3300
gcgtgttgcc tgtatatata tatacatgag aagaacggca tagtgcgtgt ttatgcttaa  3360
atgcgtactt atatgcgtct atttatgtag gatgaaaggt agtctagtac ctcctgtgat  3420
attatcccat tccatgcggg gtatcgtatg cttccttcag cactaccctt tagctgttct  3480
atatgctgcc actcctcaat tggattagtc tcatccttca atgctatcat ttcctttgat  3540
attggatcat ctaagaaacc attattatca tgacattaac ctataaaaat aggcgtatca  3600
cgaggccctt tcgtctcgcg cgtttcggtg atgacggtga aaacctctga cacatgcagc  3660
tcccggagac ggtcacagct tgtctgtaag cggatgccgg gagcagacaa gcccgtcagg  3720
gcgcgtcagc gggtgttggc gggtgtcggg gctggcttaa ctatgcggca tcagagcaga  3780
```

```
ttgtactgag agtgcaccat aaattcccgt tttaagagct tggtgagcgc taggagtcac     3840
tgccaggtat cgtttgaaca cggcattagt cagggaagtc ataacacagt cctttcccgc     3900
aattttcttt ttctattact cttggcctcc tctagtacac tctatatttt tttatgcctc     3960
ggtaatgatt ttcattttt tttttcccct agcggatgac tcttttttt tcttagcgat      4020 tggcattatc acataatgaa ttatacatta tataaagtaa tgtgatttct tcgaagaata     4080
tactaaaaaa tgagcaggca agataaacga aggcaaagat gacagagcag aaagccctag    4140
taaagcgtat tacaaatgaa accaagattc agattgcgat ctctttaaag ggtggtcccc    4200
tagcgataga gcactcgatc ttcccagaaa aagaggcaga agcagtagca gaacaggcca    4260
cacaatcgca agtgattaac gtccacacag gtatagggtt tctggaccat atgatacatg    4320
ctctggccaa gcattccggc tggtcgctaa tcgttgagtg cattggtgac ttacacatag    4380
acgaccatca caccactgaa gactgcggga ttgctctcgg tcaagctttt aaagaggccc    4440
tactggcgcg tggagtaaaa aggtttggat caggatttgc gcctttggat gaggcacttt    4500
ccagagcggt ggtagatctt tcgaacaggc cgtacgcagt tgtcgaactt ggtttgcaaa    4560
gggagaaagt aggagatctc tcttgcgaga tgatcccgca ttttcttgaa agcttttgcag   4620 aggctagcag aattaccctc cacgttgatt gtctgcgagg caagaatgat catcaccgta    4680
gtgagagtgc gttcaaggct cttgcggttg ccataagaga agccacctcg cccaatggta    4740
ccaacgatgt tccctccacc aaaggtgttc ttatgtagtg acaccgatta tttaaagctg    4800
cagcatacga tatatataca tgtgtatata tgtataccta tgaatgtcag taagtatgta    4860
tacgaacagt atgatactga agatgacaag gtaatgcatc attctatacg tgtcattctg    4920
aacgaggcgc gctttccttt tttcttttg cttttctttt tttttctct tgaactcgac     4980 ggatctatgc ggtgtgaaat accgcacaga tgcgtaagga gaaataccg catcaggaaa    5040 ttgtaaacgt taatattttg ttaaaattcg cgttaaattt ttgttaaatc agctcatttt    5100
ttaaccaata ggccgaaatc ggcaaaatcc cttataaatc aaaagaatag accgagatag    5160
ggttgagtgt tgttccagtt tggaacaaga gtccactatt aaagaacgtg gactccaacg    5220
tcaaagggcg aaaaaccgtc tatcagggcg atggcccact acgtgaacca tcaccctaat    5280
caagtttttt ggggtcgagg tgccgtaaag cactaaatcg gaaccctaaa gggagccccc    5340
gatttagagc ttgacgggga agccggcga acgtggcgag aaaggaaggg aagaaagcga    5400
aaggagcggg cgctagggcg ctggcaagtg tagcggtcac gctgcgcgta accaccacac    5460
ccgccgcgct taatgcgccg ctacaggcg cgtcgcgcca ttcgccattc aggctgcgca    5520
actgttggga agggcgatcg gtgcgggcct cttcgctatt acgccagctg gcgaaagggg    5580
gatgtgctgc aaggcgatta agttgggtaa cgccagggtt ttcccagtca cgacgttgta    5640
aaacgacggc cagtgagcgc gcgtaatacg actcactata gggcgaattg ggtaccgggc    5700 ccccctcga ggtattagaa gccgccgagc gggcgacagc cctccgacgg aagactctcc    5760
tccgtgcgtc ctcgtcttca ccggtcgcgt tcctgaaacg cagatgtgcc tcgcgccgca    5820
ctgctccgaa caataaagat tctacaatac tagcttttat ggttatgaag aggaaaaatt    5880
ggcagtaacc tggccccaca aaccttcaaa ttaacgaatc aaattaacaa ccataggatg    5940
ataatgcgat tagttttta gccttatttc tggggtaatt aatcagcgaa gcgatgattt    6000
ttgatctatt aacagatata taatggaaa agctgcataa ccactttaac taatactttc      6060
aacattttca gtttgtatta cttcttattc aaatgtcata aaagtatcaa caaaaaattg    6120
```

-continued

| | |
|---|---|
| ttaatatacc tctatacttt aacgtcaagg agaaaaatgt ccaatttact gcccgtacac | 6180 |
| caaaatttgc ctgcattacc ggtcgatgca acgagtgatg aggttcgcaa gaacctgatg | 6240 |
| gacatgttca gggatcgcca ggcgttttct gagcatacct ggaaaatgct tctgtccgtt | 6300 |
| tgccggtcgt gggcggcatg gtgcaagttg aataaccgga aatggtttcc cgcagaacct | 6360 |
| gaagatgttc gcgattatct tctatatctt caggcgcgcg gtctggcagt aaaaactatc | 6420 |
| cagcaacatt tgggccagct aaacatgctt catcgtcggt ccgggctgcc acgaccaagt | 6480 |
| gacagcaatg ctgtttcact ggttatgcgg cggatccgaa agaaaacgt tgatgccggt | 6540 |
| gaacgtgcaa acaggctct agcgttcgaa cgcactgatt tcgaccaggt tcgttcactc | 6600 |
| atggaaaata gcgatcgctg ccaggatata cgtaatctgg catttctggg gattgcttat | 6660 |
| aacaccctgt tacgtatagc cgaaattgcc aggatcaggg ttaaagatat ctcacgtact | 6720 |
| gacggtggga gaatgttaat ccatattggc agaacgaaaa cgctggttag caccgcaggt | 6780 |
| gtagagaagg cacttagcct gggggtaact aaactggtcg agcgatggat ttccgtctct | 6840 |
| ggtgtagctg atgatccgaa taactacctg ttttgccggg tcagaaaaaa tggtgttgcc | 6900 |
| gcgccatctg ccaccagcca gctatcaact cgcgccctgg aagggatttt tgaagcaact | 6960 |
| catcgattga tttacggcgc taaggatgac tctggtcaga gatacctggc ctggtctgga | 7020 |
| cacagtgccc gtgtcggagc cgcgcgagat atggcccgcg ctggagtttc aataccggag | 7080 |
| atcatgcaag ctggtggctg gaccaatgta aatattgtca tgaactatat ccgtaacctg | 7140 |
| gatagtgaaa caggggcaat ggtgcgcctg ctggaagatg gcgattagga gtaagcgaat | 7200 |
| ttcttatgat ttatgatttt tattattaaa taagttataa aaaaaataag tgtatacaaa | 7260 |
| ttttaaagtg actcttaggt tttaaaacga aaattcttat tcttgagtaa ctctttcctg | 7320 |
| taggtcaggt tgctttctca ggtatagcat gaggtcgctc ttattgacca cacctctacc | 7380 |
| ggcatgccga gcaaatgcct gcaaatcgct ccccatttca cccaattgta gatatgctaa | 7440 |
| ctccagcaat gagttgatga atctcggtgt gtattttatg tcctcagagg acaacacctg | 7500 |
| tggtccgcca ccgcggtgga gct | 7523 |

<210> SEQ ID NO 122
<211> LENGTH: 96
<212> TYPE: DNA
<213> ORGANISM: Artificial Sequence
<220> FEATURE:
<223> OTHER INFORMATION: LA722

<400> SEQUENCE: 122

| | |
|---|---|
| tgccaattat ttacctaaac atctataacc ttcaaaagta aaaaaataca caaacgttga | 60 |
| atcatcacct tggctaactc gttgtatcat cactgg | 96 |

<210> SEQ ID NO 123
<211> LENGTH: 80
<212> TYPE: DNA
<213> ORGANISM: Artificial Sequence
<220> FEATURE:
<223> OTHER INFORMATION: LA733

<400> SEQUENCE: 123

| | |
|---|---|
| cataatcaat ctcaaagaga acaacacaat acaataacaa gaagaacaaa gcattgcgga | 60 |
| ttacgtattc taatgttcag | 80 |

<210> SEQ ID NO 124
<211> LENGTH: 30

```
<212> TYPE: DNA
<213> ORGANISM: Artificial Sequence
<220> FEATURE:
<223> OTHER INFORMATION: LA453

<400> SEQUENCE: 124
caccgaagaa gaatgcaaaa atttcagctc                                    30

<210> SEQ ID NO 125
<211> LENGTH: 25
<212> TYPE: DNA
<213> ORGANISM: Artificial Sequence
<220> FEATURE:
<223> OTHER INFORMATION: LA694

<400> SEQUENCE: 125
gctgaagttg ttagaactgt tgttg                                         25

<210> SEQ ID NO 126
<211> LENGTH: 21
<212> TYPE: DNA
<213> ORGANISM: Artificial Sequence
<220> FEATURE:
<223> OTHER INFORMATION: LA695

<400> SEQUENCE: 126
tgttagctgg agtagacttg g                                             21

<210> SEQ ID NO 127
<211> LENGTH: 22
<212> TYPE: DNA
<213> ORGANISM: Artificial Sequence
<220> FEATURE:
<223> OTHER INFORMATION: oBP594

<400> SEQUENCE: 127
agctgtctcg tgttgtgggt tt                                            22

<210> SEQ ID NO 128
<211> LENGTH: 49
<212> TYPE: DNA
<213> ORGANISM: Artificial Sequence
<220> FEATURE:
<223> OTHER INFORMATION: oBP595

<400> SEQUENCE: 128
cttaataata gaacaatatc atcctttacg ggcatcttat agtgtcgtt               49

<210> SEQ ID NO 129
<211> LENGTH: 49
<212> TYPE: DNA
<213> ORGANISM: Artificial Sequence
<220> FEATURE:
<223> OTHER INFORMATION: oBP596

<400> SEQUENCE: 129
gcgccaacga cactataaga tgcccgtaaa ggatgatatt gttctatta               49

<210> SEQ ID NO 130
<211> LENGTH: 49
<212> TYPE: DNA
<213> ORGANISM: Artificial Sequence
<220> FEATURE:
<223> OTHER INFORMATION: oBP597

<400> SEQUENCE: 130
```
tatggaccct gaaaccacag ccacattgca acgacgacaa tgccaaacc                49

<210> SEQ ID NO 131
<211> LENGTH: 49
<212> TYPE: DNA
<213> ORGANISM: Artificial Sequence
<220> FEATURE:
<223> OTHER INFORMATION: oBP598

<400> SEQUENCE: 131
tccttggttt ggcattgtcg tcgttgcaat gtggctgtgg tttcagggt                49

<210> SEQ ID NO 132
<211> LENGTH: 49
<212> TYPE: DNA
<213> ORGANISM: Artificial Sequence
<220> FEATURE:
<223> OTHER INFORMATION: oBP599

<400> SEQUENCE: 132
atcctctcgc ggagtccctg ttcagtaaag gccatgaagc tttttctttt              49

<210> SEQ ID NO 133
<211> LENGTH: 49
<212> TYPE: DNA
<213> ORGANISM: Artificial Sequence
<220> FEATURE:
<223> OTHER INFORMATION: oBP600

<400> SEQUENCE: 133
attggaaaga aaaagcttca tggcctttac tgaacaggga ctccgcgag                49

<210> SEQ ID NO 134
<211> LENGTH: 22
<212> TYPE: DNA
<213> ORGANISM: Artificial Sequence
<220> FEATURE:
<223> OTHER INFORMATION: oBP601

<400> SEQUENCE: 134
tcataccaca atcttagacc at                                             22

<210> SEQ ID NO 135
<211> LENGTH: 21
<212> TYPE: DNA
<213> ORGANISM: Artificial Sequence
<220> FEATURE:
<223> OTHER INFORMATION: oBP602

<400> SEQUENCE: 135
tgttcaaacc cctaaccaac c                                              21

<210> SEQ ID NO 136
<211> LENGTH: 22
<212> TYPE: DNA
<213> ORGANISM: Artificial Sequence
<220> FEATURE:
<223> OTHER INFORMATION: oBP603

<400> SEQUENCE: 136
tgttcccaca atctattacc ta                                             22

<210> SEQ ID NO 137
<211> LENGTH: 31
<212> TYPE: DNA
<213> ORGANISM: Artificial Sequence

```
<220> FEATURE:
<223> OTHER INFORMATION: LA811

<400> SEQUENCE: 137
aacgaagcat ctgtgcttca ttttgtagaa c                              31

<210> SEQ ID NO 138
<211> LENGTH: 59
<212> TYPE: DNA
<213> ORGANISM: Artificial Sequence
<220> FEATURE:
<223> OTHER INFORMATION: LA817

<400> SEQUENCE: 138
cgatccactt gtatatttgg atgaattttt gaggaattct gaaccagtcc taaaacgag    59

<210> SEQ ID NO 139
<211> LENGTH: 31
<212> TYPE: DNA
<213> ORGANISM: Artificial Sequence
<220> FEATURE:
<223> OTHER INFORMATION: LA812

<400> SEQUENCE: 139
aacaaagata tgctattgaa gtgcaagatg g                              31

<210> SEQ ID NO 140
<211> LENGTH: 33
<212> TYPE: DNA
<213> ORGANISM: Artificial Sequence
<220> FEATURE:
<223> OTHER INFORMATION: LA818

<400> SEQUENCE: 140
ctcaaaaatt catccaaata tacaagtgga tcg                            33

<210> SEQ ID NO 141
<211> LENGTH: 90
<212> TYPE: DNA
<213> ORGANISM: Artificial Sequence
<220> FEATURE:
<223> OTHER INFORMATION: LA512

<400> SEQUENCE: 141
gtattttggt agattcaatt ctctttccct ttccttttcc ttcgctcccc ttccttatca    60
gcattgcgga ttacgtattc taatgttcag                                   90

<210> SEQ ID NO 142
<211> LENGTH: 90
<212> TYPE: DNA
<213> ORGANISM: Artificial Sequence
<220> FEATURE:
<223> OTHER INFORMATION: LA513

<400> SEQUENCE: 142
ttggttgggg gaaaaagagg caacaggaaa gatcagaggg ggaggggggg ggagagtgtc    60
accttggcta actcgttgta tcatcactgg                                   90

<210> SEQ ID NO 143
<211> LENGTH: 29
<212> TYPE: DNA
<213> ORGANISM: Artificial Sequence
<220> FEATURE:
<223> OTHER INFORMATION: LA516
```

<400> SEQUENCE: 143
ctcgaaacaa taagacgacg atggctctg                                    29

<210> SEQ ID NO 144
<211> LENGTH: 30
<212> TYPE: DNA
<213> ORGANISM: Artificial Sequence
<220> FEATURE:
<223> OTHER INFORMATION: LA514

<400> SEQUENCE: 144
cactatctgg tgcaaacttg gcaccggaag                                   30

<210> SEQ ID NO 145
<211> LENGTH: 29
<212> TYPE: DNA
<213> ORGANISM: Artificial Sequence
<220> FEATURE:
<223> OTHER INFORMATION: LA515

<400> SEQUENCE: 145
tgtttgtagc cactcgtgaa cttctctgc                                    29

<210> SEQ ID NO 146
<211> LENGTH: 6903
<212> TYPE: DNA
<213> ORGANISM: Artificial Sequence
<220> FEATURE:
<223> OTHER INFORMATION: pLA71

<400> SEQUENCE: 146
aaacgccagc aacgcggcct ttttacggtt cctggccttt tgctggcctt ttgctcacat      60
gttctttcct gcgttatccc ctgattctgt ggataaccgt attaccgcct ttgagtgagc     120
tgataccgct cgccgcagcc gaacgaccga gcgcagcgag tcagtgagcg aggaagcgga     180
agagcgccca atacgcaaac cgcctctccc cgcgcgttgg ccgattcatt aatgcagctg     240
gcacgacagg tttcccgact ggaaagcggg cagtgagcgc aacgcaatta atgtgagtta     300
gctcactcat taggcacccc aggctttaca ctttatgctt ccggctcgta tgttgtgtgg     360
aattgtgagc ggataacaat ttcacacagg aaacagctat gaccatgatt acgccaagct     420
tgcatgcgat ctgaaatgaa taacaatact gacagtagat ctgaaatgaa taacaatact     480
gacagtacta ataattgcc tacttggctt cacatacgtt gcatacgtcg atatagataa      540
taatgataat gacagcagga ttatcgtaat acgtaatagt tgaaaatctc aaaaatgtgt     600
gggtcattac gtaaataatg ataggaatgg gattcttcta ttttttcctttt tccattcta    660 gcagccgtcg ggaaaacgtg gcatcctctc tttcgggctc aattggagtc acgctgccgt     720
gagcatcctc tctttccata tctaacaact gagcacgtaa ccaatggaaa agcatgagct     780
tagcgttgct ccaaaaaagt attggatggt taataccatt tgtctgttct cttctgactt     840
tgactcctca aaaaaaaaa atctacaatc aacagatcgc ttcaattacg ccctcacaaa      900
aacttttttc cttcttcttc gcccacgtta aattttatcc ctcatgttgt ctaacggatt     960
tctgcacttg atttattata aaagacaaa gacataaatc ttctctatca atttcagtta    1020
ttgttcttcc ttgcgttatt cttctgttct tcttttttctt ttgtcatata taaccataac    1080
caagtaatac atattcaaat ctagagctga ggatgttgac aaaagcaaca aaagaacaaa    1140
aatcccttgt gaaaaacaga ggggcggagc ttgttgttga ttgcttagtg gagcaaggtg    1200
tcacacatgt atttggcatt ccaggtgcaa aaattgatgc ggtatttgac gctttacaag    1260

```
ataaaggacc tgaaattatc gttgcccggc acgaacaaaa cgcagcattc atggcccaag   1320
cagtcggccg tttaactgga aaaccgggag tcgtgttagt cacatcagga ccgggtgcct   1380
ctaacttggc aacaggcctg ctgacagcga acactgaagg agaccctgtc gttgcgcttg   1440
ctggaaacgt gatccgtgca gatcgtttaa aacggacaca tcaatctttg gataatgcgg   1500
cgctattcca gccgattaca aaatacagtg tagaagttca agatgtaaaa aatataccgg   1560
aagctgttac aaatgcattt aggatagcgt cagcagggca ggctggggcc gcttttgtga   1620
gctttccgca agatgttgtg aatgaagtca caaatacgaa aaacgtgcgt gctgttgcag   1680
cgccaaaact cggtcctgca gcagatgatg caatcagtgc ggccatagca aaaatccaaa   1740
cagcaaaact tcctgtcgtt ttggtcggca tgaaaggcgg aagaccggaa gcaattaaag   1800
cggttcgcaa gcttttgaaa aaggttcagc ttccatttgt tgaaacatat caagctgccg   1860 gtacccttc tagagattta gaggatcaat attttggccg tatcggtttg ttccgcaacc    1920
agcctggcga tttactgcta gagcaggcag atgttgttct gacgatcggc tatgacccga   1980
ttgaatatga tccgaaattc tggaatatca atggagaccg gacaattatc catttagacg   2040
agattatcgc tgacattgat catgcttacc agcctgatct tgaattgatc ggtgacattc   2100
cgtccacgat caatcatatc gaacacgatg ctgtgaaagt ggaatttgca gagcgtgagc   2160
agaaaatcct ttctgattta aaacaatata tgcatgaagg tgagcaggtg cctgcagatt   2220
ggaaatcaga cagagcgcac cctcttgaaa tcgttaaaga gttgcgtaat gcagtcgatg   2280
atcatgttac agtaacttgc gatatcggtt cgcacgccat ttggatgtca cgttatttcc   2340
gcagctacga gccgttaaca ttaatgatca gtaacggtat gcaaacactc ggcgttgcgc   2400
ttccttgggc aatcggcgct tcattggtga accgggagaa aaagtggtt tctgtctctg    2460 gtgacggcgg tttcttattc tcagcaatgg aattagagac agcagttcga ctaaaagcac   2520
caattgtaca cattgtatgg aacgacagca catatgacat ggttgcattc cagcaattga   2580
aaaaatataa ccgtacatct gcggtcgatt tcggaaatat cgatatcgtg aaatatgcgg   2640
aaagcttcgg agcaactggc ttgcgcgtag aatcaccaga ccagctggca gatgttctgc   2700
gtcaaggcat gaacgctgaa ggtcctgtca tcatcgatgt cccggttgac tacagtgata   2760
acattaattt agcaagtgac aagcttccga agaattcgg ggaactcatg aaaacgaaag    2820
ctctctagtt aattaatcat gtaattagtt atgtcacgct tacattcacg ccctccccc    2880 acatccgctc taaccgaaaa ggaaggagtt agacaacctg aagtctaggt ccctatttat   2940 tttttatag ttatgttagt attaagaacg ttatttatat ttcaaatttt tctttttttt    3000
ctgtacagac gcgtgtacgc atgtaacatt atactgaaaa ccttgcttga aaggttttg    3060 ggacgctcga aggctttaat ttaggttttg ggacgctcga aggctttaat ttggatccgc   3120
attgcggatt acgtattcta atgttcagta ccgttcgtat aatgtatgct atacgaagtt   3180
atgcagattg tactgagagt gcaccatacc acagctttc aattcaattc atcatttttt    3240
ttttattctt tttttgatt tcggtttctt tgaaatttt ttgattcggt aatctccgaa     3300
cagaaggaag aacgaaggaa ggagcacaga cttagattgg tatatatacg catatgtagt   3360
gttgaagaaa catgaaattg cccagtattc ttaacccaac tgcacagaac aaaaacctgc   3420
aggaaacgaa gataaatcat gtcgaaagct acatataagg aacgtgctgc tactcatcct   3480
agtcctgttg ctgccaagct atttaatatc atgcacgaaa agcaaacaaa cttgtgtgct   3540
tcattggatg ttcgtaccac caaggaatta ctggagttag ttgaagcatt aggtcccaaa   3600
```

```
atttgtttac taaaaacaca tgtggatatc ttgactgatt tttccatgga gggcacagtt    3660
aagccgctaa aggcattatc cgccaagtac aattttttac tcttcgaaga cagaaaattt    3720
gctgacattg gtaatacagt caaattgcag tactctgcgg gtgtatacag aatagcagaa    3780
tgggcagaca ttacgaatgc acacggtgtg gtgggcccag gtattgttag cggttttgaag   3840
caggcggcag aagaagtaac aaaggaacct agaggccttt tgatgttagc agaattgtca    3900
tgcaagggct ccctatctac tggagaatat actaagggta ctgttgacat tgcgaagagc    3960
gacaaagatt ttgttatcgg ctttattgct caaagagaca tgggtggaag agatgaaggt    4020
tacgattggt tgattatgac acccggtgtg ggtttagatg acaagggaga cgcattgggt    4080
caacagtata gaaccgtgga tgatgtggtc tctacaggat ctgacattat tattgttgga    4140
agaggactat ttgcaaaggg aagggatgct aaggtagagg gtgaacgtta cagaaaagca    4200
ggctgggaag catatttgag aagatgcggc cagcaaaact aaaaaactgt attataagta    4260
aatgcatgta tactaaactc acaaattaga gcttcaattt aattatatca gttattaccc    4320
tatgcggtgt gaaataccgc acagatgcgt aaggagaaaa taccgcatca ggaaattgta    4380
aacgttaata ttttgttaaa attcgcgtta aattttttgtt aaatcagctc attttttaac   4440
caataggccg aaatcggcaa aatcccttat aaatcaaaag aatagaccga datagggttg   4500
agtgttgttc cagtttggaa caagagtcca ctattaaaga acgtggactc caacgtcaaa    4560
gggcgaaaaa ccgtctatca gggcgatggc ccactacgtg aaccatcacc ctaatcaaga    4620
taacttcgta taatgtatgc tatacgaacg gtaccagtga tgatacaacg agttagccaa    4680
ggtgaattca ctggccgtcg ttttacaacg tcgtgactgg gaaaaccctg gcgttaccca    4740
acttaatcgc cttgcagcac atccccctttt cgccagctgg cgtaatagcg aagaggcccg   4800
caccgatcgc ccttcccaac agttgcgcag cctgaatggc gaatggcgcc tgatgcggta    4860
ttttctcctt acgcatctgt gcggtatttc acaccgcata tggtgcactc tcagtacaat    4920
ctgctctgat gccgcatagt taagccagcc ccgacacccg ccaacacccg ctgacgcgcc    4980
ctgacgggct tgtctgctcc cggcatccgc ttacagacaa gctgtgaccg tctccgggag    5040
ctgcatgtgt cagaggtttt caccgtcatc accgaaacgc gcgagacgaa agggcctcgt    5100
gatacgccta ttttttatagg ttaatgtcat gataataatg gtttcttaga cgtcaggtgg    5160
cacttttcgg ggaaatgtgc gcggaacccc tatttgttta ttttttctaaa tacattcaaa    5220
tatgtatccg ctcatgagac aataaccctg ataaatgctt caataatatt gaaaaaggaa    5280
gagtatgagt attcaacatt tccgtgtcgc ccttattccc ttttttgcgg cattttgcct    5340
tcctgttttt gctcacccag aaacgctggt gaaagtaaaa gatgctgaag atcagttggg    5400
tgcacgagtg ggttacatcg aactggatct caacagcggt aagatccttg agagttttcg    5460
ccccgaagaa cgttttccaa tgatgagcac ttttaaagtt ctgctatgtg gcgcggtatt    5520
atcccgtatt gacgccgggc aagagcaact cggtcgccgc atacactatt ctcagaatga    5580
cttggttgag tactcaccag tcacagaaaa gcatcttacg gatggcatga cagtaagaga    5640
attatgcagt gctgccataa ccatgagtga taacactgcg gccaacttac ttctgacaac    5700
gatcggagga ccgaaggagc taaccgcttt tttgcacaac atggggggatc atgtaactcg    5760
ccttgatcgt tgggaaccgg agctgaatga agccataccca aacgacgagc gtgacaccac    5820
gatgcctgta gcaatggcaa caacgttgcg caaactatta actggcgaac tacttactct    5880
agcttcccgg caacaattaa tagactggat ggaggcggat aaagttgcag gaccacttct    5940
gcgctcggcc cttccggctg gctggtttat tgctgataaa tctggagccg gtgagcgtgg    6000
```

```
gtctcgcggt atcattgcag cactgggggcc agatggtaag ccctcccgta tcgtagttat   6060
ctacacgacg gggagtcagg caactatgga tgaacgaaat agacagatcg ctgagatagg    6120
tgcctcactg attaagcatt ggtaactgtc agaccaagtt tactcatata tactttagat   6180
tgatttaaaa cttcattttt aatttaaaag gatctaggtg aagatccttt ttgataatct   6240
catgaccaaa atcccttaac gtgagttttc gttccactga gcgtcagacc ccgtagaaaa   6300
gatcaaagga tcttcttgag atcctttttt tctgcgcgta atctgctgct tgcaaacaaa   6360
aaaaccaccg ctaccagcgg tggtttgttt gccggatcaa gagctaccaa ctcttttttcc  6420
gaaggtaact ggcttcagca gagcgcagat accaaatact gtccttctag tgtagccgta   6480
gttaggccac cacttcaaga actctgtagc accgcctaca tacctcgctc tgctaatcct   6540
gttaccagtg gctgctgcca gtggcgataa gtcgtgtctt accgggttgg actcaagacg   6600
atagttaccg gataaggcgc agcggtcggg ctgaacgggg ggttcgtgca cacagcccag   6660
cttggagcga acgacctaca ccgaactgag atacctacag cgtgagctat gagaaagcgc   6720
cacgcttccc gaagggagaa aggcggacag gtatccggta agcggcaggg tcggaacagg   6780
agagcgcacg agggagcttc caggggggaaa cgcctggtat ctttatagtc ctgtcgggtt   6840
tcgccacctc tgacttgagc gtcgattttt gtgatgctcg tcagggggggc ggagcctatg  6900
gaa                                                                 6903

<210> SEQ ID NO 147
<211> LENGTH: 6924
<212> TYPE: DNA
<213> ORGANISM: Artificial Sequence
<220> FEATURE:
<223> OTHER INFORMATION: pLA78

<400> SEQUENCE: 147
gatccgcatt gcggattacg tattctaatg ttcagtaccg ttcgtataat gtatgctata     60
cgaagttatg cagattgtac tgagagtgca ccataccacc ttttcaattc atcatttttt    120
ttttattctt tttttttgatt tcggtttcct tgaaattttt ttgattcggt aatctccgaa   180
cagaaggaag aacgaaggaa ggagcacaga cttagattgg tatatatacg catatgtagt   240
gttgaagaaa catgaaattg cccagtattc ttaacccaac tgcacagaac aaaaacctgc   300
aggaaacgaa gataaatcat gtcgaaagct acatataagg aacgtgctgc tactcatcct   360
agtcctgttg ctgccaagct atttaatatc atgcacgaaa agcaaacaaa cttgtgtgct   420
tcattggatg ttcgtaccac caaggaatta ctggagttag ttgaagcatt aggtcccaaa   480
atttgtttac taaaaacaca tgtggatatc ttgactgatt tttccatgga gggcacagtt   540
aagccgctaa aggcattatc cgccaagtac aattttttac tcttcgaaga cagaaaattt   600
gctgacattg gtaatacagt caaattgcag tactctgcgg gtgtatacag aatagcagaa   660
tgggcagaca ttacgaatgc acacggtgtg gtgggcccag gtattgttag cggtttgaag   720
caggcggcag aagaagtaac aaaggaacct agaggccttt tgatgttagc agaattgtca   780
tgcaagggct ccctatctac tggagaatat actaagggta ctgttgacat tgcgaagagc   840
gacaaagatt ttgttatcgg ctttattgct caaagagaca tgggtggaag agatgaaggt   900
tacgattggt tgattatgac acccggtgtg gtttagatg acaagggaga cgcattgggt   960
caacagtata gaaccgtgga tgatgtggtc tctacaggat ctgacattat tattgttgga   1020
agaggactat ttgcaaaggg aagggatgct aaggtagagg gtgaacgtta cagaaaagca   1080
```

```
ggctgggaag catatttgag aagatgcggc cagcaaaact aaaaaactgt attataagta    1140
aatgcatgta tactaaactc acaaattaga gcttcaattt aattatatca gttattaccc    1200
tatgcggtgt gaaataccgc acagatgcgt aaggagaaaa taccgcatca ggaaattgta    1260
aacgttaata ttttgttaaa attcgcgtta aattttttgtt aaatcagctc atttttaac    1320 caataggccg aaatcggcaa aatcccttat aaatcaaaag aatagaccga gatagggttg    1380
agtgttgttc cagtttggaa caagagtcca ctattaaaga acgtggactc caacgtcaaa    1440
gggcgaaaaa ccgtctatca gggcgatggc ccactacgtg aaccatcacc ctaatcaaga    1500
taacttcgta taatgtatgc tatacgaacg gtaccagtga tgatacaacg agttagccaa    1560
ggtgaattca ctggccgtcg ttttacaacg tcgtgactgg gaaaaccctg gcgttaccca    1620
acttaatcgc cttgcagcac atccccctttt cgccagctgg cgtaatagcg aagaggcccg    1680
caccgatcgc ccttcccaac agttgcgcag cctgaatggc gaatggcgcc tgatgcggta    1740
ttttctcctt acgcatctgt gcggtatttc acaccgcata tggtgcactc tcagtacaat    1800
ctgctctgat gccgcatagt taagccagcc ccgacacccg ccaacacccg ctgacgcgcc    1860
ctgacgggct tgtctgctcc cggcatccgc ttacagacaa gctgtgaccg tctccgggag    1920
ctgcatgtgt cagaggtttt caccgtcatc accgaaacgc gcgagacgaa agggcctcgt    1980
gatacgccta ttttttatagg ttaatgtcat gataataatg gtttcttaga cgtcaggtgg    2040
cacttttcgg ggaaatgtgc gcggaacccc tatttgttta ttttttctaaa tacattcaaa    2100 tatgtatccg ctcatgagac aataaccctg ataaatgctt caataatatt gaaaaaggaa    2160
gagtatgagt attcaacatt tccgtgtcgc ccttattccc ttttttgcgg cattttgcct    2220
tcctgttttt gctcacccag aaacgctggt gaaagtaaaa gatgctgaag atcagttggg    2280
tgcacgagtg ggttacatcg aactggatct caacagcggt aagatccttg agagttttcg    2340
ccccgaagaa cgttttccaa tgatgagcac ttttaaagtt ctgctatgtg gcgcggtatt    2400
atcccgtatt gacgccgggc aagagcaact cggtcgccgc atacactatt ctcagaatga    2460
cttggttgag tactcaccag tcacagaaaa gcatcttacg gatggcatga cagtaagaga    2520
attatgcagt gctgccataa ccatgagtga taacactgcg gccaacttac ttctgacaac    2580
gatcggagga ccgaaggagc taaccgcttt tttgcacaac atgggggatc atgtaactcg    2640
ccttgatcgt tgggaaccgg agctgaatga agccatacca aacgacgagc gtgacaccac    2700
gatgcctgta gcaatggcaa caacgttgcg caaactatta actggcgaac tacttactct    2760
agcttcccgg caacaattaa tagactggat ggaggcggat aaagttgcag gaccacttct    2820
gcgctcggcc cttccggctg gctggtttat tgctgataaa tctggagccg gtgagcgtgg    2880
gtctcgcggt atcattgcag cactggggcc agatggtaag ccctcccgta tcgtagttat    2940
ctacacgacg gggagtcagg caactatgga tgaacgaaat agacagatcg ctgagatagg    3000
tgcctcactg attaagcatt ggtaactgtc agaccaagtt tactcatata cttttagat    3060 tgatttaaaa cttcattttt aatttaaaag gatctaggtg aagatccttt ttgataatct    3120
catgaccaaa atcccttaac gtgagttttc gttccactga gcgtcagacc ccgtagaaaa    3180
gatcaaagga tcttcttgag atcctttttt tctgcgcgta atctgctgct tgcaaacaaa    3240
aaaaccaccg ctaccagcgg tggtttgttt gccggatcaa gagctaccaa ctcttttttcc    3300 gaaggtaact ggcttcagca gagcgcagat accaaatact gtccttctag tgtagccgta    3360
gttaggccac cacttcaaga actctgtagc accgcctaca tacctcgctc tgctaatcct    3420
gttaccagtg gctgctgcca gtggcgataa gtcgtgtctt accgggttgg actcaagacg    3480
```

```
atagttaccg gataaggcgc agcggtcggg ctgaacgggg ggttcgtgca cacagcccag    3540
cttggagcga acgacctaca ccgaactgag atacctacag cgtgagctat gagaaagcgc    3600
cacgcttccc gaagggagaa aggcggacag gtatccggta agcggcaggg tcggaacagg    3660
agagcgcacg agggagcttc caggggaaa cgcctggtat ctttatagtc ctgtcgggtt     3720
tcgccacctc tgacttgagc gtcgatttt gtgatgctcg tcagggggc ggagcctatg      3780 gaaaacgcc agcaacgcgg cctttttacg gttcctggcc ttttgctggc cttttgctca    3840
catgttcttt cctgcgttat cccctgattc tgtggataac cgtattaccg cctttgagtg    3900
agctgatacc gctcgccgca gccgaacgac cgagcgcagc gagtcagtga gcgaggaagc    3960
ggaagagcgc ccaatacgca aaccgcctct ccccgcgcgt tggccgattc attaatgcag    4020
ctggcacgac aggtttcccg actggaaagc gggcagtgag cgcaacgcaa ttaatgtgag    4080
ttagctcact cattaggcac cccaggcttt acactttatg cttccggctc gtatgttgtg    4140
tggaattgtg agcggataac aatttcacac aggaaacagc tatgaccatg attacgccaa    4200
gcttccaatt accgtcgctc gtgatttgtt tgcaaaaaga caaaactga aaaaacccag     4260 acacgctcga cttcctgtct tcctattgat tgcagcttcc aatttcgtca cacaacaagg    4320
tcctgtcgac gcctacttgg cttcacatac gttgcatacg tcgatataga taataatgat    4380
aatgacagca ggattatcgt aatacgtaat agttgaaaat ctcaaaaatg tgtgggtcat    4440
tacgtaaata atgataggaa tgggattctt ctatttttcc ttttccatt ctagcagccg     4500 tcgggaaaac gtggcatcct ctctttcggg ctcaattgga gtcacgctgc cgtgagcatc    4560
ctctctttcc atatctaaca actgagcacg taaccaatgg aaaagcatga gcttagcgtt    4620
gctccaaaaa agtattggat ggttaatacc atttgtctgt tctcttctga ctttgactcc    4680
tcaaaaaaaa aaaatctaca atcaacagat cgcttcaatt acgccctcac aaaaactttt    4740
ttccttcttc ttcgcccacg ttaaattta tccctcatgt tgtctaacgg atttctgcac     4800
ttgatttatt ataaaaagac aaagacataa tacttctcta tcaatttcag ttattgttct    4860
tccttgcgtt attcttctgt tcttcttttt cttttgtcat atataaccat aaccaagtaa    4920
tacatattca agtttaaaca tgtataccgt aggacagtac ttggtagata gactagaaga    4980
gattggtatc gataaggttt tcggtgtgcc aggggattac aatttgactt ttctagatta    5040
cattcaaaat cacgaaggac tttcctggca agggaatact aatgaactaa acgcagcata    5100
tgcagcagat ggctacgccc gtgaaagagg cgtatcagct cttgttacta cattcggagt    5160
gggtgaactg tcagccatta acggaacagc tggtagtttt gcagaacaag tccctgtcat    5220
ccacatcgtg ggttctccaa ctatgaatgt gcaatccaac aaaaagctgg ttcatcattc    5280
cttaggaatg ggtaactttc ataactttag tgaaatggct aaggaagtca ctgccgctac    5340
aaccatgctt actgaagaga atgcagcttc agagatcgac agagtattag aaacagcctt    5400
gttgaaaaag aggccagtat acatcaatct tccaattgat atagctcata agcaatagt     5460 taaacctgca aaagcactac aaacagagaa atcatctggt gagagagagg cacaacttgc    5520
agaaatcata ctatcacact agaaaaggc cgctcaacct atcgtaatcg ccggtcatga     5580
gatcgcccgt ttccagataa gagaaagatt tgaaaactgg ataaaccaaa caagttgcc     5640 agtaaccaat ttggcatatg gcaaaggctc tttcaatgaa gagaacgaac atttcattgg    5700
tacctattac ccagcttttt ctgacaaaaa cgttctggat tacgttgaca atagtgactt    5760
cgttttacat tttggtggga aaatcattga caattctacc tcctcatttt ctcaaggctt    5820
```

| | |
|---|---|
| taagactgaa aacactttaa ccgctgcaaa tgacatcatt atgctgccag atgggtctac | 5880 |
| ttactctggg atttctctta acggtctttt ggcagagctg gaaaaactaa actttacttt | 5940 |
| tgctgatact gctgctaaac aagctgaatt agctgttttc gaaccacagg ccgaaacacc | 6000 |
| actaaagcaa gacagatttc accaagctgt tatgaacttt ttgcaagctg atgatgtgtt | 6060 |
| ggtcactgag caggggacat catctttcgg tttgatgttg gcacctctga aaaagggtat | 6120 |
| gaatttgatc agtcaaacat tatgggctc cataggatac acattacctg ctatgattgg | 6180 |
| ttcacaaatt gctgcccag aaaggagaca cattctatcc atcggtgatg gatcttttca | 6240 |
| actgacagca caggaaatgt ccaccatctt cagagagaaa ttgacaccag tgatattcat | 6300 |
| tatcaataac gatggctata cagtcgaaag agccatccat ggagaggatg agagttacaa | 6360 |
| tgatatacca acttggaact tgcaattagt tgctgaaaca tttggtggtg atgccgaaac | 6420 |
| tgtcgacact cacaacgttt tcacagaaac agacttcgct aatactttag ctgctatcga | 6480 |
| tgctactcct caaaaagcac atgtcgttga agttcatatg gaacaaatgg atatgccaga | 6540 |
| atcattgaga cagattggct tagccttatc taagcaaaac tcttaagttt aaactaagcg | 6600 |
| aatttcttat gatttatgat ttttattatt aaataagtta taaaaaaaat aagtgtatac | 6660 |
| aaattttaaa gtgactctta ggttttaaaa cgaaaattct tattcttgag taactctttc | 6720 |
| ctgtaggtca ggttgctttc tcaggtatag catgaggtcg ctcttattga ccacacctct | 6780 |
| accggcatgc cgagcaaatg cctgcaaatc gctccccatt tcacccaatt gtagatatgc | 6840 |
| taactccagc aatgagttga tgaatctcgg tgtgtatttt atgtcctcag aggacaacac | 6900 |
| ctgttgtaat cgttcttcca cacg | 6924 |

<210> SEQ ID NO 148
<211> LENGTH: 6761
<212> TYPE: DNA
<213> ORGANISM: Artificial Sequence
<220> FEATURE:
<223> OTHER INFORMATION: pLA65

<400> SEQUENCE: 148

| | |
|---|---|
| gatccgcatt gcggattacg tattctaatg ttcagtaccg ttcgtataat gtatgctata | 60 |
| cgaagttatg cagattgtac tgagagtgca ccataccacc ttttcaattc atcattttt | 120 |
| ttttattctt ttttttgatt tcggtttcct tgaaattttt ttgattcggt aatctccgaa | 180 |
| cagaaggaag aacgaaggaa ggagcacaga cttagattgg tatatatacg catatgtagt | 240 |
| gttgaagaaa catgaaattg cccagtattc ttaacccaac tgcacagaac aaaaacctgc | 300 |
| aggaaacgaa gataaatcat gtcgaaagct acatataagg aacgtgctgc tactcatcct | 360 |
| agtcctgttg ctgccaagct atttaatatc atgcacgaaa agcaaacaaa cttgtgtgct | 420 |
| tcattggatg ttcgtaccac caaggaatta ctggagttag ttgaagcatt aggtcccaaa | 480 |
| atttgtttac taaaaacaca tgtggatatc ttgactgatt tttccatgga gggcacagtt | 540 |
| aagccgctaa aggcattatc cgccaagtac aatttttac tcttcgaaga cagaaaattt | 600 |
| gctgacattg gtaatacagt caaattgcag tactctgcgg gtgtatacag aatagcagaa | 660 |
| tgggcagaca ttacgaatgc acacggtgtg gtgggcccag gtattgttag cggtttgaag | 720 |
| caggcggcag aagaagtaac aaaggaacct agaggccttt tgatgttagc agaattgtca | 780 |
| tgcaagggct ccctatctac tggagaatat actaagggta ctgttgacat tgcgaagagc | 840 |
| gacaaagatt ttgttatcgg ctttattgct caaagagaca tgggtggaag agatgaaggt | 900 |
| tacgattggt tgattatgac acccggtgtg gtttagatg acaagggaga cgcattgggt | 960 |

```
caacagtata gaaccgtgga tgatgtggtc tctacaggat ctgacattat tattgttgga    1020
agaggactat ttgcaaaggg aagggatgct aaggtagagg gtgaacgtta cagaaaagca    1080
ggctgggaag catatttgag aagatgcggc cagcaaaact aaaaaactgt attataagta    1140
aatgcatgta tactaaactc acaaattaga gcttcaattt aattatatca gttattaccc    1200
tatgcggtgt gaaataccgc acagatgcgt aaggagaaaa taccgcatca ggaaattgta    1260
aacgttaata ttttgttaaa attcgcgtta aattttttgtt aaatcagctc atttttaac    1320 caataggccg aaatcggcaa atcccttat aaatcaaaag aatagaccga datagggttg    1380
agtgttgttc cagtttggaa caagagtcca ctattaaaga acgtggactc caacgtcaaa    1440
gggcgaaaaa ccgtctatca gggcgatggc ccactacgtg aaccatcacc ctaatcaaga    1500
taacttcgta taatgtatgc tatacgaacg gtaccagtga tgatacaacg agttagccaa    1560
ggtgaattca ctggccgtcg ttttacaacg tcgtgactgg gaaaaccctg gcgttaccca    1620
acttaatcgc cttgcagcac atcccccttt cgccagctgg cgtaatagcg aagaggcccg    1680
caccgatcgc ccttcccaac agttgcgcag cctgaatggc gaatggcgcc tgatgcggta    1740
ttttctcctt acgcatctgt gcggtatttc acaccgcata tggtgcactc tcagtacaat    1800
ctgctctgat gccgcatagt taagccagcc ccgacacccg ccaacacccg ctgacgcgcc    1860
ctgacgggct tgtctgctcc cggcatccgc ttacagacaa gctgtgaccg tctccgggag    1920
ctgcatgtgt cagaggtttt caccgtcatc accgaaacgc gcgagacgaa agggcctcgt    1980
gatacgccta ttttttatagg ttaatgtcat gataataatg gtttcttaga cgtcaggtgg    2040
cacttttcgg ggaaatgtgc gcggaaccc tatttgttta ttttttctaaa tacattcaaa    2100 tatgtatccg ctcatgagac aataaccctg ataaatgctt caataatatt gaaaaggaa    2160 gagtatgagt attcaacatt tccgtgtcgc ccttattccc ttttttgcgg cattttgcct    2220
tcctgttttt gctcacccag aaacgctggt gaaagtaaaa gatgctgaag atcagttggg    2280
tgcacgagtg ggttacatcg aactggatct caacagcggt aagatccttg agagttttcg    2340
ccccgaagaa cgttttccaa tgatgagcac ttttaaagtt ctgctatgtg gcgcggtatt    2400
atcccgtatt gacgccgggc aagagcaact cggtcgccgc atacactatt ctcagaatga    2460
cttggttgag tactcaccag tcacagaaaa gcatcttacg gatggcatga cagtaagaga    2520
attatgcagt gctgccataa ccatgagtga taacactgcg gccaacttac ttctgacaac    2580
gatcggagga ccgaaggagc taaccgcttt tttgcacaac atgggggatc atgtaactcg    2640
ccttgatcgt tgggaaccgg agctgaatga agccatacca aacgacgagc gtgacaccac    2700
gatgcctgta gcaatggcaa caacgttgcg caaactatta actggcgaac tacttactct    2760
agcttcccgg caacaattaa tagactggat ggaggcggat aaagttgcag gaccacttct    2820
gcgctcggcc cttccggctg gctggtttat tgctgataaa tctggagccg gtgagcgtgg    2880
gtctcgcggt atcattgcag cactggggcc agatggtaag ccctcccgta tcgtagttat    2940
ctacacgacg gggagtcagg caactatgga tgaacgaaat agacagatcg ctgagatagg    3000
tgcctcactg attaagcatt ggtaactgtc agaccaagtt tactcatata ctttagat    3060 tgatttaaaa cttcattttt aatttaaaag gatctaggtg aagatccttt ttgataatct    3120
catgaccaaa atcccttaac gtgagttttc gttccactga gcgtcagacc ccgtagaaaa    3180
gatcaaagga tcttcttgag atcctttttt tctgcgcgta atctgctgct tgcaaacaaa    3240
aaaaccaccg ctaccagcgg tggtttgttt gccggatcaa gagctaccaa ctctttttcc    3300
```

```
gaaggtaact ggcttcagca gagcgcagat accaaatact gtccttctag tgtagccgta    3360
gttaggccac cacttcaaga actctgtagc accgcctaca tacctcgctc tgctaatcct    3420
gttaccagtg gctgctgcca gtggcgataa gtcgtgtctt accgggttgg actcaagacg    3480
atagttaccg gataaggcgc agcggtcggg ctgaacgggg ggtcgtgca cacagcccag     3540
cttggagcga acgacctaca ccgaactgag atacctacag cgtgagctat gagaaagcgc    3600
cacgcttccc gaagggagaa aggcggacag gtatccggta agcggcaggg tcggaacagg    3660
agagcgcacg agggagcttc caggggaaa cgcctggtat ctttatagtc ctgtcgggtt     3720
tcgccacctc tgacttgagc gtcgattttt gtgatgctcg tcaggggggc ggagcctatg    3780
gaaaaacgcc agcaacgcgg cctttttacg gttcctggcc ttttgctggc cttttgctca    3840
catgttcttt cctgcgttat ccctgattc tgtggataac cgtattaccg cctttgagtg     3900
agctgatacc gctcgccgca gccgaacgac cgagcgcagc gagtcagtga gcgaggaagc    3960
ggaagagcgc ccaatacgca aaccgcctct ccccgcgcgt tggccgattc attaatgcag    4020
ctggcacgac aggtttcccg actggaaagc gggcagtgag cgcaacgcaa ttaatgtgag    4080
ttagctcact cattaggcac cccaggcttt acactttatg cttccggctc gtatgttgtg    4140
tggaattgtg agcggataac aatttcacac aggaaacagc tatgaccatg attacgccaa    4200
gcttacctgg taaaacctct agtggagtag tagatgtaat caatgaagcg gaagccaaaa    4260
gaccagagta gaggcctata gaagaaactg cgataccttt tgtgatggct aaacaaacag    4320
acatcttttt atatgttttt acttctgtat atcgtgaagt agtaagtgat aagcgaattt    4380
ggctaagaac gttgtaagtg aacaagggac ctcttttgcc tttcaaaaaa ggattaaatg    4440
gagttaatca ttgagattta gttttcgtta gattctgtat ccctaaataa ctcccttacc    4500
cgacgggaag gcacaaaaga cttgaataat agcaaacggc cagtagccaa gaccaaataa    4560
tactagagtt aactgatggt cttaaacagg cattacgtgg tgaactccaa gaccaatata    4620
caaaatatcg ataagttatt cttgcccacc aatttaagga gcctacatca ggacagtagt    4680
accattcctc agagaagagg tatacataac aagaaaatcg cgtgaacacc ttatataact    4740
tagcccgtta ttgagctaaa aaaccttgca aaatttccta tgaataagaa tacttcagac    4800
gtgataaaaa tttactttct aactcttctc acgctgcccc tatctgttct tccgctctac    4860
cgtgagaaat aaagcatcga gtacggcagt tcgctgtcac tgaactaaaa caataaggct    4920
agttcgaatg atgaacttgc ttgctgtcaa acttctgagt tgccgctgat gtgacactgt    4980
gacaataaat tcaaaccggt tatagcggtc tcctccggta ccggttctgc cacctccaat    5040
agagctcagt aggagtcaga acctctgcgg tggctgtcag tgactcatcc gcgtttcgta    5100
agttgtgcgc gtgcacattt cgcccgttcc cgctcatctt gcagcaggcg gaaattttca    5160
tcacgctgta ggacgcaaaa aaaaataat taatcgtaca agaatcttgg aaaaaaaatt    5220
gaaaatttt gtataaaagg gatgacctaa cttgactcaa tggctttttac acccagtatt    5280
ttccctttcc ttgtttgtta caattataga agcaagacaa aaacatatag acaacctatt    5340
cctaggagtt atattttttt accctaccag caatataagt aaaaaactgt ttatgaaagc    5400
attagtgtat aggggcccag gccagaagtt ggtggaagag agacagaagc cagagcttaa    5460
ggaacctggt gacgctatag tgaaggtaac aaagactaca atttgcggaa ccgatctaca    5520
cattcttaaa ggtgacgttg cgacttgtaa accccggtcgt gtattagggc atgaaggagt    5580
gggggttatt gaatcagtcg gatctggggt tactgctttc caaccaggcg atagagtttt    5640
gatatcatgt atatcgagtt gcggaaagtg ctcattttgt agaagaggaa tgttcagtca    5700
```

```
ctgtacgacc gggggttgga ttctgggcaa cgaaattgat ggtacccaag cagagtacgt    5760
aagagtacca catgctgaca catcccttta tcgtattccg gcaggtgcgg atgaagaggc    5820
cttagtcatg ttatcagata ttctaccaac gggttttgag tgcggagtcc taaacggcaa    5880
agtcgcacct ggttcttcgg tggctatagt aggtgctggt cccgttggtt tggccgcctt    5940
actgacagca caattctact ccccagctga aatcataatg atcgatcttg atgataacag    6000
gctgggatta gccaaacaat tggtgccac cagaacagta aactccacgg gtggtaacgc    6060
cgcagccgaa gtgaaagctc ttactgaagg cttaggtgtt gatactgcga ttgaagcagt    6120
tgggatacct gctacatttg aattgtgtca gaatatcgta gctcccggtg aactatcgc    6180 taatgtcggc gttcacggta gcaaagttga tttgcatctt gaaagtttat ggtcccataa    6240
tgtcacgatt actacaaggt tggttgacac ggctaccacc ccgatgttac tgaaaactgt    6300
tcaaagtcac aagctagatc catctagatt gataacacat agattcagcc tggaccagat    6360
cttggacgca tatgaaactt ttggccaagc tgcgtctact caagcactaa aagtcatcat    6420
ttcgatggag gcttgattaa ttaagagtaa gcgaatttct tatgatttat gatttttatt    6480
attaaataag ttataaaaaa ataagtgta tacaaatttt aaagtgactc ttaggtttta    6540
aaacgaaaat tcttattctt gagtaactct ttcctgtagg tcaggttgct ttctcaggta    6600
tagcatgagg tcgctcttat tgaccacacc tctaccggca tgccgagcaa atgcctgcaa    6660
atcgctcccc atttcaccca attgtagata tgctaactcc agcaatgagt tgatgaatct    6720
cggtgtgtat tttatgtcct cagaggacaa cacctgtggt g                       6761

<210> SEQ ID NO 149
<211> LENGTH: 90
<212> TYPE: DNA
<213> ORGANISM: Artificial Sequence
<220> FEATURE:
<223> OTHER INFORMATION: 895

<400> SEQUENCE: 149
tctcaattat tattttctac tcataacctc acgcaaaata acacagtcaa atcaatcaaa    60
atgttgacaa aagcaacaaa agaacaaaaa                                    90

<210> SEQ ID NO 150
<211> LENGTH: 81
<212> TYPE: DNA
<213> ORGANISM: Artificial Sequence
<220> FEATURE:
<223> OTHER INFORMATION: 679

<400> SEQUENCE: 150
gtggagcatc gaagactggc aacatgattt caatcattct gatcttagag caccttggct    60
aactcgttgt atcatcactg g                                             81

<210> SEQ ID NO 151
<211> LENGTH: 20
<212> TYPE: DNA
<213> ORGANISM: Artificial Sequence
<220> FEATURE:
<223> OTHER INFORMATION: 681

<400> SEQUENCE: 151
ttattgctta gcgttggtag                                               20

<210> SEQ ID NO 152
```

```
<211> LENGTH: 22
<212> TYPE: DNA
<213> ORGANISM: Artificial Sequence
<220> FEATURE:
<223> OTHER INFORMATION: 92

<400> SEQUENCE: 152
gagaagatgc ggccagcaaa ac                                              22

<210> SEQ ID NO 153
<211> LENGTH: 25
<212> TYPE: DNA
<213> ORGANISM: Artificial Sequence
<220> FEATURE:
<223> OTHER INFORMATION: N245

<400> SEQUENCE: 153
agggtagcct ccccataaca taaac                                           25

<210> SEQ ID NO 154
<211> LENGTH: 25
<212> TYPE: DNA
<213> ORGANISM: Artificial Sequence
<220> FEATURE:
<223> OTHER INFORMATION: N246

<400> SEQUENCE: 154
tctccaaata tacctctt gtgtg                                             25

<210> SEQ ID NO 155
<211> LENGTH: 90
<212> TYPE: DNA
<213> ORGANISM: Artificial Sequence
<220> FEATURE:
<223> OTHER INFORMATION: 896

<400> SEQUENCE: 155
ttttatatac agtataaata aaaacccac gtaatatagc aaaaacatat tgccaacaaa      60
aattaccgtc gctcgtgatt tgtttgcaaa                                      90

<210> SEQ ID NO 156
<211> LENGTH: 90
<212> TYPE: DNA
<213> ORGANISM: Artificial Sequence
<220> FEATURE:
<223> OTHER INFORMATION: 897

<400> SEQUENCE: 156
caaactgtgt aagtttattt atttgcaaca ataattcgtt tgagtacact actaatggcc     60
accttggcta actcgttgta tcatcactgg                                      90

<210> SEQ ID NO 157
<211> LENGTH: 28
<212> TYPE: DNA
<213> ORGANISM: Artificial Sequence
<220> FEATURE:
<223> OTHER INFORMATION: 365

<400> SEQUENCE: 157
ctctatctcc gctcaggcta agcaattg                                        28

<210> SEQ ID NO 158
<211> LENGTH: 26
<212> TYPE: DNA
<213> ORGANISM: Artificial Sequence
```

```
<220> FEATURE:
<223> OTHER INFORMATION: 366

<400> SEQUENCE: 158
cagccgactc aacggcctgt ttcacg                                            26

<210> SEQ ID NO 159
<211> LENGTH: 28
<212> TYPE: DNA
<213> ORGANISM: Artificial Sequence
<220> FEATURE:
<223> OTHER INFORMATION: N638

<400> SEQUENCE: 159
aaaagatagt gtagtagtga taaactgg                                          28

<210> SEQ ID NO 160
<211> LENGTH: 22
<212> TYPE: DNA
<213> ORGANISM: Artificial Sequence
<220> FEATURE:
<223> OTHER INFORMATION: 740

<400> SEQUENCE: 160
cgataatcct gctgtcatta tc                                                22

<210> SEQ ID NO 161
<211> LENGTH: 83
<212> TYPE: DNA
<213> ORGANISM: Artificial Sequence
<220> FEATURE:
<223> OTHER INFORMATION: 856

<400> SEQUENCE: 161
gcttatttag aagtgtcaac aacgtatcta ccaacgattt gaccctttc cacaccttgg        60 ctaactcgtt gtatcatcac tgg                                               83

<210> SEQ ID NO 162
<211> LENGTH: 80
<212> TYPE: DNA
<213> ORGANISM: Artificial Sequence
<220> FEATURE:
<223> OTHER INFORMATION: 857

<400> SEQUENCE: 162
gcacaatatt tcaagctata ccaagcatac aatcaactat ctcatataca atgaaagcat       60
tagtgtatag gggcccaggc                                                   80

<210> SEQ ID NO 163
<211> LENGTH: 25
<212> TYPE: DNA
<213> ORGANISM: Artificial Sequence
<220> FEATURE:
<223> OTHER INFORMATION: BK415

<400> SEQUENCE: 163
gcctcattga tggtggtaca taacg                                             25

<210> SEQ ID NO 164
<211> LENGTH: 26
<212> TYPE: DNA
<213> ORGANISM: Artificial Sequence
<220> FEATURE:
<223> OTHER INFORMATION: N1092
```

```
<400> SEQUENCE: 164
agagttttga tatcatgtat atcgag                                          26

<210> SEQ ID NO 165
<211> LENGTH: 92
<212> TYPE: DNA
<213> ORGANISM: Artificial Sequence
<220> FEATURE:
<223> OTHER INFORMATION: 906

<400> SEQUENCE: 165
atgacaggtg aaagaattga aaaggtgaaa ataaatgacg aatttgcaaa atcacatttc      60
acctggtaaa acctctagtg gagtagtaga tg                                   92

<210> SEQ ID NO 166
<211> LENGTH: 87
<212> TYPE: DNA
<213> ORGANISM: Artificial Sequence
<220> FEATURE:
<223> OTHER INFORMATION: 907

<400> SEQUENCE: 166
aaaaagattc aatgccgtct cctttcgaaa cttaataata gaacaatatc atccttcacc      60
ttggctaact cgttgtatca tcactgg                                         87

<210> SEQ ID NO 167
<211> LENGTH: 70
<212> TYPE: DNA
<213> ORGANISM: Artificial Sequence
<220> FEATURE:
<223> OTHER INFORMATION: 667

<400> SEQUENCE: 167
tctcctttcg aaacttaata atagaacaat atcatccttt tgtaaaacga cggccagtga     60
attcaccttg                                                            70

<210> SEQ ID NO 168
<211> LENGTH: 25
<212> TYPE: DNA
<213> ORGANISM: Artificial Sequence
<220> FEATURE:
<223> OTHER INFORMATION: 749

<400> SEQUENCE: 168
caagtctttt gtgccttccc gtcgg                                           25

<210> SEQ ID NO 169
<211> LENGTH: 25
<212> TYPE: DNA
<213> ORGANISM: Artificial Sequence
<220> FEATURE:
<223> OTHER INFORMATION: 413

<400> SEQUENCE: 169
ggacataaaa tacacaccga gattc                                           25

<210> SEQ ID NO 170
<211> LENGTH: 10934
<212> TYPE: DNA
<213> ORGANISM: Artificial Sequence
<220> FEATURE:
<223> OTHER INFORMATION: pRS423::TEF(M4)-xpk1+ENO1-eutD

<400> SEQUENCE: 170
```

-continued

```
ggtggagctc cagcttttgt tccctttagt gagggttaat tgcgcgcttg gcgtaatcat    60
ggtcatagct gtttcctgtg tgaaattgtt atccgctcac aattccacac aacataggag   120
ccggaagcat aaagtgtaaa gcctggggtg cctaatgagt gaggtaactc acattaattg   180
cgttgcgctc actgcccgct ttccagtcgg gaaacctgtc gtgccagctg cattaatgaa   240
tcggccaacg cgcggggaga ggcggtttgc gtattgggcg ctcttccgct tcctcgctca   300
ctgactcgct gcgctcggtc gttcggctgc ggcgagcggt atcagctcac tcaaaggcgg   360
taatacggtt atccacagaa tcaggggata acgcaggaaa gaacatgtga gcaaaaggcc   420
agcaaaaggc caggaaccgt aaaaaggccg cgttgctggc gtttttccat aggctccgcc   480
cccctgacga gcatcacaaa aatcgacgct caagtcagag gtggcgaaac ccgacaggac   540
tataaagata ccaggcgttt ccccctggaa gctccctcgt gcgctctcct gttccgaccc   600
tgccgcttac cggatacctg tccgcctttc tcccttcggg aagcgtggcg ctttctcata   660
gctcacgctg taggtatctc agttcggtgt aggtcgttcg ctccaagctg ggctgtgtgc   720
acgaaccccc cgttcagccc gaccgctgcg ccttatccgg taactatcgt cttgagtcca   780
acccggtaag acacgactta tcgccactgg cagcagccac tggtaacagg attagcagag   840
cgaggtatgt aggcggtgct acagagttct tgaagtggtg gcctaactac ggctacacta   900
gaaggacagt atttggtatc tgcgctctgc tgaagccagt taccttcgga aaaagagttg   960
gtagctcttg atccggcaaa caaaccaccg ctggtagcgg tggtttttt gtttgcaagc   1020
agcagattac gcgcagaaaa aaaggatctc aagaagatcc tttgatcttt tctacggggt   1080
ctgacgctca gtggaacgaa aactcacgtt aagggatttt ggtcatgaga ttatcaaaaa   1140
ggatcttcac ctagatcctt ttaaattaaa aatgaagttt taaatcaatc taagtatat   1200
atgagtaaac ttggtctgac agttaccaat gcttaatcag tgaggcacct atctcagcga   1260
tctgtctatt tcgttcatcc atagttgcct gactccccgt cgtgtagata actacgatac   1320
gggagggctt accatctggc cccagtgctg caatgatacc gcgagaccca cgctcaccgg   1380
ctccagattt atcagcaata aaccagccag ccggaagggc cgagcgcaga agtggtcctg   1440
caactttatc cgcctccatc cagtctatta attgttgccg gaagctaga gtaagtagtt   1500
cgccagttaa tagtttgcgc aacgttgttg ccattgctac aggcatcgtg gtgtcacgct   1560
cgtcgtttgg tatggcttca ttcagctccg gttcccaacg atcaaggcga gttacatgat   1620
cccccatgtt gtgcaaaaaa gcggttagct ccttcggtcc tccgatcgtt gtcagaagta   1680
agttggccgc agtgttatca ctcatggtta tggcagcact gcataattct cttactgtca   1740
tgccatccgt aagatgcttt tctgtgactg gtgagtactc aaccaagtca ttctgagaat   1800
agtgtatgcg gcgaccgagt tgctcttgcc cggcgtcaat acgggataat accgcgccac   1860
atagcagaac tttaaaagtg ctcatcattg gaaaacgttc ttcggggcga aaactctcaa   1920
ggatcttacc gctgttgaga tccagttcga tgtaacccac tcgtgcaccc aactgatctt   1980
cagcatcttt tactttcacc agcgtttctg ggtgagcaaa aacaggaagg caaaatgccg   2040
caaaaaaggg aataagggcg acacggaaat gttgaatact catactcttc ctttttcaat   2100
attattgaag catttatcag ggttattgtc tcatgagcgg atacatattt gaatgtattt   2160
agaaaaataa acaaataggg gttccgcgca catttccccg aaaagtgcca cctgaacgaa   2220
gcatctgtgc ttcattttgt agaacaaaaa tgcaacgcga gagcgctaat ttttcaaaca   2280
aagaatctga gctgcatttt tacagaacag aaatgcaacg cgaaagcgct atttaccaa   2340
```

```
cgaagaatct gtgcttcatt tttgtaaaac aaaaatgcaa cgcgagagcg ctaattttc      2400
aaacaaagaa tctgagctgc attttacag aacagaaatg caacgcgaga gcgctatttt      2460
accaacaaag aatctatact tcttttttgt tctacaaaaa tgcatcccga gagcgctatt     2520
tttctaacaa agcatcttag attactttt ttctcctttg tgcgctctat aatgcagtct      2580
cttgataact ttttgcactg taggtccgtt aaggttagaa gaaggctact tggtgtcta      2640
ttttctcttc cataaaaaaa gcctgactcc acttcccgcg tttactgatt actagcgaag     2700
ctgcgggtgc atttttttcaa gataaaggca tccccgatta tattctatac cgatgtggat    2760
tgcgcatact ttgtgaacag aaagtgatag cgttgatgat tcttcattgg tcagaaaatt    2820
atgaacggtt tcttctatt tgtctctata tactacgtat aggaaatgtt tacattttcg      2880
tattgttttc gattcactct atgaatagtt cttactacaa ttttttttgtc taaagagtaa    2940
tactagagat aaacataaaa aatgtagagg tcgagtttag atgcaagttc aaggagcgaa    3000
aggtggatgg gtaggttata tagggatata gcacagagat atatagcaaa gagatacttt    3060
tgagcaatgt ttgtggaagc ggtattcgca atatttagt agctcgttac agtccggtgc     3120
gtttttggtt ttttgaaagt gcgtcttcag agcgcttttg gttttcaaaa gcgctctgaa    3180
gttcctatac tttctagaga ataggaactt cggaatagga acttcaaagc gtttccgaaa    3240
acgagcgctt ccgaaaatgc aacgcgagct gcgcacatac agctcactgt tcacgtcgca    3300
cctatatctg cgtgttgcct gtatatatat atacatgaga gaacggcat agtgcgtgtt     3360
tatgcttaaa tgcgtactta tgcgtctcta tttatgtagg atgaaaggta gtctagtacc    3420
tcctgtgata ttatcccatt ccatgcgggg tatcgtatgc ttccttcagc actacccttt    3480
agctgttcta tatgctgcca ctcctcaatt ggattagtct catccttcaa tgctatcatt    3540
tcctttgata ttgatcatc taagaaacca ttattatcat gacattaacc tataaaaata    3600
ggcgtatcac gaggcccttt cgtctcgcgc gtttcggtga tgacggtgaa aacctctgac    3660
acatgcagct cccggagacg gtcacagctt gtctgtaagc ggatgccggg agcagacaag    3720
cccgtcaggg cgcgtcagcg ggtgttggcg ggtgtcgggg ctggcttaac tatgcggcat    3780
cagagcagat tgtactgaga gtgcaccata aattcccgtt ttaagagctt ggtgagcgct    3840
aggagtcact gccaggtatc gtttgaacac ggcattagtc agggaagtca taacacagtc    3900
cttcccgca atttcttt tctattactc ttggcctcct ctagtacact ctatattttt       3960
ttatgcctcg gtaatgattt tcatttttt ttttcccta gcggatgact cttttttttt      4020
cttagcgatt ggcattatca cataatgaat tatacattat ataaagtaat gtgatttctt    4080
cgaagaatat actaaaaaat gagcaggcaa gataaacgaa ggcaaagatg acagagcaga    4140
aagccctagt aaagcgtatt acaaatgaaa ccaagattca gattgcgatc tctttaaagg    4200
gtggtcccct agcgatagag cactcgatct tcccagaaaa agaggcagaa gcagtagcag    4260
aacaggccac acaatcgcaa gtgattaacg tccacacagg tatagggttt ctggaccata    4320
tgatacatgc tctggccaag cattccgct ggtcgctaat cgttgagtgc attggtgact     4380
tacacataga cgaccatcac accactgaag actgcgggat tgctctcggt caagctttta    4440
aagaggccct actggcgcgt ggagtaaaaa ggtttggatc aggatttgcg cctttggatg    4500
aggcactttc cagagcggtg gtagatctt cgaacaggcc gtacgcagtt gtcgaacttg     4560
gtttgcaaag ggagaaagta ggagatctct cttgcgagat gatcccgcat tttcttgaaa    4620
gctttgcaga ggctagcaga attaccctcc acgttgattg tctgcgaggc aagaatgatc    4680
atcaccgtag tgagagtgcg ttcaaggctc ttgcggttgc cataagagaa gccacctcgc    4740
```

```
ccaatggtac caacgatgtt ccctccacca aggtgttct tatgtagtga caccgattat    4800
ttaaagctgc agcatacgat atatatacat gtgtatatat gtatacctat gaatgtcagt    4860
aagtatgtat acgaacagta tgatactgaa gatgacaagg taatgcatca ttctatacgt    4920
gtcattctga acgaggcgcg cttcctttt ttctttttgc tttttctttt tttttctctt     4980
gaactcgacg gatctatgcg gtgtgaaata ccgcacagat gcgtaaggag aaaataccgc    5040
atcaggaaat tgtaaacgtt aatattttgt taaaattcgc gttaaatttt tgttaaatca    5100 gctcatttt taaccaatag gccgaaatcg gcaaaatccc ttataaatca aagaataga     5160 ccgagatagg gttgagtgtt gttccagttt ggaacaagag tccactatta aagaacgtgg    5220
actccaacgt caagggcga aaaccgtct atcagggcga tggcccacta cgtgaaccat     5280
caccctaatc aagtttttg gggtcgaggt gccgtaaagc actaaatcgg aaccctaaag    5340
ggagcccccg atttagagct tgacggggaa agccggcgaa cgtggcgaga aggaaggga    5400 agaaagcgaa aggagcgggc gctagggcgc tggcaagtgt agcggtcacg ctgcgcgtaa   5460
ccaccacacc cgccgcgctt aatgcgccgc tacagggcgc gtcgcgccat cgccattca    5520 ggctgcgcaa ctgttgggaa gggcgatcgg tgcgggcctc ttcgctatta cgccagctgg   5580
cgaaaggggg atgtgctgca aggcgattaa gttgggtaac gccagggttt tcccagtcac    5640
gacgttgtaa aacgacggcc agtgagcgcg cgtaatacga ctcactatag gcgaattgg    5700 gtaccgggcc ccccctcgag gtcgacggta tcgataagct tgatatcgaa ttcctgcgcc    5760
cgggccacta gtcagatgcc gcgggcactt gagcacctca tgcacagcaa taacacaaca    5820
caatggttag tagcaacctg aattcggtca ttgatgcatg catgtgccgt gaagcgggac    5880
aaccagaaaa gtcgtctata aatgccggca cgtgcgatca tcgtggcggg gttttaagag    5940
tgcatatcac aaattgtcgc attaccgcgg aaccgccaga tattcattac ttgacgcaaa    6000
agcgtttgaa ataatgacga aaagaagga agaaaaaaaa agaaaaatac cgcttctagg    6060
cgggttatct actgatccga gcttccacta ggatagcacc caaacacctg catatttgga    6120
cgacctttac ttacaccacc aaaaaccact ttcgcctctc ccgccctga taacgtccac    6180 taattgagcg attacctgag cggtcctctt ttgtttgcag catgagactt gcatactgca    6240
aatcgtaagt agcaacgtct caaggtcaaa actgtatgga aaccttgtca cctcacttaa    6300
ttctagctag cctaccctgc aagtcaagag gtctccgtga ttcctagcca cctcaaggta    6360
tgcctctccc cggaaactgt ggccttttct ggcacacatg atctccacga tttcaacata    6420
taaatagctt ttgataatgg caatattaat caaatttatt ttacttcttt cttgtaacat    6480
ctctcttgta atcccttatt ccttctagct attttcata aaaaccaag caactgctta     6540 tcaacacaca aacactaaat caaagctgag gatggattta tttgagtcat tagcacaaaa    6600
aattactggt aaagatcaaa caattgtttt ccctgaagga actgaacccc gaattgtcgg    6660
tgcggcagcg cgattagctg cagacggctt ggttaagccg attgttttag gtgcaacgga    6720
caaagttcag gctgtggcta acgatttgaa tgcggattta acaggcgttc aagtccttga    6780
tcctgcgaca tacccggctg aagataagca agcaatgctt gatgcctcg ttaacggcg     6840 gaaaggtaag aatacgccag aacaagcggc taaaatgctg aagatgaaa actactttgg    6900 cacgatgctc gtttatatgg gcaaagcgga tgggatggtt tcaggtgcaa tccatccaac    6960
tggtgatacg gtacggccag cgttacaaat tattaagacc aagcccggtt cacaccgaat    7020
ctcgggtgca tttatcatgc aaaagggtga ggaacgctac gtctttgctg actgtgccat    7080
```

```
caatattgat cccgatgccg atacgttagc ggaaattgcc actcagagtg cggctactgc   7140
taaggtcttc gatattgacc cgaaagttgc gatgctcagc ttctcaacta agggttcggc   7200
taagggtgaa atggtcacta aagtgcaaga agcaacggcc aaggcgcaag ctgctgaacc   7260
ggaattggct atcgatggtg aacttcaatt tgacgcggcc ttcgttgaaa agttggttt    7320 gcaaaaggct cctggttcca aagtagctgg tcatgccaat gtctttgtat ttccagagct   7380
tcagtctggt aatattggct ataagattgc gcaacgattt ggtcattttg aagcggtggg   7440
tcctgtcttg caaggcctga acaagccggt ctccgacttg tcacgtggat gcagtgaaga   7500
agacgtttat aaggttgcga ttattacagc agcccaagga ttagcttaat taattaagag   7560
taagcgaatt tcttatgatt tatgattttt attattaaat aagttataaa aaaaataagt   7620
gtatacaaat tttaaagtga ctcttaggtt ttaaaacgaa aattcttatt cttgagtaac   7680
tctttcctgt aggtcaggtt gctttctcag gtatagcatg aggtcgctct tattgaccac   7740
acctctaccg gcatgccgag caaatgcctg caaatcgctc cccatttcac ccaattgtag   7800
atatgctaac tccagcaatg agttgatgaa tctcggtgtg tattttatgt cctcaggaga   7860
caacacctgt ggtactagtt ctagagcggc cgcccgcaaa ttaaagcctt cgagcgtccc   7920
aaaaccttct caagcaaggt tttcagtata atgttacatg cgtacacgcg tttgtacaga   7980
aaaaaaagaa aaatttgaaa tataaataac gttcttaata ctaacataac tattaaaaaa   8040
aataaatagg gacctagact tcaggttgtc taactccttc cttttcggtt agagcggatg   8100
tgggaggagg gcgtgaatgt aagcgtgaca taactaatta catgattaat taattatttt   8160 aaaccctcc attgccaatc attaacttct ggcaagtcag ttccggcatc ccggatatag   8220
gcattgtgtt tagcaagcat attatccatg gattgaacga aggccgcacc agtgttttcc   8280
attgctggtt gcgccgcaat tgccgactta gctaagtcga agcggtccat ctggttcatg   8340
acccgtacgt cgaatggtgt ggtaatatca ccattttcac ggtaaccgtg gacgtataag   8400
ttatggttgt gacgatcaaa gaagatgtca cgaactaagt cttcgtaacc gtggaaagca   8460
aagaccactg gtttgtcctt agtaaagtaa tggtcaaact cagcatctga caagccccgc   8520
ggatcctttt caggactacg taacttcaag atgtcgacca cgttcacgaa acgaatcttc   8580
atctctggga aactgtcgtg tagtaattgg atggcagcca acgtttcaag cgttggttcc   8640
gtcccagcag ctgcaaagac aatgtctggt tcgctacctt ggtccgtact tgcccaatca   8700
atgataccaa gaccattgtc aactaattgc ttagcttctt caatgctgaa ccattgttga   8760
cgtgggtgtt ttgacgtaac cacgtagttg atcttttctt ggctccggaa aatgacgtca   8820
ccgacagcta ataacgtgtt ggcatcggct ggtaaatatt cacgaatgta ttctggtttc   8880
ttttcggcca aatgagttaa tgcacctgga tcttggtggg tataaccatt atggtcttgt   8940
tggaatacag ttgaagccgc gataatgtta agtgatgggt actttttacg ccaatcaagt   9000
tcattggctt tacgtaacca cttgaagtgt tgcgtcaaca ttgagtccac aacgcgtagg   9060
aaggcttcat aactggcaaa taccccatga cgtccagtta agacgtaacc ttctaaccaa   9120
ccttcagctt ggtgttcaga taactgagca tctaagaccc ggccagctgg tgcttcatat   9180
tggtcactat ctggatgaat gtcttccatc cattgacgat tagtggtttc gaagacacca   9240
tataaacggt tagacatggt ttcatcaggt ccgaacaacc ggaagttatc aggattttc    9300 ttgatgacat cccgcaaata gtctgaccaa acgatcatat cttgcttaac attcgcgcct   9360
tctttggacg tatcgaccgc ataatcacgg aagtttggta agttcaaggc tttcggatcg   9420
accccaccat tggtgattgg gttagcagcc atccgactgt ccccagtagg aataatttct   9480
```

```
ttaatatcat ccttcaaaga gccatcttca ttgaagagtt cttttggttg atatgattcg    9540
agccaatcaa ctaaagcatc cgcatgttcc atgtcatttt gatcaacagg aatcggaatt    9600
tgatgagcac ggaatgaacc ttcgatctta tcaccgtccc atgacttcgg accagtccag    9660
cccttaggtg cgcggaagac gatcattggc catactggca atgttgcatc gttattttcg    9720
cgagcatgct tctggattgc cttgatcttt tcaacggctt catccatggc cttagctaag    9780
gctgggtgaa ccttttcagg atcgtcacct tcaacgaaga ttggttccca attcatgctt    9840
tcgaagtatt ccttaatctt agcatcagaa gtccgaccaa aaatcgttgg attagaaatc    9900
ttaaaaccat ttaagttcaa gattggtaaa acagccccgt cgttgattgg gttaatgaac    9960
ttcgttgatt gccatgaagt tgctaatgga cccgtttcgg attccccatc accaacaaca    10020
accgcggcga tttcgtcagg attgtcaaga attgccccaa ccccgtgtga aattgagtaa    10080
ccaagttcgc caccttcgtg gattgaaccg ggtgtttcag gtgccgcatg ggaagcaacc    10140
ccacctggga atgagaattg cttgaagagc ttttgcatcc cttcaacatc ctgcgtaatt    10200
tctgataaaa tatcggtgta agtaccgtca aggtaagagt ttgaaaccat cacttgacca    10260
ccatgacctg gaccttcaac gtagaacatc ttcaaaccgt acttgttgat gacccggtta    10320
agatgagcat agataaagtt tgaccggca atcgtccccc agtgaccaat tggatgaacc    10380
ttaacgtcac tggccttcaa tggccgttgt aatagtggat tatcttttaa ataaagttga    10440
ccaactgata agtagttggc agcacgccag tacttatcaa cttttttgcaa atatgctggt    10500 gatgagtaat ctgttgtcat cctcagctgg aacttagatt agattgctat gctttctctc    10560
taacgagcaa gaagtaaaaa aagttgtaat agaacaagaa aaatgaaact gaagcttgag    10620
aaattgaaga ccgtttatta gcttaaatat caatgggagg tcatcgaaag agaaaaaaat    10680
caagaaagaa actctcaaga aaaagaaacg tgataaaaat ttttattgcc tctctcgacg    10740
aagagaaaga aacgaggcgg tccctttttt cttttccaaa cctttagtac gggtaattag    10800 cgacaccta gaggaagaaa gaggggaaat ttagtatgct gtgcttgggt gtcttgaagt    10860
ggtacggcga tgcgcggagt ccgagaaaat ctggaagagt aaaagggggg tagaagcgtt    10920
ttgaagctat ccgc                                                     10934
```

```
<210> SEQ ID NO 171
<211> LENGTH: 80
<212> TYPE: DNA
<213> ORGANISM: Artificial Sequence
<220> FEATURE:
<223> OTHER INFORMATION: N1341

<400> SEQUENCE: 171
gttgcaagaa atgcattatg caattttttg attatgacaa tctctcgaaa atagcttcaa    60
aacgcttcta ccccctttt                                                80

<210> SEQ ID NO 172
<211> LENGTH: 80
<212> TYPE: DNA
<213> ORGANISM: Artificial Sequence
<220> FEATURE:
<223> OTHER INFORMATION: N1338

<400> SEQUENCE: 172
catacattat acgaacggta ctgaacatta gaatacgtaa tccgcaatgc ccgcaaatta    60
aagccttcga gcgtcccaaa                                               80
```

<210> SEQ ID NO 173
<211> LENGTH: 30
<212> TYPE: DNA
<213> ORGANISM: Artificial Sequence
<220> FEATURE:
<223> OTHER INFORMATION: N1033c

<400> SEQUENCE: 173
gcattgcgga ttacgtattc taatgttcag         30

<210> SEQ ID NO 174
<211> LENGTH: 81
<212> TYPE: DNA
<213> ORGANISM: Artificial Sequence
<220> FEATURE:
<223> OTHER INFORMATION: N1342

<400> SEQUENCE: 174
acatatgtga aaaaaatag ttgatatttt aaaccaaatc agaaatttat caccttggct         60
aactcgttgt atcatcactg g         81

<210> SEQ ID NO 175
<211> LENGTH: 30
<212> TYPE: DNA
<213> ORGANISM: Artificial Sequence
<220> FEATURE:
<223> OTHER INFORMATION: N1364

<400> SEQUENCE: 175
atgacaacag attactcatc accagcatat         30

<210> SEQ ID NO 176
<211> LENGTH: 604
<212> TYPE: DNA
<213> ORGANISM: Artificial Sequence
<220> FEATURE:
<223> OTHER INFORMATION: L8

<400> SEQUENCE: 176
gcctacttgg cttcacatac gttgcatacg acgatataga aaataatgat aatgacagca         60
ggattatcgt ataacgtaat agtcgaaaaa tctcaaaaat ctgtgggtca ttacgtaaat        120
aatgatagga atgtgattct tctatttttc ctttttccat tctggcagcc gtcgggaaaa        180
cgtggcttcc tctctttcgg gctctattgg agtaacgctg ccgtgagctt cctctctttc        240
catatctaac aactgagcac gtaaccaatg gtaaagcatg agcttagcgt tgctccaaag        300
aagtattgga aggttaatac catgtgtctg ttctcttctg actttgactc ctcaaataaa        360
aaaaaattct acaatcaaca gatcgcttca attcgctct cacaaaaact tttttccttc        420
ttcttcgccc acgttaaatt ttaaccctca tgctgtctaa cggatttctg cacttaattt        480
attataaaac gacaaagaca taatacttct ctatcaattt cagttattgt tcttcattgc        540
attactcttc tgttcttctt tttcatttgt catatacaac cataaccaaa taatacatat        600
tcaa         604

<210> SEQ ID NO 177
<211> LENGTH: 80
<212> TYPE: DNA
<213> ORGANISM: Artificial Sequence
<220> FEATURE:
<223> OTHER INFORMATION: N1366

<400> SEQUENCE: 177

```
gttgcaagaa atgcattatg caatttttg attatgacaa tctctcgaaa gcctacttgg    60
cttcacatac gttgcatacg                                               80
```

<210> SEQ ID NO 178
<211> LENGTH: 65
<212> TYPE: DNA
<213> ORGANISM: Artificial Sequence
<220> FEATURE:
<223> OTHER INFORMATION: N1368

<400> SEQUENCE: 178

```
atatgctggt gatgagtaat ctgttgtcat tttgaatatg tattatttgg ttatggttgt    60
atatg                                                               65
```

<210> SEQ ID NO 179
<211> LENGTH: 80
<212> TYPE: DNA
<213> ORGANISM: Artificial Sequence
<220> FEATURE:
<223> OTHER INFORMATION: N1371

<400> SEQUENCE: 179

```
aaaaactaat acgtaaacct gcattaaggt aagattatat cagaaaatgt gttgcaagaa    60
atgcattatg caatttttg                                                80
```

<210> SEQ ID NO 180
<211> LENGTH: 85
<212> TYPE: DNA
<213> ORGANISM: Artificial Sequence
<220> FEATURE:
<223> OTHER INFORMATION: N1372

<400> SEQUENCE: 180

```
tagaagctaa tctttaacct ggaagacagg acagaaaagt aattacaaga acatatgtga    60 aaaaaatag ttgatatttt aaacc                                          85
```

<210> SEQ ID NO 181
<211> LENGTH: 25
<212> TYPE: DNA
<213> ORGANISM: Artificial Sequence
<220> FEATURE:
<223> OTHER INFORMATION: BK93

<400> SEQUENCE: 181

```
aaaaattgat tctcatcgta aatgc                                         25
```

<210> SEQ ID NO 182
<211> LENGTH: 30
<212> TYPE: DNA
<213> ORGANISM: Artificial Sequence
<220> FEATURE:
<223> OTHER INFORMATION: N1114

<400> SEQUENCE: 182

```
atatgctggt gatgagtaat ctgttgtcat                                    30
```

<210> SEQ ID NO 183
<211> LENGTH: 6728
<212> TYPE: DNA
<213> ORGANISM: Artificial Sequence
<220> FEATURE:
<223> OTHER INFORMATION: pJT254

<400> SEQUENCE: 183

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgcgtg     120
ttggcgggtg tcggggctgg cttaactatg cggcatcaga gcagattgta ctgagagtgc     180
accataaatt cccgttttaa gagcttggtg agcgctagga gtcactgcca ggtatcgttt     240
gaacacggca ttagtcaggg aagtcataac acagtccttt cccgcaattt tctttttcta     300
ttactcttgg cctcctctag tacactctat attttttat gcctcggtaa tgattttcat      360
ttttttttt cccctagcgg atgactcttt tttttctta gcgattggca ttatcacata       420
atgaattata cattatataa agtaatgtga tttcttcgaa gaatatacta aaaaatgagc     480
aggcaagata aacgaaggca aagatgacag agcagaaagc cctagtaaag cgtattacaa     540
atgaaaccaa gattcagatt gcgatctctt taaagggtgg tccctagcg atagagcact      600
cgatcttccc agaaaagag gcagaagcag tagcagaaca ggccacacaa tcgcaagtga     660
ttaacgtcca cacaggtata gggtttctgg accatatgat acatgctctg gccaagcatt    720
ccggctggtc gctaatcgtt gagtgcattg gtgacttaca catagacgac catcacacca    780
ctgaagactg cgggattgct ctcggtcaag cttttaaaga ggccctactg gcgcgtggag    840
taaaaaggtt tggatcagga tttgcgcctt tggatgaggc actttccaga gcggtggtag    900
atctttcgaa caggccgtac gcagttgtcg aacttggttt gcaaagggag aaagtaggag   960
atctctcttg cgagatgatc ccgcattttc ttgaaagctt tgcagaggct agcagaatta   1020
ccctccacgt tgattgtctg cgaggcaaga atgatcatca ccgtagtgag agtgcgttca   1080
aggctcttgc ggttgccata agagaagcca cctcgcccaa tggtaccaac gatgttccct   1140
ccaccaaagg tgttcttatg tagtgacacc gattatttaa agctgcagca tacgatatat   1200
atacatgtgt atatatgtat acctatgaat gtcagtaagt atgtatacga acagtatgat   1260
actgaagatg acaaggtaat gcatcattct atacgtgtca ttctgaacga ggcgcgcttt   1320
ccttttttct ttttgctttt tcttttttt tctcttgaac tcgacggatc tatgcggtgt   1380
gaaataccgc acagatgcgt aaggagaaaa taccgcatca ggaaattgta aacgttaata   1440
ttttgttaaa attcgcgtta aatttttgtt aaatcagctc attttttaac caataggccg   1500
aaatcggcaa aatcccttat aaatcaaaag aatagaccga gatagggttg agtgttgttc   1560
cagtttggaa caagagtcca ctattaaaga acgtggactc caacgtcaaa gggcgaaaaa   1620
ccgtctatca gggcgatggc ccactacgtg aaccatcacc ctaatcaagt ttttgtgggt   1680
cgaggtgccg taaagcacta atcggaacc ctaaagggag cccccgattt agagcttgac    1740
ggggaaagcc ggcgaacgtg gcgagaaagg aagggaagaa agcgaaagga gcgggcgcta   1800
gggcgctggc aagtgtagcg gtcacgctgc gcgtaaccac cacacccgcc gcgcttaatg   1860
cgccgctaca gggcgcgtcg cgccattcgc cattcaggct gcgcaactgt tgggaagggc   1920
gatcggtgcg ggcctcttcg ctattacgcc agctggcgaa aggggggatgt gctgcaaggc   1980
gattaagttg ggtaacgcca gggttttccc agtcacgacg ttgtaaaacg acggccagtg   2040
agcgcgcgta atacgactca ctataggcg aattgggtac cgggcccccc ctcgaggtcg    2100
acggtatcga taagcttgat tagaagccgc cgagcgggcg acagccctcc gacggaagac   2160
tctcctccgt gcgtcctcgt cttccaccgg cgcgttcctg aaacgcagat gtgcctcgcg   2220
ccgcactgct ccgaacaata aagattctac aatactagct tttatggtta tgaagaggaa   2280
aaattggcag taacctggcc ccacaaacct tcaaattaac gaatcaaatt aacaaccata   2340
```

```
ggatgataat gcgattagtt ttttagcctt atttctgggg taattaatca gcgaagcgat    2400
gatttttgat ctattaacag atatataaat ggaaaagctg cataaccact ttaactaata    2460
ctttcaacat tttcagtttg tattacttct tattcaaatg tcataaaagt atcaacaaaa    2520
aattgttaat atacctctat actttaacgt caaggagaaa aatgtccaat ttactgcccg    2580
tacaccaaaa tttgcctgca ttaccggtcg atgcaacgag tgatgaggtt cgcaagaacc    2640
tgatggacat gttcagggat cgccaggcgt tttctgagca tacctggaaa atgcttctgt    2700
ccgtttgccg gtcgtgggcg gcatggtgca agttgaataa ccggaaatgg tttcccgcag    2760
aacctgaaga tgttcgcgat tatcttctat atcttcaggc gcgcggtctg gcagtaaaaa    2820
ctatccagca acatttgggc cagctaaaca tgcttcatcg tcggtccggg ctgccacgac    2880
caagtgacag caatgctgtt tcactggtta tgcggcggat ccgaaaagaa acgttgatg    2940
ccggtgaacg tgcaaaacag gctctagcgt tcgaacgcac tgatttcgac caggttcgtt    3000
cactcatgga aaatagcgat cgctgccagg atatacgtaa tctggcattt ctggggattg    3060
cttataacac cctgttacgt atagccgaaa ttgccaggat cagggttaaa gatatctcac    3120
gtactgacgg tgggagaatg ttaatccata ttggcagaac gaaaacgctg gttagcaccg    3180
caggtgtaga gaaggcactt agcctggggg taactaaact ggtcgagcga tggatttccg    3240
tctctggtgt agctgatgat ccgaataact acctgttttg ccgggtcaga aaaaatggtg    3300
ttgccgcgcc atctgccacc agccagctat caactcgcgc cctggaaggg attttttgaag   3360
caactcatcg attgatttac ggcgctaagg atgactctgg tcagagatac ctggcctggt    3420
ctggacacag tgcccgtgtc ggagccgcgc gagatatggc ccgcgctgga gtttcaatac    3480
cggagatcat gcaagctggt ggctggacca atgtaaatat tgtcatgaac tatatccgta    3540
acctggatag tgaaacaggg gcaatggtgc gcctgctgga agatggcgat taggagtaag    3600
cgaatttctt atgatttatg attttttatta ttaaataagt tataaaaaaa ataagtgtat    3660
acaaatttta aagtgactct taggttttaa aacgaaaatt cttattcttg agtaactctt    3720
tcctgtaggt caggttgctt tctcaggtat agcatgaggt cgctcttatt gaccacacct    3780
ctaccggcat gccgagcaaa tgcctgcaaa tcgctcccca tttcacccaa ttgtagatat    3840
gctaactcca gcaatgagtt gatgaatctc ggtgtgtatt ttatgtcctc agaggacaac    3900
acctgtggtg ttctagagcg gccgccaccg cggtggagct ccagcttttg ttccctttag    3960
tgagggttaa ttgcgcgctt ggcgtaatca tggtcatagc tgtttcctgt gtgaaattgt    4020
tatccgctca caattccaca caacatagga gccggaagca taaagtgtaa agcctggggt    4080
gcctaatgag tgaggtaact cacattaatt gcgttgcgct cactgcccgc tttccagtcg    4140
ggaaacctgt cgtgccagct gcattaatga atcggccaac gcgcggggag aggcggtttg    4200
cgtattgggc gctcttccgc ttcctcgctc actgactcgc tgcgctcggt cgttcggctg    4260
cggcgagcgg tatcagctca ctcaaaggcg gtaatacggt tatccacaga atcaggggat    4320
aacgcaggaa agaacatgtg agcaaaaggc cagcaaaagg ccaggaaccg taaaaaggcc    4380
gcgttgctgg cgtttttcca taggctccgc cccctgacg agcatcacaa aaatcgacgc    4440
tcaagtcaga ggtggcgaaa cccgacagga ctataaagat accaggcgtt tccccctgga    4500
agctccctcg tgcgctctcc tgttccgacc ctgccgctta ccggatacct gtccgccttt    4560
ctcccttcgg gaagcgtggc gctttctcat agctcacgct gtaggtatct cagttcggtg    4620
taggtcgttc gctccaagct gggctgtgtg cacgaacccc ccgttcagcc cgaccgctgc    4680
```

```
gccttatccg gtaactatcg tcttgagtcc aacccggtaa gacacgactt atcgccactg    4740
gcagcagcca ctggtaacag gattagcaga gcgaggtatg taggcggtgc tacagagttc    4800
ttgaagtggt ggcctaacta cggctacact agaaggacag tatttggtat ctgcgctctg    4860
ctgaagccag ttaccttcgg aaaaagagtt ggtagctctt gatccggcaa acaaaccacc    4920
gctggtagcg gtggtttttt tgtttgcaag cagcagatta cgcgcagaaa aaaggatct    4980 caagaagatc ctttgatctt ttctacgggg tctgacgctc agtggaacga aaactcacgt    5040
taagggattt tggtcatgag attatcaaaa aggatcttca cctagatcct tttaaattaa    5100
aaatgaagtt ttaaatcaat ctaaagtata tatgagtaaa cttggtctga cagttaccaa    5160
tgcttaatca gtgaggcacc tatctcagcg atctgtctat ttcgttcatc catagttgcc    5220
tgactccccg tcgtgtagat aactacgata cgggagggct taccatctgg ccccagtgct    5280
gcaatgatac cgcgagaccc acgctcaccg gctccagatt tatcagcaat aaaccagcca    5340
gccggaaggg ccgagcgcag aagtggtcct gcaactttat ccgcctccat ccagtctatt    5400
aattgttgcc gggaagctag agtaagtagt tcgccagtta atagtttgcg caacgttgtt    5460
gccattgcta caggcatcgt ggtgtcacgc tcgtcgtttg gtatggcttc attcagctcc    5520
ggttcccaac gatcaaggcg agttacatga tcccccatgt tgtgcaaaaa agcggttagc    5580
tccttcggtc ctccgatcgt tgtcagaagt aagttggccg cagtgttatc actcatggtt    5640
atggcagcac tgcataattc tcttactgtc atgccatccg taagatgctt ttctgtgact    5700
ggtgagtact caaccaagtc attctgagaa tagtgtatgc ggcgaccgag ttgctcttgc    5760
ccggcgtcaa tacgggataa taccgcgcca catagcagaa ctttaaaagt gctcatcatt    5820
ggaaaacgtt cttcggggcg aaaactctca aggatcttac cgctgttgag atccagttcg    5880
atgtaaccca ctcgtgcacc caactgatct tcagcatctt ttactttcac cagcgtttct    5940
gggtgagcaa aaacaggaag gcaaaatgcc gcaaaaaagg aataagggc gacacggaaa    6000 tgttgaatac tcatactctt cctttttcaa tattattgaa gcatttatca gggttattgt    6060
ctcatgagcg gatacatatt tgaatgtatt tagaaaaata acaaataggg gttccgcgc    6120 acatttcccc gaaaagtgcc acctgggtcc ttttcatcac gtgctataaa aataattata    6180
atttaaattt tttaatataa atatataaat taaaaataga agtaaaaaa agaaattaaa    6240 gaaaaaatag ttttgttttt ccgaagatgt aaaagactct aggggatcg ccaacaaata    6300 ctacctttta tcttgctctt cctgctctca ggtattaatg ccgaattgtt tcatcttgtc    6360
tgtgtagaag accacacacg aaaatcctgt gattttacat tttacttatc gttaatcgaa    6420
tgtatatcta tttaatctgc ttttcttgtc taataaatat atatgtaaag tacgcttttt    6480
gttgaaattt tttaaacctt tgtttatttt tttttcttca ttccgtaact cttctacctt    6540
ctttatttac tttctaaaat ccaaatacaa aacataaaaa taaataaaca cagagtaaat    6600
tcccaaatta ttccatcatt aaaagatacg aggcgcgtgt aagttacagg caagcgatcc    6660
gtcctaagaa accattatta tcatgacatt aacctataaa aataggcgta tcacgaggcc    6720
ctttcgtc                                                            6728
```

<210> SEQ ID NO 184
<211> LENGTH: 22
<212> TYPE: DNA
<213> ORGANISM: Artificial Sequence
<220> FEATURE:
<223> OTHER INFORMATION: N160Seq F5

<400> SEQUENCE: 184

```
cctgaagtct aggtccctat tt                                              22
```

<210> SEQ ID NO 185
<211> LENGTH: 1650
<212> TYPE: DNA
<213> ORGANISM: Artificial Sequence
<220> FEATURE:
<223> OTHER INFORMATION: Amn1

<400> SEQUENCE: 185

```
atgaagctgg agcgcgtgag ttctaacggg agctttaagc gtggccgtga catccaaagt    60
ttggagagtc cgtgtacccg cccattaaag aaaatgtcgc catcaccttc atttacgagc   120
ctgaagatgg aaaaaccgtt taaggacatt gttcgaaaat acggggtca cctgcaccag   180
tcctcgtata acccaggttc ttcaaaagtt gaactcgtgc gtccggacct gagcttgaaa   240
acggaccaat cattttttgca gagcagcgtg cagacaaccc cgaacaaaaa gagttgtaac   300
gagtatctgt ccacacccga agccactccc cttaagaaca cggccaccga gaatgcgtgg   360
gctacgtcaa gggtggtgag cgcatcaagc ctgtcaatcg tcacgccgac cgaaatcaaa   420
aatatactgg ttgacgagtt tagtgaacta aaacttggtc agcccttaac agcccagcac   480
caacggagcc atgcagtttt cgagatacct gagatcgtag agaacataat caagatgatc   540
gtttccctcg agagcgccaa tattccgaaa aacgtccgt gcctgcgtcg caacccgcag   600
agttatgagc attcccttct gatgtataaa gacgaggaac gcgcgaagaa agcatggtcc   660
gcggctcaac aactgcgcga tccgccgctg gtgggtcata aggaaaaaaa acagggcgct   720
ctgtttagct gcatgatggt caaccgcctg tggttgaatg tcacgcgtcc gttcttatt   780
aagtctctgc atttcaaatc agtgcacaac ttcaaagaat ttctgcgcac aagtcaggaa   840
accacgcaag tgatgaggcc atcgcacttt atcctgcata aattgcacca ggtaacgcag   900
ccggatattg agagactgtc tagaatggaa tgccagaacc tcaagtggtt ggaattttat   960
gtatgtcccc gtattacacc tccactgtct tggttcgaca atttgcataa gttagaaaaa  1020
ttaatcatcc ccggaaacaa gaatatcgac gataatttcc tcttacggct gtctcagagt  1080
attcctaacc tgaaacacct cgtgcttcgt gcttgcgaca atgtttccga tagtggtgta  1140
gtttgtatcg ccctgaactg ccctaagctg aagacgttca acatcggacg tcatcgccgc  1200
ggcaatctga ttacatcagt tagccttggtt gccctgggta gtatacgca agttgagacc  1260
gttggttttg caggctgcga tgtggacgac gcaggcatat gggagttcgc gcgtttaaac  1320
gggaaaaacg tcgagcgcct gtcactcaac agttgccggc ttttaaccga ctatagcttg  1380
ccaatcctgt ttgcccttaa tagttttccg aaccttgcgg tgttggaaat tcgaaacctc  1440
gataaaatta cagatgtccg ccattttgtg aaatataatc tgtggaagaa atcactggat  1500
gctcctatcc tgattgaggc gtgcgaacgc ataacaaagc tgattgatca ggaagagaac  1560
cgggtcaaac gcataaatag cctggtcgct ttaaaggata tgaccgcgtg ggtgaacgct  1620
gacgatgaaa ttgaaaacaa cgtcgattga                                   1650
```

<210> SEQ ID NO 186
<211> LENGTH: 549
<212> TYPE: PRT
<213> ORGANISM: Artificial Sequence
<220> FEATURE:
<223> OTHER INFORMATION: Amn1

<400> SEQUENCE: 186

```
Met Lys Leu Glu Arg Val Ser Ser Asn Gly Ser Phe Lys Arg Gly Arg
1               5                   10                  15

Asp Ile Gln Ser Leu Glu Ser Pro Cys Thr Arg Pro Leu Lys Lys Met
            20                  25                  30

Ser Pro Ser Pro Ser Phe Thr Ser Leu Lys Met Glu Lys Pro Phe Lys
            35                  40                  45

Asp Ile Val Arg Lys Tyr Gly Gly His Leu His Gln Ser Ser Tyr Asn
50                  55                  60

Pro Gly Ser Ser Lys Val Glu Leu Val Arg Pro Asp Leu Ser Leu Lys
65                  70                  75                  80

Thr Asp Gln Ser Phe Leu Gln Ser Ser Val Gln Thr Thr Pro Asn Lys
                85                  90                  95

Lys Ser Cys Asn Glu Tyr Leu Ser Thr Pro Glu Ala Thr Pro Leu Lys
                100                 105                 110

Asn Thr Ala Thr Glu Asn Ala Trp Ala Thr Ser Arg Val Val Ser Ala
                115                 120                 125

Ser Ser Leu Ser Ile Val Thr Pro Thr Glu Ile Lys Asn Ile Leu Val
130                 135                 140

Asp Glu Phe Ser Glu Leu Lys Leu Gly Gln Pro Leu Thr Ala Gln His
145                 150                 155                 160

Gln Arg Ser His Ala Val Phe Glu Ile Pro Glu Ile Val Glu Asn Ile
                165                 170                 175

Ile Lys Met Ile Val Ser Leu Glu Ser Ala Asn Ile Pro Lys Glu Arg
                180                 185                 190

Pro Cys Leu Arg Arg Asn Pro Gln Ser Tyr Glu His Ser Leu Leu Met
                195                 200                 205

Tyr Lys Asp Glu Glu Arg Ala Lys Lys Ala Trp Ser Ala Ala Gln Gln
210                 215                 220

Leu Arg Asp Pro Pro Leu Val Gly His Lys Glu Lys Gln Gly Ala
225                 230                 235                 240

Leu Phe Ser Cys Met Met Val Asn Arg Leu Trp Leu Asn Val Thr Arg
                245                 250                 255

Pro Phe Leu Phe Lys Ser Leu His Phe Lys Ser Val His Asn Phe Lys
                260                 265                 270

Glu Phe Leu Arg Thr Ser Gln Glu Thr Thr Gln Val Met Arg Pro Ser
                275                 280                 285

His Phe Ile Leu His Lys Leu His Gln Val Thr Gln Pro Asp Ile Glu
                290                 295                 300

Arg Leu Ser Arg Met Glu Cys Gln Asn Leu Lys Trp Leu Glu Phe Tyr
305                 310                 315                 320

Val Cys Pro Arg Ile Thr Pro Pro Leu Ser Trp Phe Asp Asn Leu His
                325                 330                 335

Lys Leu Glu Lys Leu Ile Ile Pro Gly Asn Lys Asn Ile Asp Asp Asn
                340                 345                 350

Phe Leu Leu Arg Leu Ser Gln Ser Ile Pro Asn Leu Lys His Leu Val
                355                 360                 365

Leu Arg Ala Cys Asp Asn Val Ser Asp Ser Gly Val Val Cys Ile Ala
370                 375                 380

Leu Asn Cys Pro Lys Leu Lys Thr Phe Asn Ile Gly Arg His Arg Arg
385                 390                 395                 400

Gly Asn Leu Ile Thr Ser Val Ser Leu Val Ala Leu Gly Lys Tyr Thr
                405                 410                 415

Gln Val Glu Thr Val Gly Phe Ala Gly Cys Asp Val Asp Asp Ala Gly
```

```
                420             425             430
Ile Trp Glu Phe Ala Arg Leu Asn Gly Lys Asn Val Glu Arg Leu Ser
            435                 440                 445

Leu Asn Ser Cys Arg Leu Leu Thr Asp Tyr Ser Leu Pro Ile Leu Phe
450                 455                 460

Ala Leu Asn Ser Phe Pro Asn Leu Ala Val Leu Glu Ile Arg Asn Leu
465                 470                 475                 480

Asp Lys Ile Thr Asp Val Arg His Phe Val Lys Tyr Asn Leu Trp Lys
            485                 490                 495

Lys Ser Leu Asp Ala Pro Ile Leu Ile Glu Ala Cys Glu Arg Ile Thr
            500                 505                 510

Lys Leu Ile Asp Gln Glu Gly Asn Arg Val Lys Arg Ile Asn Ser Leu
            515                 520                 525

Val Ala Leu Lys Asp Met Thr Ala Trp Val Asn Ala Asp Asp Glu Ile
            530                 535                 540

Glu Asn Asn Val Asp
545

<210> SEQ ID NO 187
<211> LENGTH: 6638
<212> TYPE: DNA
<213> ORGANISM: Artificial Sequence
<220> FEATURE:
<223> OTHER INFORMATION: pLA67

<400> SEQUENCE: 187
aaacgccagc aacgcggcct ttttacggtt cctggccttt tgctggcctt ttgctcacat    60
gttctttcct gcgttatccc ctgattctgt ggataaccgt attaccgcct ttgagtgagc   120
tgataccgct cgccgcagcc gaacgaccga gcgcagcgag tcagtgagcg aggaagcgga   180
agagcgccca atacgcaaac cgcctctccc cgcgcgttgg ccgattcatt aatgcagctg   240
gcacgacagg tttcccgact ggaaagcggg cagtgagcgc aacgcaatta atgtgagtta   300
gctcactcat taggcacccc aggctttaca ctttatgctt ccggctcgta tgttgtgtgg   360
aattgtgagc ggataacaat ttcacacagg aaacagctat gaccatgatt acgccaagct   420
tgcatgcctg caggtcgact ctagaggatc cgcattgcgg attacgtatt ctaatgttca   480
gtaccgttcg tataatgtat gctatacgaa gttatgcaga ttgtactgag agtgcaccat   540
accacagctt tcaattcaa ttcatcattt ttttttatt ctttttttg atttcggttt      600 ctttgaaatt tttttgattc ggtaatctcc gaacagaagg aagaacgaag gaaggagcac   660
agacttagat tggtatatat acgcatatgt agtgttgaag aaacatgaaa ttgcccagta   720
ttcttaaccc aactgcacag aacaaaaacc tgcaggaaac gaagataaat catgtcgaaa   780
gctacatata aggaacgtgc tgctactcat cctagtcctg ttgctgccaa gctatttaat   840
atcatgcacg aaaagcaaac aaacttgtgt gcttcattgg atgttcgtac caccaaggaa   900
ttactggagt tagttgaagc attaggtccc aaaatttgtt tactaaaaac acatgtggat   960
atcttgactg attttttcat ggagggcaca gttaagccgc taaaggcatt atccgccaag  1020 tacaatttt tactcttcga agacagaaaa tttgctgaca ttggtaatac agtcaaattg  1080
cagtactctg cgggtgtata cagaatagca gaatgggcag acattacgaa tgcacacggt  1140
gtggtgggcc caggtattgt tagcggtttg aagcaggcgg cagaagaagt aacaaaggaa  1200
cctagaggcc ttttgatgtt agcagaattg tcatgcaagg ctccctatc tactggagaa   1260 tatactaagg gtactgttga cattgcgaag agcgacaaag attttgttat cggctttatt  1320
```

```
gctcaaagag acatgggtgg aagagatgaa ggttacgatt ggttgattat gacacccggt   1380
gtgggtttag atgacaaggg agacgcattg ggtcaacagt atagaaccgt ggatgatgtg   1440
gtctctacag gatctgacat tattattgtt ggaagaggac tatttgcaaa gggaagggat   1500
gctaaggtag agggtgaacg ttacagaaaa gcaggctggg aagcatattt gagaagatgc   1560
ggccagcaaa actaaaaaac tgtattataa gtaaatgcat gtatactaaa ctcacaaatt   1620
agagcttcaa tttaattata tcagttatta ccctatgcgg tgtgaaatac cgcacagatg   1680
cgtaaggaga aaataccgca tcaggaaatt gtaaacgtta atattttgtt aaaattcgcg   1740
ttaaattttt gttaaatcag ctcattttt aaccataggc cgaaatcgg caaatccct   1800 tataaatcaa aagaatagac cgagataggg ttgagtgttg ttccagtttg gaacaagagt   1860
ccactattaa agaacgtgga ctccaacgtc aaagggcgaa aaaccgtcta tcagggcgat   1920
ggcccactac gtgaaccatc accctaatca agataacttc gtataatgta tgctatacga   1980
acggtaccag tgatgataca acgagttagc caaggtgaat tcgacttagg atgtctcatc   2040
aatcatctta ttcctgctgg tgttttttgt atcgccttgc cttggagtgt ttatgcttgt   2100
cctttgttca gtaaccattc ttcaagtttg tttcaagtag taggatacct tcagatatac   2160
gaaagaaagg gagtatagtt gtggatatat atatatatag caacccttct ttataagggt   2220
cctatagact atactcttca cactttaaag tacggaatta aggcccaagg gaactaacaa   2280
aaacgttcaa aaagttttaa aactatatgt gttaactgta caaaaataac ttatttatca   2340
tatcattttt ttctctgttt atttcttcta gaacttatac ctgtcttttc cttttattct   2400
ttgaatttgk tttaatatcc cttttttgktt taatatccat ccattccttt cacttagaac   2460
taataattcc cttcgtttga taatttatca ttttcctttt ctgttagtaa agtacccatt   2520
aaatgaagct ggagcgcgtg agttctaacg ggagcttaa gcgtggccgt gacatccaaa   2580
gtttggagag tccgtgtacc cgcccattaa agaaaatgtc gccatcacct tcatttacga   2640
gcctgaagat ggaaaaaccg tttaaggaca ttgttcgaaa atacgggggt cacctgcacc   2700
agtcctcgta taacccaggt tcttcaaaag ttgaactcgt gcgtccggac ctgagcttga   2760
aaacggacca atcatttttg cagagcagcg tgcagacaac cccgaacaaa aagagttgta   2820
acgagtatct gtccacaccc gaagccactc cccttaagaa cacggccacc gagaatgcgt   2880
gggctacgtc aagggtggtg agcgcatcaa gcctgtcaat cgtcacgccg accgaaatca   2940
aaaatatact ggttgacgag tttagtgaac taaaacttgg tcagcccta acagcccagc   3000 accaacggag ccatgcagtt ttcgagatac ctgagatcgt agagaacata atcaagatga   3060
tcgtttccct cgagagcgcc aatattccga agaacgtcc gtgcctgcgt cgcaacccgc   3120
agagttatga gcattccctt ctgatgtata agacgagga acgcgcgaag aaagcatggt   3180
ccgcggctca acaactgcgc gatccgccgc tggtgggtca taaggaaaaa aaacagggcg   3240
ctctgtttag ctgcatgatg gtcaaccgcc tgtggttgaa tgtcacgcgt ccgttcttat   3300
ttaagtctct gcatttcaaa tcagtgcaca acttcaaaga atttctgcgc acaagtcagg   3360
aaaccacgca agtgatgagg ccatcgcact ttatcctgca taaattgcac caggtaacgc   3420
agccggatat tgagagactg tctagaatgg aatgccagaa cctcaagtgg ttggaatttt   3480
atgtatgtcc ccgtattaca cctccactgt cttggttcga caatttgcat aagttagaaa   3540
aattaatcat ccccggaaac aagaatatcg acgataattt cctcttacgg ctgtctcaga   3600
gtattcctaa cctgaaacac ctcgtgcttc gtgcttgcga caatgtttcc gatagtggtg   3660
```

```
tagtttgtat cgccctgaac tgccctaagc tgaagacgtt caacatcgga cgtcatcgcc   3720
gcggcaatct gattacatca gttagcttgg ttgccctggg taagtatacg caagttgaga   3780
ccgttggttt tgcaggctgc gatgtggacg acgcaggcat atgggagttc gcgcgtttaa   3840
acgggaaaaa cgtcgagcgc ctgtcactca acagttgccg gcttttaacc gactatagct   3900
tgccaatcct gtttgccctt aatagtttcc cgaaccttgc ggtgttggaa attcgaaacc   3960
tcgataaaat tacagatgtc cgccattttg tgaaatataa tctgtggaag aaatcactgg   4020
atgctcctat cctgattgag gcgtgcgaac gcataacaaa gctgattgat caggaagaga   4080
accgggtcaa acgcataaat agcctggtcg ctttaaagga tatgaccgcg tgggtgaacg   4140
ctgacgatga aattgaaaac aacgtcgatt gagacgatga aattgaaaac aacgtcgatt   4200
gaggtaccat ggttttgtg actttaccta taaatagtac acaacagacc accagtaatt   4260
ctacacactt cttaactgat aatattatta taattgtaac ttttagcag cactaaattt   4320 aatgaataca tagattttta actagcattt tactattctg tacttttac ttgaaattcc   4380 agaagggccg aagaaaccag aattccttca cagaaaacga attcactggc cgtcgtttta   4440
caacgtcgtg actgggaaaa ccctggcgtt acccaactta atcgccttgc agcacatccc   4500
cctttcgcca gctggcgtaa tagcgaagag gcccgcaccg atcgcccttc ccaacagttg   4560
cgcagcctga atggcgaatg gcgcctgatg cggtattttc tccttacgca tctgtgcggt   4620
atttcacacc gcatatggtg cactctcagt acaatctgct ctgatgccgc atagttaagc   4680
cagccccgac acccgccaac acccgctgac gcgccctgac gggcttgtct gctcccggca   4740
tccgcttaca gacaagctgt gaccgtctcc gggagctgca tgtgtcagag gttttcaccg   4800
tcatcaccga aacgcgcgag acgaaagggc ctcgtgatac gcctattttt ataggttaat   4860
gtcatgataa taatggtttc ttagacgtca ggtggcactt tcggggaaa tgtgcgcgga   4920 acccctattt gtttattttt ctaaatacat tcaaatatgt atccgctcat gagacaataa   4980
ccctgataaa tgcttcaata atattgaaaa aggaagagta tgagtattca acatttccgt   5040
gtcgccctta ttccctttt tgcggcattt tgccttcctg tttttgctca cccagaaacg   5100
ctggtgaaag taaagatgc tgaagatcag ttgggtgcac gagtgggtta catcgaactg   5160
gatctcaaca gcggtaagat ccttgagagt tttcgccccg aagaacgttt tccaatgatg   5220
agcactttta aagttctgct atgtggcgcg gtattatccc gtattgacgc cgggcaagag   5280
caactcggtc gccgcataca ctattctcag aatgacttgg ttgagtactc accagtcaca   5340
gaaaagcatc ttacggatgg catgacagta agagaattat gcagtgctgc cataaccatg   5400
agtgataaca ctgcggccaa cttacttctg acaacgatcg gaggaccgaa ggagctaacc   5460
gcttttttgc acaacatggg ggatcatgta actcgccttg atcgttggga accggagctg   5520
aatgaagcca taccaaacga cgagcgtgac accacgatgc ctgtagcaat ggcaacaacg   5580
ttgcgcaaac tattaactgg cgaactactt actctagctt cccggcaaca attaatagac   5640
tggatggagg cggataaagt tgcaggacca cttctgcgct cggcccttcc ggctggctgg   5700
tttattgctg ataaatctgg agccggtgag cgtgggtctc gcggtatcat tgcagcactg   5760
gggccagatg gtaagccctc ccgtatcgta gttatctaca cgacggggag tcaggcaact   5820
atggatgaac gaaatagaca gatcgctgag ataggtgcct cactgattaa gcattggtaa   5880
ctgtcagacc aagtttactc atatatactt tagattgatt taaaacttca ttttaattt    5940 aaaaggatct aggtgaagat ccttttgat aatctcatga ccaaaatccc ttaacgtgag   6000
ttttcgttcc actgagcgtc agaccccgta gaaaagatca aggatcttc ttgagatcct   6060
```

```
tttttctgc gcgtaatctg ctgcttgcaa acaaaaaaac caccgctacc agcggtggtt    6120
tgtttgccgg atcaagagct accaactctt tttccgaagg taactggctt cagcagagcg    6180
cagataccaa atactgtcct tctagtgtag ccgtagttag ccaccactt caagaactct     6240 gtagcaccgc ctacatacct cgctctgcta atcctgttac cagtggctgc tgccagtggc    6300
gataagtcgt gtcttaccgg gttggactca agacgatagt taccggataa ggcgcagcgg    6360
tcgggctgaa cggggggttc gtgcacacag cccagcttgg agcgaacgac ctacaccgaa    6420
ctgagatacc tacagcgtga gctatgagaa agcgccacgc ttcccgaagg gagaaaggcg    6480
gacaggtatc cggtaagcgg cagggtcgga acaggagagc gcacgaggga gcttccaggg    6540
ggaaacgcct ggtatcttta tagtcctgtc gggtttcgcc acctctgact tgagcgtcga    6600
tttttgtgat gctcgtcagg ggggcggagc ctatggaa                            6638
```

<210> SEQ ID NO 188
<211> LENGTH: 100
<212> TYPE: DNA
<213> ORGANISM: Artificial Sequence
<220> FEATURE:
<223> OTHER INFORMATION: LA712

<400> SEQUENCE: 188

```
cttaattgaa agaaagaatt tccttcaact tcggtttcct ggttccgcta tttctcgctt    60
gtttcttcta gcattgcgga ttacgtattc taatgttcag                           100
```

<210> SEQ ID NO 189
<211> LENGTH: 30
<212> TYPE: DNA
<213> ORGANISM: Artificial Sequence
<220> FEATURE:
<223> OTHER INFORMATION: LA746

<400> SEQUENCE: 189

```
gttttctgtg aaggaattct ggtttcttcg                                      30
```

<210> SEQ ID NO 190
<211> LENGTH: 66
<212> TYPE: PRT
<213> ORGANISM: Homo sapiens

<400> SEQUENCE: 190

Arg Val Thr Met Trp Val Phe Glu Glu Asp Ile Gly Gly Lys Lys Leu
1               5                   10                  15

Thr Glu Ile Ile Asn Thr Gln His Glu Asn Val Lys Tyr Leu Pro Gly
            20                  25                  30

His Lys Leu Pro Pro Asn Val Val Ala Val Pro Asp Val Val Gln Ala
        35                  40                  45

Ala Glu Asp Ala Asp Ile Leu Ile Phe Val Val Pro His Gln Phe Ile
    50                  55                  60

Gly Lys
65

<210> SEQ ID NO 191
<211> LENGTH: 66
<212> TYPE: PRT
<213> ORGANISM: Saccharomyces cerevisiae

<400> SEQUENCE: 191

Ile Val Gln Met Trp Val Phe Glu Glu Glu Ile Asn Gly Glu Lys Leu

-continued

```
                1               5                  10                  15
Thr Glu Ile Ile Asn Thr Arg His Gln Asn Val Lys Tyr Leu Pro Gly
                        20                  25                  30
Ile Thr Leu Pro Asp Asn Leu Val Ala Asn Pro Asp Leu Ile Asp Ser
                35                  40                  45
Val Lys Asp Val Asp Ile Ile Val Phe Asn Ile Pro His Gln Phe Leu
        50                  55                  60
Pro Arg
65

<210> SEQ ID NO 192
<211> LENGTH: 60
<212> TYPE: PRT
<213> ORGANISM: Rickettsia prowazekii

<400> SEQUENCE: 192

Asn Val Thr Leu Phe Leu Arg Asp Glu Ile Ile Leu Lys Glu Ile Leu
1               5                   10                  15
Tyr Lys Lys Thr Asn Ala Gln Tyr Leu Gly Asp Ile Glu Leu Pro Thr
                20                  25                  30
Asn Leu Gln Ala Thr Thr Asn Leu Ser Val Ile Lys Asp Phe Glu Leu
            35                  40                  45
Ile Ile Ile Ala Val Pro Ser Tyr Ala Phe Asp Asp
        50                  55                  60

<210> SEQ ID NO 193
<211> LENGTH: 61
<212> TYPE: PRT
<213> ORGANISM: Beggiatoa alba

<400> SEQUENCE: 193

Pro Ile Tyr Leu Trp Gly Lys Asp Pro Ala His Val His Thr Leu Gln
1               5                   10                  15
Ile Gln Arg Cys Asn Gln Arg Phe Leu Pro Asn Ala Val Phe Pro Asp
                20                  25                  30
Asn Leu Tyr Ala Ile Thr Asp Phe Val Thr Leu Met Pro Ile Val Glu
            35                  40                  45
Asp Ile Ile Ile Val Val Pro Ser His Gly Phe Arg Glu
        50                  55                  60

<210> SEQ ID NO 194
<211> LENGTH: 61
<212> TYPE: PRT
<213> ORGANISM: Kangiella koreensis

<400> SEQUENCE: 194

Ser Val Gln Leu Trp Ala Arg Asn Ser Gln His Val Val Glu Met Gln
1               5                   10                  15
Gln Ala Lys Gln Asn Thr Lys Tyr Leu Pro Asp Val Ala Phe Pro Asp
                20                  25                  30
Asn Leu Ser Val Thr Asp Gln Ile Asp Val Ala Leu Lys His His Pro
            35                  40                  45
Ile Ile Leu Val Ala Val Pro Ser His Ala Phe Arg Asp
        50                  55                  60

<210> SEQ ID NO 195
<211> LENGTH: 391
<212> TYPE: PRT
<213> ORGANISM: Saccharomyces cerevisiae
```

<400> SEQUENCE: 195

```
Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
            35                  40                  45

Ile Ala Lys Val Val Ala Glu Asn Cys Lys Gly Tyr Pro Glu Val Phe
        50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
            115                 120                 125

Phe Leu Pro Arg Ile Cys Ser Gln Leu Lys Gly His Val Asp Ser His
130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
            195                 200                 205

Glu Gly Lys Asp Val Asp His Lys Val Leu Lys Ala Leu Phe His Arg
            210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
            275                 280                 285

Glu Glu Thr Tyr Tyr Gln Glu Ser Ala Gly Val Ala Asp Leu Ile Thr
            290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
            355                 360                 365

Ile Val Tyr Asn Asn Tyr Pro Met Lys Asn Leu Pro Asp Met Ile Glu
        370                 375                 380

Glu Leu Asp Leu His Glu Asp
385                 390
```

```
<210> SEQ ID NO 196
<211> LENGTH: 391
<212> TYPE: PRT
<213> ORGANISM: Artificial Sequence
<220> FEATURE:
<223> OTHER INFORMATION: F73G

<400> SEQUENCE: 196

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
            35                  40                  45

Ile Ala Lys Val Val Ala Glu Asn Cys Lys Gly Tyr Pro Glu Val Phe
        50                  55                  60

Ala Pro Ile Val Gln Met Trp Val Gly Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
```

```
               370                 375                 380
Glu Leu Asp Leu His Glu Asp
385                 390

<210> SEQ ID NO 197
<211> LENGTH: 391
<212> TYPE: PRT
<213> ORGANISM: Artificial Sequence
<220> FEATURE:
<223> OTHER INFORMATION: F73A

<400> SEQUENCE: 197

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Ala Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
```

```
                    340                 345                 350
Thr Cys Gly Ser Val Glu Asp Phe Pro Leu Phe Glu Ala Val Tyr Gln
            355                 360                 365

Ile Val Tyr Asn Asn Tyr Pro Met Lys Asn Leu Pro Asp Met Ile Glu
        370                 375                 380

Glu Leu Asp Leu His Glu Asp
385                 390
```

<210> SEQ ID NO 198
<211> LENGTH: 391
<212> TYPE: PRT
<213> ORGANISM: Artificial Sequence
<220> FEATURE:
<223> OTHER INFORMATION: F73R

<400> SEQUENCE: 198

```
Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
            35                  40                  45

Ile Ala Lys Val Val Ala Glu Asn Cys Lys Gly Tyr Pro Glu Val Phe
50                  55                  60

Ala Pro Ile Val Gln Met Trp Val Arg Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
290                 295                 300

Thr Cys Ala Gly Gly Arg Asn Val Lys Val Ala Arg Leu Met Ala Thr
```

```
                305                 310                 315                 320
Ser Gly Lys Asp Ala Trp Glu Cys Glu Lys Glu Leu Leu Asn Gly Gln
                    325                 330                 335

Ser Ala Gln Gly Leu Ile Thr Cys Lys Glu Val His Glu Trp Leu Glu
                340                 345                 350

Thr Cys Gly Ser Val Glu Asp Phe Pro Leu Phe Glu Ala Val Tyr Gln
                355                 360                 365

Ile Val Tyr Asn Asn Tyr Pro Met Lys Asn Leu Pro Asp Met Ile Glu
            370                 375                 380

Glu Leu Asp Leu His Glu Asp
385                 390

<210> SEQ ID NO 199
<211> LENGTH: 391
<212> TYPE: PRT
<213> ORGANISM: Artificial Sequence
<220> FEATURE:
<223> OTHER INFORMATION: F73K

<400> SEQUENCE: 199

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
                20                  25                  30

Lys Pro Phe Lys Val Thr Val Ile Gly Ser Gly Asn Trp Gly Thr Thr
                35                  40                  45

Ile Ala Lys Val Val Ala Glu Asn Cys Lys Gly Tyr Pro Glu Val Phe
        50                  55                  60

Ala Pro Ile Val Gln Met Trp Val Lys Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
                100                 105                 110

Asp Ser Val Lys Asp Val Asp Ile Ile Val Phe Asn Ile Pro His Gln
                115                 120                 125

Phe Leu Pro Arg Ile Cys Ser Gln Leu Lys Gly His Val Asp Ser His
            130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
                180                 185                 190

Trp Ser Glu Thr Thr Val Ala Tyr His Ile Pro Lys Asp Phe Arg Gly
            195                 200                 205

Glu Gly Lys Asp Val Asp His Lys Val Leu Lys Ala Leu Phe His Arg
                210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
                260                 265                 270

Leu Gly Glu Ile Ile Arg Phe Gly Gln Met Phe Phe Pro Glu Ser Arg
```

```
                      275                 280                 285
Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

<210> SEQ ID NO 200
<211> LENGTH: 391
<212> TYPE: PRT
<213> ORGANISM: Artificial Sequence
<220> FEATURE:
<223> OTHER INFORMATION: F129G

<400> SEQUENCE: 200

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Gly Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
```

```
                   245                 250                 255
Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

<210> SEQ ID NO 201
<211> LENGTH: 391
<212> TYPE: PRT
<213> ORGANISM: Artificial Sequence
<220> FEATURE:
<223> OTHER INFORMATION: F129A

<400> SEQUENCE: 201

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Ala Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
```

```
                210                 215                 220
Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
                260                 265                 270

Leu Gly Glu Ile Ile Arg Phe Gly Gln Met Phe Phe Pro Glu Ser Arg
                275                 280                 285

Glu Glu Thr Tyr Tyr Gln Glu Ser Ala Gly Val Ala Asp Leu Ile Thr
                290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
                340                 345                 350

Thr Cys Gly Ser Val Glu Asp Phe Pro Leu Phe Glu Ala Val Tyr Gln
                355                 360                 365

Ile Val Tyr Asn Asn Tyr Pro Met Lys Asn Leu Pro Asp Met Ile Glu
                370                 375                 380

Glu Leu Asp Leu His Glu Asp
385                 390

<210> SEQ ID NO 202
<211> LENGTH: 391
<212> TYPE: PRT
<213> ORGANISM: Artificial Sequence
<220> FEATURE:
<223> OTHER INFORMATION: F129R

<400> SEQUENCE: 202

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
                20                  25                  30

Lys Pro Phe Lys Val Thr Val Ile Gly Ser Gly Asn Trp Gly Thr Thr
            35                  40                  45

Ile Ala Lys Val Val Ala Glu Asn Cys Lys Gly Tyr Pro Glu Val Phe
        50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
                100                 105                 110

Asp Ser Val Lys Asp Val Asp Ile Ile Val Phe Asn Ile Pro His Gln
            115                 120                 125

Arg Leu Pro Arg Ile Cys Ser Gln Leu Lys Gly His Val Asp Ser His
        130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
```

```
                180             185             190
Trp Ser Glu Thr Thr Val Ala Tyr His Ile Pro Lys Asp Phe Arg Gly
            195                 200                 205
Glu Gly Lys Asp Val Asp His Lys Val Leu Lys Ala Leu Phe His Arg
        210                 215                 220
Pro Tyr Phe His Val Ser Val Ile Glu Asp Val Ala Gly Ile Ser Ile
225                 230                 235                 240
Cys Gly Ala Leu Lys Asn Val Val Ala Leu Gly Cys Gly Phe Val Glu
                245                 250                 255
Gly Leu Gly Trp Gly Asn Asn Ala Ser Ala Ala Ile Gln Arg Val Gly
            260                 265                 270
Leu Gly Glu Ile Ile Arg Phe Gly Gln Met Phe Phe Pro Glu Ser Arg
        275                 280                 285
Glu Glu Thr Tyr Tyr Gln Glu Ser Ala Gly Val Ala Asp Leu Ile Thr
        290                 295                 300
Thr Cys Ala Gly Gly Arg Asn Val Lys Val Ala Arg Leu Met Ala Thr
305                 310                 315                 320
Ser Gly Lys Asp Ala Trp Glu Cys Glu Lys Glu Leu Leu Asn Gly Gln
                325                 330                 335
Ser Ala Gln Gly Leu Ile Thr Cys Lys Glu Val His Glu Trp Leu Glu
            340                 345                 350
Thr Cys Gly Ser Val Glu Asp Phe Pro Leu Phe Glu Ala Val Tyr Gln
        355                 360                 365
Ile Val Tyr Asn Asn Tyr Pro Met Lys Asn Leu Pro Asp Met Ile Glu
        370                 375                 380
Glu Leu Asp Leu His Glu Asp
385                 390

<210> SEQ ID NO 203
<211> LENGTH: 391
<212> TYPE: PRT
<213> ORGANISM: Artificial Sequence
<220> FEATURE:
<223> OTHER INFORMATION: F129K

<400> SEQUENCE: 203

Met Ser Ala Ala Ala Asp Arg Leu Asn Leu Thr Ser Gly His Leu Asn
1               5                   10                  15
Ala Gly Arg Lys Arg Ser Ser Ser Val Ser Leu Lys Ala Ala Glu
            20                  25                  30
Lys Pro Phe Lys Val Thr Val Ile Gly Ser Gly Asn Trp Gly Thr Thr
        35                  40                  45
Ile Ala Lys Val Val Ala Glu Asn Cys Lys Gly Tyr Pro Glu Val Phe
50                  55                  60
Ala Pro Ile Val Gln Met Trp Val Phe Glu Glu Glu Ile Asn Gly Glu
65                  70                  75                  80
Lys Leu Thr Glu Ile Ile Asn Thr Arg His Gln Asn Val Lys Tyr Leu
                85                  90                  95
Pro Gly Ile Thr Leu Pro Asp Asn Leu Val Ala Asn Pro Asp Leu Ile
            100                 105                 110
Asp Ser Val Lys Asp Val Asp Ile Ile Val Phe Asn Ile Pro His Gln
        115                 120                 125
Lys Leu Pro Arg Ile Cys Ser Gln Leu Lys Gly His Val Asp Ser His
        130                 135                 140
Val Arg Ala Ile Ser Cys Leu Lys Gly Phe Glu Val Gly Ala Lys Gly
```

```
                 145                 150                 155                 160
Val Gln Leu Leu Ser Ser Tyr Ile Thr Glu Glu Leu Gly Ile Gln Cys
                 165                 170                 175

Gly Ala Leu Ser Gly Ala Asn Ile Ala Thr Glu Val Ala Gln Glu His
                 180                 185                 190

Trp Ser Glu Thr Thr Val Ala Tyr His Ile Pro Lys Asp Phe Arg Gly
                 195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
                260                 265                 270

Leu Gly Glu Ile Ile Arg Phe Gly Gln Met Phe Phe Pro Glu Ser Arg
                275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
                340                 345                 350

Thr Cys Gly Ser Val Glu Asp Phe Pro Leu Phe Glu Ala Val Tyr Gln
                355                 360                 365

Ile Val Tyr Asn Asn Tyr Pro Met Lys Asn Leu Pro Asp Met Ile Glu
                370                 375                 380

Glu Leu Asp Leu His Glu Asp
385                 390

<210> SEQ ID NO 204
<211> LENGTH: 391
<212> TYPE: PRT
<213> ORGANISM: Artificial Sequence
<220> FEATURE:
<223> OTHER INFORMATION: F73A F129G

<400> SEQUENCE: 204

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Glu
                20                  25                  30

Lys Pro Phe Lys Val Thr Val Ile Gly Ser Gly Asn Trp Gly Thr Thr
                35                  40                  45

Ile Ala Lys Val Val Ala Glu Asn Cys Lys Gly Tyr Pro Glu Val Phe
    50                  55                  60

Ala Pro Ile Val Gln Met Trp Val Ala Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
                100                 105                 110

Asp Ser Val Lys Asp Val Asp Ile Ile Val Phe Asn Ile Pro His Gln
```

```
            115                 120                 125
Gly Leu Pro Arg Ile Cys Ser Gln Leu Lys Gly His Val Asp Ser His
        130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

<210> SEQ ID NO 205
<211> LENGTH: 391
<212> TYPE: PRT
<213> ORGANISM: Artificial Sequence
<220> FEATURE:
<223> OTHER INFORMATION: F73A F129A

<400> SEQUENCE: 205

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Ala Glu Glu Ile Asn Gly Glu
65                  70                  75                  80

Lys Leu Thr Glu Ile Ile Asn Thr Arg His Gln Asn Val Lys Tyr Leu
```

```
                  85                  90                  95

Pro Gly Ile Thr Leu Pro Asp Asn Leu Val Ala Asn Pro Asp Leu Ile
                100                 105                 110

Asp Ser Val Lys Asp Val Asp Ile Ile Val Phe Asn Ile Pro His Gln
            115                 120                 125

Ala Leu Pro Arg Ile Cys Ser Gln Leu Lys Gly His Val Asp Ser His
        130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
                180                 185                 190

Trp Ser Glu Thr Thr Val Ala Tyr His Ile Pro Lys Asp Phe Arg Gly
            195                 200                 205

Glu Gly Lys Asp Val Asp His Lys Val Leu Lys Ala Leu Phe His Arg
        210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
                260                 265                 270

Leu Gly Glu Ile Ile Arg Phe Gly Gln Met Phe Phe Pro Glu Ser Arg
            275                 280                 285

Glu Glu Thr Tyr Tyr Gln Glu Ser Ala Gly Val Ala Asp Leu Ile Thr
        290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
                340                 345                 350

Thr Cys Gly Ser Val Glu Asp Phe Pro Leu Phe Glu Ala Val Tyr Gln
            355                 360                 365

Ile Val Tyr Asn Asn Tyr Pro Met Lys Asn Leu Pro Asp Met Ile Glu
        370                 375                 380

Glu Leu Asp Leu His Glu Asp
385                 390

<210> SEQ ID NO 206
<211> LENGTH: 391
<212> TYPE: PRT
<213> ORGANISM: Artificial Sequence
<220> FEATURE:
<223> OTHER INFORMATION: F73A F129R

<400> SEQUENCE: 206

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
```

```
            50                  55                  60
Ala Pro Ile Val Gln Met Trp Val Ala Glu Glu Ile Asn Gly Glu
 65                  70                  75                  80

Lys Leu Thr Glu Ile Ile Asn Thr Arg His Gln Asn Val Lys Tyr Leu
                 85                  90                  95

Pro Gly Ile Thr Leu Pro Asp Asn Leu Val Ala Asn Pro Asp Leu Ile
             100                 105                 110

Asp Ser Val Lys Asp Val Asp Ile Ile Val Phe Asn Ile Pro His Gln
             115                 120                 125

Arg Leu Pro Arg Ile Cys Ser Gln Leu Lys Gly His Val Asp Ser His
             130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                 165                 170                 175

Gly Ala Leu Ser Gly Ala Asn Ile Ala Thr Glu Val Ala Gln Glu His
             180                 185                 190

Trp Ser Glu Thr Thr Val Ala Tyr His Ile Pro Lys Asp Phe Arg Gly
             195                 200                 205

Glu Gly Lys Asp Val Asp His Lys Val Leu Lys Ala Leu Phe His Arg
             210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                 245                 250                 255

Gly Leu Gly Trp Gly Asn Asn Ala Ser Ala Ala Ile Gln Arg Val Gly
             260                 265                 270

Leu Gly Glu Ile Ile Arg Phe Gly Gln Met Phe Phe Pro Glu Ser Arg
             275                 280                 285

Glu Glu Thr Tyr Tyr Gln Glu Ser Ala Gly Val Ala Asp Leu Ile Thr
             290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                 325                 330                 335

Ser Ala Gln Gly Leu Ile Thr Cys Lys Glu Val His Glu Trp Leu Glu
             340                 345                 350

Thr Cys Gly Ser Val Glu Asp Phe Pro Leu Phe Glu Ala Val Tyr Gln
             355                 360                 365

Ile Val Tyr Asn Asn Tyr Pro Met Lys Asn Leu Pro Asp Met Ile Glu
             370                 375                 380

Glu Leu Asp Leu His Glu Asp
385                 390

<210> SEQ ID NO 207
<211> LENGTH: 391
<212> TYPE: PRT
<213> ORGANISM: Artificial Sequence
<220> FEATURE:
<223> OTHER INFORMATION: F73A F129K

<400> SEQUENCE: 207

Met Ser Ala Ala Ala Asp Arg Leu Asn Leu Thr Ser Gly His Leu Asn
 1               5                  10                  15

Ala Gly Arg Lys Arg Ser Ser Ser Ser Val Ser Leu Lys Ala Ala Glu
```

```
                20              25              30
Lys Pro Phe Lys Val Thr Val Ile Gly Ser Gly Asn Trp Gly Thr Thr
            35              40              45
Ile Ala Lys Val Val Ala Glu Asn Cys Lys Gly Tyr Pro Glu Val Phe
        50              55              60
Ala Pro Ile Val Gln Met Trp Val Ala Glu Glu Ile Asn Gly Glu
65              70              75              80
Lys Leu Thr Glu Ile Ile Asn Thr Arg His Gln Asn Val Lys Tyr Leu
                85              90              95
Pro Gly Ile Thr Leu Pro Asp Asn Leu Val Ala Asn Pro Asp Leu Ile
            100             105             110
Asp Ser Val Lys Asp Val Asp Ile Ile Val Phe Asn Ile Pro His Gln
        115             120             125
Lys Leu Pro Arg Ile Cys Ser Gln Leu Lys Gly His Val Asp Ser His
130             135             140
Val Arg Ala Ile Ser Cys Leu Lys Gly Phe Glu Val Gly Ala Lys Gly
145             150             155             160
Val Gln Leu Leu Ser Ser Tyr Ile Thr Glu Glu Leu Gly Ile Gln Cys
                165             170             175
Gly Ala Leu Ser Gly Ala Asn Ile Ala Thr Glu Val Ala Gln Glu His
            180             185             190
Trp Ser Glu Thr Thr Val Ala Tyr His Ile Pro Lys Asp Phe Arg Gly
        195             200             205
Glu Gly Lys Asp Val Asp His Lys Val Leu Lys Ala Leu Phe His Arg
210             215             220
Pro Tyr Phe His Val Ser Val Ile Glu Asp Val Ala Gly Ile Ser Ile
225             230             235             240
Cys Gly Ala Leu Lys Asn Val Val Ala Leu Gly Cys Gly Phe Val Glu
                245             250             255
Gly Leu Gly Trp Gly Asn Asn Ala Ser Ala Ala Ile Gln Arg Val Gly
            260             265             270
Leu Gly Glu Ile Ile Arg Phe Gly Gln Met Phe Phe Pro Glu Ser Arg
        275             280             285
Glu Glu Thr Tyr Tyr Gln Glu Ser Ala Gly Val Ala Asp Leu Ile Thr
        290             295             300
Thr Cys Ala Gly Gly Arg Asn Val Lys Val Ala Arg Leu Met Ala Thr
305             310             315             320
Ser Gly Lys Asp Ala Trp Glu Cys Glu Lys Glu Leu Leu Asn Gly Gln
            325             330             335
Ser Ala Gln Gly Leu Ile Thr Cys Lys Glu Val His Glu Trp Leu Glu
        340             345             350
Thr Cys Gly Ser Val Glu Asp Phe Pro Leu Phe Glu Ala Val Tyr Gln
        355             360             365
Ile Val Tyr Asn Asn Tyr Pro Met Lys Asn Leu Pro Asp Met Ile Glu
        370             375             380
Glu Leu Asp Leu His Glu Asp
385             390

<210> SEQ ID NO 208
<211> LENGTH: 391
<212> TYPE: PRT
<213> ORGANISM: Artificial Sequence
<220> FEATURE:
<223> OTHER INFORMATION: F73G F129G
```

<400> SEQUENCE: 208

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
                35                  40                  45

Ile Ala Lys Val Val Ala Glu Asn Cys Lys Gly Tyr Pro Glu Val Phe
    50                  55                  60

Ala Pro Ile Val Gln Met Trp Val Gly Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Ala Asn Pro Asp Leu Ile
            100                 105                 110

Asp Ser Val Lys Asp Val Asp Ile Ile Val Phe Asn Ile Pro His Gln
            115                 120                 125

Gly Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
    195                 200                 205

Glu Gly Lys Asp Val Asp His Lys Val Leu Lys Ala Leu Phe His Arg
210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
            245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
    275                 280                 285

Glu Glu Thr Tyr Tyr Gln Glu Ser Ala Gly Val Ala Asp Leu Ile Thr
290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
            325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
    355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

<210> SEQ ID NO 209

<211> LENGTH: 391
<212> TYPE: PRT
<213> ORGANISM: Artificial Sequence
<220> FEATURE:
<223> OTHER INFORMATION: F73G F129A

<400> SEQUENCE: 209

```
Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
                35                  40                  45

Ile Ala Lys Val Val Ala Glu Asn Cys Lys Gly Tyr Pro Glu Val Phe
    50                  55                  60

Ala Pro Ile Val Gln Met Trp Val Gly Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Val Phe Asn Ile Pro His Gln
        115                 120                 125

Ala Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
                195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
    275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380
```

```
Glu Leu Asp Leu His Glu Asp
385                 390
```

<210> SEQ ID NO 210
<211> LENGTH: 391
<212> TYPE: PRT
<213> ORGANISM: Artificial Sequence
<220> FEATURE:
<223> OTHER INFORMATION: F73G F129R

<400> SEQUENCE: 210

```
Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
            35                  40                  45

Ile Ala Lys Val Val Ala Glu Asn Cys Lys Gly Tyr Pro Glu Val Phe
    50                  55                  60

Ala Pro Ile Val Gln Met Trp Val Gly Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Arg Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350
```

```
Thr Cys Gly Ser Val Glu Asp Phe Pro Leu Phe Glu Ala Val Tyr Gln
            355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

<210> SEQ ID NO 211
<211> LENGTH: 390
<212> TYPE: PRT
<213> ORGANISM: Artificial Sequence
<220> FEATURE:
<223> OTHER INFORMATION: F73G F129K

<400> SEQUENCE: 211

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
            35                  40                  45

Ile Ala Lys Val Val Ala Glu Asn Cys Lys Gly Tyr Pro Glu Val Phe
    50                  55                  60

Ala Pro Ile Val Gln Met Trp Val Gly Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
            115                 120                 125

Lys Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
    195                 200                 205

Glu Gly Lys Asp Val Asp His Lys Val Leu Lys Ala Leu Phe His Arg
210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
    275                 280                 285

Glu Glu Thr Tyr Tyr Gln Glu Ser Ala Gly Val Ala Asp Leu Ile Thr
290                 295                 300

Thr Cys Ala Gly Gly Arg Asn Val Lys Val Ala Arg Leu Met Ala Thr
305                 310                 315                 320
```

Ser Gly Lys Asp Ala Trp Glu Cys Glu Lys Glu Leu Leu Asn Gly Gln
            325                 330                 335

Ser Ala Gln Gly Leu Ile Thr Cys Lys Glu Val His Glu Trp Leu Glu
        340                 345                 350

Thr Cys Gly Ser Val Glu Asp Phe Pro Leu Phe Glu Ala Val Tyr Gln
            355                 360                 365

Ile Val Tyr Asn Asn Tyr Pro Met Lys Asn Leu Pro Asp Met Ile Glu
        370                 375                 380

Glu Leu Asp Leu His Glu
385                 390

<210> SEQ ID NO 212
<211> LENGTH: 391
<212> TYPE: PRT
<213> ORGANISM: Artificial Sequence
<220> FEATURE:
<223> OTHER INFORMATION: N44A

<400> SEQUENCE: 212

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Ala Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

-continued

```
Glu Glu Thr Tyr Tyr Gln Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390
```

<210> SEQ ID NO 213
<211> LENGTH: 391
<212> TYPE: PRT
<213> ORGANISM: Artificial Sequence
<220> FEATURE:
<223> OTHER INFORMATION: N44C

<400> SEQUENCE: 213

```
Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Cys Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255
```

-continued

```
Gly Leu Gly Trp Gly Asn Asn Ala Ser Ala Ile Gln Arg Val Gly
            260                 265                 270

Leu Gly Glu Ile Ile Arg Phe Gly Gln Met Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

<210> SEQ ID NO 214
<211> LENGTH: 391
<212> TYPE: PRT
<213> ORGANISM: Artificial Sequence
<220> FEATURE:
<223> OTHER INFORMATION: N44G

<400> SEQUENCE: 214

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220
```

```
Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
            245                 250                 255

Gly Leu Gly Trp Gly Asn Asn Ala Ser Ala Ala Ile Gln Arg Val Gly
        260                 265                 270

Leu Gly Glu Ile Ile Arg Phe Gly Gln Met Phe Phe Pro Glu Ser Arg
    275                 280                 285

Glu Glu Thr Tyr Tyr Gln Glu Ser Ala Gly Val Ala Asp Leu Ile Thr
290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
            325                 330                 335

Ser Ala Gln Gly Leu Ile Thr Cys Lys Glu Val His Glu Trp Leu Glu
        340                 345                 350

Thr Cys Gly Ser Val Glu Asp Phe Pro Leu Phe Glu Ala Val Tyr Gln
    355                 360                 365

Ile Val Tyr Asn Asn Tyr Pro Met Lys Asn Leu Pro Asp Met Ile Glu
370                 375                 380

Glu Leu Asp Leu His Glu Asp
385                 390
```

<210> SEQ ID NO 215
<211> LENGTH: 391
<212> TYPE: PRT
<213> ORGANISM: Artificial Sequence
<220> FEATURE:
<223> OTHER INFORMATION: N44I

<400> SEQUENCE: 215

```
Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Ile Trp Gly Thr Thr
            35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190
```

```
Trp Ser Glu Thr Thr Val Ala Tyr His Ile Pro Lys Asp Phe Arg Gly
        195                 200                 205
Glu Gly Lys Asp Val Asp His Lys Val Leu Lys Ala Leu Phe His Arg
    210                 215                 220
Pro Tyr Phe His Val Ser Val Ile Glu Asp Val Ala Gly Ile Ser Ile
225                 230                 235                 240
Cys Gly Ala Leu Lys Asn Val Val Ala Leu Gly Cys Gly Phe Val Glu
                245                 250                 255
Gly Leu Gly Trp Gly Asn Asn Ala Ser Ala Ala Ile Gln Arg Val Gly
            260                 265                 270
Leu Gly Glu Ile Ile Arg Phe Gly Gln Met Phe Phe Pro Glu Ser Arg
        275                 280                 285
Glu Glu Thr Tyr Tyr Gln Glu Ser Ala Gly Val Ala Asp Leu Ile Thr
    290                 295                 300
Thr Cys Ala Gly Gly Arg Asn Val Lys Val Ala Arg Leu Met Ala Thr
305                 310                 315                 320
Ser Gly Lys Asp Ala Trp Glu Cys Glu Lys Glu Leu Leu Asn Gly Gln
                325                 330                 335
Ser Ala Gln Gly Leu Ile Thr Cys Lys Glu Val His Glu Trp Leu Glu
            340                 345                 350
Thr Cys Gly Ser Val Glu Asp Phe Pro Leu Phe Glu Ala Val Tyr Gln
        355                 360                 365
Ile Val Tyr Asn Asn Tyr Pro Met Lys Asn Leu Pro Asp Met Ile Glu
    370                 375                 380
Glu Leu Asp Leu His Glu Asp
385                 390

<210> SEQ ID NO 216
<211> LENGTH: 391
<212> TYPE: PRT
<213> ORGANISM: Artificial Sequence
<220> FEATURE:
<223> OTHER INFORMATION: N44L

<400> SEQUENCE: 216

Met Ser Ala Ala Ala Asp Arg Leu Asn Leu Thr Ser Gly His Leu Asn
1               5                   10                  15
Ala Gly Arg Lys Arg Ser Ser Ser Val Ser Leu Lys Ala Ala Glu
            20                  25                  30
Lys Pro Phe Lys Val Thr Val Ile Gly Ser Gly Leu Trp Gly Thr Thr
        35                  40                  45
Ile Ala Lys Val Val Ala Glu Asn Cys Lys Gly Tyr Pro Glu Val Phe
    50                  55                  60
Ala Pro Ile Val Gln Met Trp Val Phe Glu Glu Ile Asn Gly Glu
65                  70                  75                  80
Lys Leu Thr Glu Ile Ile Asn Thr Arg His Gln Asn Val Lys Tyr Leu
                85                  90                  95
Pro Gly Ile Thr Leu Pro Asp Asn Leu Val Ala Asn Pro Asp Leu Ile
            100                 105                 110
Asp Ser Val Lys Asp Val Asp Ile Ile Val Phe Asn Ile Pro His Gln
        115                 120                 125
Phe Leu Pro Arg Ile Cys Ser Gln Leu Lys Gly His Val Asp Ser His
    130                 135                 140
Val Arg Ala Ile Ser Cys Leu Lys Gly Phe Glu Val Gly Ala Lys Gly
145                 150                 155                 160
```

-continued

```
Val Gln Leu Leu Ser Ser Tyr Ile Thr Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
            195                 200                 205

Glu Gly Lys Asp Val Asp His Lys Val Leu Lys Ala Leu Phe His Arg
        210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

<210> SEQ ID NO 217
<211> LENGTH: 391
<212> TYPE: PRT
<213> ORGANISM: Artificial Sequence
<220> FEATURE:
<223> OTHER INFORMATION: N44M

<400> SEQUENCE: 217

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Met Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125
```

-continued

```
Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
                180                 185                 190

Trp Ser Glu Thr Thr Val Ala Tyr His Ile Pro Lys Asp Phe Arg Gly
                195                 200                 205

Glu Gly Lys Asp Val Asp His Lys Val Leu Lys Ala Leu Phe His Arg
210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
                260                 265                 270

Leu Gly Glu Ile Ile Arg Phe Gly Gln Met Phe Phe Pro Glu Ser Arg
                275                 280                 285

Glu Glu Thr Tyr Tyr Gln Glu Ser Ala Gly Val Ala Asp Leu Ile Thr
290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
                340                 345                 350

Thr Cys Gly Ser Val Glu Asp Phe Pro Leu Phe Glu Ala Val Tyr Gln
                355                 360                 365

Ile Val Tyr Asn Asn Tyr Pro Met Lys Asn Leu Pro Asp Met Ile Glu
                370                 375                 380

Glu Leu Asp Leu His Glu Asp
385                 390
```

<210> SEQ ID NO 218
<211> LENGTH: 391
<212> TYPE: PRT
<213> ORGANISM: Artificial Sequence
<220> FEATURE:
<223> OTHER INFORMATION: N44S

<400> SEQUENCE: 218

```
Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
                20                  25                  30

Lys Pro Phe Lys Val Thr Val Ile Gly Ser Gly Ser Trp Gly Thr Thr
                35                  40                  45

Ile Ala Lys Val Val Ala Glu Asn Cys Lys Gly Tyr Pro Glu Val Phe
            50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95
```

-continued

```
Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

<210> SEQ ID NO 219
<211> LENGTH: 391
<212> TYPE: PRT
<213> ORGANISM: Artificial Sequence
<220> FEATURE:
<223> OTHER INFORMATION: N44V

<400> SEQUENCE: 219

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Val Trp Gly Thr Thr
        35                  40                  45

Ile Ala Lys Val Val Ala Glu Asn Cys Lys Gly Tyr Pro Glu Val Phe
    50                  55                  60
```

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
            85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
            115                 120                 125

Phe Leu Pro Arg Ile Cys Ser Gln Leu Lys Gly His Val Asp Ser His
            130                 135             140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
                180                 185                 190

Trp Ser Glu Thr Thr Val Ala Tyr His Ile Pro Lys Asp Phe Arg Gly
                195                 200                 205

Glu Gly Lys Asp Val Asp His Lys Val Leu Lys Ala Leu Phe His Arg
210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
                260                 265                 270

Leu Gly Glu Ile Ile Arg Phe Gly Gln Met Phe Phe Pro Glu Ser Arg
                275                 280                 285

Glu Glu Thr Tyr Tyr Gln Glu Ser Ala Gly Val Ala Asp Leu Ile Thr
            290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
                340                 345                 350

Thr Cys Gly Ser Val Glu Asp Phe Pro Leu Phe Glu Ala Val Tyr Gln
                355                 360                 365

Ile Val Tyr Asn Asn Tyr Pro Met Lys Asn Leu Pro Asp Met Ile Glu
                370                 375                 380

Glu Leu Asp Leu His Glu Asp
385                 390

<210> SEQ ID NO 220
<211> LENGTH: 391
<212> TYPE: PRT
<213> ORGANISM: Artificial Sequence
<220> FEATURE:
<223> OTHER INFORMATION: W45A

<400> SEQUENCE: 220

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Ala Gly Thr Thr
        35                  40                  45

Ile Ala Lys Val Val Ala Glu Asn Cys Lys Gly Tyr Pro Glu Val Phe
 50                  55                  60

Ala Pro Ile Val Gln Met Trp Val Phe Glu Glu Ile Asn Gly Glu
 65                  70                  75                  80

Lys Leu Thr Glu Ile Ile Asn Thr Arg His Gln Asn Val Lys Tyr Leu
                 85                  90                  95

Pro Gly Ile Thr Leu Pro Asp Asn Leu Val Ala Asn Pro Asp Leu Ile
             100                 105                 110

Asp Ser Val Lys Asp Val Asp Ile Ile Val Phe Asn Ile Pro His Gln
             115                 120                 125

Phe Leu Pro Arg Ile Cys Ser Gln Leu Lys Gly His Val Asp Ser His
             130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                 165                 170                 175

Gly Ala Leu Ser Gly Ala Asn Ile Ala Thr Glu Val Ala Gln Glu His
             180                 185                 190

Trp Ser Glu Thr Thr Val Ala Tyr His Ile Pro Lys Asp Phe Arg Gly
             195                 200                 205

Glu Gly Lys Asp Val Asp His Lys Val Leu Lys Ala Leu Phe His Arg
210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                 245                 250                 255

Gly Leu Gly Trp Gly Asn Asn Ala Ser Ala Ala Ile Gln Arg Val Gly
             260                 265                 270

Leu Gly Glu Ile Ile Arg Phe Gly Gln Met Phe Phe Pro Glu Ser Arg
             275                 280                 285

Glu Glu Thr Tyr Tyr Gln Glu Ser Ala Gly Val Ala Asp Leu Ile Thr
             290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                 325                 330                 335

Ser Ala Gln Gly Leu Ile Thr Cys Lys Glu Val His Glu Trp Leu Glu
             340                 345                 350

Thr Cys Gly Ser Val Glu Asp Phe Pro Leu Phe Glu Ala Val Tyr Gln
             355                 360                 365

Ile Val Tyr Asn Asn Tyr Pro Met Lys Asn Leu Pro Asp Met Ile Glu
             370                 375                 380

Glu Leu Asp Leu His Glu Asp
385                 390

<210> SEQ ID NO 221
<211> LENGTH: 391
<212> TYPE: PRT
<213> ORGANISM: Artificial Sequence
<220> FEATURE:
<223> OTHER INFORMATION: W45C

<400> SEQUENCE: 221

```
Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Cys Gly Thr Thr
            35                  40                  45

Ile Ala Lys Val Val Ala Glu Asn Cys Lys Gly Tyr Pro Glu Val Phe
50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
            115                 120                 125

Phe Leu Pro Arg Ile Cys Ser Gln Leu Lys Gly His Val Asp Ser His
130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
            195                 200                 205

Glu Gly Lys Asp Val Asp His Lys Val Leu Lys Ala Leu Phe His Arg
210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
            275                 280                 285

Glu Glu Thr Tyr Tyr Gln Glu Ser Ala Gly Val Ala Asp Leu Ile Thr
290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
            355                 360                 365

Ile Val Tyr Asn Asn Tyr Pro Met Lys Asn Leu Pro Asp Met Ile Glu
370                 375                 380

Glu Leu Asp Leu His Glu Asp
385                 390

<210> SEQ ID NO 222
<211> LENGTH: 391
```

<212> TYPE: PRT
<213> ORGANISM: Artificial Sequence
<220> FEATURE:
<223> OTHER INFORMATION: W45G

<400> SEQUENCE: 222

| | | | | | | | | | | | | | | |
|---|---|---|---|---|---|---|---|---|---|---|---|---|---|---|
| Met | Ser | Ala | Ala | Ala | Asp | Arg | Leu | Asn | Leu | Thr | Ser | Gly | His | Leu | Asn |
| 1 | | | | 5 | | | | | 10 | | | | | 15 |
| Ala | Gly | Arg | Lys | Arg | Ser | Ser | Ser | Val | Ser | Leu | Lys | Ala | Ala | Glu |
| | | | 20 | | | | | 25 | | | | | 30 | |
| Lys | Pro | Phe | Lys | Val | Thr | Val | Ile | Gly | Ser | Gly | Asn | Gly | Thr | Thr |
| | | 35 | | | | | 40 | | | | | 45 | | |
| Ile | Ala | Lys | Val | Val | Ala | Glu | Asn | Cys | Lys | Gly | Tyr | Pro | Glu | Val | Phe |
| 50 | | | | | 55 | | | | | 60 | | | | | |
| Ala | Pro | Ile | Val | Gln | Met | Trp | Val | Phe | Glu | Glu | Ile | Asn | Gly | Glu |
| 65 | | | | | 70 | | | | 75 | | | | | 80 |
| Lys | Leu | Thr | Glu | Ile | Ile | Asn | Thr | Arg | His | Gln | Asn | Val | Lys | Tyr | Leu |
| | | | | 85 | | | | | 90 | | | | | 95 | |
| Pro | Gly | Ile | Thr | Leu | Pro | Asp | Asn | Leu | Val | Ala | Asn | Pro | Asp | Leu | Ile |
| | | | 100 | | | | | 105 | | | | | 110 | | |
| Asp | Ser | Val | Lys | Asp | Val | Asp | Ile | Ile | Val | Phe | Asn | Ile | Pro | His | Gln |
| | | 115 | | | | | 120 | | | | | 125 | | | |
| Phe | Leu | Pro | Arg | Ile | Cys | Ser | Gln | Leu | Lys | Gly | His | Val | Asp | Ser | His |
| 130 | | | | | 135 | | | | | 140 | | | | | |
| Val | Arg | Ala | Ile | Ser | Cys | Leu | Lys | Gly | Phe | Glu | Val | Gly | Ala | Lys | Gly |
| 145 | | | | | 150 | | | | | 155 | | | | | 160 |
| Val | Gln | Leu | Leu | Ser | Ser | Tyr | Ile | Thr | Glu | Glu | Leu | Gly | Ile | Gln | Cys |
| | | | | 165 | | | | | 170 | | | | | 175 | |
| Gly | Ala | Leu | Ser | Gly | Ala | Asn | Ile | Ala | Thr | Glu | Val | Ala | Gln | Glu | His |
| | | | 180 | | | | | 185 | | | | | 190 | | |
| Trp | Ser | Glu | Thr | Thr | Val | Ala | Tyr | His | Ile | Pro | Lys | Asp | Phe | Arg | Gly |
| | | 195 | | | | | 200 | | | | | 205 | | | |
| Glu | Gly | Lys | Asp | Val | Asp | His | Lys | Val | Leu | Lys | Ala | Leu | Phe | His | Arg |
| 210 | | | | | 215 | | | | | 220 | | | | | |
| Pro | Tyr | Phe | His | Val | Ser | Val | Ile | Glu | Asp | Val | Ala | Gly | Ile | Ser | Ile |
| 225 | | | | | 230 | | | | | 235 | | | | | 240 |
| Cys | Gly | Ala | Leu | Lys | Asn | Val | Val | Ala | Leu | Gly | Cys | Gly | Phe | Val | Glu |
| | | | | 245 | | | | | 250 | | | | | 255 | |
| Gly | Leu | Gly | Trp | Gly | Asn | Asn | Ala | Ser | Ala | Ala | Ile | Gln | Arg | Val | Gly |
| | | | 260 | | | | | 265 | | | | | 270 | | |
| Leu | Gly | Glu | Ile | Ile | Arg | Phe | Gly | Gln | Met | Phe | Phe | Pro | Glu | Ser | Arg |
| | | 275 | | | | | 280 | | | | | 285 | | | |
| Glu | Glu | Thr | Tyr | Tyr | Gln | Glu | Ser | Ala | Gly | Val | Ala | Asp | Leu | Ile | Thr |
| 290 | | | | | 295 | | | | | 300 | | | | | |
| Thr | Cys | Ala | Gly | Gly | Arg | Asn | Val | Lys | Val | Ala | Arg | Leu | Met | Ala | Thr |
| 305 | | | | | 310 | | | | | 315 | | | | | 320 |
| Ser | Gly | Lys | Asp | Ala | Trp | Glu | Cys | Glu | Lys | Glu | Leu | Leu | Asn | Gly | Gln |
| | | | | 325 | | | | | 330 | | | | | 335 | |
| Ser | Ala | Gln | Gly | Leu | Ile | Thr | Cys | Lys | Glu | Val | His | Glu | Trp | Leu | Glu |
| | | | 340 | | | | | 345 | | | | | 350 | | |
| Thr | Cys | Gly | Ser | Val | Glu | Asp | Phe | Pro | Leu | Phe | Glu | Ala | Val | Tyr | Gln |
| | | 355 | | | | | 360 | | | | | 365 | | | |
| Ile | Val | Tyr | Asn | Asn | Tyr | Pro | Met | Lys | Asn | Leu | Pro | Asp | Met | Ile | Glu |
| 370 | | | | | 375 | | | | | 380 | | | | | |

Glu Leu Asp Leu His Glu Asp
385                 390

<210> SEQ ID NO 223
<211> LENGTH: 391
<212> TYPE: PRT
<213> ORGANISM: Artificial Sequence
<220> FEATURE:
<223> OTHER INFORMATION: W45H

<400> SEQUENCE: 223

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn His Gly Thr Thr
            35                  40                  45

Ile Ala Lys Val Val Ala Glu Asn Cys Lys Gly Tyr Pro Glu Val Phe
50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
            115                 120                 125

Phe Leu Pro Arg Ile Cys Ser Gln Leu Lys Gly His Val Asp Ser His
130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
            195                 200                 205

Glu Gly Lys Asp Val Asp His Lys Val Leu Lys Ala Leu Phe His Arg
210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
            275                 280                 285

Glu Glu Thr Tyr Tyr Gln Glu Ser Ala Gly Val Ala Asp Leu Ile Thr
290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

```
Thr Cys Gly Ser Val Glu Asp Phe Pro Leu Phe Glu Ala Val Tyr Gln
            355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

<210> SEQ ID NO 224
<211> LENGTH: 391
<212> TYPE: PRT
<213> ORGANISM: Artificial Sequence
<220> FEATURE:
<223> OTHER INFORMATION: W45I

<400> SEQUENCE: 224

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Ile Gly Thr Thr
            35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
            115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
    195                 200                 205

Glu Gly Lys Asp Val Asp His Lys Val Leu Lys Ala Leu Phe His Arg
210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320
```

```
Ser Gly Lys Asp Ala Trp Glu Cys Glu Lys Glu Leu Leu Asn Gly Gln
            325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
            355                 360                 365

Ile Val Tyr Asn Asn Tyr Pro Met Lys Asn Leu Pro Asp Met Ile Glu
            370                 375                 380

Glu Leu Asp Leu His Glu Asp
385                 390

<210> SEQ ID NO 225
<211> LENGTH: 391
<212> TYPE: PRT
<213> ORGANISM: Artificial Sequence
<220> FEATURE:
<223> OTHER INFORMATION: W45K

<400> SEQUENCE: 225

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Lys Gly Thr Thr
            35                  40                  45

Ile Ala Lys Val Val Ala Glu Asn Cys Lys Gly Tyr Pro Glu Val Phe
        50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
            115                 120                 125

Phe Leu Pro Arg Ile Cys Ser Gln Leu Lys Gly His Val Asp Ser His
        130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
            195                 200                 205

Glu Gly Lys Asp Val Asp His Lys Val Leu Lys Ala Leu Phe His Arg
        210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285
```

```
Glu Glu Thr Tyr Tyr Gln Glu Ser Ala Gly Val Ala Asp Leu Ile Thr
            290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
            325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
            355                 360                 365

Ile Val Tyr Asn Asn Tyr Pro Met Lys Asn Leu Pro Asp Met Ile Glu
            370                 375                 380

Glu Leu Asp Leu His Glu Asp
385                 390

<210> SEQ ID NO 226
<211> LENGTH: 391
<212> TYPE: PRT
<213> ORGANISM: Artificial Sequence
<220> FEATURE:
<223> OTHER INFORMATION: W45L

<400> SEQUENCE: 226

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Leu Gly Thr Thr
            35                  40                  45

Ile Ala Lys Val Val Ala Glu Asn Cys Lys Gly Tyr Pro Glu Val Phe
50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
            85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
            115                 120                 125

Phe Leu Pro Arg Ile Cys Ser Gln Leu Lys Gly His Val Asp Ser His
            130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
            165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
            195                 200                 205

Glu Gly Lys Asp Val Asp His Lys Val Leu Lys Ala Leu Phe His Arg
            210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
            245                 250                 255
```

```
Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

<210> SEQ ID NO 227
<211> LENGTH: 391
<212> TYPE: PRT
<213> ORGANISM: Artificial Sequence
<220> FEATURE:
<223> OTHER INFORMATION: W45M

<400> SEQUENCE: 227

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Met Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220
```

```
Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
            245                 250                 255

Gly Leu Gly Trp Gly Asn Asn Ala Ser Ala Ala Ile Gln Arg Val Gly
        260                 265                 270

Leu Gly Glu Ile Ile Arg Phe Gly Gln Met Phe Phe Pro Glu Ser Arg
    275                 280                 285

Glu Glu Thr Tyr Tyr Gln Glu Ser Ala Gly Val Ala Asp Leu Ile Thr
290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
            325                 330                 335

Ser Ala Gln Gly Leu Ile Thr Cys Lys Glu Val His Glu Trp Leu Glu
        340                 345                 350

Thr Cys Gly Ser Val Glu Asp Phe Pro Leu Phe Glu Ala Val Tyr Gln
    355                 360                 365

Ile Val Tyr Asn Asn Tyr Pro Met Lys Asn Leu Pro Asp Met Ile Glu
370                 375                 380

Glu Leu Asp Leu His Glu Asp
385                 390

<210> SEQ ID NO 228
<211> LENGTH: 391
<212> TYPE: PRT
<213> ORGANISM: Artificial Sequence
<220> FEATURE:
<223> OTHER INFORMATION: W45N

<400> SEQUENCE: 228

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Asn Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190
```

```
Trp Ser Glu Thr Thr Val Ala Tyr His Ile Pro Lys Asp Phe Arg Gly
            195                 200                 205

Glu Gly Lys Asp Val Asp His Lys Val Leu Lys Ala Leu Phe His Arg
210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
                260                 265                 270

Leu Gly Glu Ile Ile Arg Phe Gly Gln Met Phe Phe Pro Glu Ser Arg
                275                 280                 285

Glu Glu Thr Tyr Tyr Gln Glu Ser Ala Gly Val Ala Asp Leu Ile Thr
290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
                340                 345                 350

Thr Cys Gly Ser Val Glu Asp Phe Pro Leu Phe Glu Ala Val Tyr Gln
                355                 360                 365

Ile Val Tyr Asn Asn Tyr Pro Met Lys Asn Leu Pro Asp Met Ile Glu
                370                 375                 380

Glu Leu Asp Leu His Glu Asp
385                 390

<210> SEQ ID NO 229
<211> LENGTH: 391
<212> TYPE: PRT
<213> ORGANISM: Artificial Sequence
<220> FEATURE:
<223> OTHER INFORMATION: W45Q

<400> SEQUENCE: 229

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Glu
                20                  25                  30

Lys Pro Phe Lys Val Thr Val Ile Gly Ser Gly Asn Gln Gly Thr Thr
                35                  40                  45

Ile Ala Lys Val Val Ala Glu Asn Cys Lys Gly Tyr Pro Glu Val Phe
50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
                100                 105                 110

Asp Ser Val Lys Asp Val Asp Ile Ile Val Phe Asn Ile Pro His Gln
                115                 120                 125

Phe Leu Pro Arg Ile Cys Ser Gln Leu Lys Gly His Val Asp Ser His
                130                 135                 140

Val Arg Ala Ile Ser Cys Leu Lys Gly Phe Glu Val Gly Ala Lys Gly
145                 150                 155                 160
```

```
Val Gln Leu Leu Ser Ser Tyr Ile Thr Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
            195                 200                 205

Glu Gly Lys Asp Val Asp His Lys Val Leu Lys Ala Leu Phe His Arg
210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
            245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
            275                 280                 285

Glu Glu Thr Tyr Tyr Gln Glu Ser Ala Gly Val Ala Asp Leu Ile Thr
            290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
            325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
            355                 360                 365

Ile Val Tyr Asn Asn Tyr Pro Met Lys Asn Leu Pro Asp Met Ile Glu
            370                 375                 380

Glu Leu Asp Leu His Glu Asp
385                 390

<210> SEQ ID NO 230
<211> LENGTH: 391
<212> TYPE: PRT
<213> ORGANISM: Artificial Sequence
<220> FEATURE:
<223> OTHER INFORMATION: W45R

<400> SEQUENCE: 230

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
                20                  25                  30

Lys Pro Phe Lys Val Thr Val Ile Gly Ser Gly Asn Arg Gly Thr Thr
            35                  40                  45

Ile Ala Lys Val Val Ala Glu Asn Cys Lys Gly Tyr Pro Glu Val Phe
50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
            85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
            115                 120                 125
```

Phe Leu Pro Arg Ile Cys Ser Gln Leu Lys Gly His Val Asp Ser His
130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
                180                 185                 190

Trp Ser Glu Thr Thr Val Ala Tyr His Ile Pro Lys Asp Phe Arg Gly
                195                 200                 205

Glu Gly Lys Asp Val Asp His Lys Val Leu Lys Ala Leu Phe His Arg
210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
                260                 265                 270

Leu Gly Glu Ile Ile Arg Phe Gly Gln Met Phe Phe Pro Glu Ser Arg
                275                 280                 285

Glu Glu Thr Tyr Tyr Gln Glu Ser Ala Gly Val Ala Asp Leu Ile Thr
290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
                340                 345                 350

Thr Cys Gly Ser Val Glu Asp Phe Pro Leu Phe Glu Ala Val Tyr Gln
                355                 360                 365

Ile Val Tyr Asn Asn Tyr Pro Met Lys Asn Leu Pro Asp Met Ile Glu
                370                 375                 380

Glu Leu Asp Leu His Glu Asp
385                 390

<210> SEQ ID NO 231
<211> LENGTH: 391
<212> TYPE: PRT
<213> ORGANISM: Artificial Sequence
<220> FEATURE:
<223> OTHER INFORMATION: W45S

<400> SEQUENCE: 231

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Glu
                20                  25                  30

Lys Pro Phe Lys Val Thr Val Ile Gly Ser Gly Asn Ser Gly Thr Thr
                35                  40                  45

Ile Ala Lys Val Val Ala Glu Asn Cys Lys Gly Tyr Pro Glu Val Phe
50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

```
Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

<210> SEQ ID NO 232
<211> LENGTH: 391
<212> TYPE: PRT
<213> ORGANISM: Artificial Sequence
<220> FEATURE:
<223> OTHER INFORMATION: W45T

<400> SEQUENCE: 232

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Thr Gly Thr Thr
        35                  40                  45

Ile Ala Lys Val Val Ala Glu Asn Cys Lys Gly Tyr Pro Glu Val Phe
    50                  55                  60
```

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
            115                 120                 125

Phe Leu Pro Arg Ile Cys Ser Gln Leu Lys Gly His Val Asp Ser His
        130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

<210> SEQ ID NO 233
<211> LENGTH: 391
<212> TYPE: PRT
<213> ORGANISM: Artificial Sequence
<220> FEATURE:
<223> OTHER INFORMATION: W45V

<400> SEQUENCE: 233

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Val Gly Thr Thr
             35                  40                  45

Ile Ala Lys Val Val Ala Glu Asn Cys Lys Gly Tyr Pro Glu Val Phe
 50                  55                  60

Ala Pro Ile Val Gln Met Trp Val Phe Glu Glu Ile Asn Gly Glu
65                   70                  75                  80

Lys Leu Thr Glu Ile Ile Asn Thr Arg His Gln Asn Val Lys Tyr Leu
                 85                  90                  95

Pro Gly Ile Thr Leu Pro Asp Asn Leu Val Ala Asn Pro Asp Leu Ile
             100                 105                 110

Asp Ser Val Lys Asp Val Asp Ile Ile Val Phe Asn Ile Pro His Gln
             115                 120                 125

Phe Leu Pro Arg Ile Cys Ser Gln Leu Lys Gly His Val Asp Ser His
130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Leu Gly Ile Gln Cys
                 165                 170                 175

Gly Ala Leu Ser Gly Ala Asn Ile Ala Thr Glu Val Ala Gln Glu His
             180                 185                 190

Trp Ser Glu Thr Thr Val Ala Tyr His Ile Pro Lys Asp Phe Arg Gly
             195                 200                 205

Glu Gly Lys Asp Val Asp His Lys Val Leu Lys Ala Leu Phe His Arg
             210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                 245                 250                 255

Gly Leu Gly Trp Gly Asn Asn Ala Ser Ala Ala Ile Gln Arg Val Gly
             260                 265                 270

Leu Gly Glu Ile Ile Arg Phe Gly Gln Met Phe Phe Pro Glu Ser Arg
             275                 280                 285

Glu Glu Thr Tyr Tyr Gln Glu Ser Ala Gly Val Ala Asp Leu Ile Thr
290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                 325                 330                 335

Ser Ala Gln Gly Leu Ile Thr Cys Lys Glu Val His Glu Trp Leu Glu
             340                 345                 350

Thr Cys Gly Ser Val Glu Asp Phe Pro Leu Phe Glu Ala Val Tyr Gln
             355                 360                 365

Ile Val Tyr Asn Asn Tyr Pro Met Lys Asn Leu Pro Asp Met Ile Glu
             370                 375                 380

Glu Leu Asp Leu His Glu Asp
385                 390

<210> SEQ ID NO 234
<211> LENGTH: 90
<212> TYPE: DNA
<213> ORGANISM: Artificial Sequence
<220> FEATURE:
<223> OTHER INFORMATION: F1

<400> SEQUENCE: 234
tcaagaaaca attgtatatt gtacaccccc ccctccaca aacacaaata ttgataatat    60
aaagatgaac caacgtaatg cttcaatgac    90

<210> SEQ ID NO 235
<211> LENGTH: 52
<212> TYPE: DNA
<213> ORGANISM: Artificial Sequence
<220> FEATURE:
<223> OTHER INFORMATION: R1

<400> SEQUENCE: 235
ctgaacatta gaatacgtaa tccgcaatgc ttagtggctg ctgcgctcgt cc    52

<210> SEQ ID NO 236
<211> LENGTH: 52
<212> TYPE: DNA
<213> ORGANISM: Artificial Sequence
<220> FEATURE:
<223> OTHER INFORMATION: F2

<400> SEQUENCE: 236
ggacgagcgc agcagccact aagcattgcg gattacgtat tctaatgttc ag    52

<210> SEQ ID NO 237
<211> LENGTH: 93
<212> TYPE: DNA
<213> ORGANISM: Artificial Sequence
<220> FEATURE:
<223> OTHER INFORMATION: R2

<400> SEQUENCE: 237
gatatagaag agcctcgaaa aaagtggggg aaagtatgat atgttatctt tctccaataa    60
atcaccttgg ctaactcgtt gtatcatcac tgg    93

<210> SEQ ID NO 238
<211> LENGTH: 42
<212> TYPE: DNA
<213> ORGANISM: Artificial Sequence
<220> FEATURE:
<223> OTHER INFORMATION: Ptrc-gpsA NcoI F

<400> SEQUENCE: 238
taaggaggaa taaccatga accaacgtaa tgcttcaatg ac    42

<210> SEQ ID NO 239
<211> LENGTH: 36
<212> TYPE: DNA
<213> ORGANISM: Artificial Sequence
<220> FEATURE:
<223> OTHER INFORMATION: Ptrc-gpsA PstI R

<400> SEQUENCE: 239
atggtaccag ctgcattagt ggctgctgcg ctcgtc    36

<210> SEQ ID NO 240
<211> LENGTH: 11222
<212> TYPE: DNA
<213> ORGANISM: Artificial Sequence
<220> FEATURE:
<223> OTHER INFORMATION: pLMH11-JM44

<400> SEQUENCE: 240
tcccattacc gacatttggg cgctatacgt gcatatgttc atgtatgtat ctgtatttaa    60 aacactttg tattatttttt cctcatatat gtgtataggt ttatacggat gatttaatta    120

-continued

```
ttacttcacc acccttttatt tcaggctgat atcttagcct tgttactaga ttaatcatgt    180
aattagttat gtcacgctta cattcacgcc ctccccccac atccgctcta accgaaaagg    240
aaggagttag acaacctgaa gtctaggtcc ctatttattt ttttatagtt atgttagtat    300
taagaacgtt atttatattt caaattttc ttttttttct gtacagacgc gtgtacgcat     360
gtaacattat actgaaaacc ttgcttgaga aggttttggg acgctcgaag gctttaattt    420
gcgggcggcc gcacctggta aaacctctag tggagtagta gatgtaatca atgaagcgga    480
agccaaaaga ccagagtaga ggcctataga agaaactgcg atacctttg tgatggctaa     540
acaaacagac atcttttat atgttttac ttctgtatat cgtgaagtag taagtgataa      600
gcgaatttgg ctaagaacgt tgtaagtgaa caagggacct cttttgcctt tcaaaaaagg    660
attaaatgga gttaatcatt gagatttagt tttcgttaga ttctgtatcc ctaaataact    720
cccttacccg acgggaaggc acaaaagact tgaataatag caaacggcca gtagccaaga    780
ccaaataata ctagagttaa ctgatggtct taaacaggca ttacgtggtg aactccaaga    840
ccaatataca aaatatcgat aagttattct tgcccaccaa tttaaggagc ctacatcagg    900
acagtagtac cattcctcag agaagaggta tacataacaa gaaaatcgcg tgaacaccatt    960
atataactta gcccgttatt gagctaaaaa accttgcaaa atttcctatg aataagaata   1020
cttcagacgt gataaaaatt tactttctaa ctcttctcac gctgcccta tctgttcttc    1080
cgctctaccg tgagaaataa agcatcgagt acggcagttc gctgtcactg aactaaaaca   1140
ataaggctag ttcgaatgat gaacttgctt gctgtcaaac ttctgagttg ccgctgatgt   1200
gacactgtga caataaattc aaaccggtta tagcggtctc ctccggtacc ggttctgcca   1260
cctccaatag agctcagtag gagtcagaac ctctgcggtg gctgtcagtg actcatccgc   1320
gtttcgtaag ttgtgcgcgt gcacatttcg cccgttcccg ctcatcttgc agcaggcgga   1380
aattttcatc acgctgtagg acgcaaaaaa aaaataatta atcgtacaag aatcttggaa   1440
aaaaaattga aaaattttgt ataaagggga tgacctaact tgactcaatg gcttttacac   1500
ccagtatttt ccctttcctt gtttgttaca attatagaag caagacaaaa acatatagac   1560
aacctattcc taggagttat attttttttac cctaccagca atataagtaa aaaactgttt   1620
aaacagtatg gctaagattt actaccaaga agactgtaac ttgtccttgt tggatggtaa   1680
gactatcgcc gttatcggtt acggttctca aggtcacgct catgccctga atgctaagga   1740
atccggttgt aacgttatca ttggtttatt cgaaggtgcg gaggagtgga aaagagctga   1800
agaacaaggt ttcgaagtct acaccgctgc tgaagctgct aagaaggctg acatcattat   1860
gatcttgatc ccagatgaat accaggctgt catgtacaaa acgacatcg aaccaaactt    1920
ggaagccggt aacatgttga tgttcgctca cggtttcaac atccatttcg ttgtattgt    1980
tccaccaaag gacgttgatg tcactatgat cgctccaaag ggtccaggtc acaccgttag   2040
atccgaatac gaagaaggta aaggtgtccc atgcttggtt gctgtcgaac aagacgctac   2100
tggcaaggct ttggatatgg ctttggccta cgctttagcc atcggtggtg ctagagccgg   2160
tgtcttggaa actaccttca gaaccgaaac tgaaaccgac ttgttcggtg aacaagctgt   2220
tttatgtggt ggtgtctgcg ctttgatgca ggccggtttt gaaacttgg ttgaagccgg    2280
ttacgaccca agaaacgctt acttcgaatg tatccacgaa atgaagttga tcgttgactt   2340
gatctaccaa tctggtttct ccggtatgcg ttactctatc tccaacactg ctgaatacgg   2400
tgactacatt accggtccaa agatcattac tgaagatacc aagaaggcta tgaagaagat   2460
```

| | |
|---|---|
| tttgtctgac attcaagatg gtacctttgc caaggacttc ttggttgaca tgtctgatgc | 2520 |
| tggttcccag gtccacttca aggctatgag aaagttggcc tccgaacacc cagctgaagt | 2580 |
| tgtcggtgaa gaaattagat ccttgtactc ctggtccgac gaagacaagt tgattaacaa | 2640 |
| ctgaggccct gcaggccaga ggaaaataat atcaagtgct ggaaactttt tctcttggaa | 2700 |
| tttttgcaac atcaagtcat agtcaattga attgacccaa tttcacattt aagattttt | 2760 |
| tttttttcatc cgacatacat ctgtacacta ggaagccctg ttttctgaa gcagcttcaa | 2820 |
| atatatatat tttttacata tttattatga ttcaatgaac aatctaatta aatcgaaaac | 2880 |
| aagaaccgaa acgcgaataa ataatttatt tagatggtga caagtgtata agtcctcatc | 2940 |
| gggacagcta cgatttctct ttcggttttg gctgagctac tggttgctgt gacgcagcgg | 3000 |
| cattagcgcg gcgttatgag ctaccctcgt ggcctgaaag atggcgggaa taaagcggaa | 3060 |
| ctaaaaatta ctgactgagc catattgagg tcaatttgtc aactcgtcaa gtcacgtttg | 3120 |
| gtggacggcc cctttccaac gaatcgtata tactaacatg cgcgcgcttc ctatatacac | 3180 |
| atatacatat atatatatat atatatgtgt gcgtgtatgt gtacacctgt atttaatttc | 3240 |
| cttactcgcg ggttttctt ttttctcaat tcttggcttc ctctttctcg agcggaccgg | 3300 |
| atcctcgcga actccaaaat gagctatcaa aaacgataga tcgattagga tgactttgaa | 3360 |
| atgactccgc agtggactgg ccgttaattt caagcgtgag taaaatagtg catgacaaaa | 3420 |
| gatgagctag gcttttgtaa aaatatctta cgttgtaaaa ttttagaaat cattattcc | 3480 |
| ttcatatcat tttgtcattg accttcagaa gaaagagcc gaccaataat ataaataaat | 3540 |
| aaataaaaat aatattccat tatttctaaa cagattcaat actcattaaa aaactatatc | 3600 |
| aattaatttg aattaacgcg gccgcttaac cacagcaacc aggacaacat ttttgccag | 3660 |
| tttcttcagg cttccaaaag tctgttacgg ctcccctaga agcagacgaa acgatgtgag | 3720 |
| catatttacc aaggataccg cgtgaataga gcggtggcaa ttcaatggtc tcttgacgat | 3780 |
| gttttaactc ttcatcggag atatcaaagt gtaattcctt agtgtcttgg tcaatagtga | 3840 |
| ctatgtctcc tgtttgcagg taggcgattg gaccgccatc ttgtgcttca ggagcgatat | 3900 |
| gacccacgac aagaccataa gtaccacctg agaagcggcc atctgtcaga agggcaactt | 3960 |
| tttcaccttg ccctttacca acaatcattg atgaaaggga aagcatttca ggcataccag | 4020 |
| gaccgccctt tggtcctaca aaacgtacga caacaacatc accatcaaca atatcatcat | 4080 |
| tcaagacagc ttcaatggct tcttcttcag aattaaagac cttagcagga ccgacatgac | 4140 |
| gacgcacttt tacaccagaa actttggcaa cggcaccgtc tggagccaag ttaccatgga | 4200 |
| gaataatgac cggaccatct tcacgtttag gattttcaag cggcataata accttttgac | 4260 |
| caggtgttaa atcatcaaaa gccttcaaat tttcagcgac tgttttgcca gtacaagtga | 4320 |
| tacggtcacc atgaaggaag ccatttttaa ggagatattt cataactgct ggtacccctc | 4380 |
| cgaccttgta aaggtcttgg aatacatatt gaccagaagg tttcaaatca gccaaatgag | 4440 |
| gaacttttc ttggaaagta ttgaaatcat caagtgtcaa ttccacatta gcagcatggg | 4500 |
| caatagctaa gaggtgaagg gttgagttgg ttgaacctcc cagagccata gttacagtaa | 4560 |
| tagcatcttc aaaagcttca cgcgttaaaa tgtcagaagg ttttaagccc atttcgagca | 4620 |
| ttttgacaac agcgcgacca gcttcttcaa tatctgcttt cttttctgcg gattcagccg | 4680 |
| ggtgagaaga tgaacccgga aggctaagtc ccaaaacttc aatagctgtc gccattgtgt | 4740 |
| tagcagtata cataccaccg cagcctccag gaccgggaca agcattacat tccaaagctt | 4800 |
| taacttcttc tttggtcata tcgccgtggt tccaatggcc gacaccttca aagacagaga | 4860 |

```
ctaaatcgat atctttgccg tctaaattac caggtgcaat tgttccgccg taagcaaaaa    4920
tggctgggat atccatgtta gccatagcga taacagaacc gggcatgttt ttatcacaac    4980
cgccaatggc tacaaaagca tccgcattat gacctcccat ggctgcttca atagaatctg    5040
caataatatc acgagatgtc aaggagaaac gcattccttg ggttcccatg gcgattccat    5100
cagaaaccgt gattgttccg aactgaactg gccaagcacc agcttcctta acaccgactt    5160
tggctagttt accaaagtca tgtaagtgga tattacaagg tgtgttttca gcccaagttg    5220
aaatgacacc gacgataggt ttttcaaagt cttcatcttg cataccagtt gcacgcaaca    5280
tagcacgatt aggtgattta accattgaat cgtaaacaga actacgattt cttaagtctt    5340
taagagtttt tttgtcagtc atactcacgt gaaacttaga ttagattgct atgctttctt    5400
tccaatgagc aagaagtaaa aaagttgta atagaacagg aaaatgaag ctgaaacttg    5460
agaaattgaa gaccgtttgt taactcaaat atcaatggga ggtcgtcgaa agagaacaaa    5520
atcgaaaaaa aagttttcaa gagaaagaaa cgtgataaaa attttattg ccttctccga    5580
cgaagaaaaa gggacgaggc ggtctctttt tccttttcca aacctttagt acgggtaatt    5640
aacggcaccc tagaggaagg aggaggggga atttagtatg ctgtgcttgg gtgttttgaa    5700
gtggtacggc ggtgcgcgga gtccgagaaa atctggaaga gtaaaaaagg agtagagaca    5760
ttttgaagct atgccggcag atctatttaa atggcgcgcc gacgtcaggt ggcacttttc    5820
ggggaaatgt gcgcggaacc cctatttgtt tattttttcta aatacattca aatatgtatc    5880
cgctcatgag acaataaccc tgataaatgc ttcaataata ttgaaaaagg aagagtatga    5940
gtattcaaca tttccgtgtc gcccttattc cttttttgc ggcattttgc cttcctgttt    6000
ttgctcaccc agaaacgctg gtgaaagtaa aagatgctga agatcagttg ggtgcacgag    6060
tgggttacat cgaactggat ctcaacagcg gtaagatcct tgagagtttt cgccccgaag    6120
aacgttttcc aatgatgagc acttttaaag ttctgctatg tggcgcggta ttatcccgta    6180
ttgacgccgg gcaagagcaa ctcggtcgcc gcatacacta ttctcagaat gacttggttg    6240
agtactcacc agtcacagaa aagcatctta cggatggcat gacagtaaga gaattatgca    6300
gtgctgccat aaccatgagt gataacactg cggccaactt acttctgaca acgatcggag    6360
gaccgaagga gctaaccgct ttttgcaca acatggggga tcatgtaact cgccttgatc    6420
gttgggaacc ggagctgaat gaagccatac caaacgacga gcgtgacacc acgatgcctg    6480
tagcaatggc aacaacgttg cgcaaactat taactggcga actacttact ctagcttccc    6540
ggcaacaatt aatagactgg atggaggcgg ataaagttgc aggaccactt ctgcgctcgg    6600
cccttccggc tggctggttt attgctgata atctggagc cggtgagcgt gggtctcgcg    6660
gtatcattgc agcactgggg ccagatggta agccctcccg tatcgtagtt atctacacga    6720
cggggagtca ggcaactatg gatgaacgaa atagacagat cgctgagata ggtgcctcac    6780
tgattaagca ttggtaactg tcagaccaag tttactcata tactttag attgatttaa    6840
aacttcattt ttaatttaaa aggatctagg tgaagatcct ttttgataat ctcatgacca    6900
aaatccctta acgtgagttt tcgttccact gagcgtcaga ccccgtagaa aagatcaaag    6960
gatcttcttg agatcctttt tttctgcgcg taatctgctg cttgcaaaca aaaaaaccac    7020
cgctaccagc ggtggtttgt ttgccggatc aagagctacc aactcttttt ccgaaggtaa    7080
ctggcttcag cagagcgcag ataccaaata ctgttcttct agtgtagccg tagttaggcc    7140
accacttcaa gaactctgta gcaccgccta catacctcgc tctgctaatc ctgttaccag    7200
```

```
tggctgctgc cagtggcgat aagtcgtgtc ttaccgggtt ggactcaaga cgatagttac    7260
cggataaggc gcagcggtcg ggctgaacgg ggggttcgtg cacacagccc agcttggagc    7320
gaacgaccta caccgaactg agatacctac agcgtgagct atgagaaagc gccacgcttc    7380
ccgaagggag aaaggcggac aggtatccgg taagcggcag ggtcggaaca ggagagcgca    7440
cgagggagct tccaggggga aacgcctggt atctttatag tcctgtcggg tttcgccacc    7500
tctgacttga gcgtcgattt tgtgatgct cgtcaggggg gcggagccta tggaaaaacg    7560
ccagcaacgc ggccttttta cggttcctgg ccttttgctg ccttttgct cacatgttct    7620 ttcctgcgtt atccctgat tctgtggata accgtattac cgcctttgag tgagctgata    7680
ccgctcgccg cagccgaacg accgagcgca gcgagtcagt gagcgaggaa gcggaagagc    7740
gcccaatacg caaaccgcct ctccccgcgc gttggccgat tcattaatgc agctggcacg    7800
acaggtttcc cgactggaaa gcgggcagtg agcgcaacgc aattaatgtg agttagctca    7860
ctcattaggc accccaggct ttacacttta tgcttccggc tcgtatgttg tgtggaattg    7920
tgagcggata acaatttcac acaggaaaca gctatgacca tgattacgcc aagcttttc     7980 tttccaattt ttttttttc gtcattataa aaatcattac gaccgagatt cccgggtaat     8040
aactgatata attaaattga agctctaatt tgtgagttta gtatacatgc atttacttat    8100
aatacagttt tttagttttg ctggccgcat cttctcaaat atgcttccca gcctgctttt    8160
ctgtaacgtt caccctctac cttagcatcc cttccctttg caaatagtcc tcttccaaca    8220
ataataatgt cagatcctgt agagaccaca tcatccacgg ttctatactg ttgacccaat    8280
gcgtctccct tgtcatctaa acccacaccg ggtgtcataa tcaaccaatc gtaaccttca    8340
tctcttccac ccatgtctct ttgagcaata aagccgataa caaaatcttt gtcgctcttc    8400
gcaatgtcaa cagtacccct tagtatattct ccagtagata gggagcccct gcatgacaat    8460
tctgctaaca tcaaaaggcc tctaggttcc tttgttactt cttctgccgc ctgcttcaaa    8520
ccgctaacaa tacctgggcc caccacaccg tgtgcattcg taatgtctgc ccattctgct    8580
attctgtata caccgcaga gtactgcaat tgactgtat taccaatgtc agcaaatttt     8640
ctgtcttcga agagtaaaaa attgtacttg gcggataatg cctttagcgg cttaactgtg    8700
ccctccatgg aaaaatcagt caagatatcc acatgtgttt ttagtaaaca aattttggga    8760
cctaatgctt caactaactc cagtaattcc ttggtggtac gaacatccaa tgaagcacac    8820
aagtttgttt gcttttcgtg catgatatta aatagcttgg cagcaacagg actaggatga    8880
gtagcagcac gttccttata tgtagctttc gacatgattt atcttcgttt cctgcaggtt    8940
tttgttctgt gcagttgggt taagaatact gggcaatttc atgtttcttc aacactacat    9000
atgcgtatat ataccaatct aagtctgtgc tccttccttc gttcttcctt ctgttcggag    9060
attaccgaat caaaaaaatt tcaaggaaac cgaaatcaaa aaaagaata aaaaaaaat      9120 gatgaattga aaagcttgca tgcctgcagg tcgactctag tatactccgt ctactgtacg    9180
atacacttcc gctcaggtcc ttgtccttta acgaggcctt accactcttt tgttactcta    9240
ttgatccagc tcagcaaagg cagtgtgatc taagattcta tcttcgcgat gtagtaaaac    9300
tagctagacc gagaaagaga ctagaaatgc aaaaggcact tctacaatgg ctgccatcat    9360
tattatccga tgtgacgctg cattttttt ttttttttt ttttttttt ttttttttt       9420 tttttttttt ttttgtacgt cacctggcaa aacgacgatc ttcttagggg cagacattac    9480
aatggtatat ccttgaaata tatataaaaa aaaaaaaaa aaaaaaaaa aaaatgcag      9540 cttctcaatg atattcgaat acgctttgag gagatacagc ctaatatccg acaaactgtt    9600
```

```
ttacagattt acgatcgtac ttgttaccca tcattgaatt ttgaacatcc gaacctggga   9660
gttttccctg aaacagatag tatatttgaa cctgtataat aatatatagt ctagcgcttt   9720
acggaagaca atgtatgtat ttcggttcct ggagaaacta ttgcatctat tgcataggta   9780
atcttgcacg tcgcatcccc ggttcatttt ctgcgtttcc atcttgcact tcaatagcat   9840
atctttgtta acgaagcatc tgtgcttcat tttgtagaac aaaaatgcaa cgcgagagcg   9900 ctaattttc aaacaaagaa tctgagctgc atttttacag aacagaaatg caacgcgaaa    9960
gcgctatttt accaacgaag aatctgtgct tcattttgt aaaacaaaaa tgcaacgcga    10020
gagcgctaat ttttcaaaca aagaatctga gctgcatttt tacagaacag aaatgcaacg   10080
cgagagcgct attttaccaa caaagaatct atacttcttt tttgttctac aaaaatgcat   10140
cccgagagcg ctattttct aacaaagcat cttagattac tttttttctc ctttgtgcgc    10200
tctataatgc agtctcttga taacttttg cactgtaggt ccgttaaggt tagaagaagg    10260
ctactttggt gtctattttc tcttccataa aaaaagcctg actccacttc ccgcgtttac   10320
tgattactag cgaagctgcg ggtgcatttt ttcaagataa aggcatcccc gattatattc   10380
tataccgatg tggattgcgc atactttgtg aacagaaagt gatagcgttg atgattcttc   10440
attggtcaga aaattatgaa cggttcttc tattttgtct ctatatacta cgtataggaa    10500
atgtttacat tttcgtattg ttttcgattc actctatgaa tagttcttac tacaatttt    10560 ttgtctaaag agtaatacta gagataaaca taaaaaatgt agaggtcgag tttagatgca   10620
agttcaagga gcgaaaggtg gatgggtagg ttatataggg atatagcaca gagatatata   10680
gcaaagagat acttttgagc aatgtttgtg gaagcggtat tcgcaatatt ttagtagctc   10740
gttacagtcc ggtgcgtttt tggttttttg aaagtgcgtc ttcagagcgc ttttggtttt   10800
caaaagcgct ctgaagttcc tatactttct agagaatagg aacttcggaa taggaacttc   10860
aaagcgtttc cgaaaacgag cgcttccgaa aatgcaacgc gagctgcgca catacagctc   10920
actgttcacg tcgcacctat atctgcgtgt tgcctgtata tatatataca tgagaagaac   10980
ggcatagtgc gtgtttatgc ttaaatgcgt acttatatgc gtctatttat gtaggatgaa   11040
aggtagtcta gtacctcctg tgatattatc ccattccatg cggggtatcg tatgcttcct   11100
tcagcactac cctttagctg ttctatatgc tgccactcct caattggatt agtctcatcc   11160
ttcaatgcta tcatttcctt tgatattgga tcatatgcat agtaccgaga aactagagga   11220
tc                                                                  11222
```

<210> SEQ ID NO 241
<211> LENGTH: 54
<212> TYPE: DNA
<213> ORGANISM: Artificial Sequence
<220> FEATURE:
<223> OTHER INFORMATION: oBP1350

<400> SEQUENCE: 241
gattgaggcg atcggctgcg gcggacatct ttatattatc aatatttgtg tttg       54

<210> SEQ ID NO 242
<211> LENGTH: 53
<212> TYPE: DNA
<213> ORGANISM: Artificial Sequence
<220> FEATURE:
<223> OTHER INFORMATION: oBP1351

<400> SEQUENCE: 242

-continued aaacacaaat attgataata taaagatgtc cgccgcagcc gatcgcctca atc    53

<210> SEQ ID NO 243
<211> LENGTH: 40
<212> TYPE: DNA
<213> ORGANISM: Artificial Sequence
<220> FEATURE:
<223> OTHER INFORMATION: oBP1352

<400> SEQUENCE: 243
ttaagtttaa acttaatcct catgcagatc cagttcttcg    40

<210> SEQ ID NO 244
<211> LENGTH: 53
<212> TYPE: DNA
<213> ORGANISM: Artificial Sequence
<220> FEATURE:
<223> OTHER INFORMATION: oBP1353

<400> SEQUENCE: 244
gtttaatcta tcagcagcag cagacatctt tatattatca atatttgtgt ttg    53

<210> SEQ ID NO 245
<211> LENGTH: 52
<212> TYPE: DNA
<213> ORGANISM: Artificial Sequence
<220> FEATURE:
<223> OTHER INFORMATION: oBP1354

<400> SEQUENCE: 245
aaacacaaat attgataata taaagatgtc tgctgctgct gatagattaa ac    52

<210> SEQ ID NO 246
<211> LENGTH: 39
<212> TYPE: DNA
<213> ORGANISM: Artificial Sequence
<220> FEATURE:
<223> OTHER INFORMATION: oBP1355

<400> SEQUENCE: 246
ttaagtttaa acctaatctt catgtagatc taattcttc    39

<210> SEQ ID NO 247
<211> LENGTH: 27
<212> TYPE: DNA
<213> ORGANISM: Artificial Sequence
<220> FEATURE:
<223> OTHER INFORMATION: oBP1356

<400> SEQUENCE: 247
agaaacgtca aggttgctag gctaatg    27

<210> SEQ ID NO 248
<211> LENGTH: 26
<212> TYPE: DNA
<213> ORGANISM: Artificial Sequence
<220> FEATURE:
<223> OTHER INFORMATION: oBP1357

<400> SEQUENCE: 248
gtgaagaaac gtattatcag gagtcg    26

<210> SEQ ID NO 249
<211> LENGTH: 7063
<212> TYPE: DNA
<213> ORGANISM: Artificial Sequence
<220> FEATURE:
<223> OTHER INFORMATION: pBP3518GPD1_EcOpt

<400> SEQUENCE: 249

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acccggggat     420
ccggcgcgcc gtgtagacgt agtataacag tatatctgac acgcacgtga tgaccacgta     480
atcgcatcgc ccctcacatc tcacctctca ccgctgactc agcttcacta aaaggaaaa     540
tatatactct ttcccaggca aggtgacagc ggtccccgtc tcctccacaa aggcctctcc     600
tggggtttga gcaagtctaa gtttacgtag cataaaaatt ctcggattgc gtcaaataat     660
aaaaaaagta actccacttc tacttctaca tcggaaaaac attccattca catatcgtct     720
ttggcctatc ttgttttgtc cttggtagat caggtcagta caaacgcaac acgaaagaac     780
aaaaaaagaa gaaaacagaa ggccaagaca gggtcaatga gactgttgtc ctcctactgt     840
ccctatgtct ctggccgatc acgcgccatt gtccctcaga aacaaatcaa acacccacac     900
cccgggcacc caaagtcccc acccacacca ccaatacgta aacggggcgc ccctgcagg     960
ccctcctgcg cgcggcctcc cgccttgctt ctctcccctc ccttttcttt ttccagtttt    1020
ccctattttg tccctttttc cgcacaacaa gtatcagaat gggttcatca aatctatcca    1080
acctaattcg cacgtagact ggcttggtat tggcagtttc gcagttatat atatactacc    1140
atgagtgaaa ctgttacgtt accttaaatt ctttctccct ttaattttct tttatcttac    1200
tctcctacat aagacatcaa gaaacaattg tatattgtac ccccccccc tccacaaaca    1260
caaatattga taatataaag atgtccgccg cagccgatcg cctcaatctc acgtccggtc    1320
atttgaacgc aggtcgtaaa cgcagcagca gctccgttag cttgaaagcg gcggagaagc    1380
cgtttaaagt gaccgtgatt ggtagcggta actgggcac caccattgcg aaagtggtcg    1440
cagagaactg taagggctac ccggaagtgt tcgctccgat tgttcagatg tgggtgtttg    1500
aagaagagat caatggtgaa aaactgacgg agatcatcaa caccgccac caaaacgtca    1560
aatatctgcc tggcatcacc ttgccggaca atctggtggc gaatccggac ctgatcgatt    1620
ctgtcaaaga cgttgacatt attgttttca acatcccgca ccagtttctg ccgcgtattt    1680
gcagccagct gaagggtcac gtcgatagcc acgtccgcgc gattagctgc ctgaaaggct    1740
tcgaggtggg cgcgaagggt gttcaattgc tgtctagcta catcaccgaa gagctgggca    1800
ttcagtgcgg tgcgctgtcc ggtgctaata tcgctaccga agttcacaa gagcattgga    1860
gcgagactac ggtcgcgtat cacattccga aggacttccg tggcgaaggc aaggatgtcg    1920
accataaagt tctgaaggcg ctgtttcacc gtccgtactt tcatgtcagc gtcatcgaag    1980
atgttgccgg tatcagcatt tgtggtgcgt tgaagaacgt tgttgcactg ggttgcggtt    2040
ttgttgaggg tctgggttgg ggtaacaacg cgtctgcggc aattcaacgt gtgggtctgg    2100
gcgagatcat ccgtttcggc cagatgttct tcccagagag ccgtgaagaa cgtattatc    2160
aggagtcggc cggtgtggcc gacctgatca ccacttgcgc tggtggccgc aatgttaagg    2220
```

```
tagcgcgtct gatggcgacc agcggcaagg acgcctggga gtgcgagaaa gagctgctga    2280
atggtcagag cgcacaaggt ctgattacct gtaaagaagt gcacgaatgg ctggaaacgt    2340
gtggcagcgt cgaggacttc cgctgtttg aggcagtgta ccaaattgtg tacaacaatt     2400
acccgatgaa gaatctgccg gatatgatcg aagaactgga tctgcatgag gattaagttt    2460
aaactcatgt aattagttat gtcacgctta cattcacgcc ctcctcccac atccgctcta    2520
accgaaaagg aaggagttag acaacctgaa gtctaggtcc ctatttattt ttttttaatag   2580 ttatgttagt attaagaacg ttatttatat ttcaaatttt tcttttttt ctgtacaaac     2640 gcgtgtacgc atgtaacatt atactgaaaa ccttgcttga aaggttttg ggacgctcga     2700 aggctttaat ttgcgggcc ggccgcattg cggattacgt attctaatgt tcagtaccgt     2760
tcgtataatg tatgctatac gaagttatgc agattgtact gagagtgcac cataccacct    2820
tttcaattca tcattttttt tttattcttt tttttgattt cggtttcctt gaaattttt     2880 tgattcggta atctccgaac agaaggaaga acgaaggaag gagcacagac ttagattggt    2940
atatatacgc atatgtagtg ttgaagaaac atgaaattgc ccagtattct aacccaact     3000 gcacagaaca aaaacctgca ggaaacgaag ataaatcatg tcgaaagcta catataagga    3060
acgtgctgct actcatccta gtcctgttgc tgccaagcta tttaatatca tgcacgaaaa    3120
gcaaacaaac ttgtgtgctt cattggatgt tcgtaccacc aaggaattac tggagttagt    3180
tgaagcatta ggtcccaaaa tttgtttact aaaaacacat gtggatatct tgactgattt    3240
ttccatggag ggcacagtta agccgctaaa ggcattatcc gccaagtaca atttttact     3300 cttcgaagac agaaaatttg ctgacattgg taatacagtc aaattgcagt actctgcggg    3360
tgtatacaga atagcagaat gggcagacat tacgaatgca cacggtgtgg tgggcccagg    3420
tattgttagc ggtttgaagc aggcggcaga agaagtaaca aaggaaccta gaggccttt    3480 gatgttagca gaattgtcat gcaagggctc cctatctact ggagaatata ctaagggtac    3540
tgttgacatt gcgaagagcg acaaagattt tgttatcggc tttattgctc aaagagacat    3600
gggtggaaga gatgaaggtt acgattggtt gattatgaca cccggtgtgg gtttagatga    3660
caagggagac gcattgggtc aacagtatag aaccgtggat gatgtggtct ctacaggatc    3720
tgacattatt attgttggaa gaggactatt tgcaaaggga agggatgcta aggtagaggg    3780
tgaacgttac agaaaagcag gctgggaagc atatttgaga gatgcggcc agcaaaacta    3840 aaaaactgta ttaagtaa atgcatgtat actaaactca caaattagag cttcaattta     3900
attatatcag ttattaccct atgcggtgtg aaataccgca cagatgcgta aggagaaaat    3960
accgcatcag gaaattgtaa gcgttaatat tttgttaaaa ttcgcgttaa attttgtta    4020 aatcagctca tttttaacc aataggccga aatcggcaaa atcccttata atcaaaaga     4080 atagaccgag atagggttga gtgttgttcc agtttggaac aagagtccac tattaaagaa    4140
cgtggactcc aacgtcaaag ggcgaaaaac cgtctatcag gcgatggcc cactacgtga    4200 accatcaccc taatcaagat aacttcgtat aatgtatgct atacgaacgg taccagtgat    4260
gatacaacga gttagccaag gtggcggccg catttattgg agaaagataa catatcatac    4320
tttcccccac tttttcgag gctcttctat atcatattca taaattagca ttatgtcatt    4380
tctcataact actttatcac gttagaaatt acttattatt attaaattaa tacaaaattt    4440
agtaaccaaa taaatataaa taaatatgca tatttaaatt ttaaaaaaaa aatcctatag   4500
agcaaaagga ttctccatta taatatgagc tatacacctc ttacgcattt tttgagggtg    4560
gttacaacac cactcattca gaggctgtcg gcacagttgc ttccagcatc tggcgtccgt    4620
```

```
atgtatgggt gtattttaaa taataaacaa agtgccacac cttcaccaat tatgtcttta    4680
agaaatggac aagttccaaa gagcttgccc aaggctcgac aaggatgtac tttagaatat    4740
ctatattcaa gtacgtggcg cgcatatgtt tgagtgtgca cacaataaag gttaattaat    4800
ctagagtcga cctgcaggca tgcaagcttg gcgtaatcat ggtcatagct gtttcctgtg    4860
tgaaattgtt atccgctcac aattccacac aacatacgag ccggaagcat aaagtgtaaa    4920
gcctggggtg cctaatgagt gagctaactc acattaattg cgttgcgctc actgcccgct    4980
ttccagtcgg gaaacctgtc gtgccagctg cattaatgaa tcggccaacg cgcggggaga    5040
ggcggtttgc gtattgggcg ctcttccgct tcctcgctca ctgactcgct gcgctcggtc    5100
gttcggctgc ggcgagcggt atcagctcac tcaaaggcgg taatacggtt atccacagaa    5160
tcagggggata acgcaggaaa gaacatgtga gcaaaaggcc agcaaaaggc caggaaccgt    5220
aaaaaggccg cgttgctggc gtttttccat aggctccgcc cccctgacga gcatcacaaa    5280
aatcgacgct caagtcagag gtggcgaaac ccgacaggac tataaagata ccaggcgttt    5340
ccccctggaa gctccctcgt gcgctctcct gttccgaccc tgccgcttac cggatacctg    5400
tccgcctttc tcccttcggg aagcgtggcg ctttctcata gctcacgctg taggtatctc    5460
agttcggtgt aggtcgttcg ctccaagctg ggctgtgtgc acgaaccccc cgttcagccc    5520
gaccgctgcg ccttatccgg taactatcgt cttgagtcca acccggtaag acacgactta    5580
tcgccactgg cagcagccac tggtaacagg attagcagag cgaggtatgt aggcggtgct    5640
acagagttct tgaagtggtg gcctaactac ggctacacta aaggacagt atttggtatc    5700
tgcgctctgc tgaagccagt taccttcgga aaaagagttg gtagctcttg atccggcaaa    5760
caaaccaccg ctggtagcgg tggttttttt gtttgcaagc agcagattac gcgcagaaaa    5820
aaaggatctc aagaagatcc tttgatcttt tctacggggt ctgacgctca gtggaacgaa    5880
aactcacgtt aagggatttt ggtcatgaga ttatcaaaaa ggatcttcac ctagatcctt    5940
ttaaattaaa aatgaagttt taaatcaatc taaagtatat atgagtaaac ttggtctgac    6000
agttaccaat gcttaatcag tgaggcacct atctcagcga tctgtctatt tcgttcatcc    6060
atagttgcct gactccccgt cgtgtagata actacgatac gggagggctt accatctggc    6120
cccagtgctg caatgatacc gcgagaccca cgctcaccgg ctccagattt atcagcaata    6180
aaccagccag ccggaagggc cgagcgcaga agtggtcctg caactttatc cgcctccatc    6240
cagtctatta attgttgccg ggaagctaga gtaagtagtt cgccagttaa tagtttgcgc    6300
aacgttgttg ccattgctac aggcatcgtg gtgtcacgct cgtcgtttgg tatggcttca    6360
ttcagctccg gttcccaacg atcaaggcga gttacatgat cccccatgtt gtgcaaaaaa    6420
gcggttagct ccttcggtcc tccgatcgtt gtcagaagta agttggccgc agtgttatca    6480
ctcatggtta tggcagcact gcataattct cttactgtca tgccatccgt aagatgcttt    6540
tctgtgactg gtgagtactc aaccaagtca ttctgagaat agtgtatgcg gcgaccgagt    6600
tgctcttgcc cggcgtcaat acgggataat accgcgccac atagcagaac tttaaaagtg    6660
ctcatcattg gaaaacgttc ttcggggcga aaactctcaa ggatcttacc gctgttgaga    6720
tccagttcga tgtaacccac tcgtgcaccc aactgatctt cagcatcttt tactttcacc    6780
agcgtttctg ggtgagcaaa aacaggaagg caaaatgccg caaaaaaggg aataagggcg    6840
acacggaaat gttgaatact catactcttc ctttttcaat attattgaag catttatcag    6900
ggttattgtc tcatgagcgg atacatattt gaatgtattt agaaaaataa acaaataggg    6960
```

```
gttccgcgca catttccccg aaaagtgcca cctgacgtct aagaaaccat tattatcatg      7020
acattaacct ataaaaatag gcgtatcacg aggccctttc gtc                       7063

<210> SEQ ID NO 250
<211> LENGTH: 7063
<212> TYPE: DNA
<213> ORGANISM: Artificial Sequence
<220> FEATURE:
<223> OTHER INFORMATION: pBP3518GPD1_Native

<400> SEQUENCE: 250
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcggggctgg cttaactatg cggcatcaga gcagattgta ctgagagtgc       180
accatatgcg gtgtgaaata ccgcacagat gcgtaaggag aaaataccgc atcaggcgcc       240
attcgccatt caggctgcgc aactgttggg aagggcgatc ggtgcgggcc tcttcgctat       300
tacgccagct ggcgaaaggg ggatgtgctg caaggcgatt aagttgggta acgccagggt       360
tttcccagtc acgacgttgt aaaacgacgg ccagtgaatt cgagctcggt acccggggat       420
ccggcgcgcc gtgtagacgt agtataacag tatatctgac acgcacgtga tgaccacgta       480
atcgcatcgc ccctcacatc tcacctctca ccgctgactc agcttcacta aaaaggaaaa       540
tatatactct ttcccaggca aggtgacagc ggtccccgtc cctccacaa aggcctctcc        600 tggggtttga gcaagtctaa gtttacgtag cataaaaatt ctcggattgc gtcaaataat       660
aaaaaaagta actccacttc tacttctaca tcggaaaaac attccattca catatcgtct       720
ttggcctatc ttgttttgtc cttggtagat caggtcagta caaacgcaac acgaaagaac       780
aaaaaaagaa gaaaacagaa ggccaagaca gggtcaatga gactgttgtc ctcctactgt       840
ccctatgtct ctggccgatc acgcgccatt gtccctcaga aacaaatcaa acacccacac       900
cccgggcacc caaagtcccc acccacacca ccaatacgta aacggggcgc ccctgcagg       960 ccctcctgcg cgcggcctcc cgccttgctt ctctcccctc cctttcttt ttccagtttt      1020 ccctattttg tccctttttc cgcacaacaa gtatcagaat gggttcatca aatctatcca      1080
acctaattcg cacgtagact ggcttggtat tggcagtttc gcagttatat atatactacc      1140
atgagtgaaa ctgttacgtt accttaaatt ctttctccct ttaatttct tttatcttac       1200 tctcctacat aagacatcaa gaaacaattg tatattgtac cccccccc tccacaaaca       1260 caaatattga taatataaag atgtctgctg ctgctgatag attaaactta acttccggcc      1320
acttgaatgc tggtagaaag agaagttcct cttctgtttc tttgaaggct gccgaaaagc      1380
ctttcaaggt tactgtgatt ggatctggta actggggtac tactattgcc aaggtggttg      1440
ccgaaaattg taagggatac ccagaagttt cgctccaat agtacaaatg tgggtgttcg       1500
aagaagagat caatggtgaa aaattgactg aaatcataaa tactagacat caaaacgtga      1560
aatacttgcc tggcatcact ctacccgaca atttggttgc taatccagac ttgattgatt      1620
cagtcaagga tgtcgacatc atcgttttca acattccaca tcaatttttg ccccgtatct      1680
gtagccaatt gaaaggtcat gttgattcac acgtcagagc tatctcctgt ctaaagggtt      1740
ttgaagttgg tgctaaaggt gtccaattgc tatcctctta catcactgag gaactaggta      1800
ttcaatgtgg tgctctatct ggtgctaaca ttgccaccga agtcgctcaa gaacactggt      1860
ctgaaacaac agttgcttac cacattccaa aggatttcag aggcgagggc aaggacgtcg      1920
accataaggt tctaaaggcc ttgttccaca gaccttactt ccacgttagt gtcatcgaag      1980
```

```
atgttgctgg tatctccatc tgtggtgctt tgaagaacgt tgttgcctta ggttgtggtt    2040
tcgtcgaagg tctaggctgg ggtaacaacg cttctgctgc catccaaaga gtcggtttgg    2100
gtgagatcat cagattcggt caaatgtttt tcccagaatc tagagaagaa acatactacc    2160
aagagtctgc tggtgttgct gatttgatca ccacctgcgc tggtggtaga aacgtcaagg    2220
ttgctaggct aatggctact tctggtaagg acgcctggga atgtgaaaag gagttgttga    2280
atggccaatc cgctcaaggt ttaattacct gcaaagaagt tcacgaatgg ttggaaacat    2340
gtggctctgt cgaagacttc ccattatttg aagccgtata ccaaatcgtt tacaacaact    2400
acccaatgaa gaacctgccg acatgatgg aagaattaga tctacatgaa gattaggttt    2460
aaactcatgt aattagttat gtcacgctta cattcacgcc ctcctcccac atccgctcta    2520
accgaaaagg aaggagttag acaacctgaa gtctaggtcc ctatttattt ttttttaatag   2580
ttatgttagt attaagaacg ttatttatat ttcaaatttt tctttttttt ctgtacaaac    2640
gcgtgtacgc atgtaacatt atactgaaaa ccttgcttga aaggttttg ggacgctcga     2700
aggctttaat ttgcggggcc ggccgcattg cggattacgt attctaatgt tcagtaccgt    2760
tcgtataatg tatgctatac gaagttatgc agattgtact gagagtgcac cataccacct    2820
tttcaattca tcattttttt tttattcttt tttttgattt cggtttcctt gaaatttttt    2880
tgattcggta atctccgaac agaaggaaga acgaaggaag gagcacagac ttagattggt    2940
atatatacgc atatgtagtg ttgaagaaac atgaaattgc ccagtattct aacccaact     3000
gcacagaaca aaaacctgca ggaaacgaag ataaatcatg tcgaaagcta catataagga    3060
acgtgctgct actcatccta gtcctgttgc tgccaagcta tttaatatca tgcacgaaaa    3120
gcaaacaaac ttgtgtgctt cattggatgt tcgtaccacc aaggaattac tggagttagt    3180
tgaagcatta ggtcccaaaa tttgtttact aaaaacacat gtggatatct tgactgattt    3240
ttccatggag ggcacagtta agccgctaaa ggcattatcc gccaagtaca atttttttact  3300
cttcgaagac agaaaatttg ctgacattgg taatacagtc aaattgcagt actctgcggg    3360
tgtatacaga atagcagaat gggcagacat tacgaatgca cacggtgtgg tgggcccagg    3420
tattgttagc ggtttgaagc aggcggcaga agaagtaaca aaggaaccta gaggccttt     3480
gatgttagca gaattgtcat gcaagggctc cctatctact ggagaatata ctaagggtac    3540
tgttgacatt gcgaagagcg acaaagattt tgttatcggc tttattgctc aaagagacat    3600
gggtggaaga gatgaaggtt acgattggtt gattatgaca cccggtgtgg gtttagatga    3660
caagggagac gcattgggtc aacagtatag aaccgtggat gatgtggtct ctacaggatc    3720
tgacattatt attgttggaa gaggactatt tgcaaggga agggatgcta aggtagaggg    3780
tgaacgttac agaaaagcag gctgggaagc atatttgaga agatgcggcc agcaaaacta    3840
aaaaactgta ttataagtaa atgcatgtat actaaactca caaattagag cttcaattta    3900
attatatcag ttattacccct atgcggtgtg aaataccgca cagatgcgta aggagaaaat    3960
accgcatcag gaaattgtaa gcgttaatat tttgttaaaa ttcgcgttaa attttttgtta    4020
aatcagctca ttttttaacc aataggccga atcggcaaa atcccttata atcaaaaga     4080
atagaccgag atagggttga gtgttgttcc agtttggaac aagagtccac tattaaagaa    4140
cgtggactcc aacgtcaaag ggcgaaaaac cgtctatcag ggcgatggcc cactacgtga    4200
accatcaccc taatcaagat aacttcgtat aatgtatgct atacgaacgg taccagtgat    4260
gatacaacga gttagccaag gtggcggccg catttattgg agaaagataa catatcatac    4320
```

```
tttcccccac ttttttcgag gctcttctat atcatattca taaattagca ttatgtcatt     4380
tctcataact actttatcac gttagaaatt acttattatt attaaattaa tacaaaattt     4440
agtaaccaaa taaatataaa taaatatgca tatttaaatt ttaaaaaaaa aatcctatag     4500
agcaaaagga ttctccatta taatatgagc tatacacctc ttacgcattt tttgagggtg     4560
gttacaacac cactcattca gaggctgtcg gcacagttgc ttccagcatc tggcgtccgt     4620
atgtatgggt gtattttaaa taataaacaa agtgccacac cttcaccaat tatgtcttta     4680
agaaatggac aagttccaaa gagcttgccc aaggctcgac aaggatgtac tttagaatat     4740
ctatattcaa gtacgtggcg cgcatatgtt tgagtgtgca cacaataaag gttaattaat     4800
ctagagtcga cctgcaggca tgcaagcttg gcgtaatcat ggtcatagct gtttcctgtg     4860
tgaaattgtt atccgctcac aattccacac aacatacgag ccggaagcat aaagtgtaaa     4920
gcctgggtg cctaatgagt gagctaactc acattaattg cgttgcgctc actgcccgct     4980
ttccagtcgg gaaacctgtc gtgccagctg cattaatgaa tcggccaacg cgcgggaga     5040
ggcggtttgc gtattgggcg ctcttccgct tcctcgctca ctgactcgct gcgctcggtc     5100
gttcggctgc ggcgagcggt atcagctcac tcaaaggcgg taatacggtt atccacagaa     5160
tcaggggata acgcaggaaa gaacatgtga gcaaaaggcc agcaaaaggc caggaaccgt     5220
aaaaaggccg cgttgctggc gttttttccat aggctccgcc cccctgacga gcatcacaaa     5280
aatcgacgct caagtcagag gtggcgaaac ccgacaggac tataaagata ccaggcgttt     5340
cccccctggaa gctccctcgt gcgctctcct gttccgaccc tgccgcttac cggatacctg     5400
tccgcctttc tcccttcggg aagcgtggcg ctttctcata gctcacgctg taggtatctc     5460
agttcggtgt aggtcgttcg ctccaagctg ggctgtgtgc acgaaccccc cgttcagccc     5520
gaccgctgcg ccttatccgg taactatcgt cttgagtcca acccggtaag acacgactta     5580
tcgccactgg cagcagccac tggtaacagg attagcagag cgaggtatgt aggcggtgct     5640
acagagttct tgaagtggtg gcctaactac ggctacacta aggacagt atttggtatc      5700
tgcgctctgc tgaagccagt taccttcgga aaaagagttg gtagctcttg atccggcaaa     5760
caaaccaccg ctggtagcgg tggttttttt gtttgcaagc agcagattac gcgcagaaaa     5820
aaaggatctc aagaagatcc tttgatcttt tctacggggt ctgacgctca gtggaacgaa     5880
aactcacgtt aagggatttt ggtcatgaga ttatcaaaaa ggatcttcac ctagatcctt     5940
ttaaattaaa aatgaagttt taaatcaatc taaagtatat atgagtaaac ttggtctgac     6000
agttaccaat gcttaatcag tgaggcacct atctcagcga tctgtctatt tcgttcatcc     6060
atagttgcct gactccccgt cgtgtagata actacgatac gggagggctt accatctggc     6120
cccagtgctg caatgatacc gcgagaccca cgctcaccgg ctccagattt atcagcaata     6180
aaccagccag ccggaagggc cgagcgcaga agtggtcctg caactttatc cgcctccatc     6240
cagtctatta attgttgccg ggaagctaga gtaagtagtt cgccagttaa tagtttgcgc     6300
aacgttgttg ccattgctac aggcatcgtg gtgtcacgct cgtcgtttgg tatggcttca     6360
ttcagctccg gttcccaacg atcaaggcga gttacatgat cccccatgtt gtgcaaaaaa     6420
gcggttagct ccttcggtcc tccgatcgtt gtcagaagta agttggccgc agtgttatca     6480
ctcatggtta tggcagcact gcataattct cttactgtca tgccatccgt aagatgcttt     6540
tctgtgactg gtgagtactc aaccaagtca ttctgagaat agtgtatgcg gcgaccgagt     6600
tgctcttgcc cggcgtcaat acgggataat accgcgccac atagcagaac tttaaaagtg     6660
ctcatcattg gaaaacgttc ttcggggcga aaactctcaa ggatcttacc gctgttgaga     6720
```

```
tccagttcga tgtaacccac tcgtgcaccc aactgatctt cagcatcttt tactttcacc    6780
agcgtttctg ggtgagcaaa aacaggaagg caaaatgccg caaaaaaggg aataagggcg    6840
acacggaaat gttgaatact catactcttc ctttttcaat attattgaag catttatcag    6900
ggttattgtc tcatgagcgg atacatattt gaatgtattt agaaaaataa acaaataggg    6960
gttccgcgca catttccccg aaaagtgcca cctgacgtct aagaaaccat tattatcatg    7020
acattaacct ataaaaatag gcgtatcacg aggcccttc gtc                       7063
```